(12) United States Patent
Bernardelli et al.

(10) Patent No.: US 7,214,676 B2
(45) Date of Patent: May 8, 2007

(54) SPIROTRICYCLIC DERIVATIVES AND THEIR USE AS PHOSPHODIESTERASE-7 INHIBITORS

(75) Inventors: Patrick Bernardelli, Fontenay Aux Roses (FR); Pierre Ducrot, Verrieres Le Buisson (FR); Edwige Lorthiois, Paris (FR); Febrice Vergne, Chevry (FR)

(73) Assignee: Warner-Lambert Company LLC, Morris Plains, NJ (US)

( * ) Notice: Subject to any disclaimer, the term of this patent is extended or adjusted under 35 U.S.C. 154(b) by 139 days.

(21) Appl. No.: 10/852,404

(22) Filed: May 24, 2004

(65) Prior Publication Data

US 2004/0214843 A1 Oct. 28, 2004

Related U.S. Application Data

(63) Continuation of application No. 10/101,996, filed on Mar. 19, 2002, now abandoned.

(30) Foreign Application Priority Data

Mar. 21, 2001 (WO) .................. PCT/EP01/03355

(51) Int. Cl.
A61K 31/535 (2006.01)
A61K 31/497 (2006.01)
A61K 31/517 (2006.01)
C07D 273/01 (2006.01)

(52) U.S. Cl. .............. 514/234.5; 514/252.15; 514/266.3; 514/266.31; 544/70; 544/231

(58) Field of Classification Search ........ 544/70, 544/231; 514/234.5, 252.15, 266.3, 266.31
See application file for complete search history.

(56) References Cited

U.S. PATENT DOCUMENTS

| 5,536,716 A | 7/1996 | Chen et al. |
| 5,578,593 A | 11/1996 | Chen et al. |
| 5,652,235 A | 7/1997 | Chen et al. |
| 6,358,948 B1 | 3/2002 | Zhang et al. |
| 6,693,103 B2 | 2/2004 | Zhang et al. |

FOREIGN PATENT DOCUMENTS

| EP | 0 070 171 A1 | 1/1983 |
| WO | WO 00/66560 | 11/1920 |
| WO | WO 88/01508 | 3/1988 |
| WO | WO 1994/13696 A1 | 6/1994 |
| WO | WO 1994/19367 A1 | 9/1994 |
| WO | WO 1997/14686 A1 | 4/1997 |
| WO | WO 00/66164 | 11/2000 |
| WO | WO 00/66570 | 11/2000 |
| WO | WO 00/66571 | 11/2000 |
| WO | WO 2000/66165 A1 | 11/2000 |
| WO | WO 2001/45707 A1 | 6/2001 |

OTHER PUBLICATIONS

Takai et al., Chemical Abstracts, vol. 111:7312, 1989.*
Teranishi et al., Chemical Abstracts, vol. 99:70751, 1983.*
Carretero, Juan C., et al., "A Practical Route to C-8 Substituted Fluoroquinolones", Tetrahedron, vol. 48, No. 32, 1992, pp. 7373-7382.
H. Takai, et al., "Cyclofunction alization of Olefinic Urethanes and Ureas with Halogens. Synthesis of 1-2ubstituted spiro[piperidine-4,4'(3'H)-quinazolun]-2'(1'H)-one derivatives", Chem Pharm. Bull., 1998 pp. 4659-4670, vol. 36, No. 12.

* cited by examiner

*Primary Examiner*—Peter O'Sullivan
(74) *Attorney, Agent, or Firm*—Charles W. Ashbrook; David R. Kurlandsky

(57) ABSTRACT

The invention provides compounds which are PDE7 inhibitors, having the following formula (I), (II) and (III)

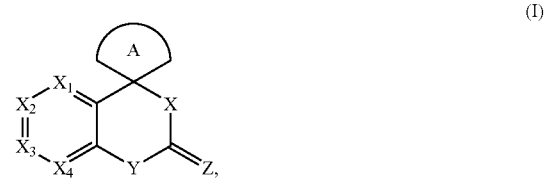

(I)

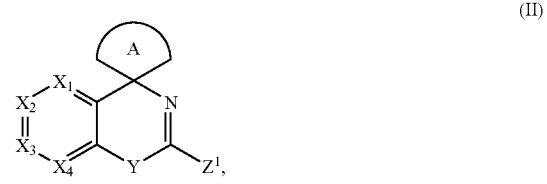

(II)

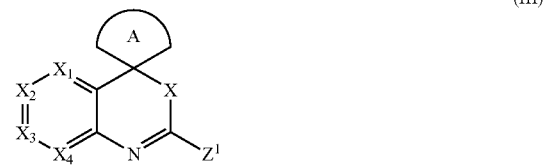

(III)

in which $X_1$, $X_2$, $X_3$, $X_4$, X, Y, Z, A and $Z^1$ are as defined in the description, methods for preparing them and their use for the treatment of disorders for which therapy by a PDE7 inhibitor is relevant.

18 Claims, No Drawings

SPIROTRICYCLIC DERIVATIVES AND THEIR USE AS PHOSPHODIESTERASE-7 INHIBITORS

CROSS REFERENCE TO RELATED APPLICATION

This is a continuation of U.S. patent application Ser. No. 10/101,996, filed on Mar. 19, 2002 now abandoned, which claims the benefit of priority from PCT International Application Number PCT/EP01/03355, filed Mar. 21, 2001.

FIELD OF THE INVENTION

The invention relates to spirotricyclic derivatives, the process for their preparation, and their use as phosphodiesterase 7 (PDE7) inhibitors.

BACKGROUND OF THE INVENTION

Phosphodiesterases (PDE) play an important role in various biological processes by hydrolysing the key second messengers adenosine and guanosine 3',5'-cyclic monophosphates (cAMP and cGMP respectively) into their corresponding 5'-monophosphate nucleotides. Therefore, inhibition of PDE activity produces an increase of cAMP and cGMP intracellular levels that activate specific protein phosphorylation pathways involved in a variety of functional responses.

At least eleven isoenzymes of mammalian cyclic nucleotide phosphodiesterases, numbered PDE 1 through PDE 11, have been identified on the basis of primary structure, substrate specificity or sensitivity to cofactors or inhibitory drugs.

Among these phosphodiesterases, PDE7 is a cAMP-specific PDE. The biochemical and pharmacological characterization showed a high-affinity cAMP-specific PDE ($Km=0.2$ μM), that was not affected by cGMP potent selective PDE isoenzyme inhibitors.

PDE7 activity or protein has been detected in T-cell lines, B-cell lines, airway epithelial (AE) cell lines and several foetal tissues.

Increasing cAMP levels by selective PDE7 inhibition appears to be a potentially promising approach to specifically block T-cell mediated immune responses. Further studies have demonstrated that elevation of intracellular -cAMP levels can modulate inflammatory and immunological processes. This selective approach could presumably be devoid of the side effects associated with known selective PDE inhibitors (e.g. PDE3 or PDE4 selective inhibitors) and which limit their use.

A functional role of PDE7 in T-cell activation has also been disclosed; therefore selective PDE7 inhibitors would be candidates for the treatment of T-cell-related diseases.

AE cells actively participate in inflammatory airway diseases by liberating mediators such as arachidonate metabolites and cytokines. Selective inhibition of PDE7 may be a useful anti-inflammatory approach for treating AE cells related diseases.

Thus, there is a need for selective PDE7 inhibitors, which are active at very low concentrations, i.e. preferably nanomolar inhibitors.

WO 88/01508 discloses compounds of formula

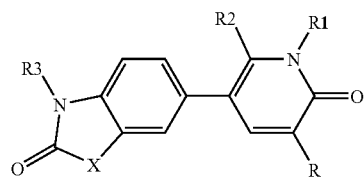

where R is hydrogen, alkyl, alkoxyalkyl, hydroxyalkyl, halo, cyano, carbamoyl, alkyl carbamoyl, formyl, alkylamino or amino;
X is —(CR4R5)a-NR6-(CR4R5)b-;
R1, R2, R3, and R5 are hydrogen or alkyl;
R4 and R6 are hydrogen, alkyl or aralkyl; a and b are 0, 1 or 2 and a+b=0, 1 or 2; R4 and R5 groups on vicinal carbon atoms may together form a carbon-carbon double bond; and geminal R4 and R5 groups may together form a spiro substitutent, —(CH2)d-, where d is 2 to 5; or a pharmaceutically acceptable salt thereof. These compounds are described as cardiotonics.

WO 00/66560 discloses compounds of formula

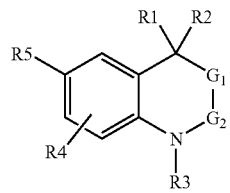

These compounds are described as progesterone receptor modulators

SUMMARY OF THE INVENTION

The invention provides the use of spirotricyclic derivatives, which are PDE inhibitors and more particularly PDE7 inhibitors, having the following formula (I), (II) or

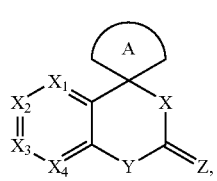

(I)

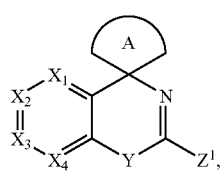

(II)

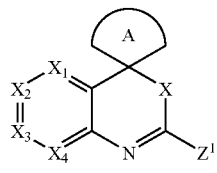

(III)

in which,
a) $X_1$, $X_2$, $X_3$ and $X_4$ are the same or different and are selected from:
N, provided that not more than two of the groups $X_1$, $X_2$, $X_3$ and $X_4$ simultaneously represent a nitrogen atom, or, C—$R^1$, in which $R^1$ is selected from:
Q1, or
lower alkyl, lower alkenyl or lower alkynyl, these groups being unsubstituted or substituted with one or several groups Q2;
the group $X^5$—$R^5$ in which,
$X^5$ is selected from:
a single bond,
lower alkylene, lower alkenylene or lower alkynylene, optionally interrupted with 1 or 2 heteroatoms chosen from O, S, S(=O), $SO_2$ or N, the carbon atoms of these groups being unsubstituted or substituted with one or several groups, identical or different, selected from $SR^6$, $OR^6$, $NR^6R^7$, =O, =S or =N—$R^6$ in which $R^6$ and $R^7$ are the same or different and are selected from hydrogen or lower alkyl, and,
$R^5$ is selected from aryl, heteroaryl, cycloalkyl optionally interrupted with C(=O) or with 1, 2, or 3 heteroatoms chosen from O, S, S(=O), $SO_2$ or N, cycloalkenyl optionally interrupted with C(=O) or with 1, 2, or 3 heteroatoms chosen from O, S, S(=O), $SO_2$ or N, or a bicyclic group, these groups being unsubstituted or substituted with one or several groups selected from Q3, heteroaryl or lower alkyl optionally substituted with Q3;
in which Q1, Q2, Q3 are the same or different and are selected from
hydrogen, halogen, CN, $NO_2$, $SO_3H$, P(=O)(OH)$_2$ $OR^2$, OC(=O)$R^2$, C(=O)$OR^2$, $SR^2$, S(=O)$R^2$, C(=O)—NH—$SO_2$—$CH_3$, $NR^3R^4$, Q-$R^2$, Q-$NR^3R^4$, $NR^2$-Q-$NR^3R^4$ or $NR^3$-Q-$R^2$ in which Q is selected from C(=NR), C(=O), C(=S) or $SO_2$, R is selected from hydrogen, CN, $SO_2NH_2$ or lower alkyl and $R^2$, $R^3$ and $R^4$ are the same or different and are selected from:
hydrogen,
lower alkyl optionally interrupted with C(=O), Q4-aryl, Q4-heteroaryl, Q4-cycloalkyl optionally interrupted with C(=O) or with 1 or 2 heteroatoms chosen from O, S, S(=O), $SO_2$ or N, or Q4-cycloalkenyl optionally interrupted with C(=O) or with 1 or 2 heteroatoms chosen from O, S, S(=O), $SO_2$ or N, in which
Q4 is selected from (CH$_2$)$_n$, lower alkyl interrupted with one heteroatom selected from O, S or N, lower alkenyl or lower alkynyl, these groups being optionally substituted with lower alkyl, OR' or NR'R" in which R' and R" are the same or different and are selected from hydrogen or lower alkyl;
n is an integer selected from 0, 1, 2, 3 or 4;
these groups being unsubstituted or substituted with one or several groups selected from lower alkyl, halogen, CN, $CH_3$, $SO_3H$, $SO_2CH_3$, C(=O)—NH—$SO_2$—$CH_3$, $CF_3$, $OR^6$, $COOR^6$, C(=O)$R^6$, $NR^6R^7$, $NR^6C$(=O)$R^7$, C(=O)$NR^6R^7$ or $SO_2NR^6R^7$, in which $R^6$ and $R^7$ are the same or different and are selected from hydrogen or lower alkyl optionally substituted with one or two groups selected from OR, COOR or NRR$^8$ in which R and $R^8$ are hydrogen or lower alkyl, and, $R^6$ and $R^7$, and/or, $R^3$ and $R^4$, together with the nitrogen atom to which they are linked, can form a 4- to 8-membered heterocyclic ring, which may have one or two heteroatoms selected from O, S, S(=O), $SO_2$ or N, and which may be substituted with,
(CH$_2$)$_n$-Q5, in which n is an integer selected from 0, 1, 2 and 3, and Q5 is a 4- to 8-membered heterocyclic ring which may have one or two heteroatoms selected from O, S or N and which may be substituted with a lower alkyl, or,
a lower alkyl optionally substituted with OR', NR'R", C(=O)NR'R" or COOR' in which R' and R" are the same or different and are selected from,
H, or,
lower alkyl optionally substituted with OR or COOR in which R is hydrogen or lower alkyl and,
R' and R" together with the nitrogen atom to which they are linked, can form a 4- to 8-membered heterocyclic ring, which may have one or two heteroatoms selected from O, S or N; or,
when $X_1$, and $X_2$ both represent C—$R^1$, the 2 substituents $R^1$ may form together with the carbon atoms to which they are attached, a 5-membered heterocyclic ring comprising a nitrogen atom and optionally a second heteroatom selected from O, S or N;
b) X is O, S or $NR^9$, in which $R^9$ is selected from,
hydrogen, CN, OH, $NH_2$,
lower alkyl, lower alkenyl or lower alkynyl, these groups being unsubstituted or substituted with cycloalkyl optionally interrupted with 1 or 2 heteroatoms chosen from O, S, S(=O), $SO_2$ or N, cycloalkenyl optionally interrupted with 1 or 2 heteroatoms chosen from O, S, S(=O), $SO_2$ or N, aryl, heteroaryl, $OR^{10}$, $COOR^{10}$ or $NR^{10}R^{11}$ in which $R^{10}$ and $R^{11}$ are the same or different and are selected from hydrogen or lower alkyl;
c) Y is selected from O, S or N—$R^{12}$, in which $R^{12}$ is selected from:
hydrogen, CN, OH, $NH_2$,
lower alkyl, lower alkenyl or lower alkynyl, these groups being unsubstituted or substituted with cycloalkyl optionally interrupted with 1 or 2 heteroatoms chosen from O, S, S(=O), $SO_2$ or N, cycloalkenyl optionally interrupted with 1 or 2 heteroatoms chosen from O, S, S(=O), $SO_2$ or N, aryl, heteroaryl, $OR^{10}$, $COOR^{10}$ or $NR^{10}R^{11}$ in which $R^{10}$ and $R^{11}$ are the same or different and are selected from hydrogen or lower alkyl;
d) Z is chosen from CH—$NO_2$, O, S or $NR^{13}$ in which $R^{13}$ is selected from:
hydrogen, CN, OH, $NH_2$, aryl, heteroaryl, cycloalkyl optionally interrupted with one or several heteroatoms chosen from O, S, S(=O), $SO_2$ or N, cycloalkenyl optionally interrupted with one or several heteroatoms chosen from O, S, S(=O), $SO_2$ or N, C(=O)$R^{14}$, C(=O)$NR^{14}R^{15}$, $OR^{14}$, or,
lower alkyl, unsubstituted or substituted with one or several groups which are the same or different and which are selected $OR^{14}$, $COOR^{14}$ or $NR^{14}R^{15}$;
$R^{14}$ and $R^{15}$ being independently selected from hydrogen or lower alkyl, or, $R^{14}$ and $R^{15}$, together with the nitrogen atom to which they are linked, can form a 4- to 8-membered heterocyclic ring which may have one or two heteroatoms chosen from O, S or N, and which may be substituted with a lower alkyl, or, when Y is N—$R^{12}$ and Z is N—$R^{13}$, $R^{12}$ and $R^{13}$ may form together a —CH=N— group or a —C=C— group, when X is N—$R^9$ and Z is N—$R^{13}$, $R^9$ and $R^{13}$ may form together a —CH=N— group or a —C=C— group;

e) $Z^1$ is chosen from H, $CH_3$ or $NR^{16}R^{17}$ in which $R^{16}$ and $R^{17}$ are the same or different and are selected from:

hydrogen, CN, aryl, heteroaryl, cycloalkyl optionally interrupted with one or several heteroatoms chosen from O, S, S(=O), $SO_2$ or N, cycloalkenyl optionally interrupted with one or several heteroatoms chosen from O, S, S(=O), $SO_2$ or N, C(=O)$R^{14}$, C(=O)$NR^{14}R^{15}$, $OR^{14}$, or, lower alkyl unsubstituted or substituted with one or several groups selected from $OR^{14}$, $COOR^{14}$ or $NR^{14}R^{15}$, $R^{14}$ and $R^{15}$ being chosen from hydrogen or lower alkyl, and, $R^{14}$ and $R^{15}$, and/or, $R^{16}$ and $R^{17}$, together with the nitrogen atom to which they are linked, can form a 4- to 8-membered heterocyclic ring which may have one or two heteroatoms chosen from O, S or N, and which may be substituted with a lower alkyl;

f) A is a cycle chosen from:

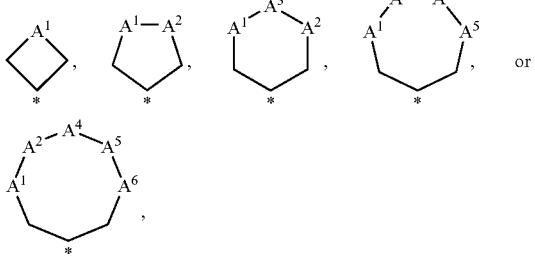

in which, $A^1$, $A^2$, $A^3$, $A^4$, $A^5$ and $A^6$ are the same or different and are selected from O, S, C, C(=O), SO, $SO_2$ or N—$R^{18}$ in which $R^{18}$ is selected from:

hydrogen, aryl, heteroaryl, cycloalkyl optionally interrupted with one or several heteroatoms chosen from O, S, S(=O), $SO_2$ or N, cycloalkenyl optionally interrupted with one or several heteroatoms chosen from O, S, S(=O), $SO_2$ or N, lower alkyl unsubstituted or substituted with aryl, heteroaryl, cycloalkyl optionally interrupted with one or several heteroatoms chosen from O, S, S(=O), $SO_2$ or N, cycloalkenyl optionally interrupted with one or several heteroatoms chosen from O, S, S(=O), $SO_2$ or N, CN, $NR^{19}R^{20}$, C(=O)$NR^{19}R^{20}$, $OR^{19}$, C(=O)$R^{19}$ or C(=O)$OR^{19}$ in which $R^{19}$ and $R^{20}$ are identical or different and are selected from hydrogen or lower alkyl;

* represents the carbon atom which is shared between the cycle A and the backbone cycle containing X and/or Y;

each carbon atom of the cycle A is unsubstituted or substituted with 1 or 2 groups, identical or different, selected from lower alkyl optionally substituted with $OR^{21}$, $NR^{21}R^{22}$, $COOR^{21}$ or $CONR^{21}R^{22}$, lower haloalkyl, CN, F, =O, $SO_2NR^{19}R^{20}$, $OR^{19}$, $SR^{19}$, C(=O)$OR^{19}$, C(=O)$NR^{19}R^{20}$ or $NR^{19}R^{20}$ in which $R^{19}$ and $R^{20}$ are identical or different and are selected from hydrogen or lower alkyl optionally substituted with $OR^{21}$, $NR^{21}R^{22}$, $COOR^{21}$ or $CONR^{21}R^{22}$ in which $R^{21}$ and $R^{22}$ are identical or different and are selected from hydrogen or lower alkyl, and, $R^{19}$ and $R^{20}$, and/or, $R^{21}$ and $R^{22}$, together with the nitrogen atom to which they are linked, can form a 4- to 8-membered heterocyclic ring;

2 atoms of the cycle A, which are not adjacent, may be linked by a 2, 3 or 4 carbon atom chain which may be interrupted with 1 heteroatom chosen from O, S or N;

provided that not more than two of the groups $A^1$, $A^2$, $A^3$, $A^4$, $A^5$ and $A^6$ simultaneously represent a heteroatom;

of their tautomeric forms, their racemic forms or their isomers and of their pharmaceutically acceptable derivatives, for the prevention or the treatment of disorders for which therapy by a PDE7 inhibitor is relevant.

The invention also relates to compounds, which are PDE7 inhibitors, having the following formula (I), (II) or (III)

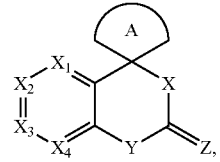
(I)

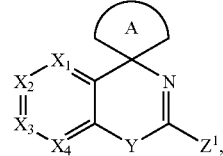
(II)

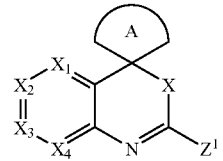
(III)

in which, a) $X_1$, $X_2$, $X_3$ and $X_4$ are the same or different and are selected from:

N, provided that not more than two of the groups $X_1$, $X_2$, $X_3$ and $X_4$ simultaneously represent a nitrogen atom, or, C—$R^1$, in which $R^1$ is selected from:

Q1, or lower alkyl, lower alkenyl or lower alkynyl, these groups being unsubstituted or substituted with one or several groups Q2;

the group $X^5$—$R^5$ in which, $X^5$ is selected from:

a single bond, lower alkylene, lower alkenylene or lower alkynylene, optionally interrupted with 1 or 2 heteroatoms chosen from O, S, S(=O), $SO_2$ or N, the carbon atoms of these groups being unsubstituted or substituted with one or several groups, identical or different, selected from $SR^6$, $OR^6$, $NR^6R^7$, =O, =S or =N—$R^6$ in which $R^6$ and $R^7$ are the same or different and are selected from hydrogen or lower alkyl, and, $R^5$ is selected from aryl, heteroaryl, cycloalkyl optionally interrupted with C(=O) or with 1, 2, or 3 heteroatoms chosen from O, S, S(=O), $SO_2$ or N, cycloalkenyl optionally interrupted with C(=O) or with 1, 2, or 3 heteroatoms chosen from O, S, S(=O), $SO_2$ or N, or a bicyclic group, these groups being unsubstituted or substituted with one or several groups selected from Q3, heteroaryl or lower alkyl optionally substituted with Q3;

in which Q1, Q2, Q3 are the same or different and are selected from hydrogen, halogen, CN, $NO_2$, $SO_3H$, P(=O)(OH)$_2$ $OR^2$, OC(=O)$R^2$, C(=O)O$R^2$, $SR^2$, S(=O)$R^2$, C(=O)—NH—$SO_2$—$CH_3$, $NR^3R^4$, Q-$R^2$, Q-$NR^3R^4$, $NR^2$-Q-$NR^3R^4$ or $NR^3$-Q-$R^2$ in which Q is selected from C(=NR), C(=O), C(=S) or $SO_2$, R is selected from hydrogen, CN, $SO_2NH_2$ or lower alkyl and $R^2$, $R^3$ and $R^4$ are the same or different and are selected from:

hydrogen, lower alkyl optionally interrupted with C(=O), Q4-aryl, Q4-heteroaryl, Q4-cycloalkyl optionally interrupted with C(=O) or with 1 or 2 heteroatoms chosen from O, S, S(=O), $SO_2$ or N, or Q4-cycloalkenyl optionally interrupted with C(=O) or with 1 or 2 heteroatoms chosen from O, S, S(=O), $SO_2$ or N, in which Q4 is selected from $(CH_2)_n$, lower alkyl interrupted with one heteroatom selected from O, S or N, lower alkenyl or lower alkynyl, these groups being optionally substituted with lower alkyl, OR' or NR'R" in which R' and R" are the same or different and are selected from hydrogen or lower lower alkyl;

n is an integer selected from 0, 1, 2, 3 or 4;

these groups being unsubstituted or substituted with one or several groups selected from lower alkyl, halogen, CN, $CH_3$, $SO_3H$, $SO_2CH_3$, C(=O)—NH—$SO_2$—$CH_3$, $CF_3$, $OR^6$, $COOR^6$, C(=O)$R^6$, $NR^6R^7$, $NR^6C(=O)R^7$, C(=O)$NR^6R^7$ or $SO_2NR^6R^7$, in which $R^6$ and $R^7$ are the same or different and are selected from hydrogen or lower alkyl optionally substituted with one or two groups selected from OR, COOR or $NRR^8$ in which R and $R^8$ are hydrogen or lower alkyl, and, $R^6$ and $R^7$, and/or, $R^3$ and $R^4$, together with the nitrogen atom to which they are linked, can form a 4- to 8-membered heterocyclic ring, which may have one or two heteroatoms selected from O, S, S(=O), $SO_2$, or N, and which may be substituted with, $(CH_2)_n$-Q5, in which n is an integer selected from 0, 1, 2 and 3, and Q5 is a 4- to 8-membered heterocyclic ring which may contain one or two heteroatoms selected from O, S or N and which may be substituted with a lower alkyl, or, a lower alkyl optionally substituted with OR', NR'R", C(=O)NR'R" or COOR' in which R' and R" are the same or different and are selected from, H, or, lower alkyl optionally substituted with OR or COOR in which R is hydrogen or lower alkyl and, R' and R" together with the nitrogen atom to which they are linked, can form a 4- to 8-membered heterocyclic ring, which may contain one or two heteroatoms selected from O, S or N; or, when $X_1$ and $X_2$ both represent C—$R^1$, the 2 substituents $R^1$ may form together with the carbon atoms to which they are attached, a 5-membered heterocyclic ring comprising a nitrogen atom and optionally a second heteroatom selected from O, S or N;

b) X is O or $NR^9$, in which $R^9$ is selected from, hydrogen, CN, OH, $NH_2$, lower alkyl, lower alkenyl or lower alkynyl, these groups being unsubstituted or substituted with cycloalkyl optionally interrupted with 1 or 2 heteroatoms chosen from O, S, S(=O), $SO_2$ or N, cycloalkenyl optionally interrupted with 1 or 2 heteroatoms chosen from O, S, S(=O), $SO_2$ or N, aryl, heteroaryl, $OR^{10}$, $COOR^{10}$ or $NR^{10}R^{11}$ in which $R^{10}$ and $R^{11}$ are the same or different and are selected from hydrogen or lower alkyl;

c) Y is selected from O, S or N—$R^{12}$, in which $R^{12}$ is selected from:

hydrogen, CN, OH, $NH_2$, lower alkyl, lower alkenyl or lower alkynyl, these groups being unsubstituted or substituted with, cycloalkyl optionally interrupted with 1 or 2 heteroatoms chosen from O, S, S(=O), $SO_2$ or N, cycloalkenyl optionally interrupted with 1 or 2 heteroatoms chosen from O, S, S(=O), $SO_2$ or N, aryl, heteroaryl, $OR^{10}$, $COOR^{10}$ or $NR^{10}R^{11}$ in which $R^{10}$ and $R^{11}$ are the same or different and are selected from hydrogen or lower alkyl;

d) Z is chosen from CH—$NO_2$, O, S or $NR^{13}$ in which $R^{13}$ is selected from:

hydrogen, CN, OH, $NH_2$, aryl, heteroaryl, cycloalkyl optionally interrupted with one or several heteroatoms chosen from O, S, S(=O), $SO_2$ or N, cycloalkenyl optionally interrupted with one or several heteroatoms chosen from O, S, S(=O), $SO_2$ or N, C(=O)$R^{14}$, C(=O)$NR^{14}R^{15}$, $OR^{14}$, or, lower alkyl, unsubstituted or substituted with one or several groups which are the same or different and which are selected $OR^{14}$, $COOR^{10}$ or $NR^{14}R^{15}$;

$R^{14}$ and $R^{15}$ being independently selected from hydrogen or lower alkyl, or, $R^{14}$ and $R^{15}$, together with the nitrogen atom to which they are linked, can form a 4- to 8-membered heterocyclic ring which may contain one or two heteroatoms chosen from O, S or N, and which may be substituted with a lower alkyl, or, when Y is N—$R^{12}$ and Z is N—$R^{13}$, may form together a —CH=N— group or a —C=C— group, when X is N—$R^9$ and Z is N—$R^{13}$, $R^9$ and $R^{13}$ may form together a —CH=N— group or a —C=C— group;

e) $Z^1$ is chosen from H, $CH_3$ or $NR^{16}R^{17}$ in which $R^{16}$ and $R^{17}$ are the same or different and are selected from:

hydrogen, CN, aryl, heteroaryl, cycloalkyl optionally interrupted with one or several heteroatoms chosen from O, S, S(=O), $SO_2$ or N, cycloalkenyl optionally interrupted with one or several heteroatoms chosen from O, S, S(=O), $SO_2$ or N, C(=O)$R^{14}$, C(=O)$NR^{14}R^{15}$, $OR^{14}$ or, lower alkyl unsubstituted or substituted with one or several groups selected from $OR^{14}$, $COOR^{14}$ or $NR^{14}R^{15}$, $R^{14}$ and $R^{15}$ being chosen from hydrogen or lower alkyl, and, $R^{14}$ and $R^{15}$, and/or, $R^{16}$ and $R^{17}$, together with the nitrogen atom to which they are linked, can form a 4- to 8-membered heterocyclic ring which may contain one or two heteroatoms chosen from O, S or N, and which may be substituted with a lower alkyl;

f) A is a cycle chosen from:

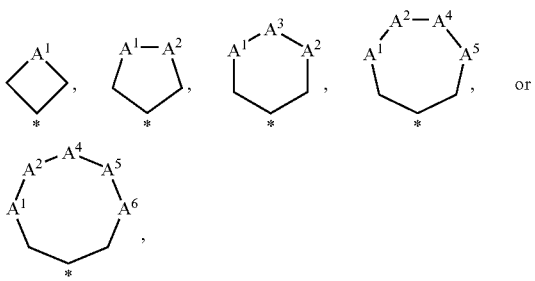

in which,
A¹, A², A⁴, A⁵ and A⁶ are the same or different and are selected from O, S, C, C(=O), SO, SO₂ or N—R¹⁸ in which R¹⁸ is selected from:
hydrogen, aryl, heteroaryl, cycloalkyl optionally interrupted with one or several heteroatoms chosen from O, S, S(=O), SO₂ or N, cycloalkenyl optionally interrupted with one or several heteroatoms chosen from O, S, S(=O), SO₂ or N,
lower alkyl unsubstituted or substituted with aryl, heteroaryl, cycloalkyl optionally interrupted with one or several heteroatoms chosen from O, S, S(=O), SO₂ or N, cycloalkenyl optionally interrupted with one or several heteroatoms chosen from O, S, S(=O), SO₂ or N, CN, NR¹⁹R²⁰, C(=O)NR¹⁹R²⁰, OR¹⁹, C(=O)R¹⁹ or C(=O)OR¹⁹ in which R¹⁹ and R²⁰ are identical or different and are selected from hydrogen or lower alkyl;
A³ is selected from O, S, C, C(=O), SO or SO₂, or N—R¹⁸ when A¹ and/or A² are C(=O) or when Y is O or S, wherein R¹⁸ is as defined above;
* represents the carbon atom which is shared between the cycle A and the backbone cycle containing X and/or Y;
each carbon atom of the cycle A is unsubstituted or substituted with 1 or 2 groups, identical or different, selected from lower alkyl optionally substituted with OR²¹, NR²¹R²², COOR²¹ or CONR²¹R²², lower haloalkyl, CN, F, =O, SO₂NR¹⁹R²⁰, OR¹⁹, SR¹⁹, C(=O)OR¹⁹, C(=O)NR¹⁹R²⁰ or NR¹⁹R²⁰ in which R¹⁹ and R²⁰ are identical or different and are selected from hydrogen or lower alkyl optionally substituted with OR²¹, NR²¹R²², COOR²¹ or CONR²¹R²² in which R²¹ and R²² are identical or different and are selected from hydrogen or lower alkyl, and, R¹⁹ and R²⁰, and/or, R²¹ and R²², together with the nitrogen atom to which they are linked, can form a 4- to 8-membered heterocyclic ring;
2 atoms of the cycle A, which are not adjacent, may be linked by a 2, 3 or 4 carbon atom chain which may be interrupted with 1 heteroatom chosen from O, S or N;
provided that:
not more than two of the groups A¹, A², A³, A⁴, A⁵ and A⁶ simultaneously represent a heteroatom;
the cycle A does not contain more than 2 carbon atoms in an sp² hybridization state;
when X is O, X₂ is not C—R¹ in which R¹ is
a thienyl substituted with CN or with CN and CH₃,
a phenyl substituted with CN, Cl, NO₂ or CN and F, Br
F;

or their tautomeric forms, their racemic forms or their isomers and their pharmaceutically acceptable derivatives.

These compounds are selective PDE7 inhibitors. They can be used in the treatment of various diseases, such as T-cell-related diseases, autoimmune diseases, osteoarthritis, rheumatoid arthritis, multiple sclerosis, osteoporosis, chronic obstructive pulmonary disease (COPD), asthma, cancer, acquired immune deficiency syndrome (AIDS), allergy or inflammatory bowel disease (IBD).

The invention also relates to a process for preparing the above compounds.

The invention further concerns the use of a compound of formula (I), (II) or (III) for the preparation of a medicament for the prevention or the treatment of disorders for which therapy by a PDE7 inhibitor is relevant.

The invention also provides a method for the treatment of a disorder for which therapy by a PDE7 inhibitor is relevant, comprising administering to a mammal in need thereof an effective amount of compound of formula (I), (II) or (III).

The invention also provides a method for the treatment of T-cell-related diseases, autoimmune diseases, osteoarthritis, rheumatoid arthritis, multiple sclerosis, osteoporosis, chronic obstructive pulmonary disease (COPD), asthma, cancer, acquired immune deficiency syndrome (AIDS), allergy or inflammatory bowel disease (IBD), comprising administering to a mammal in need thereof an effective amount of compound of formula (I), (II) or (III).

The invention also concerns a pharmaceutical composition comprising a compound of formula (I), (II) or (III) together with a pharmaceutically acceptable carrier, excipient, diluent or delivery system.

DETAILED DESCRIPTION OF THE INVENTION

The present invention provides the use of compounds, which are PDE7 inhibitors, having formula (I), (II) or (III),

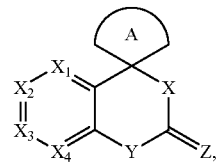

(I)

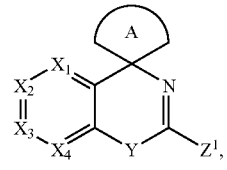

(II)

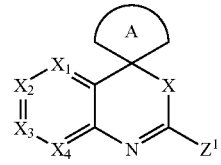

(III)

in which
a) X₁, X₂, X₃ and X₄ are the same or different and are selected from:
N, provided that not more than two of the groups X₁, X₂, X₃ and X₄ simultaneously represent a nitrogen atom, or,
C—R¹, in which R¹ is selected from:
Q1, or
lower alkyl, lower alkenyl or lower alkynyl, these groups being unsubstituted or substituted with one or several groups Q2;

the group $X^5$—$R^5$ in which, $X^5$ is selected from:
- a single bond,
- lower alkyl, lower alkenylene or lower alkynylene, optionally interrupted with 1 or 2 heteroatoms chosen from O, S, S(=O), SO$_2$ or N, , the carbon atoms of these groups being unsubstituted or substituted with one or several groups, identical or different, selected from SR$^6$, OR$^6$, NR$^6$R$^7$, =O, =S or =N—R$^6$ in which R$^6$ and R$^7$ are the same or different and are selected from hydrogen or lower alkyl, and, $R^5$ is selected from aryl, heteroaryl, cycloalkyl optionally interrupted with C(=O) or with 1, 2, or 3 heteroatoms chosen from O, S, S(=O), SO$_2$ or N, cycloalkenyl optionally interrupted with C(=O) or with 1, 2, or 3 heteroatoms chosen from O, S, S(=O), SO$_2$ or N, or a bicyclic group, these groups being unsubstituted or substituted with one or several groups selected from Q3, heteroaryl or lower alkyl optionally substituted with Q3;

in which Q1, Q2, Q3 are the same or different and are selected from hydrogen, halogen, CN, NO$_2$, SO$_3$H, P(=O)(OH)$_2$ OR$^2$, OC(=O)R$^2$, C(=O)OR$^2$, SR$^2$, S(=O)R$^2$, NR$^3$R$^4$, Q-R$^2$, Q-NR$^3$R$^4$, NR$^2$-Q-NR$^3$R$^4$ or NR$^3$-Q-R$^2$ in which Q is selected from C(=NR), C(=O), C(=S) or SO$_2$, R is selected from hydrogen or lower alkyl and R$^2$, R$^3$ and R$^4$ are the same or different and are selected from:

hydrogen, lower alkyl optionally interrupted with C(=O), (CH$_2$)$_n$-aryl, (CH$_2$)$_n$-heteroaryl, (CH$_2$)$_n$-cycloalkyl optionally interrupted with C(=O) or with 1 or 2 heteroatoms chosen from O, S, S(=O), SO$_2$ or N or (CH$_2$)$_n$-cycloalkenyl optionally interrupted with C(=O) or with 1 or 2 heteroatoms chosen from O, S, S(=O), SO$_2$ or N, in which n is an integer selected from 0, 1, 2, 3 or 4;

these groups being unsubstituted or substituted with one or several groups selected from lower alkyl, halogen, CN, SO$_3$H, CH$_3$, SO$_2$CH$_3$, CF$_3$, C(=O)—NH—SO$_2$—CH$_3$, OR$^6$, COOR$^6$, NR$^6$R$^7$, C(=O)NR$^6$R$^7$ or SO$_2$NR$^6$R$^7$, in which R$^6$ and R$^7$ are the same or different and are selected from hydrogen or lower alkyl optionally substituted with one or two groups selected from OR, COOR or NRR$^8$ in which R and R$^8$ are hydrogen or lower alkyl, and, R$^6$ and R$^7$, and/or, R$^3$ and R$^4$, together with the nitrogen atom to which they are linked, can form a 4- to 8-membered heterocyclic ring, which may contain one or two heteroatoms selected from O, S, S(=O), SO$_2$ or N, and which may be substituted with, a 4- to 8-membered heterocyclic ring, which may contain one or two heteroatoms selected from O, S or N and which may be substituted with a lower alkyl, or, a lower alkyl optionally substituted with OR', NR'R", C(=O)NR'R" or COOR' in which R' and R" are the same or different and are selected from, H, or, lower alkyl optionally substituted with OR or COOR in which R is hydrogen or lower alkyl and, R' and R" together with the nitrogen atom to which they are linked, can form a 4- to 8-membered heterocyclic ring, which may contain one or two heteroatoms selected from O, S or N;

b) X is O, S or NR$^9$, in which R$^9$ is selected from, hydrogen, CN, OH, NH$_2$, lower alkyl, lower alkenyl or lower alkynyl, these groups being unsubstituted or substituted with cycloalkyl optionally interrupted with 1 or 2 heteroatoms chosen from O, S, S(=O), SO$_2$ or N, cycloalkenyl optionally interrupted with 1 or 2 heteroatoms chosen from O, S, S(=O), SO$_2$ or N, aryl, heteroaryl, OR$^{10}$ or NR$^{10}$R$^{11}$ in which R$^{10}$ and R$^{11}$ are the same or different and are selected from hydrogen or lower alkyl;

c) Y is selected from O, S or N—R$^{12}$, in which R$^{12}$ is selected from:

hydrogen, CN, OH, NH$_2$, lower alkyl, lower alkenyl or lower alkynyl, these groups being unsubstituted or substituted with, cycloalkyl optionally interrupted with 1 or 2 heteroatoms chosen from O, S, S(=O), SO$_2$ or N, cycloalkenyl optionally interrupted with 1 or 2 heteroatoms chosen from O, S, S(=O), SO$_2$ or N, aryl, heteroaryl, OR$^{10}$or NR$^{10}$R$^{11}$ in which R$^{10}$ and R$^{11}$ are the same or different and are selected from hydrogen or lower alkyl;

d) Z is chosen from CH—NO$_2$, O, S or NR$^{13}$ in which R$^{13}$ is selected from:

hydrogen, CN, OH, NH$_2$, aryl, heteroaryl, cycloalkyl optionally interrupted with one or several heteroatoms chosen from O, S, S(=O), SO$_2$ or N, cycloalkenyl optionally interrupted with one or several heteroatoms chosen from O, S, S(=O), SO$_2$ or N, C(=O)R$^{14}$, C(=O)NR$^{14}$R$^{15}$, OR$^{14}$, or, lower alkyl, unsubstituted or substituted with one or several groups which are the same or different and which are selected OR$^{14}$ or NR$^{14}$R$^{15}$;

R$^{14}$ and R$^{15}$ being independently selected from hydrogen or lower alkyl, or, R$^{14}$ and R$^{15}$, together with the nitrogen atom to which they are linked, can form a 4- to 8-membered heterocyclic ring which may contain one or two heteroatoms chosen from O, S or N, and which may be substituted with a lower alkyl;

e) Z$^1$ is chosen from H, CH$_3$ or NR$^{16}$R$^{17}$ in which R$^{16}$ and R$^{17}$ are the same or different and are selected from:

hydrogen, CN, aryl, heteroaryl, cycloalkyl optionally interrupted with one or several heteroatoms chosen from O, S, S(=O), SO$_2$ or N, cycloalkenyl optionally interrupted with one or several heteroatoms chosen from O, S, S(=O), SO$_2$ or N, C(=O)R$^{14}$, C(=O)NR$^{14}$R$^{15}$, OR$^{14}$ or, lower alkyl unsubstituted or substituted with one or several groups selected from OR$^{14}$ or NR$^{14}$R$^{15}$, R$^{14}$ and R$^{15}$ being chosen from hydrogen or lower alkyl, and, R$^{14}$ and R$^{15}$, and/or, R$^{16}$ and R$^{17}$, together with the nitrogen atom to which they are linked, can form a 4- to 8-membered heterocyclic ring which may contain one or two heteroatoms chosen from O, S or N, and which may be substituted with a lower alkyl;

f) A is a cycle chosen from:

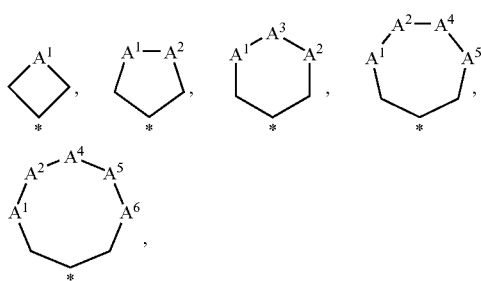

in which,

A$^1$, A$^2$, A$^3$, A$^4$, A$^5$ and A$^6$ are the same or different and are selected from O, S, C, C(=O), SO, SO$_2$ or N—R$^{18}$ in which R$^{18}$ is selected from:

hydrogen, aryl, heteroaryl, cycloalkyl optionally interrupted with one or several heteroatoms chosen from O, S, S(=O), SO$_2$ or N, cycloalkenyl optionally interrupted with one or several heteroatoms chosen from O, S, S(=O), SO$_2$ or N, lower alkyl unsubstituted or substituted with aryl, heteroaryl, cycloalkyl optionally interrupted with one or several heteroatoms chosen from O, S, S(=O), SO$_2$ or N, cycloalkenyl optionally interrupted with one or several heteroatoms chosen from O, S, S(=O), SO$_2$ or N, CN, NR$^{19}$R$^{20}$, C(=O)NR$^{19}$R$^{20}$, OR$^{19}$, C(=O)R$^{19}$ or C(=O)OR$^{19}$ in which R$^{19}$ and R$^{20}$ are identical or different and are selected from hydrogen or lower alkyl;

\* represents the carbon atom which is shared between the cycle A and the backbone cycle containing X and/or Y;

each carbon atom of the cycle A is unsubstituted or substituted with 1 or 2 groups, identical or different, selected from lower alkyl optionally substituted with OR$^2$, NR$^{21}$R$^{22}$, COOR$^{21}$ or CONR$^{21}$R$^{22}$, lower haloalkyl, CN, F, =O, SO$_2$NR$^{19}$R$^{20}$, OR$^{19}$, SR$^{19}$, C(=O)OR$^{19}$, C(=O)NR$^{19}$R$^{20}$ or NR$^{19}$R$^{20}$ in which R$^{19}$ and R$^{20}$ are identical or different and are selected from hydrogen or lower alkyl optionally substituted with OR$^{21}$, NR$^{21}$R$^{22}$, COOR$^{21}$ or COONR$^{21}$R$^{22}$ in which R$^{21}$ and R$^{22}$ are identical or different and are selected from hydrogen or lower alkyl, and, R$^{19}$ and R$^{20}$, and/or, R$^{21}$ and R$^{22}$, together with the nitrogen atom to which they are linked, can form a 4- to 8-membered heterocyclic ring;

2 atoms of the cycle A, which are not adjacent, may be linked by a 2, 3 or 4 carbon atom chain which may be interrupted with 1 heteroatom chosen from O, S or N;

provided that not more than two of the groups A$^1$, A$^2$, A$^3$, A$^4$, A$^5$ and A$^6$ simultaneously represent a heteroatom;

of their tautomeric forms, their racemic forms or their isomers and of their pharmaceutically acceptable derivatives, for the prevention or the treatment of disorders for which therapy by a PDE7 inhibitor is relevant.

A preferred use concerns the PDE7 inhibitors of formula (I),

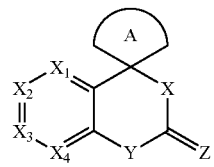

in which X$_1$, X$_2$, X$_3$, X$_4$, X, Y, Z and A are as defined above, for the prevention or the treatment of disorders for which therapy by a PDE7 inhibitor is relevant.

A more preferred use concerns the PDE7 inhibitors of formula (II) or (III) in which, a) X$_1$, X$_2$ and X$_3$ are the same or different and are C—R$^1$, in which R$^1$ is selected from:

hydrogen, halogen, CN, SO$_3$H, NO$_2$, CF$_3$, OR$^2$, SR$^2$, NR$^2$R$^3$, COR$^2$, COOR$^2$, CONR$^2$R$^3$, SO$_2$CH$_3$, SO$_2$NR$^2$R$^3$ in which R$^2$ and R$^3$ are the same or different and are selected from hydrogen or lower alkyl optionally substituted with halogen, CN, SO$_3$H, OR$^6$, COOR$^6$, NR$^6$R$^7$, SO$_2$NR$^6$R$^7$ or C(=O)NR$^6$R$^7$ in which R$^6$ and R$^7$ are the same or different and are selected from hydrogen or lower alkyl, and, R$^6$ and R$^7$, together with the nitrogen atom to which they are linked, can form a 4- to 8-membered heterocyclic ring lower alkyl, lower alkenyl or lower alkynyl, these groups being unsubstituted or substituted with 1, 2 or 3 groups selected from halogen, CN, OR$^2$, COOR$^2$, NR$^3$R$^4$, SO$_2$NR$^3$R$^4$ or C(=O)NR$^3$R$^4$ in which R$^2$, R$^3$ and R$^4$ are the same or different and are selected from hydrogen or lower alkyl, and, R$^3$ and R$^4$, together with the nitrogen atom to which they are linked, can form a 4- to 8-membered heterocyclic ring;

the group X$^5$—R$^5$ in which,

X$^5$ is selected from a lower alkylene or a single bond, and,

R$^5$ is selected from phenyl, pyridyl or indolyl, these groups being unsubstituted or substituted with one or several groups selected from Q3, heteroaryl or lower alkyl optionally substituted with Q3 in which Q3 is selected from:

halogen, CN, SO$_3$H, NO$_2$, CF$_3$, OR$^2$, OC(=O)R$^2$, C(=O)R$^2$, C(=O)OR$^2$, NH—C(=O)R$^2$, NR$^3$R$^4$, SO$_2$NR$^3$R$^4$ or C(=O)NR$^3$R$^4$ in which R$^2$, R$^3$ and R$^4$ are the same or different and are selected from:

hydrogen, lower alkyl unsubstituted or substituted with one or several groups selected from halogen, OR$^6$, COOR$^6$ or NR$^6$R$^7$ in which R$^6$ and R$^7$ are the same or different and are selected from hydrogen or lower alkyl and, R$^6$ and R$^7$, and/or, R$^3$ and R$^4$, together with the nitrogen atom to which they are linked, can form a 4- to 8-membered heterocyclic ring, which may contain one or two heteroatoms selected from O, S or N, and which may be substituted with a 4- to 8-membered heterocyclic ring, which may contain one or two heteroatoms selected from O, S or N and which may be substituted with a lower alkyl, or, a lower alkyl optionally substituted with OR', NR'R'', C(=O)NR'R'' or COOR' in which R' and R'' are the same or different and are selected from H, or, lower alkyl optionally substituted with OR or COOR in which R is hydrogen or lower alkyl and, R' and R" together with the nitrogen atom to which they are linked, can form a 4- to 8-membered heterocyclic ring, which may contain one or two heteroatoms selected from O, S or N;

b) $X_4$ is C—$R^1$ in which $R^1$ is selected from hydrogen, halogen, CN, $NO_2$, $SO_2CH_3$, $SO_3H$, $CH_3$, $CF_3$, $OR^2$, $SR^2$, $NR^2R^3$, $COOR^2$, $CONR^2R^3$, $SO_2NR^2R^3$ in which $R^2$ and $R^3$ are the same or different and are selected from hydrogen or lower alkyl;

c) X is NH;

d) Y is NH;

e) $Z^1$ is chosen from $NR^{16}R^{17}$ in which $R^{16}$ and $R^{17}$ are the same or different and are selected from:
hydrogen, CN, C(=O)$R^{14}$, (C=O)$NR^{14}R^{15}$, $OR^{14}$, or,
lower alkyl unsubstituted or substituted with one or several groups selected from $OR^{14}$ or $NR^{14}R^{15}$, $R^{14}$ and $R^{15}$ being chosen from hydrogen or lower alkyl, and, $R^{14}$ and $R^{15}$, and/or, $R^{16}$ and $R^{17}$, together with the nitrogen atom to which they are linked, can form a 4- to 8-membered heterocyclic ring which may contain one or two heteroatoms selected from O, S or N, and which may be substituted with a lower alkyl;

f) A is a cycle chosen from:

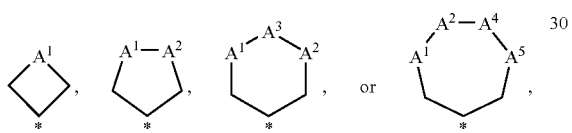

in which, $A^1$, $A^2$, $A^3$, $A^4$ and $A^5$ are the same or different and are selected from:
a carbon atom, unsubstituted or substituted with 1 or 2 groups, identical or different, selected from lower alkyl, OH or F, or,
an oxygen atom;

* represents the carbon atom which is shared between the cycle A and the backbone cycle containing X and/or Y;

2 atoms of the cycle A, which are not adjacent, may be linked by a 2, 3 or 4 carbon atom chain, provided that:
not more than one of the groups $A^1$, $A^2$, $A^3$, $A^4$ and $A^5$ simultaneously represent an oxygen atom;

for the prevention or the treatment of disorders for which therapy by a PDE7 inhibitor is relevant.

A particularly preferred use concerns the PDE7 inhibitors of formula (I), in which, a) $X_1$, $X_2$ and $X_3$ are the same or different and are C—$R^1$, in which $R^1$ is selected from:
hydrogen, halogen, CN, $SO_3H$, $NO_2$, $CF_3$, $OR^2$, $SR^2$, $NR^2R^3$, $COR^2$, $COOR^2$, $CONR^2R^3$, $SO_2CH_3$, $SO_2NR^2R^3$ in which $R^2$ and $R^3$ are the same or different and are selected from hydrogen or lower alkyl optionally substituted with halogen, CN, $OR^6$, $COOR^6$, $NR^6R^7$, $SO_2NR^6R^7$ or C(=O)$NR^6R^7$ in which $R^6$ and $R^7$ are the same or different and are selected from hydrogen or lower alkyl, and, $R^6$ and $R^7$, together with the nitrogen atom to which they are linked, can form a 4- to 8-membered heterocyclic ring;

lower alkyl, lower alkenyl or lower alkynyl, these groups being unsubstituted or substituted with 1, 2 or 3 groups selected from halogen, CN, $SO_3H$, $OR^2$, $COOR^2$, $NR^3R^4$, $SO_2NR^3R^4$ or C(=O)$NR^3R^4$ in which $R^2$, $R^3$ and $R^4$ are the same or different and are selected from hydrogen or lower alkyl, and, $R^3$ and $R^4$, together with the nitrogen atom to which they are linked, can form a 4- to 8-membered heterocyclic ring;

the group $X^5$—$R^5$ in which,
$X^5$ is selected from a lower alkylene or a single bond, and,
$R^5$ is selected from phenyl, pyridyl or indolyl, these groups being unsubstituted or substituted with 1, 2 or 3 groups selected from Q3, heteroaryl or lower alkyl optionally substituted with Q3 in which Q3 is selected from:
halogen, CN, $SO_3H$, $NO_2$, $CF_3$, $OR^2$, OC(=O)$R^2$, C(=O)$R^2$, C(=O)$OR^2$, NH—C(=O)$R^2$, $NR^3R^4$, $SO_2NR^3R^4$, C(=O)$NR^3R^4$ in which $R^2$, $R^3$ and $R^4$ are the same or different and are selected from:
hydrogen, lower alkyl unsubstituted or substituted with one or several groups selected from halogen, $OR^6$, $COOR^6$ or $NR^6R^7$ in which $R^6$ and $R^7$ are the same or different and are selected from hydrogen or lower alkyl and, $R^6$ and $R^7$, and/or, $R^3$ and $R^4$, together with the nitrogen atom to which they are linked, can form a 4- to 8-membered heterocyclic ring, which may contain one or two heteroatoms selected from O, S or N, and which may be substituted with,
a 4- to 8-membered heterocyclic ring, which may contain one or two heteroatoms selected from O, S or N and which may be substituted with a lower alkyl, or,
a lower alkyl optionally substituted with OR', NR'R", C(=O)NR'R" or COOR' in which R' and R" are the same or different and are selected from, H, or
lower alkyl optionally substituted with OR or COOR in which R is hydrogen or lower alkyl and,
R' and R" together with the nitrogen atom to which they are linked, can form a 4- to 8-membered heterocyclic ring, which may contain one or two heteroatoms selected from O, S or N;

b) $X_4$ is C—$R^1$ in which $R^1$ is selected from hydrogen, halogen, CN, $NO_2$, $SO_2CH_3$, $SO_3H$, $CH_3$, $CF_3$, $OR^2$, $SR^2$, $NR^2R^3$, $COOR^2$, $CONR^2R^3$, $SO_2NR^2R^3$ in which $R^2$ and $R^3$ are the same or different and are selected from hydrogen or lower alkyl;

c) X is NH;
d) Y is NH;
e) Z is chosen from O, S or $NH^{13}$ in which $H^{13}$ is hydrogen or CN;
f) A is a cycle chosen from:

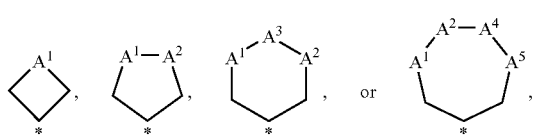

in which,
$A^1$, $A^2$, $A^3$, $A^4$ and $A^5$ are the same or different and are selected from:

a carbon atom, unsubstituted or substituted with 1 or 2 groups, identical or different, selected from lower alkyl, OH or F, or, an oxygen atom;

* represents the carbon atom which is shared between the cycle A and the backbone cycle containing X and/or Y;

2 atoms of the cycle A, which are not adjacent, may be linked by a 2, 3 or 4 carbon atom chain, provided that:

not more than one of the groups $A^1$, $A^2$, $A^3$, $A^4$ and $A^5$ simultaneously represent an oxygen atom;

for the prevention or the treatment of disorders for which therapy by a PDE7 inhibitor is relevant.

A preferred group of compounds of formula (II) or (III) are those in which, a) $X_1$, $X_2$ and $X_3$ are the same or different and are C—$R^1$, in which $R^1$ is selected from:

hydrogen, halogen, CN, $SO_3H$, $NO_2$, $CF_3$, $OR^2$, $SR^2$, $NR^2R^3$, $COR^2$, $COOR^2$, $CONR^2R^3$, $SO_2CH_3$, $SO_2NR^2R^3$ in which $R^2$ and $R^3$ are the same or different and are selected from hydrogen or lower alkyl optionally substituted with halogen, CN, $SO_3H$, $OR^6$, COOR, $NR^6R^7$, $SO_2NR^6R^7$ or $C(=O)NR^6R^7$ in which $R^6$ and $R^7$ are the same or different and are selected from hydrogen or lower alkyl, and, $R^6$ and $R^7$, together with the nitrogen atom to which they are linked, can form a 4- to 8-membered heterocyclic ring;

lower alkyl, lower alkenyl or lower alkynyl, these groups being unsubstituted or substituted with 1, 2 or 3 groups selected from halogen, CN, $OR^2$, $COOR^2$, $NR^3R^4$, $SO_2NR^3R^4$ or $C(=O)NR^3R^4$ in which $R^2$, $R^3$ and $R^4$ are the same or different and are selected from hydrogen or lower alkyl, and, $R^3$ and $R^4$, together with the nitrogen atom to which they are linked, can form a 4- to 8-membered heterocyclic ring;

the group $X^5$—$R^5$ in which, $X^5$ is selected from a lower alkylene or a single bond, and, $R^5$ is selected from phenyl, pyridyl or indolyl, these groups being unsubstituted or substituted with one or several groups selected from Q3, heteroaryl or lower alkyl optionally substituted with Q3 in which Q3 is selected from:

halogen, CN, $SO_3H$, $NO_2$, $CF_3$, $OR^2$, $OC(=O)R^2$, $C(=O)R^2$, $C(=O)OR^2$, NH—$C(=O)R^2$, $NR^3R^4$, $SO_2NR^3R^4$ or $C(=O)NR^3R^4$ in which $R^2$, $R^3$ and $R^4$ are the same or different and are selected from:

hydrogen, lower alkyl unsubstituted or substituted with one or several groups selected from halogen, $OR^6$, $COOR^6$ or $NR^6R^7$ in which $R^6$ and $R^7$ are the same or different and are selected from hydrogen or lower alkyl and, $R^6$ and $R^7$, and/or, $R^3$ and $R^4$, together with the nitrogen atom to which they are linked, can form a 4- to 8-membered heterocyclic ring, which may contain one or two heteroatoms selected from O, S or N, and which may be substituted with a 4- to 8-membered heterocyclic ring, which may contain one or two heteroatoms selected from O, S or N and which may be substituted with a lower alkyl, or, a lower alkyl optionally substituted with OR', NR'R", $C(=O)NR'R"$ or COOR' in which R' and R" are the same or different and are selected from H, or lower alkyl optionally substituted with OR or COOR in which R is hydrogen or lower alkyl and, R' and R" together with the nitrogen atom to which they are linked, can form a 4- to 8-membered heterocyclic ring, which may contain one or two heteroatoms selected from O, S or N;

b) $X_4$ is C—$R^1$ in which $R^1$ is selected from hydrogen, halogen, CN, $NO_2$, $SO_2CH_3$, $SO_3H$, $CH_3$, $CF_3$, $OR^2$, $SR^2$, $NR^2R^3$, $COOR^2$, $CONR^2R^3$ or $SO_2NR^2R^3$ in which $R^2$ and $R^3$ are the same or different and are selected from hydrogen or lower alkyl;

c) X is NH;

d) Y is NH;

e) $Z^1$ is chosen from $NR^{16}R^{17}$ in which $R^{16}$ and $R^{17}$ are the same or different and are selected from:

hydrogen, CN, $C(=O)R^{14}$, $(C=O)NR^{14}R^{15}$, $OR^{14}$, lower alkyl unsubstituted or substituted with one or several groups selected from $OR^{14}$ or $NR^{14}H^{15}$, $R^{14}$ and $R^{15}$ being chosen from hydrogen or lower alkyl, and, $R^{14}$ and $R^{15}$, and/or, $R^{16}$ and $R^{17}$, together with the nitrogen atom to which they are linked, can form a 4- to 8-membered heterocyclic ring which may contain one or two heteroatoms selected from O, S or N, and which may be substituted with a lower alkyl;

f) A is a cycle chosen from:

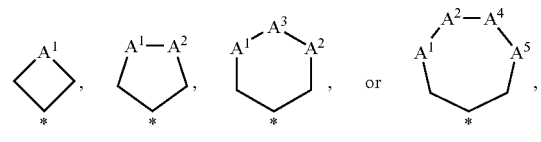

in which, $A^1$, $A^2$, $A^3$, $A^4$ and $A^5$ are the same or different and are selected from:

a carbon atom, unsubstituted or substituted with 1 or 2 groups, identical or different selected from lower alkyl, OH or F, or, an oxygen atom;

* represents the carbon atom which is shared between the cycle A and the backbone cycle containing X and/or Y;

2 atoms of the cycle A, which are not adjacent, may be linked by a 2, 3 or 4 carbon atom chain;

provided that:

not more than one of the groups $A^1$, $A^2$, $A^3$, $A^4$ and $A^5$ simultaneously represent an oxygen atom.

A preferred group of compounds of formula (II) or (III) are the one in which $X_1$, $X_2$, $X_3$, $X_4$, X, Y, $Z_1$ and A are as disclosed hereabove wherein when $X_2$ is C—$R^1$ and $R^1$ is $X^5$—$R^5$, then $X^5$ is not a single bond;

Another preferred group of compounds are compounds of formula (I) in which, a) $X_1$, $X_2$, $X_3$ and $X_4$ are the same or different and are selected from:

N, provided that not more than two of the groups $X_1$, $X_2$, $X_3$ and $X_4$ simultaneously represent a nitrogen atom, or, C—$R_1$, in which $R^1$ is selected from:

Q1, or lower alkyl, lower alkenyl or lower alkynyl, these groups being unsubstituted or substituted with one or several groups Q2;

the group $X^5$—$R^5$ in which,
$X^5$ is selected from
a single bond,
lower alkylene, lower alkenylene or lower alkynylene, optionally interrupted with 1 or 2 heteroatoms chosen from O, S, S(=O), SO$_2$ or N, the carbon atoms of these groups being unsubstituted or substituted with one or several groups, identical or different, selected from SR$^6$, OR$^6$, NR$^6$R$^7$, =O, =S or =N—R$^6$ in which R$^6$ and R$^7$ are the same or different and are selected from hydrogen or lower alkyl, and,
$R^5$ is selected from aryl, heteroaryl, cycloalkyl optionally interrupted with C(=O) or with 1, 2, or 3 heteroatoms chosen from O, S, S(=O), SO$_2$ or N, cycloalkenyl optionally interrupted with C(=O) or with 1, 2, or 3 heteroatoms chosen from O, S, S(=O), SO$_2$ or N, or a bicyclic group, these groups being unsubstituted or substituted with one or several groups selected from Q3, heteroaryl or lower alkyl optionally substituted with Q3;
in which Q1, Q2, Q3 are the same or different and are selected from
hydrogen, halogen, CN, NO$_2$, SO$_3$H,
OR$^2$, OC(=O)R$^2$, C(=O)OR$^2$, SR$^2$, S(=O)R$^2$, NR$^3$R$^4$, Q-R$^2$, Q-NR$^3$R$^4$, NR$^2$-Q-NR$^3$R$^3$ or NR$^2$-Q-R$^2$ in which Q is selected from C(=NR), C(=O), C(=S) or SO$_2$, R is selected from hydrogen or lower alkyl and R$^2$, R$^3$ and R$^4$ are the same or different and are selected from:
hydrogen,
lower alkyl optionally interrupted with C(=O), (CH$_2$)$_n$-aryl, (CH$_2$)$_n$-heteroaryl, (CH$_2$)$_n$-cycloalkyl optionally interrupted with C(=O) or with 1 or 2 heteroatoms chosen from O, S, S(=O), SO$_2$ or N or (CH$_2$)$_n$-cycloalkenyl optionally interrupted with C(=O) or with 1 or 2 heteroatoms chosen from O, S, S(=O), SO$_2$ or N, in which n is an integer selected from 0, 1, 2 or 3; these groups being unsubstituted or substituted with one or several groups selected from lower alkyl, halogen, CN, SO$_3$H, CH$_3$, SO$_2$CH$_3$, CF$_3$, C(=O)—NH—SO$_2$—CH$_3$, OR$^6$, COOR$^6$, NR$^6$R$^7$, C(=O)NR$^6$R$^7$ or SO$_2$NR$^6$R$^7$, in which R$^6$ and R$^7$ are the same or different and are selected from hydrogen or lower alkyl optionally substituted with one or two groups selected from OR, COOR or NRR$^8$ in which R and R$^8$ are hydrogen or lower alkyl, and,
R$^6$ and R$^7$, and/or, R$^3$ and R$^4$, together with the nitrogen atom to which they are linked, can form a 4- to 8-membered heterocyclic ring, which may contain one or two heteroatoms selected from O, S, S(=O), SO$_2$ or N, and which may be substituted with
a 4- to 8-membered heterocyclic ring, which may contain one or two heteroatoms selected from O, S or N and which may be substituted with a lower alkyl, or,
a lower alkyl optionally substituted with OR', NR'R'', C(=O)NR'R'' or COOR' in which R' and R'' are the same or different and are selected from H, or
lower alkyl optionally substituted with OR or COOR in which R is hydrogen or lower alkyl and,
R' and R'' together with the nitrogen atom to which they are linked, can form a 4- to 8-membered heterocyclic ring, which may contain one or two heteroatoms selected from O, S or N;
b) X is NR$^9$, in which R$^9$ is selected from,
hydrogen, CN, OH, NH$_2$,
lower alkyl, lower alkenyl or lower alkynyl, these groups being unsubstituted or substituted with cycloalkyl optionally interrupted with 1 or 2 heteroatoms chosen from O, S, S(=O), SO$_2$ or N, cycloalkenyl optionally interrupted with 1 or 2 heteroatoms chosen from O, S, S(=O), SO$_2$ or N, aryl, heteroaryl, OR$^{10}$ or NR$^{10}$OR$^{11}$ in which R$^{10}$ and R$^{11}$ are the same or different and are selected from hydrogen or lower alkyl;
c) Y is selected from O, S or N—R$^{12}$, in which R$^{12}$ is selected from:
hydrogen, CN, OH, NH$_2$,
lower alkyl, lower alkenyl or lower alkynyl, these groups being unsubstituted or substituted with, cycloalkyl optionally interrupted with 1 or 2 heteroatoms chosen from O, S, S(=O), SO$_2$ or N, cycloalkenyl optionally interrupted with 1 or 2 heteroatoms chosen from O, S, S(=O), SO$_2$ or N, aryl, heteroaryl, OR$^{10}$or NR$^{10}$R$^{11}$ in which R$^{10}$ and R$^{11}$ are the same or different and are selected from hydrogen or lower alkyl;
d) Z is chosen from CH—NO$_2$, O, S or NR$^{13}$ in which R$^{13}$ is selected from:
hydrogen, CN, OH, NH$_2$, aryl, heteroaryl, cycloalkyl optionally interrupted with one or several heteroatoms chosen from O, S, S(=O), SO$_2$ or N, cycloalkenyl optionally interrupted with one or several heteroatoms chosen from O, S, S(=O), SO$_2$ or N, C(=O)R$^{14}$, C(=O)NR$^{14}$R$^{15}$ OH$^{14}$ or,
lower alkyl, unsubstituted or substituted with one or several groups which are the same or different and which are selected OR$^{14}$ or NR$^{14}$R$^{15}$;
R$^{14}$ and R$^{15}$ being independently selected from hydrogen or lower alkyl, or, R$^{14}$ and R$^{15}$, together with the nitrogen atom to which they are linked, can form a 4- to 8-membered heterocyclic ring which may contain one or two heteroatoms chosen from O, S or N, and which may be substituted with a lower alkyl;
e) A is a cycle chosen from:

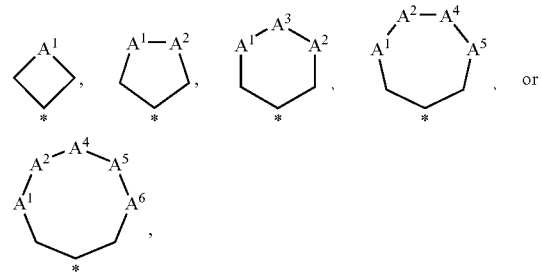

in which,
A$^1$, A$^2$, A$^4$, A$^5$ and A$^6$ are the same or different and are selected from O, S, C, C(=O), SO, SO$_2$ or N—R$^{18}$ in which R$^{18}$ is selected from:
hydrogen, aryl, heteroaryl, cycloalkyl optionally interrupted with one or several heteroatoms chosen from O, S, S(=O), SO$_2$ or N, cycloalkenyl optionally interrupted with one or several heteroatoms chosen from O, S, S(=O), SO$_2$ or N,
lower alkyl unsubstituted or substituted with aryl, heteroaryl, cycloalkyl optionally interrupted with one or several heteroatoms chosen from O, S, S(=O), $SO_2$ or N, cycloalkenyl optionally interrupted with one or several heteroatoms chosen from O, S, S(=O), $SO_2$ or N, CN, $NR^{19}R^{20}$, $C(=O)NR^{19}R^{20}$, $OR^{19}$, $C(=O)R^{19}$ or $C(=O)OR^{19}$ in which $R^{19}$ and $R^{20}$ are identical or different and are selected from hydrogen or lower alkyl;

$A^3$ is selected from O, S, C, C(=O), SO or $SO_2$, or N—$R^{18}$ when $A^1$ and/or $A^2$ are C(=O) or when Y is O or S, wherein $R^{18}$ is as defined above;

\* represents the carbon atom which is shared between the cycle A and the backbone cycle containing X and/or Y;

each carbon atom of the cycle A is unsubstituted or substituted with 1 or 2 groups, identical or different, selected from lower alkyl optionally substituted with $OR^{21}$, $NR^{21}R^{22}$, $COOR^{21}$ or $CONR^{21}R^{22}$, lower haloalkyl, CN, F, =O, $SO_2NR^{19}R^{20}$, $OR^{19}$, $SR^{19}$, $C(=O)OR^{19}$, $C(=O)NR^{19}R^{20}$ or $NR^{19}R^{20}$ in which $R^{19}$ and $R^{20}$ are identical or different and are selected from hydrogen or lower alkyl optionally substituted with $OR^{21}$, $NR^{21}R^{22}$, $COOR^{21}$ or $CONR^{21}R^{22}$ in which $R^{21}$ and $R^{22}$ are identical or different and are selected from hydrogen or lower alkyl, and, $R^{19}$ and $R^{20}$, and/or, $R^{21}$ and $R^{22}$, together with the nitrogen atom to which they are linked, can form a 4- to 8-membered heterocyclic ring;

2 atoms of the cycle A, which are not adjacent, may be linked by a 2, 3 or 4 carbon atom chain which may be interrupted with 1 heteroatom chosen from O, S or N;

provided that:

not more than two of the groups $A^1$, $A^2$, $A^3$, $A^4$, $A^5$ and $A^6$ simultaneously represent a heteroatom;

the cycle A does not contain more than 2 carbon atoms in an $sp^2$ hybridization state.

A preferred group of compounds of formula (I) is a group in which $X_1$, $X_2$, $X_3$, $X_4$, X, Y, Z and A are as disclosed hereabove wherein when $X_2$ is C—$R^1$ and $R^1$ is $X^5$—$R^5$, then $X^5$ is not a single bond;

Preferred compounds of formula (I) are those in which, a) $X_1$, $X_2$, $X_3$ and $X_4$ are the same or different and are selected from:

N, provided that not more than two of the groups $X_1$, $X_2$, $X_3$ and $X_4$ simultaneously represent a nitrogen atom, or, C—$R_1$, in which $R^1$ is selected from:

Q1, or lower alkyl, lower alkenyl or lower alkynyl, these groups being unsubstituted or substituted with 1, 2 or 3 groups Q2;

the group $X^5$—$R^5$ in which, $X^5$ is selected from:

a single bond, lower alkylene, lower alkenylene or lower alkynylene, optionally interrupted with 1 or 2 heteroatoms chosen from O, S or N, the carbon atoms of these groups being unsubstituted or substituted with 1 or 2 groups, identical or different, selected from $SR^6$, $OR^6$, $NR^6R^7$, =O, =S or =N—$R^6$ in which $R^6$ and $R^7$ are the same or different and are selected from hydrogen or lower alkyl, and, $R^5$ is selected from aryl, heteroaryl, cycloalkyl optionally interrupted with C(=O) or with 1, 2, or 3 heteroatoms chosen from O, S or N, cycloalkenyl optionally interrupted with C(=O) or with 1, 2, or 3 heteroatoms chosen from O, S or N, or a bicyclic group, these groups being unsubstituted or substituted with 1, 2 or 3 groups selected from Q3, heteroaryl or lower alkyl optionally substituted with Q3;

in which Q1, Q2, Q3 are the same or different and are selected from:

hydrogen, halogen, CN, $NO_2$, $SO_3H$, $OR^2$, $OC(=O)R^2$, $C(=O)OR^2$, $SR^2$, $S(=O)R^2$, $NR^3R^4$, Q-$R^2$, Q-$NR^3R^4$, $NR^2$-Q-$NR^3R^4$ or $NR^3$-Q-$R^2$ in which Q is selected from C(=NR), C(=O), C(=S) or $SO_2$, R is selected from hydrogen or lower alkyl and $R^2$, $R^3$ and $R^4$ are the same or different and are selected from:

hydrogen, lower alkyl optionally interrupted with C(=O), $(CH_2)_n$-aryl, $(CH_2)_n$-heteroaryl, $(CH_2)_n$-cycloalkyl optionally interrupted with C(=O) or with 1 or 2 heteroatoms chosen from O, S or N or $(CH_2)_n$-cycloalkenyl optionally interrupted with C(=O) or with 1 or 2 heteroatoms chosen from O, S or N, in which n is an integer selected from 0, 1, 2 or 3;

these groups being unsubstituted or substituted with 1, 2 or 3 groups selected from halogen, CN, $SO_3H$, $CH_3$, $SO_2CH_3$, $CF_3$, $OR^6$, $COOR^6$, $NR^6R^7$, $C(=O)NR^6R^7$ or $SO_2NR^6R^7$, in which $R^6$ and $R^7$ are the same or different and are selected from hydrogen or lower alkyl optionally substituted with one or two groups selected from OR, COOR or $NRR^8$ in which R and $R^8$ are hydrogen or lower alkyl, and, $R^6$ and $R^7$, and/or, $R^3$ and $R^4$, together with the nitrogen atom to which they are linked, can form a 4- to 8-membered heterocyclic ring, which may contain one or two heteroatoms selected from O, S, S(=O), $SO_2$ or N, and which may be substituted with a 4- to 8-membered heterocyclic ring, which may contain one or two heteroatoms selected from O, S or N and which may be substituted with a lower alkyl, or, a lower alkyl optionally substituted with OR', NR'R", C(=O)NR'R" or COOR' in which R' and R" are the same or different and are selected from H, or lower alkyl optionally substituted with OR or COOR in which R is hydrogen or lower alkyl and, R' and R" together with the nitrogen atom to which they are linked, can form a 4- to 8-membered heterocyclic ring, which may contain one or two heteroatoms selected from O, S or N;

b) X is NH;

c) Y is NH;

d) Z is chosen from O, S or $NR^{13}$ in which $R^{13}$ is hydrogen or CN;

f) A is a cycle chosen from:

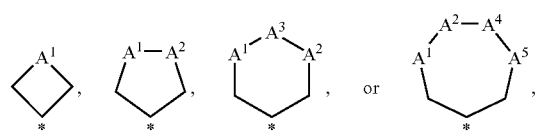

in which,

A$^1$, A$^2$, A$^4$ and A$^5$ are the same or different and are selected from O, S, C, C(=O), SO, SO$_2$ or N—R$^{18}$ in which R$^{18}$ is selected from:

hydrogen, aryl, heteroaryl, cycloalkyl optionally interrupted with 1 or 2 heteroatoms chosen from O, S, S(=O), SO$_2$ or N, cycloalkenyl optionally interrupted with 1 or 2 heteroatoms chosen from O, S, S(=O), SO$_2$ or N, lower alkyl unsubstituted or substituted with aryl, heteroaryl, cycloalkyl optionally interrupted with 1 or 2 heteroatoms chosen from O, S, S(=O), SO$_2$ or N, cycloalkenyl optionally interrupted with 1 or 2 heteroatoms chosen from O, S, S(=O), SO$_2$ or N, CN, NR$^{19}$R$^{20}$, C(=O)NR$^{19}$R$^{20}$, OR$^{19}$, C(=O)R$^{19}$ or C(=O)OR$^{19}$ in which R$^{19}$ and R$^{20}$ are identical or different and are selected from hydrogen or lower alkyl;

A$^3$ is selected from O, S, C, C(=O), SO or SO$_2$, or N—R$^{18}$ when A$^1$ and/or A$^2$ are C(=O) or when Y is O or S, wherein R$^{18}$ is as defined above;

* represents the carbon atom which is shared between the cycle A and the backbone cycle containing X and/or Y;

each carbon atom of the cycle A is unsubstituted or substituted with 1 or 2 groups, identical or different, selected from lower alkyl optionally substituted with OR$^{21}$, NR$^{21}$R$^{22}$, COOR$^{21}$ or CONR$^{21}$R$^{22}$, lower haloalkyl, CN, F, =O, SO$_2$NR$^{19}$R$^{20}$, OR$^{19}$, SR$^{19}$, C(=O)OR$^{19}$ or C(=O)NR$^{19}$R$^{20}$ or NR$^{19}$R$^{20}$ in which R$^{19}$ and R$^{20}$ are identical or different and are selected from hydrogen or lower alkyl optionally substituted with OR$^{21}$, NR$^{21}$R$^{22}$, COOR$^{21}$ or CONR$^{21}$R$^{22}$ in which R$^{21}$ and R$^{22}$ are identical or different and are selected from hydrogen or lower alkyl, and, R$^{19}$ and R$^{20}$, and/or, R$^{21}$ and R$^{22}$, together with the nitrogen atom to which they are linked, can form a 4- to 8-membered heterocyclic ring;

2 atoms of the cycle A, which are not adjacent, may be linked by a 2, 3 or 4 carbon atom chain which may be interrupted with 1 heteroatom chosen from O, S or N;

provided that:
not more than one of the groups A$^1$, A$^2$, A$^3$, A$^4$ and A$^5$ simultaneously represent a heteroatom;
the cycle A does not contain more than 2 carbon atoms in an sp$^2$ hybridization state.

A preferred group of compounds of formula (I) is a group in which X$_1$, X$_2$, X$_3$, X$_4$, X, Y, Z and A are as disclosed hereabove wherein when X$_2$ is C—R$^1$ and R$^1$ is X$^5$—R$^5$, then X$^5$ is not a single bond;

More preferred compounds of formula (I) are those in which, a) X$_1$, X$_2$ and X$_3$ are the same or different and are C—R$_1$, in which R$^1$ is selected from:
hydrogen, halogen, CN, SO$_3$H, NO$_2$, CF$_3$, OR$^2$, SR$^2$, NR$^2$R$^3$, COR$^2$, COOR$^2$, CONR$^2$R$^3$, SO$_2$CH$_3$, SO$_2$NR$^2$R$^3$ in which R$^2$ and R$^3$ are the same or different and are selected from hydrogen or lower alkyl optionally substituted with halogen, CN, OR$^6$, COOR$^6$, NR$^6$R$^7$, SO$_2$NR$^6$R$^7$ or C(=O)NR$^6$R$^7$ in which R$^6$ and R$^7$ are the same or different and are selected from hydrogen or lower alkyl, and, R$^6$ and R$^7$, together with the nitrogen atom to which they are linked, can form a 4- to 8-membered heterocyclic ring;

lower alkyl, lower alkenyl or lower alkynyl, these groups being unsubstituted or substituted with 1, 2 or 3 groups selected from halogen, CN, SO$_3$H, OR$^2$, COOR$^2$, NR$^3$R$^4$, SO$_2$NR$^3$R$^4$ or C(=O)NR$^3$R$^4$ in which R$^2$, R$^3$ and R$^4$ are the same or different and are selected from hydrogen or lower alkyl, and, R$^3$ and R$^4$, together with the nitrogen atom to which they are linked, can form a 4- to 8-membered heterocyclic ring;

the group X$^5$—R$^5$ in which,
X$^5$ is selected from a lower alkylene or a single bond, and,
R$^5$ is selected from phenyl, pyridyl or indolyl, these groups being unsubstituted or substituted with 1, 2 or 3 groups selected from Q3, heteroaryl or lower alkyl optionally substituted with Q3 in which Q3 is selected from:
halogen, CN, SO$_3$H, NO$_2$, CF$_3$, OR$^2$, OC(=O)R$^2$, C(=O)R$^2$, C(=O)OR$^2$, NH—C(=O)R$^2$, NR$^3$R$^4$, SO$_2$NR$^3$R$^4$ or C(=O)NR$^3$R$^4$ in which R$^2$, R$^3$ and R$^4$ are the same or different and are selected from:
hydrogen, lower alkyl unsubstituted or substituted with one or several groups selected from halogen, OR$^6$, COOR$^6$ or NR$^6$R$^7$ in which R$^6$ and R$^7$ are the same or different and are selected from hydrogen or lower alkyl and, R$^6$ and R$^7$, and/or, R$^3$ and R$^4$, together with the nitrogen atom to which they are linked, can form a 4- to 8-membered heterocyclic ring, which may contain one or two heteroatoms selected from O, S or N, and which may be substituted with, a 4- to 8-membered heterocyclic ring, which may contain one or two heteroatoms selected from O, S or N and which may be substituted with a lower alkyl, or, a lower alkyl optionally substituted with OR', NR'R'', C(=O)NR'R'' or COOR' in which R' and R'' are the same or different and are selected from,
H, or
lower alkyl optionally substituted with OR or COOR in which R is hydrogen or lower alkyl and, R' and R'' together with the nitrogen atom to which they are linked, can form a 4- to 8-membered heterocyclic ring, which may contain one or two heteroatoms selected from O, S or N;

b) X$_4$ is C—R$^1$ in which R$^1$ is selected from hydrogen, halogen, CN, NO$_2$, SO$_2$CH$_3$, SO$_3$H, CH$_3$, CF$_3$, OR$^2$, SR$^2$, NR$^2$R$^3$, COOR$^2$, CONR$^2$R$^3$ or SO$_2$NR$^2$R$^3$ in which R$^2$ and R$^3$ are the same or different and are selected from hydrogen or lower alkyl;

c) X is NH;

d) Y is NH;

e) Z is chosen from O, S or NR$^{13}$ in which R$^{13}$ is hydrogen or CN;

f) A is a cycle chosen from:

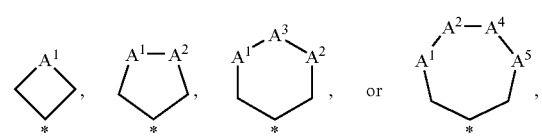

in which,
A$^1$, A$^2$, A$^3$, A$^4$ and A$^5$ are the same or different and are selected from:

a carbon atom, unsubstituted or substituted with 1 or 2 groups, identical or different selected from lower alkyl, OH or F, or, an oxygen atom;

* represents the carbon atom which is shared between the cycle A and the backbone cycle containing X and/or Y;

2 atoms of the cycle A, which are not adjacent, may be linked by a 2, 3 or 4 carbon atom chain;

provided that:

not more than one of the groups $A^1$, $A^2$, $A^3$, $A^4$ and $A^5$ simultaneously represent an oxygen atom.

A preferred group of compounds of formula (I) is a group in which $X_1$, $X_2$, $X_3$, $X_4$, X, Y, Z and A are as disclosed hereabove wherein when $X_2$ is C—$R^1$ and $R^1$ is $X^5$—$R^5$, then $X^5$ is not a single bond;

Most preferred compounds of formula (I) are those in which, a) $X_1$, $X_2$ and $X_3$ are the same or different and are C—$R_1$, in which $R^1$ is selected from:
   hydrogen, halogen, CN, $OR^2$, in which $R^2$ is selected from hydrogen or lower alkyl;
   lower alkyl, lower alkenyl or lower alkynyl, these groups being unsubstituted or substituted with 1, 2 or 3 groups selected from halogen, CN, $SO_3H$, $OR^2$, $COOR^2$, $NR^3R^4$, $SO_2NR^3R^4$ or $C(=O)NR^3R^4$ in which $R^2$, $R^3$ and $R^4$ are the same or different and are selected from hydrogen or lower alkyl, and, $R^3$ and $R^4$, together with the nitrogen atom to which they are linked, can form a 4- to 8-membered heterocyclic ring;

b) $X_4$ is C—$R^1$ in which $R^1$ is selected hydrogen, halogen, $CH_3$, CN, $OR^2$, in which $R^2$ is selected from hydrogen or lower alkyl;

c) X is NH;

d) Y is NH;

e) Z is chosen from O, S or $NR^{13}$ in which $R^{13}$ is hydrogen or CN;

f) A is a cycle chosen from:

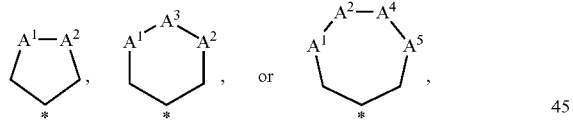

in which, $A^1$, $A^2$, $A^3$, $A^4$ and $A^5$ are the same or different and are selected from carbon atoms, unsubstituted or substituted with $CH_3$;

* represents the carbon atom which is shared between the cycle A and the backbone cycle containing X and/or Y;

2 atoms of the cycle A, which are not adjacent, may be linked by a 2, 3 or 4 carbon atom chain.

Preferably, $X_1$, $X_2$, $X_3$ and $X_4$ are the same or different and are C—$R_1$, in which $R^1$ is selected from:

Q1, or lower alkyl, lower alkenyl or lower alkynyl, these groups being unsubstituted or substituted with 1, 2 or 3 groups Q2;

the group $X^5$—$R^5$ in which, $X^5$ is selected from:
   a single bond,
   a lower alkylene, optionally interrupted with 1 heteroatoms chosen from O, S and N $R^5$ is selected from aryl, heteroaryl, cycloalkyl optionally interrupted with C(=O) or with 1, 2, or 3 heteroatoms chosen from O, S, S(=O), $SO_2$ or N, cycloalkenyl optionally interrupted with C(=O) or with 1, 2, or 3 heteroatoms chosen from O, S, S(=O), $SO_2$ or N, or a bicyclic group, these groups being unsubstituted or substituted with 1, 2 or 3 groups selected from Q3, heteroaryl or lower alkyl optionally substituted with Q3;

in which Q1, Q2, Q3 are the same or different and are selected from
   halogen, CN, $NO_2$, $SO_3H$,
   $OR^2$, $OC(=O)R^2$, $C(=O)OR^2$, $SR^2$, $S(=O)R^2$, $C(=O)$—NH—$SO_2$—$CH_3$, $NR^3R^4$, Q-$R^2$, Q-$NR^3R^4$, $NR^2$-Q-$NR^3R^4$ or $NR^3$-Q-$R^2$ in which Q is selected from C(=NR), C(=O), C(=S) or $SO_2$,
   R is selected from hydrogen or lower alkyl and $R^2$, $R^3$ and $R^4$ are the same or different and are selected from:
   hydrogen,
   lower alkyl optionally interrupted with C(=O), Q4-aryl, Q4-heteroaryl, Q4-cycloalkyl optionally interrupted with C(=O) or with 1 or 2 heteroatoms chosen from O, S, S(=O), $SO_2$ or N, or Q4-cycloalkenyl optionally interrupted with C(=O) or with 1 or 2 heteroatoms chosen from O, S, S(=O), $SO_2$ or N, in which
   Q4 is selected from $(CH_2)_n$, lower alkyl interrupted with one heteroatom selected from O, S or N, lower alkenyl or lower alkynyl, these groups being optionally substituted with lower alkyl, OR' or NR'R" in which R' and R" are the same or different and are selected from hydrogen or lower alkyl;
   n is an integer selected from 0, 1, 2, 3 or 4;
   these groups being unsubstituted or substituted with 1 or 2 groups selected from lower alkyl, halogen, CN, $CH_3$, $SO_3H$, $SO_2CH_3$, $CF_3$, C(=O)NH—$SO_2CH_3$, $OR^6$, $COOR^6$, $C(=O)R^6$, $NR^6R^7$, $C(=O)NR^6R^7$ or $SO_2NR^6R^7$, in which $R^6$ and $R^7$ are the same or different and are selected from hydrogen or lower alkyl optionally substituted with one or two groups selected from OR, COOR or $NRR^8$ in which R and $R^8$ are hydrogen or lower alkyl, and,
   $R^6$ and $R^7$, and/or, $R^3$ and $R^4$, together with the nitrogen atom to which they are linked, can form a 4- to 8-membered heterocyclic ring, which may contain one or two heteroatoms selected from O, S, S(=O), $SO_2$ or N, and which may be substituted with,
   $(CH_2)_n$-Q5, in which n is an integer selected from 0, 1, 2 and 3, and Q5 is a 4- to 8-membered heterocyclic ring which may contain one or two heteroatoms selected from O, S or N and which may be substituted with a lower alkyl, or,
   a lower alkyl optionally substituted with OR', NR'R", C(=O)NR'R" or COOR' in which R' and R" are the same or different and are selected from,
   H, or
   lower alkyl optionally substituted with OR or COOR in which R is hydrogen or lower alkyl and, R' and R" together with the nitrogen atom to which they are linked, can form a 4- to 8-membered heterocyclic ring, which may contain one or two heteroatoms selected from O, S or N.

A preferred group of compounds of formula (I) is a group in which $X_1$, $X_2$, $X_3$ and $X_4$, are as disclosed hereabove wherein when $X_2$ is C—$R^1$ and $R^1$ is $X^5$—$R^5$, then $X^5$ is not a single bond;

Preferably, $X_1$, $X_2$, $X_3$ and $X_4$ are the same or different and are C—$R^1$, in which $R^1$ is selected from:
  Q1, or
  lower alkyl or lower alkynyl, these groups being unsubstituted or substituted with 1, 2 or 3 fluor atoms, $OR^3$, $COOR^3$ or $NR^3R^4$ in which $R^3$ and $R^4$ are the same or different and are selected from hydrogen or lower alkyl;
  $R^3$ and $R^4$ together with the nitrogen atom to which they are linked, may also form a 6-membered heterocyclic ring, which may contain one or two heteroatoms selected from O or N;
  the group $X^5$—$R^5$ in which $X^5$ is a single bond and $R^5$ is selected from aryl, preferably phenyl, heteroaryl, preferably pyridyl, or a bicyclic group, preferably indolyl, these groups being unsubstituted or substituted with 1, 2 or 3 groups selected from Q3,
  in which Q1 and Q3 are the same or different and are selected from
  hydrogen, halogen, CN, lower alkyl,
  $OR^2$, $C(=O)OR^2$, $NR^3R^4$, $C(=O)NR^3R^4$ or $SO_2NR^3R^4$ in which $R^2$, $R^3$ and $R^4$ are the same or different and are selected from:
    hydrogen,
    lower alkyl, Q4-heteroaryl in which Q4 is selected from lower alkyl interrupted with one heteroatom selected from O, S or N and $(CH_2)_n$ in which n is an integer selected from 0, 1, 2 or 3;
    these groups being unsubstituted or substituted with 1 or 2 groups selected from lower alkyl, CN, $SO_3H$, $C(=O)$—NH—$SO_2$—$CH_3$, $OR^6$, $COOR^6$ or $NR^6R^7$, in which $R^6$ and $R^7$ are the same or different and are selected from hydrogen or lower alkyl optionally substituted with one or two groups selected from OR, COOR or $NRR^8$ in which R and $R^8$ are hydrogen or lower alkyl, and,
    $R^6$ and $R^7$, and/or, $R^3$ and $R^4$, together with the nitrogen atom to which they are linked, can form a 4- to 6-membered heterocyclic ring, which may contain one or two heteroatoms selected from O or N, and which may be substituted with,
    a 6-membered heterocyclic ring, which may contain one or two heteroatoms selected from O or N and which may be substituted with a lower alkyl, or,
    a lower alkyl optionally substituted with OR', NR'R", $C(=O)NR'R"$ or COOR' in which R' and R" are the same or different and are selected from,
      H, or
      lower alkyl optionally substituted with OR or COOR in which R is hydrogen or lower alkyl and,
    R' and R" together with the nitrogen atom to which they are linked, can form a 6-membered heterocyclic ring, which may contain one or two heteroatoms selected from O or N.

A preferred group of compounds of formula (I) is a group in which $X_1$, $X_2$, $X_3$ and $X_4$, are as disclosed hereabove wherein when $X_2$ is C—$R^1$ and $R^1$ is $X^5$—$R^5$, then $X^5$ is not a single bond;

A preferred group of compounds is the group in which one of $X_1$, $X_2$, $X_3$ and $X_4$ is C—$R^1$ in which $R^1$ is hydrogen while the others are identical or different and are C—$R^1$ in which $R^1$ is selected from:
  Q1, or
  lower alkyl, lower alkenyl or lower alkynyl, these groups being unsubstituted or substituted with 1, 2 or 3 groups Q2;
  the group $X^5$—$R^5$ in which,
    $X^5$ is selected from:
      a single bond,
      a lower alkylene, optionally interrupted with 1 heteroatoms chosen from O, S and N
    $R^5$ is selected from aryl, heteroaryl, cycloalkyl optionally interrupted with $C(=O)$ or with 1, 2, or 3 heteroatoms chosen from O, S, $S(=O)$, $SO_2$ or N, cycloalkenyl optionally interrupted with $C(=O)$ or with 1, 2, or 3 heteroatoms chosen from O, S, $S(=O)$, $SO_2$ or N, or a bicyclic group, these groups being unsubstituted or substituted with 1, 2 or 3 groups selected from Q3, heteroaryl or lower alkyl optionally substituted with Q3;
  in which Q1, Q2, Q3 are the same or different and are selected from
  hydrogen, halogen, CN, $NO_2$, $SO_3H$,
  $OR^2$, $OC(=O)R^2$, $C(=O)OR^2$, $SR^2$, $S(=O)R^2$, $C(=O)$—NH—$SO_2$—$CH_3$, $NR^3R^4$, Q-$R^2$, Q-$NR^3R^4$, $NR^2$-Q-$NR^3R^4$ or $NR^3$-Q-$R^2$ in which Q is selected from $C(=NR)$, $C(=O)$, $C(=S)$ or $SO_2$, R is selected from hydrogen or lower alkyl and $R^2$, $R^3$ and $R^4$ are the same or different and are selected from:
    hydrogen,
    lower alkyl optionally interrupted with $C(=O)$, Q4-aryl, Q4-heteroaryl, Q4-cycloalkyl optionally interrupted with $C(=O)$ or with 1 or 2 heteroatoms chosen from O, S, $S(=O)$, $SO_2$ or N, or Q4-cycloalkenyl optionally interrupted with $C(=O)$ or with 1 or 2 heteroatoms chosen from O, S, $S(=O)$, $SO_2$ or N, in which
    Q4 is selected from $(CH_2)_n$, lower alkyl interrupted with one heteroatom selected from O, S or N, lower alkenyl or lower alkynyl, these groups being optionally substituted with lower alkyl, OR' or NR'R" in which R' and R" are the same or different and are selected from hydrogen or lower alkyl;
    n is an integer selected from 0, 1, 2, 3 or 4;
    these groups being unsubstituted or substituted with 1 or 2 groups selected from lower alkyl, halogen, CN, $CH_3$, $SO_3H$, $SO_2CH_3$, $CF_3$, $C(=O)$—NH—$SO_2$—$CH_3$, $OR^6$, $COOR^6$, $C(=O)R^6$, $NR^6R^7$, $C(=O)NR^6R^7$ or $SO_2NR^6R^7$, in which $R^6$ and $R^7$ are the same or different and are selected from hydrogen or lower alkyl optionally substituted with one or two groups selected from OR, COOR or $NRR^8$ in which R and $R^8$ are hydrogen or lower alkyl, and,
    $R^6$ and $R^7$, and/or, $R^3$ and $R^4$, together with the nitrogen atom to which they are linked, can form a 4- to 8-membered heterocyclic ring, which may contain one or two heteroatoms selected from O, S, $S(=O)$, $SO_2$ or N, and which may be substituted with,
    $(CH_2)_n$-Q5, in which n is an integer selected from 0, 1, 2 and 3, and Q5 is a 4- to 8-membered heterocyclic ring which may contain one or two heteroatoms selected from O, S or N and which may be substituted with a lower alkyl, or, a lower alkyl optionally substituted with OR', NR'R", C(=O)NR'R" or COOR' in which R' and R" are the same or different and are selected from, H, or lower alkyl optionally substituted with OR or COOR in which R is hydrogen or lower alkyl and, R' and R" together with the nitrogen atom to which they are linked, can form a 4- to 8-membered heterocyclic ring, which may contain one or two heteroatoms selected from O, S or N.

A preferred group of compounds of formula (I) is a group in which $X_1$, $X_2$, $X_3$ and $X_4$, are as disclosed hereabove wherein when $X_2$ is C—$R^1$ and $R^1$ is $X^5$—$R^5$, then $X^5$ is not a single bond;

A preferred group of compounds is the group in which one of $X_1$, $X_2$, $X_3$ and $X_4$ is C—$R^1$ in which $R^1$ is hydrogen while the others are identical or different and are C—$R^1$ in which $R^1$ is selected from:

Q1, or lower alkyl or lower alkynyl, these groups being unsubstituted or substituted with 1, 2 or 3 groups halogen or with $OR^3$, $COOR^3$ or $NR^3R^4$ in which $R^3$ and $R^4$ are the same or different and are selected from hydrogen or lower alkyl;

$R^3$ and $R^4$ together with the nitrogen atom to which they are linked, may also form a 6-membered heterocyclic ring, which may contain one or two heteroatoms selected from O or N;

the group $X^5$—$R^5$ in which $X^5$ is a single bond and $R^5$ is selected from aryl, preferably phenyl, heteroaryl, preferably pyridyl, or a bicyclic group, preferably indolyl, these groups being unsubstituted or substituted with 1, 2 or 3 groups selected from Q3, in which Q1 and Q3 are the same or different and are selected from halogen, CN, lower alkyl $OR^2$, $C(=O)OR^2$, $NR^3R^4$, $C(=O)NR^3R^4$ or $SO_2NR^3R^4$ in which $R^2$, $R^3$ and $R^4$ are the same or different and are selected from:

hydrogen, lower alkyl, Q4-heteroaryl in which Q4 is selected from lower alkyl interrupted with one heteroatom selected from O, S or N and $(CH_2)_n$ in which n is an integer selected from 0, 1, 2 or 3;

these groups being unsubstituted or substituted with 1 or 2 groups selected from lower alkyl, CN, $SO_3H$, C(=O)—NH—$SO_2$—$CH_3$, $OR^6$, $COOR^6$ or $NR^6R^7$, in which $R^6$ and $R^7$ are the same or different and are selected from hydrogen or lower alkyl optionally substituted with one or two groups selected from OR, COOR or $NRR^8$ in which R and $R^8$ are hydrogen or lower alkyl, and, $R^6$ and $R^7$, and/or, $R^3$ and $R^4$, together with the nitrogen atom to which they are linked, can form a 4- to 6-membered heterocyclic ring, which may contain one or two heteroatoms selected from O or N, and which may be substituted with, a 6-membered heterocyclic ring, which may contain one or two heteroatoms selected from O or N and which may be substituted with a lower alkyl, or, a lower alkyl optionally substituted with OR', NR'R", C(=O)NR'R" or COOR' in which R' and R" are the same or different and are selected from, H, or lower alkyl optionally substituted with OR or COOR in which R is hydrogen or lower alkyl and, R' and R" together with the nitrogen atom to which they are linked, can form a 6-membered heterocyclic ring, which may contain one or two heteroatoms selected from O or N.

A preferred group of compound is the group disclosed hereabove in which $X^3$ is C—$R^1$ in which $R^1$ is hydrogen.

Preferably, $X_3$ is C—$R^1$, in which $R^1$ is selected from hydrogen or halogen, preferably Cl, or, $X^5$—$R^5$ in which $R^5$ is a single bond and $R^5$ is aryl, preferably phenyl or heteroaryl, preferably pyridyl, optionally substituted with one, two or three groups which are the same or different and which are selected from halogen, CN, $CF_3$, $SO_2Me$, $OR^2$, $COOR^2$, $NR^2R^3$, $SO_2NR^2R^3$ and $CONR^2R^3$ in which $R^2$ and $R^3$ are the same or different and are selected from hydrogen and lower alkyl.

Preferably, $X_3$ is C—$R^1$, in which $R^1$ is selected from hydrogen or halogen, preferably Cl.

Preferably, $X_3$ is C—$R^1$ in which $R^1$ is hydrogen.

Preferably, $X_4$ is C—$R^1$, in which $R^1$ is selected from hydrogen, halogen, $CF_3$, O-lower alkyl, $COOR^2$ or, lower alkyl optionally substituted with $OR^2$, $COOR^2$ or $SO_2NR^2R^3$ in which $R^2$ and $R^3$ are the same or different and are selected from hydrogen and lower alkyl.

Preferably, $X_4$ is C—$R^1$, in which $R^1$ is selected from hydrogen, halogen, $CF_3$, methyl and methoxy.

Preferably, $X_1$, is C—$R^1$, in which $R^1$ is selected from hydrogen, halogen, preferably Cl or Br, $OR^2$, $COR^2$, $COOR^2$, $CONR^2R^3$ in which $R^2$ and $R^3$ are the same or different and are selected from hydrogen, lower alkyl, Q4-aryl, Q4-heteroaryl, Q4-cycloalkyl optionally interrupted with C(=O) or with 1 or 2 heteroatoms chosen from O, S, or N, or Q4-cycloalkenyl optionally interrupted with C(=O) or with 1 or 2 heteroatoms chosen from O, S, or N, in which Q4 is selected from $(CH_2)_n$, lower alkyl interrupted with one heteroatom selected from O, S or N, lower alkenyl or lower alkynyl;

n is an integer selected from 0, 1, 2 or 3;

these groups being unsubstituted or substituted with lower alkyl, CN, C(=O)—NH—$SO_2$—$CH_3$, $OR_6$, $SO_3H$, $CONR^6R^7$, $COOR^6$, $COR^6$ or $NR^6R^7$, in which and $R^6$ and $R^7$ are the same or different and are selected from hydrogen or lower alkyl, optionally substituted with $NH_2$, COOH, OH;

$R^6$ and $R^7$ together with the nitrogen atom to which they are linked, can form a 4- to 8-membered heterocyclic ring, which may contain one or two heteroatoms selected from O, S or N and which may be substituted with, $(CH_2)_n$-Q5, in which n is an integer selected from 0, 1, 2 and 3, and Q5 is a 4- to 8-membered heterocyclic ring which may contain one or two heteroatoms selected from O, S or N and which may be substituted with a lower alkyl, or, COR' or lower alkyl optionally substituted with OR', NR'R", C(=O)NR'R" or COOR' in which R' and R" are the same or different and are selected from hydrogen or lower alkyl;

lower alkyl optionally substituted with CN, $SO_3H$, $OR^3$, $NR^3R^4$, $COOR^3$ or $CONR^3R^4$ in which $R^3$ and $R^4$ are the same or different and are selected from hydrogen and, lower alkyl optionally substituted with OH, COOH or NH$_2$ the group X$^5$—R$^5$ in which X$^5$ is a lower alkylene optionally interrupted with a heteroatom selected from O and N and R$^5$ is selected from aryl, heteroaryl, cycloalkyl optionally interrupted with C(=O) or with 1, 2, or 3 heteroatoms chosen from O, S or N and cycloalkenyl optionally interrupted with C(=O) or with 1, 2, or 3 heteroatoms chosen from O, S or N, these groups being unsubstituted or substituted OR$^3$ or COOR$^3$ in which R$^3$ is selected from hydrogen and lower alkyl;

R$^3$ and R$^4$, together with the nitrogen atom to which they are linked, can form a 4- to 6-membered heterocyclic ring, which may contain one or two heteroatoms selected from O or N, and which may be substituted with, (CH$_2$)$_n$-Q5, in which n is an integer selected from 0, 1, 2 and 3, and Q5 is a 4- to 8-membered heterocyclic ring which may contain one or two heteroatoms selected from O, S or N and which may be substituted with a lower alkyl, or, C(=O)—R$^1$ or a lower alkyl optionally substituted with OR', NR'R", C(=O)NR'R" or COOR' in which R' and R" are the same or different and are selected from hydrogen or lower alkyl.

Preferably, X$_1$, is C—R$^1$, in which R$^1$ is selected from hydrogen, halogen, preferably Cl or Br, or OR$^2$ in which R$^2$ is selected from hydrogen, lower alkyl, unsubstituted or substituted with CN, C(=O)—NH—SO$_2$—CH$_3$, OR$^6$, SO$_3$H, COOR$^6$ or NR$^6$R$^7$, Q4-oxadiazole, Q4-tetrazole, Q4-morpholine, Q4-furan, Q4-isoxazole, in which Q4 is selected from lower alkyl interrupted with one heteroatom selected from O, S or N and (CH$_2$)$_n$ in which n is an integer selected from 1 and 2;

these groups being unsubstituted or substituted with CH$_3$, OR$^6$ or COOR$^6$, in which R$^6$ and R$^7$ are the same or different and are selected from hydrogen or lower alkyl, optionally substituted with NH$_2$ or COOH.

Preferably, X$_2$ is C—R$_1$, in which R$^1$ is X$^5$—R$^5$, in which X$^5$ is a single bond, R$^5$ is phenyl or pyridyl, optionally substituted with a lower alkyl, and, substituted with C(=O)NR$^3$R$^4$ in which R$^3$ and R$^4$ together with the nitrogen atom to which they are linked, form a 4- to 8-membered heterocyclic ring, which may contain one or two heteroatoms selected from O, S, S(=O), SO$_2$ or N, and which may be substituted with, a 4- to 8-membered heterocyclic ring, which may contain one or two heteroatoms selected from O, S or N and which may be substituted with a lower alkyl, or, a lower alkyl optionally substituted with OR', NR'R", C(=O)NR'R" or COOR' in which R' and R" are the same or different and are selected from, H, or lower alkyl optionally substituted with OR or COOR in which R is hydrogen or lower alkyl and, R' and R" together with the nitrogen atom to which they are linked, can form a 4- to 8-membered heterocyclic ring, which may contain one or two heteroatoms selected from O, S or N.

Preferably, X$_2$ is C—R$^1$, in which R$^1$ is X$^5$—R$^5$, in which X$^5$ is a single bond, R$^5$ is phenyl, optionally substituted with a methyl, and substituted with C(=O)NR$^3$R$^4$ in which R$^3$ and R$^4$ together with the nitrogen atom to which they are linked, form a 6-membered heterocyclic ring, which may contain one or two nitrogen atoms, and which may be substituted with, a 6-membered heterocyclic ring, which may contain one or two nitrogen atoms and which may be substituted with a lower alkyl, or, a lower alkyl optionally substituted with OR', NR'R", C(=O)NR'R" or COOR' in which R' and R" are the same or different and are selected from, H, or lower alkyl optionally substituted with OR or COOR in which R is hydrogen or lower alkyl and, R' and R" together with the nitrogen atom to which they are linked, can form a 6-membered heterocyclic ring, which may contain one or two heteroatoms selected from O or N;

In each of all the group of compounds defined above, the following substitutions are further preferred:

Preferably, compounds of the invention are compounds of formula (I).

Preferably, X is NH.

Preferably, Y is NH.

Preferably, Z is O.

Preferably, X is NH, Y is NH, and Z is O.

Preferably, A is selected from cyclohexyl or cycloheptyl, optionally interrupted with C(=O) or O, and unsubstituted or substituted with CH$_3$, OH or OCH$_3$.

Preferably, A is selected from unsubstituted cyclohexyl or cycloheptyl.

Preferably, A is unsubstituted cyclohexyl.

Preferably X is NH, Y is NH, Z is O and A is unsubstituted cyclohexyl.

Preferably X is NH, Y is NH, Z is O, A is unsubstituted cyclohexyl, X$_3$ is C—R$^1$ in which R$^1$ is hydrogen and X$_4$ is C—R$^1$, in which R$^1$ is selected from hydrogen, halogen, CF$_3$, methyl or methoxy.

In the following and in the foregoing text:

Halogen includes fluoro, chloro, bromo, and iodo. Preferred halogens are F and Cl.

Lower alkyl includes straight and branched carbon chains having from 1 to 6 carbon atoms. Examples of such alkyl groups include methyl, ethyl, isopropyl, tert-butyl and the like.

Lower alkenyl includes straight and branched hydrocarbon radicals having from 2 to 6 carbon atoms and at least one double bond. Examples of such alkenyl groups are ethenyl, 3-buten-1-yl, 2-ethenylbutyl, 3-hexen-1-yl, and the like.

Lower alkynyl includes straight and branched hydrocarbon radicals having from 2 to 6 carbon atoms and at least one triple bond. Examples of such alkynyl groups are ethynyl, 3-butyn-1-yl, propynyl, 2-butyn-1-yl, 3-pentyn-1-yl, and the like.

Lower haloalkyl includes a lower alkyl as defined above, substituted with one or several halogens. A preferred haloalkyl is trifluoromethyl.

Aryl is understood to refer to an aromatic carbocycle containing between 6 and 10, preferably 6, carbon atoms. A preferred aryl group is phenyl.

Heteroaryl includes aromatic cycles which have from 5 to 10 ring atoms, from 1 to 4 of which are independently selected from the group consisting of O, S, and N. Preferred heteroaryl groups have 1, 2, 3 or 4 heteroatoms in a 5- or 6-membered aromatic ring. Examples of such groups are tetrazole, pyridyl, thienyl and the like. Preferred cycloalkyl contain from 3 to 8 carbon atoms. Examples of such groups are cyclopropyl, cyclobutyl, cyclopentyl, cyclohexyl, cycloheptyl and cyclooctyl.

The term "interrupted" means that in a backbone chain, a carbon atom is replaced by an heteroatom or a group as defined herein. For example, in "cycloalkyl or cycloalkenyl optionally interrupted with C(=O) or with 1 heteroatom chosen from O, S, S(=O), $SO_2$ or N", the term "interrupted" means that C(=O) or a heteroatom can replace a carbon atom of the ring. Example of such groups are morpholine or piperazine. Cycloalkenyl includes 3- to 10-membered cycloalkyl containing at least one double bond.

Heterocyclic ring include heteroaryl as defined above and cycloalkyl or cycloalkenyl, as defined above, interrupted with 1, 2 or 3 heteroatoms chosen from O, S, S(=O), $SO_2$, or N.

Bicyclic substituents refer to two cycles, which are the same or different and which are chosen from aryl, heterocyclic ring, cycloalkyl or cycloalkenyl, fused together to form said bicyclic substituents. A preferred bicyclic substituent is indolyl. $Sp^2$ hybridization state: carbon atoms in an $sp^2$ hybridization state are trigonal instead of tetraedric. It means that the carbon atoms in a $sp^2$ hybridization state are linked to three atoms and form a double bond with one of these three atoms.

Preferred compounds are:
Spiro[cyclohexane-1-4'-(3',4'-dihydro)quinazolin]-2'(1'H)-one,
6'-Methoxyspiro[cyclohexane-1-4'-(3',4'-dihydro)quinazolin]-2'(1'H)-one,
Spiro[cycloheptane-1-4'-(3',4'-dihydro)quinazolin]-2'(1'H)-one,
7'-Methoxyspiro[cyclohexane-1-4'-(3',4'-dihydro)quinazolin]-2'(1'H)-one,
6'-Phenylspiro[cycloheptane-1-4'-(3',4'-dihydro)quinazolin]-2'(1'H)-one,
8'-Methoxyspiro[cyclohexane-1-4'-(3',4'-dihydro)quinazolin]-2'(1'H)-one,
8'-Chlorospiro[cyclohexane-1-4'-(3',4'-dihydro)quinazolin]-2'(1'H)-one,
7'-chlorospiro[cyclohexane-1-4'-(3',4'-dihydro)quinazolin]-2'(1'H)-one,
5'-chlorospiro[cyclohexane-1-4'-(3',4'-dihydro)quinazolin]-2'(1'H)-one,
8'-methylspiro[cyclohexane-1-4'-(3',4'-dihydro)quinazolin]-2'(1'H)-one,
6'-chlorospiro[cyclohexane-1-4'-(3',4'-dihydro)quinazolin]-2'(1'H)-one,
8'-bromospiro[cyclohexane-1-4'-(3',4'-dihydro)quinazolin]-2'(1'H)-one,
8'-fluorospiro[cyclohexane-1-4'-(3',4'-dihydro)quinazolin]-2'(1'H)-one,
6'-methylspiro[cyclohexane-1-4'-(3',4'-dihydro)quinazolin]-2'(1'H)-one,
5',8'-dichlorospiro[cyclohexane-1-4'-(3',4'-dihydro)quinazolin]-2'(1'H)-one,
6',7'-dichlorospiro[cyclohexane-1-4'-(3',4'-dihydro)quinazolin]-2'(1'H)-one,
5',6'-dichlorospiro[cyclohexane-1-4'-(3',4'-dihydro)quinazolin]-2'(1'H)-one,
6'-phenylspiro[cyclohexane-1-4'-(3',4'-dihydro)quinazolin]-2'(1'H)-one,
8'-iodospiro[cyclohexane-1-4'-(3',4'-dihydro)quinazolin]-2'(1'H)-one,
8'-Bromospiro[cyclobutane-1-4'-(3',4'-dihydro)quinazolin]-2'(1'H)-one,
8'-Bromospiro[cycloheptane-1-4'-(3',4'-dihydro)quinazolin]-2'(1'H)-one,
8'-Bromo-4-methylspiro[cyclohexane-1-4'-(3',4'-dihydro)quinazolin]-2'(1'H)-one,
8'-Bromospiro[bicyclo[3,2,1]octane-2-4'-(3',4'-dihydro)quinazolin]-2'(1'H)-one,
6',8'-dichlorospiro[cyclohexane-1-4'-(3',4'-dihydro)quinazolin]-2'(1'H)-one
8'-chloro-6'-iodospiro[cyclohexane-1-4'-(3',4'-dihydro)quinazolin]-2'(1'H)-one,
8'-chloro-6'-methoxyspiro[cyclohexane-1-4'-(3',4'-dihydro)quinazolin]-2'(1'H)-one,
8'-chloro-6'-phenylspiro[cycloheptane-1-4'-(3',4'-dihydro)quinazolin]-2'(1'H)-one,
8'-chloro-6'-phenylspiro[cyclohexane-1-4'-(3',4'-dihydro)quinazolin]-2'(1'H)-one,
8'-chloro-6'-methylspiro[cyclohexane-1-4'-(3',4'-dihydro)quinazolin]-2'(1'H)-one,
8'-chloro-6'-(3-pyridyl)spiro[cyclohexane-1-4'-(3',4'-dihydro)quinazolin]-2'(1'H)-one,
8'-chloro-6'-(4-pyridyl)spiro[cyclohexane-1-4'-(3',4'-dihydro)quinazolin]-2'(1'H)-one,
6'-(4-carboxyphenyl)-8'-chlorospiro[cyclohexane-1-4'-(3',4'-dihydro)-quinazolin]-2'(1'H)-one,
6'-(3-carboxyphenyl)-8'-chlorospiro[cyclohexane-1-4'-(3',4'-dihydro)-quinazolin]-2'(1'H)-one,
8'-chloro-6'-(1H-indol-5yl)spiro[cyclohexane-1-4'-(3',4'-dihydro)-quinazolin]-2'(1'H)-one,
8'-chloro-6'-(2-pyridyl)spiro[cyclohexane-1-4'-(3',4'dihydro)quinazolin]-2'(1'H)-one,
8'-chloro-6'-(3-dimethylamino-prop-1-ynyl)spiro[cyclohexane-1-4'-(3',4'-dihydro)-quinazolin]-2'(1'H)-one,
8'-chloro-6'-(3-methylamino-prop-1-ynyl)spiro[cyclohexane-1-4'-(3',4'-dihydro)quinazolin]-2'(1'H)-one,
8'-chloro-6'-[4-(4-methyl-piperazine-1-carbonyl)phenyl]spiro[cyclohexane-1-4'-(3',4'-dihydro)quinazolin]-2'(1'H)-one,
8'-chloro-6'-[4-(3-N-dimethylamino-propylcarboxamide)phenyl]-spiro-[cyclohexane-1-4'-(3',4'-dihydro)quinazolin]-2'(1'H)-one,
8'-chloro-6'-[4-(2-N-dimethylamino-ethylcarboxamide)phenyl]-spiro-[cyclohexane-1-4'-(3',4'-dihydro)quinazolin]-2'(1'H)-one,
8'-chloro-6'-[3-(3-N-dimethylamino-propylcarboxamide)phenyl]-spiro-[cyclohexane-1-4'-(3',4'-dihydro)quinazolin]-2'(1'H)-one,
8'-chloro-6'-[3-(4-methyl-piperazine-1-carbonyl)-phenyl]spiro-[cyclohexane-1-4'-(3',4'-dihydro)quinazolin]-2'(1'H)-one,
8'-chloro-6'-[3-(2-N-dimethylamino-ethylcarboxamide)phenyl]spiro-[cyclohexane-1-4'-(3',4'-dihydro)quinazolin]-2'(1'H)-one,
8'-Chlorospiro[cyclohexane-1-4'-(3',4'-dihydro)quinazolin]-2'(1'H)-thione
8'-Chloro-2'-cyanoiminospiro[cyclohexane-1-4'-(3',4'-dihydro)quinazoline 8'-Chloro-2'-methoxyiminospiro[cyclohexane-1-4'-(3',4'-dihydro)quinazoline, 8'-Chloro-2'-dimethylaminospiro[cyclohexane-1-4'-(3',4'-dihydro)quinazoline], 8'-Chloro-1'-methylspiro[cyclohexane-1-4'-(3',4'-dihydro)quinazolin]-2'(1'H)-one, 8'-Chloro-1'-(ethoxycarbonylmethyl)spiro[cyclohexane-1-4'-(3',4'-dihydro)-quinazolin]-2'(1'H)-one, 8'-Chloro-3'-methylspiro[cyclohexane-1-4'-(3',4'-dihydro)quinazolin]-2'(1'H)-one, 8'-chloro-6'-[4-(4-pyrimidin-2-yl-piperazine-1-carbonyl)phenyl]spiro[-cyclohexane-1-4'-(3',4'-dihydro)quinazolin]-2'(1'H)-one, 8'-chloro-6'-[4-(4-(2-morpholin-4-yl-ethyl)-piperazine-1-carbonyl)-phenyl]spiro[-cyclohexane-1-4'-(3',4'-dihydro)quinazolin]-2'(1'H)-one, 8'-chloro-6'-[4-(4-(2-morpholin-4-yl-2-oxo-ethyl)-piperazine-1-carbonyl)-phenyl]spiro[-cyclohexane-1-4'-(3',4'-dihydro)quinazolin]-2'(1'H)-one, 8'-chloro-6'-[4-(4-(2-hydroxy-ethoxy)-ethyl)-piperazine-1-carbonyl)-phenyl]spiro[-cyclohexane-1-4'-(3',4'-dihydro)quinazolin]-2'(1'H)-one, 9'-Chlorospiro[cyclohexane-1-5'-(5',10'-dihydro)]-imidazo[2,1-b]quinazoline 9'-Chlorospiro[cyclohexane-1-5'-(5',10'-dihydro)]-[1,2,4]triazolo[3,4-b]quinazoline, 9'-Chlorospiro[cyclohexane-1-5'-(4',5'-dihydro)]-[1,2,4]triazolo[4,3-a]quinazoline, Spiro[cyclohexane-1-9'-(8',9'-dihydro)-pyrazolo[4',3'-f]quinazolin]-7'(6'H)-one, 8'-Chloro-5'-methoxyspiro[cyclohexane-1-4'-(3',4'-dihydro)quinazolin]-2'(1'H)-one, 5',8'-difluorospiro[cyclohexane-1-4'-(3',4'-dihydro)quinazolin]-2'(1'H)-one, 8'-Chloro-5'-methylspiro[cyclohexane-1-4'-(3',4'-dihydro)quinazolin]-2'(1'H)-one, 8'-Chloro-6'-(morpholin-4-yl)methylspiro[cyclohexane-1-4'-(3',4'-dihydro)quinazolin]-2'(1'H)-one, 8'-Chloro-5'-hydroxyspiro[cyclohexane-1-4'-(3',4'-dihydro)quinazolin]-2'(1'H)-one, 8'-Chloro-5'-hydroxy-6'-iodo-spiro[cyclohexane-1-4'-(3',4'-dihydro)quinazolin]-2'(1'H)-one, 8'-Chloro-6'-iodo-5'-methoxy-spiro[cyclohexane-1-4'-(3',4'-dihydro)quinazolin]-2'(1'H)-one, 8'-Chloro-6'-cyano-5'-methoxy-spiro[cyclohexane-1-4'-(3',4'-dihydro)quinazolin]-2'(1'H)-one, 8'-Chloro-5'-[2-(4-morpholino)ethoxy]spiro[cyclohexane-1-4'-(3',4'-dihydro)quinazolin]-2'(1'H)-one, 8'-Chloro-5'-[2-dimethylaminoethoxy]spiro[cyclohexane-1-4'-(3',4'-dihydro)quinazolin]-2'(1'H)-one, 8'-Chloro-5'-(2-aminoethoxy)-spiro[cyclohexane-1-4'-(3',4'-dihydro)quinazolin]-2'(1'H)-one, 8'-Chloro-5'-[2-(methylamino)ethoxy]-spiro[cyclohexane-1-4'-(3',4'-dihydro)quinazolin]-2'(1'H)-one, 8'-Chloro-5'-[2-(2-aminoethoxy)ethoxy]spiro[cyclohexane-1-4'-(3',4'-dihydro)quinazolin]-2'(1'H)-one, 8'-Chloro-5'-[3-dimethylaminopropoxy]spiro[cyclohexane-1-4'-(3',4'-dihydro)quinazolin]-2'(1'H)-one, 8'-Chloro-5'-ethoxycarbonylmethoxyspiro[cyclohexane-1-4'-(3',4'-dihydro)quinazolin]-2'(1'H)-one, 5'-carboxymethoxy-8'-chloro-spiro[cyclohexane-1-4'-(3',4'-dihydro)quinazolin]-2'(1'H)-one, 5'-carboxypropoxy-8'-chloro-spiro[cyclohexane-1-4'-(3',4'-dihydro)quinazolin]-2'H)-one, 8'-chloro-5'-(3-sulphopropoxy)-spiro[cyclohexane-1-4'-(3',4'-dihydro)quinazolin]-2'(1'H)-one, 8'-Chloro-5'-[2-(tetrahydro-pyran-2-yloxy)-ethoxy]-spiro[cyclohexane-1-4'-(3',4'-dihydro)quinazolin]-2'(1'H)-one, 8'-Chloro-5'-(2-hydroxy-ethoxy)-spiro[cyclohexane-1-4'-(3',4'-dihydro)quinazolin]-2'(1'H)-one, 8'-Chloro-5'-(5-ethoxycarbonyl-furan-2-ylmethoxy)-spiro[cyclohexane-1-4'-(3',4'-dihydro)quinazolin]-2'(1'H)-one, 8'-Chloro-5'-(5-carboxy-furan-2-ylmethoxy)-spiro[cyclohexane-1-4'-(3',4'-dihydro)quinazolin]-2'(1'H)-one, 8'-Chloro-5'-cyanomethoxyspiro[cyclohexane-1-4'-(3',4'-dihydro)quinazolin]-2'(1'H)-one, 8'-Chloro-5'-(1H-tetrazol-5-ylmethoxy)-spiro[cyclohexane-1-4'-(3',4'-dihydro)quinazolin]2'(1'H)-one, 8'-Chloro-5'-(5-hydroxy-[1,2,4]oxadiazol-3-ylmethoxy)-spiro[cyclohexane-1-4'-(3',440 -dihydro) quinazolin]-2'(1'H)-one, 8'-Chloro-6'-iodo-5'-[2-dimethylamino-ethoxy]spiro[cyclohexane-1-4'-(3',4'-dihydro)quinazolin]-2'(1'H)-one, 6'-(4-carboxyphenyl)-8'-chloro-5'-methoxyspiro[cyclohexane-1-4'-(3',4'-dihydro)quinazolin]-2'(1'H)-one, 6'-(3-carboxyphenyl)-8'-chloro-5'-methoxyspiro[cyclohexane-1-4'-(3',4'-dihydro)quinazolin]-2'(1'H)-one, 8'-chloro-6'-[2-(4-methyl-piperazine-1-carbonyl)phenyl]spiro[cyclohexane-1-4'-(3',4'-dihydro)quinazolin]-2'(1'H)-one, 8'-chloro-6'-[2-methyl4-(4-methyl-piperazine-1-carbonyl)phenyl]spiro[cyclohexane-1-4'-(3',4'-dihydro)quinazolin]-2'(1'H)-one, 8'-chloro-6'-[4-(piperazine-1-carbonyl)phenyl]spiro[cyclohexane-1-4'-(3',4'-dihydro)quinazolin]-2'(1'H)-one, 8'-chloro-6'-[4-carbamoyl-phenyl]spiro[cyclohexane-1-4'-(3',4'-dihydro)quinazolin]-2'(1'H)-one, 8'-chloro-6'-[4-((1-methyl-piperidin4-yl)-piperazine-1-carbonyl)phenyl]spiro[cyclohexane-1-4'-(3',4'-dihydro)quinazolin]-2'(1'H)-one, 8'-chloro-5'-methoxy-6'-[4-(4-methyl-piperazine-1-carbonyl)phenyl]spiro[cyclohexane-1-4'-(3',4'-dihydro)quinazolin]-2'(1'H)-one, 8-Chloro-5-methoxyspiro[4H-benzo[d][1,3]oxazin-2-ylamine4-4'-(tetrahydro-pyran4'-yl)], 8'-Trifluoromethylspiro[cyclohexane-1-4'-(3',4'-dihydro)quinazolin]-2'(1'H)-one, 8'-Chloro-6'-cyanomethylspiro[cyclohexane-1-4'-(3',4'-dihydro)quinazolin]-2'(1'H)-one, 8'-Chloro-5'-(3-dimethylamino-2-hydroxy-propoxy)-spiro[cyclohexane-1-4'-(3',4'-dihydro)quinazolin]-2'(1'H)-one, 8'-Chloro-5'-(3-methylamino-2-hydroxy-propoxy)-spiro[cyclohexane-1-4'-(3',4'-dihydro)quinazolin]-2'(1'H)-one, 8'-Chloro-5'-[2-(ethoxycarbonylmethyl-amino)-ethoxy]-spiro[cyclohexane-1-4'-(3',4'-dihydro)quinazolin]-2'(1'H)-one, 8'-Chloro-5'-[2-(carboxymethyl-amino)-ethoxy]-spiro[cyclohexane-1-4'-(3',4'-dihydro)quinazolin]-2'(1'H)-one hydrochloride, 8'-Chloro-5'-(2-methanesulfonylamino-2-oxo-ethoxy)-spiro[cyclohexane-1-4'-(3', 4'-dihydro)quinazolin]-2'(1'H)-one, 8'-Chloro-5'-(2-[(5-methyl-isoxazol-3-ylmethyl)-amino]ethoxy)-spiro[cyclohexane-1-4'-(3',4'-dihydro)quinazolin]-2'(1'H)-one.

Among the compounds mentioned above, the following compounds are more preferred:

6'-Phenylspiro[cycloheptane-1-4'-(3',4'-dihydro)quinazolin]-2'(1'H)-one,

8'-Chlorospiro[cyclohexane-1-4'-(3',4'-dihydro)quinazolin]-2'(1'H)-one,

5'-chlorospiro[cyclohexane-1-4'-(3',4'-dihydro)quinazolin]-2'(1'H)-one,
8'-methylspiro[cyclohexane-1-4'-(3',4'-dihydro)quinazolin]-2'(1'H)-one,
8'-bromospiro[cyclohexane-1-4'-(3',4'-dihydro)quinazolin]-2'(1'H)-one,
8'-fluorospiro[cyclohexane-1-4'-(3',4'-dihydro)quinazolin]-2'(1'H)-one,
5',8'-dichlorospiro[cyclohexane-1-4'-(3',4'-dihydro)quinazolin]-2'(1'H)-one,
5',6'-dichlorospiro[cyclohexane-1-4'-(3',4'-dihydro)quinazolin]-2'(1'H)-one,
6'-phenylspiro[cyclohexane-1-4'-(3',4'-dihydro)quinazolin]-2'(1'H)-one,
8'-Bromospiro[cycloheptane-1-4'-(3',4'-dihydro)quinazolin]-2'(1'H)-one,
8'-Bromo-4-methylspiro[cyclohexane-1-4'-(3',4'-dihydro)quinazolin]-2'(1'H)-one,
8'-Bromospiro[bicyclo[3,2,1]octane-2-4'-(3',4'-dihydro)quinazolin]-2'(1'H)-one,
6',8'-dichlorospiro[cyclohexane-1-4'-(3',4'-dihydro)quinazolin]-2'(1'H)-one
8'-chloro-6'-iodospiro[cyclohexane-1-4'-(3',4'-dihydro)quinazolin]-2'(1'H)-one,
8'-chloro-6'-methoxyspiro[cyclohexane-1-4'-(3',4'-dihydro)quinazolin]-2'(1'H)-one,
8'-chloro-6'-phenylspiro[cycloheptane-1-4'-(3',4'-dihydro)quinazolin]-2'(1'H)-one,
8'-chloro-6'-phenylspiro[cyclohexane-1-4'-(3',4'-dihydro)quinazolin]-2'(1'H)-one,
8'-chloro-6'-methylspiro[cyclohexane-1-4'-(3',4'-dihydro)quinazolin]-2'(1'H)-one,
8'-chloro-6'-(3-pyridyl)spiro[cyclohexane-1-4'-(3',4'-dihydro)quinazolin]-2'(1'H)-one,
8'-chloro-6'-(4-pyridyl)spiro[cyclohexane-1-4'-(3',4'-dihydro)quinazolin]-2'(1'H)-one,
6'-(4-carboxyphenyl)-8'-chlorospiro[cyclohexane-1-4'-(3',4'-dihydro)quinazolin]-2'(1'H)-one,
6'-(3-carboxyphenyl)-8'-chlorospiro[cyclohexane-1-4'-(3',4'-dihydro)quinazolin]-2'(1'H)-one,
8'-chloro-6'-(1H-indol-5yl)spiro[cyclohexane-1-4'-(3',4'-dihydro)-quinazolin]-2'(1'H)-one,
8'-chloro-6'-(2-pyridyl)spiro[cyclohexane-1-4'-(3',4'-dihydro)quinazolin]-2'(1'H)-one,
8'-chloro-6'-(3-dimethylamino-prop-1-ynyl)spiro[cyclohexane-1-4'-(3',4'-dihydro)quinazolin]-2'(1'H)-one,
8'-chloro-6'-(3-methylamino-prop-1-ynyl)spiro[cyclohexane-1-4'-(3',4'-dihydro)quinazolin]2'(1'H)-one,
8'-chloro-6'-[4-(4-methyl-piperazine-1-carbonyl)phenyl]spiro[cyclohexane-1-4'-(3',4'-dihydro)quinazolin]-2'(1'H)-one,
8'-chloro-6'-[4-(3-N-dimethylamino-propylcarboxamide)phenyl]-spiro-[cyclohexane-1-4'-(3',4'-dihydro)quinazolin]-2'(1'H)-one,
8'-chloro-6'-[4-(2-N-dimethylamino-ethylcarboxamide)phenyl]-spiro-[cyclohexane-1-4'-(3',4'-dihydro)quinazolin]-2'(1'H)-one,
8'-chloro-6'-[3-(3-N-dimethylamino-propylcarboxamide)phenyl]-spiro-[cyclohexane-1-4'-(3',4'-dihydro)quinazolin]-2'(1'H)-one,
8'-chloro -6'-[3-(4-methyl-piperazine-1-carbonyl)-phenyl]spiro-[cyclohexane-1-4'-(3',4'-dihydro)quinazolin]-2'(1'H)-one,
8'-chloro-6'-[3-(2-N-dimethylamino-ethylcarboxamide)phenyl]spiro-[cyclohexane-1-4'-(3',4'-dihydro)quinazolin]-2'(1'H)-one,
8'-Chlorospiro[cyclohexane-1-4'-(3',4'-dihydro)quinazolin]-2'(1'H)-thione
8'-Chloro-2'-cyanoiminospiro[cyclohexane-1-4'-(3',4'-dihydro)quinazoline
8'-chloro-6'-[4-(4-pyrimidin-2-yl-piperazine-1-carbonyl)phenyl]spiro[-cyclohexane-1-4'-(3',4'-dihydro)quinazolin]-2'(1'H)-one,
8'-chloro-6'-[4-(4-(2-morpholin-4-yl-ethyl)-piperazine-1-carbonyl)-phenyl]spiro[-cyclohexane-1-4'-(3',4'-dihydro)quinazolin]-2'(1'H)-one,
8'-chloro-6'-[4-(4-(2-morpholin-4-yl-2-oxo-ethyl)-piperazine-1-carbonyl)-phenyl]spiro[-cyclohexane-1-4'-(3',4'-dihydro)quinazolin]-2'(1'H)-one,
8'-chloro-6'-[4-(4-(2-hydroxy-ethoxy)-ethyl)-piperazine-1-carbonyl)-phenyl]spiro[-cyclohexane-1-4'-(3',4'-dihydro)quinazolin]-2'(1'H)-one,
8'-Chloro-5'-methoxyspiro[cyclohexane-1-4'-(3',4'-dihydro)quinazolin]-2'(1'H)-one,
5',8'-difluorospiro[cyclohexane-1-4'-(3',4'-dihydro)quinazolin]-2'(1'H)-one,
8'-Chloro-5'-methylspiro[cyclohexane-1-4'-(3',4'-dihydro)quinazolin]-2'(1'H)-one,
8'-Chloro-6'-(morpholin-4-yl)methylspiro[cyclohexane-1-4'-(3',4'-dihydro)quinazolin]-2'(1'H)-one,
8'-Chloro-5'-hydroxyspiro[cyclohexane-1-4'-(3',4'-dihydro)quinazolin]-2'(1'H)-one,
8'-Chloro-6'-cyano-5'-methoxy-spiro[cyclohexane-1-4'-(3',4'-dihydro)quinazolin]-2'(1'H)-one,
8'-Chloro-5'-[2-(4-morpholino)ethoxy]spiro[cyclohexane-1-4'-(3',4'-dihydro)quinazolin]-2'(1'H)-one,
8'-Chloro-5'-[2-dimethylaminoethoxy]spiro[cyclohexane-1-4'-(3',4'-dihydro)quinazolin]-2'(1'H)-one,
8'-Chloro-5'-[2-(methylamino)ethoxy]-spiro[cyclohexane-1-4'-(3',4'-dihydro)quinazolin]-2'(1'H)-one,
5'-carboxymethoxy-8'-chloro-spiro[cyclohexane-1-4'-(3',4'-dihydro)quinazolin]-2'(1'H)-one,
5'-carboxypropoxy-8'-chloro-spiro[cyclohexane-1-4'-(3',4'-dihydro)quinazolin]-2'(1'H)-one,
8'-chloro-5'-(3-sulphopropoxy)-spiro[cyclohexane-1-4'-(3',4'-dihydro)quinazolin]-2'(1'H)-one,
8'-Chloro-5'-(2-hydroxy-ethoxy)-spiro[cyclohexane-1-4'-(3',4'-dihydro)quinazolin]-2'(1'H)-one,
8'-Chloro-5'-(5-ethoxycarbonyl-furan-2-ylmethoxy)-spiro[cyclohexane-1-4'-(3',4'-dihydro)quinazolin]-2'(1'H)-one,
8'-Chloro-5'-(5-carboxy-furan-2-ylmethoxy)-spiro[cyclohexane-1-4'-(3',4'-dihydro)quinazolin]-2'(1'H)-one,
8'-Chloro-5'-cyanomethoxyspiro[cyclohexane-1-4'-(3',4'-dihydro)quinazolin]-2'(1'H)-one,
8'-Chloro-5'-(1H-tetrazol-5-ylmethoxy)-spiro[cyclohexane-1-4'-(3',4'-dihydro)quinazolin]-2'(1'H)-one,
8'-Chloro-5'-(5-hydroxy-[1,2,4]oxadiazol-3-ylmethoxy)-spiro[cyclohexane-1-4'-(3',4'-dihydro)quinazolin]-2'(1'H)-one,
6'-(4-carboxyphenyl)-8'-chloro-5'-methoxyspiro[cyclohexane-1-4'-(3',4'-dihydro)quinazolin]-2'(1'H)-one,
6'-(3-carboxyphenyl)-8'-chloro-5'-methoxyspiro[cyclohexane-1-4'-(3',4'-dihydro)quinazolin]-2'(1'H)-one,
8'-chloro-6'-[2-methyl-4-(4-methyl-piperazine-1-carbonyl)phenyl]spiro[cyclohexane-1-4'-(3',4'-dihydro)quinazolin]-2'(1'H)-one,
8'-chloro-6'-[4-(piperazine-1-carbonyl)phenyl]spiro[cyclohexane-1-4'-(3',4'-dihydro)quinazolin]-2'(1'H)-one,
8'-chloro-6'-[4-carbamoyl-phenyl]spiro[cyclohexane-1-4'-(3',4'-dihydro)quinazolin]-2'(1'H)-one,
8'-chloro-6'-[4-((1-methyl-piperidin-4-yl)-piperazine-1-carbonyl)phenyl]spiro[cyclohexane-1-4'-(3',4'-dihydro)quinazolin]-2'(1'H)-one, 8'-chloro-5'-methoxy-6'-[4-(4-methyl-piperazine-1-carbonyl)phenyl]spiro[cyclohexane-1-4'-(3',4'-dihydro)quinazolin]-2'(1'H)-one,
8'-Chloro-6'-cyanomethylspiro[cyclohexane-1-4'-(3',4'-dihydro)quinazolin]-2'(1'H)-one,
8'-Chloro-5'-(3-dimethylamino-2-hydroxy-propoxy)-spiro[cyclohexane-1-4'-(3',4'-dihydro)quinazolin]-2'(1'H)-one,
8'-Chloro-5'-(3-methylamino-2-hydroxy-propoxy)-spiro[cyclohexane-1-4'-(3',4'-dihydro)quinazolin]-2'(1'H)-one,
8'-Chloro-5'-[2-(carboxymethyl-amino)-ethoxy]-spiro[cyclohexane-1-4'-(3',4'-dihydro)quinazolin]-2'(1'H)-one hydrochloride,
8'-Chloro-5'-(2-methanesulfonylamino-2-oxo-ethoxy)-spiro[cyclohexane-1-4'-(3',4'-dihydro)quinazolin]-2'(1'H)-one,
8'-Chloro-5'-(2-[(5-methyl-isoxazol-3-ylmethyl)-amino]ethoxy)-spiro[cyclohexane-1-4'-(3',4'-dihydro)quinazolin]-2'(1'H)-one.

Among the compounds mentioned above, the following compounds are more preferred:
8'-bromospiro[cyclohexane-1-4'-(3',4'-dihydro)quinazolin]-2'(1'H)-one,
5',8'-dichlorospiro[cyclohexane-1-4'-(3',4'-dihydro)quinazolin]-2'(1'H)-one,
8'-Bromospiro[cycloheptane-1-4'-(3',4'-dihydro)quinazolin]-2'(1'H)-one,
8'-chloro-6'-methoxyspiro[cyclohexane-1-4'-(3',4'-dihydro)quinazolin]-2'(1'H)-one,
8'-chloro-6'-phenylspiro[cyclohexane-1-4'-(3',4'-dihydro)quinazolin]-2'(1'H)-one,
8'-chloro-6'-(3-pyridyl)spiro[cyclohexane-1-4'-(3',4'-dihydro)quinazolin]-2'(1'H)-one,
8'-chloro-6'-(4-pyridyl)spiro[cyclohexane-1-4'-(3',4'-dihydro)quinazolin]-2'(1'H)-one,
6'-(4-carboxyphenyl)-8'-chlorospiro[cyclohexane-1-4'-(3',4'-dihydro)quinazolin]-2'(1'H)-one,
6'-(3-carboxyphenyl)-8'-chlorospiro[cyclohexane-1-4'-(3',4'-dihydro)-quinazolin]-2'(1'H)-one,
8'-chloro-6'-(1H-indol-5yl)spiro[cyclohexane-1-4'-(3',4'-dihydro)-quinazolin]-2'(1'H)-one,
8'-chloro-6'-(2-pyridyl)spiro[cyclohexane-1-4'-(3',4'-dihydro)quinazolin]-2'(1'H)-one,
8'-chloro-6'-(3-dimethylamino-prop-1-ynyl)spiro[cyclohexane-1-4'-(3',4'-dihydro)-quinazolin]-2'(1'H)-one,
8'-chloro-6'-(3-methylamino-prop-1-ynyl)spiro[cyclohexane-1-4'-(3',4'-dihydro)quinazolin]-2'(1'H)-one,
8'-chloro-6'-[4-(4-methyl-piperazine-1-carbonyl)phenyl]spiro[cyclohexane-1-4'-(3',4'-dihydro)quinazolin]-2'(1'H)-one,
8'-chloro-6'-[4-(3-N-dimethylamino-propylcarboxamide)phenyl]-spiro-[cyclohexane-1-4'-(3',4'-dihydro)quinazolin]-2'(1'H)-one,
8'-chloro-6'-[4-(2-N-dimethylamino-ethylcarboxamide)phenyl]-spiro-[cyclohexane-1-4'-(3',4'-dihydro)quinazolin]-2'(1'H)-one,
8'-chloro-6'-[3-(3-N-dimethylamino-propylcarboxamide)phenyl]-spiro-[cyclohexane-1-4'-(3',4'-dihydro)quinazolin]-2'(1'H)-one,
8'-chloro -6'-[3-(4-methyl-piperazine-1-carbonyl)-phenyl]spiro-[cyclohexane-1-4'-(3',4'-dihydro)quinazolin]-2'(1'H)-one,
8'-chloro-6'-[3-(2-N-dimethylamino-ethylcarboxamide)phenyl]spiro-[cyclohexane-1-4'-(3',4'-dihydro)quinazolin]-2'(1'H)-one,
8'-chloro-6'-[4-(4-pyrimidin-2-yl-piperazine-1-carbonyl)phenyl]spiro[-cyclohexane -1-4'-(3',4'-dihydro)quinazolin]-2'(1'H)-one,
8'-chloro-6'-[4-(4-(2-morpholin-4-yl-ethyl)-piperazine-1-carbonyl)-phenyl]spiro[-cyclohexane-1-4'-(3',4'-dihydro)quinazolin]-2'(1'H)-one,
8'-chloro-6'-[4-(4-(2-morpholin4-yl-2-oxo-ethyl)-piperazine-1-carbonyl)-phenyl]spiro[-cyclohexane-1-4'-(3',4'-dihydro)quinazolin]-2'(1'H)-one,
8'-chloro-6'-[4-(4-(2-hydroxy-ethoxy)-ethyl)-piperazine-1-carbonyl)-phenyl]spiro[-cyclohexane-1-4'-(3',4'-dihydro)quinazolin]-2'(1'H)-one,
8'-Chloro-5'-methoxyspiro[cyclohexane-1-4'-(3',4'-dihydro)quinazolin]-2'(1'H)-one,
8'-Chloro-5'-methylspiro[cyclohexane-1-4'-(3',4'-dihydro)quinazolin]-2'(1'H)-one,
8'-Chloro-5'-hydroxyspiro[cyclohexane-1-4'-(3',4'-dihydro)quinazolin]-2'(1'H)-one,
8'-Chloro-6'-cyano-5'-methoxy-spiro[cyclohexane-1-4'-(3',4'-dihydro)quinazolin]-2'(1'H)-one,
8'-Chloro-5'-[2-(4-morpholino)ethoxy]spiro[cyclohexane-1-4'-(3',4'-dihydro)quinazolin]-2'(1'H)-one,
5'-carboxymethoxy-8'-chloro-spiro[cyclohexane-1-4'-(3',4'-dihydro)quinazolin]-2'(1'H)-one,
5'-carboxypropoxy-8'-chloro-spiro[cyclohexane-1-4'-(3',4'-dihydro)quinazolin]-2'(1'H)-one
8'-chloro-5'-(3-sulphopropoxy)-spiro[cyclohexane-1-4'-(3',4'-dihydro)quinazolin]-2'(1'H)-one,
8'-Chloro-5'-(2-hydroxy-ethoxy)-spiro[cyclohexane-1-4'-(3',4'-dihydro)quinazolin]-2'(1'H)-one,
8'-Chloro-5'-(5-ethoxycarbonyl-furan-2-ylmethoxy)-spiro[cyclohexane-1-4'-(3',4'-dihydro)quinazolin]-2'(1'H)-one,
8'-Chloro-5'-(5-carboxy-furan-2-ylmethoxy)-spiro[cyclohexane-1-4'-(3',4'-dihydro)quinazolin]-2'(1'H)-one,
8'-Chloro-5'-cyanomethoxyspiro[cyclohexane-1-4'-(3',4'-dihydro)quinazolin]-2'(1'H)-one,
8'-Chloro-5'-(1H-tetrazol-5-ylmethoxy)-spiro[cyclohexane-1-4'-(3',4'dihydro)quinazolin]2'(1'H)-one,
8'-Chloro-5'-(5-hydroxy-[1,2,4]oxadiazol-3-ylmethoxy)-spiro[cyclohexane-1-4'-(3',4'-dihydro)quinazolin]-2'(1'H)-one,
6'-(4-carboxyphenyl)-8'-chloro-5'-methoxyspiro[cyclohexane-1-4'-(3',4'-dihydro)quinazolin]-2'(1'H)-one,
6'-(3-carboxyphenyl)-8'-chloro-5'-methoxyspiro[cyclohexane-1-4'-(3',4'-dihydro)quinazolin]-2'(1'H)-one,
8'-chloro-6'-[2-methyl-4-(4-methyl-piperazine-1-carbonyl)phenyl]spiro[cyclohexane-1-4'-(3',4'-dihydro)quinazolin]-2'(1'H)-one,
8'-chloro-6'-[4-(piperazine-1-carbonyl)phenyl]spiro[cyclohexane-1-4'-(3',4'-dihydro)quinazolin]-2'(1'H)-one,
8'-chloro-6'-[4-carbamoyl-phenyl]spiro[cyclohexane-1-4'-(3',4'-dihydro)quinazolin]-2'(1'H)-one,
8'-chloro-6'-[4-((1-methyl-piperidin-4-yl)-piperazine-1-carbonyl)phenyl]spiro[cyclohexane-1-4'-(3',4'-dihydro)quinazolin]-2'(1'H)-one, and,
8'-Chloro-5'-[2-(carboxymethyl-amino)-ethoxy]-spiro[cyclohexane-1-4'-(3',4'-dihydro)quinazolin]-2'(1'H)-one hydrochloride,
8'-Chloro-5'-(2-methanesulfonylamino-2-oxo-ethoxy)-spiro[cyclohexane-1-4'-(3',4'-dihydro)quinazolin]-2'(1'H)-one,
8'-Chloro-5'-(2-[(5-methyl-isoxazol-3-ylmethyl)-amino]ethoxy)-spiro[cyclohexane-1-4'-(3',4'-dihydro)quinazolin]-2'(1'H)-one.

General Process for the Preparation of Compounds of the Invention

One method for preparing a compound of the formula (I) defined above in which Y is N—$R^{12}$, X is N—$R^9$ and Z is O comprises reacting a substituted urea of formula

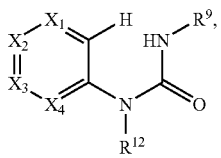

in which $X_1$, $X_2$, $X_3$, $X_4$, $R_9$ and $R_{12}$ are as defined in the summary of the invention, with a cyclic ketone of formula

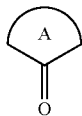

in which A is as defined in the summary of the invention, to obtain said compound of formula (I).

An alternative method for preparing a compound of formula (I) in which X is N—$R^9$, Y is O, S or NH, and $X_1$, $X_2$, $X_3$, $X_4$, A and $R^9$ are as defined in the summary of the invention and, comprises, (1) reacting a compound (2a)

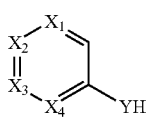

in which $X_1$, $X_2$, $X_3$, $X_4$ are as defined in the summary of the invention and Y is O, S or NH, with a group P-LG in which P is a protecting group and LG is a leaving group to obtain compound (2b)

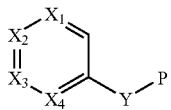

(2) reacting compound (2b) with R-Li in which R is lower alkyl and then with a ketone of formula

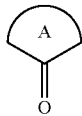

in which A is as defined in the summary of the invention to obtain compound (2c)

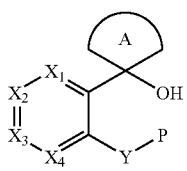

(3) removing the protecting group P either under reductive conditions, acidic condition or condition to obtain compound (2d)

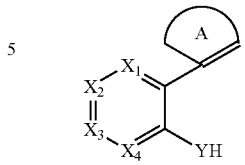

(4) reacting compound (2d) with a group O=C=N—$R^9$ in which $R^9$ is as defined in the summary of the invention to obtain compound (2e)

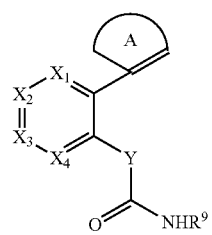

(5) reacting compound (2e) with an acid to obtain said compound of formula (I), (6) isolating said compound of formula (I).

An alternative process for the preparation of a compound of formula (I) in which X is O, S or $NR^9$, Y is O, S or $NR^{12}$, Z is O, S or $NR^{13}$, $X_1$, $X_2$, $X_3$, $X_4$, A, $R^9$, $R^{12}$ and $R^{13}$ are as defined in the summary of the invention and Y is O, S or NH, comprises, (1) reacting compound (2d)

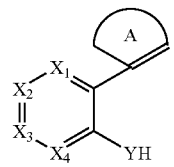

in which $X_1$, $X_2$, $X_3$, $X_4$ and A are as defined in claim 1, with a group LG-C(=X)Z' or X=C=Z' in which LG is a leaving group, X is O, S or $NR^9$, Z' is OR, SR or $NR^{13}$ in which R is lower alkyl or benzyl and $R^9$ and $R^{13}$ are as defined in the summary of the invention, to obtain compound (2'e)

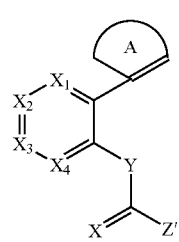

(2) reacting compound (2'e) with a source of halonium to obtain compound (2'f)

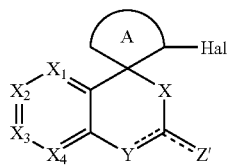

(2'f)

(3) reduction of compound (2'f) to obtain said compound of formula (I)
(4) optionally, when Z' is OR or SR, hydrolysis or hydrogenolysis of compound (2'f) is carried out to obtain compound said compound of formula (I) in which Z is O or S, and,
(5) isolating said compound of formula (I).

The compounds utilized in the invention include pharmaceutically acceptable derivatives of compounds of formula (I), (II) or (III) such as solvates, hydrates, pharmaceutically acceptable salts and polymorphs (different crystalline lattice descriptors).

Pharmaceutically acceptable salts of a compound of formula (I), (II) or (III) include salts having a basic part and salts having an acidic part.

The expression pharmaceutically acceptable salt of a compound of formula (I), (II) or (III) having a basic part should be understood to refer to the addition salts of the compounds of formula (I), (II) or (III) which may be formed from non-toxic inorganic or organic acids such as, for example, hydrobromic, hydrochloric, sulfuric, phosphoric, nitric, acetic, succinic, tartaric, citric, maleic, hydroxymaleic, benzoic, fumaric and toluenesulfonic acid salts, and the like. The various quaternary ammonium salts of the derivatives (I), (II) or (III) are also included in this category of compounds of the invention. In addition, the expression pharmaceutically acceptable salt of a compound of formula (I), (II) or (III) having an acidic part is understood to refer to the usual salts of the compounds of formula (I), (II) or (III) which may be formed from non-toxic inorganic or organic bases such as, for example, the hydroxides of alkali metals and alkaline-earth metals (sodium, potassium, magnesium and calcium), amines (dibenzylethylenediamine, trimethylamine, piperidine, pyrrolidine, benzylamine and the like) or alternatively quaternary ammonium hydroxides such as tetramethylammonium hydroxide. (See also "Pharmaceutical salts" by Berge S. M. et al. (1997) *J. Pharm. Sci.* 66: 1–19, which is incorporated herein by reference.).

Use of a prodrug of a compound of the invention such as it would occur to one skilled in the art (see Bundgaard, et al., *Acta Pharm. Suec.*, 1987; 24: 233–246), is also contemplated.

Pharmaceutical Compositions

The products of the invention are administered in the form of compositions, which are appropriate for the nature, and severity of the complaint to be treated. The daily dose in humans is usually between 1 mg and 1 g of product, which may be taken in one or more individual doses. The compositions are prepared in forms which are compatible with the intended route of administration, such as, for example, tablets, coated tablets, capsules, mouthwashes, aerosols, powders for inhalation, suppositories, enemas, foams (such as rectal foams) gels or suspensions. These compositions are prepared by methods which are familiar to those skilled in the art and comprise from 0.5 to 60% by weight of active principle (compound of the invention) and 40 to 99.5% by weight of a pharmaceutical vehicle or carrier which is appropriate and compatible with the active principle and the physical form of the intended composition.

Solid form preparations include powders, tablets, dispersible granules, capsules, cachets, and suppositories. A solid carrier can be one or more substances which may also act as diluents, flavouring agents, solubilizers, lubricants, suspending agents, binders, or tablet disintegrating agents; it can also be an encapsulating material. In powders, the carrier is a finely divided solid, which is in a mixture with the finely divided active component. In tablets, the active component is mixed with the carrier having the necessary binding properties in suitable proportions and compacted in the shape and size desired. The powders, tablets, cachets or encapsulated forms for capsules preferably contain 5% to about 70% of the active component. Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

Tablets, powders, cachets, and capsules can be used as solid dosage forms suitable for oral administration. The drug may be delivered as a spray (either in a pressurized container fitted with an appropriate valve or in a non-pressurized container fitted with a metering valve).

Liquid form preparations include solutions, suspensions, and emulsions.

Sterile water or water-propylene glycol solutions of the active compounds may be mentioned as an example of liquid preparations suitable for parenteral administration. Liquid preparations can also be formulated in solution in aqueous polyethylene glycol solution.

Aqueous solutions for oral administration can be prepared by dissolving the active component in water and adding suitable colorants, flavouring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

For preparing suppository preparations, a low-melting wax such as a mixture of fatty acid glycerides and cocoa butter is first melted and the active ingredient is dispersed therein by, for example, stirring. The molten homogeneous mixture is then poured into convenient sized molds and allowed to cool and solidify. Enemas are obtained according to known procedures to prepare solutions adapted for rectal administration. Foams are prepared according to known methods (these foams can notably be similar to those used to administer a drug such as 5-ASA for treating rectocolite).

Preferably the pharmaceutical preparation is in unit dosage form. In such form, the preparation is divided into unit doses containing appropriate quantities of drug. The unit dosage form can be a packaged preparation, the package containing discrete quantities of the preparation, for example, packaged tablets, capsules, and powders in vials or ampoules. The unit dosage form can also be a capsule, cachet, or tablet itself, or it can be the appropriate number of any of these packaged forms.

Methods of Treatment

The compounds of the invention are PDE inhibitors, and particularly PDE7 inhibitors. These compounds have low $IC_{50}$ values, typically at most 5 μM, preferably below 1 μM, and even below 100 nM.

It has been shown according to the invention that compounds of the invention are selective PDE7 inhibitors. "selective PDE7 inhibitors" refers to a compound which have an $IC_{50}$ for PDE7 at least 5 times lower than the $IC_{50}$ for a PDE distinct from PDE7, and preferably at least 10 times, 15 times, 20 times, 30 times, 40 times, 50 times or 100 times lower than the $IC_{50}$ value for a PDE distinct from PDE7.

A PDE distinct from PDE7 refers preferably to a PDE chosen from PDE1, PDE3, PDE4 or PDE5.

In particular, it has been shown according to the invention that the compounds of the invention, and more particularly the family of compounds given as examples in the present description, have an $IC_{50}$ value for the enzyme PDE7 which is often 100 times lower than the value of their $IC_{50}$ for a PDE distinct from PDE7, in particular PDE1, PDE3, PDE4 or PDE5.

Compounds of the invention can be used in the treatment of various diseases, as they can modulate inflammatory and immunological processes due to the increase of intracellular cAMP levels.

The diseases that can be treated are T-cell-related diseases, AE-cell-related diseases and immune disorders, such as autoimmune diseases, osteoarthritis, rheumatoid arthritis, multiple sclerosis, osteoporosis, asthma, COPD, cancer, AIDS, inflammation, allergy and various inflammatory disorders such as, for example, inflammatory bowel disease (IBD).

The invention finally relates to a method for the treatment of the above-mentioned diseases comprising administering to a mammal, particularly a human, in need thereof an effective amount of compound of the invention.

Processes for Synthetising the Compounds of General Formula (I), (II) and (III)

The compounds according to the present invention can be obtained by carrying out several synthetic processes. Some of these synthetic processes (protocols A-L) are described below.

The solvent, reaction time, temperature, catalyst if any, can be varied in all steps described below for all routes, as the skilled man will appreciate.

Protocol A:

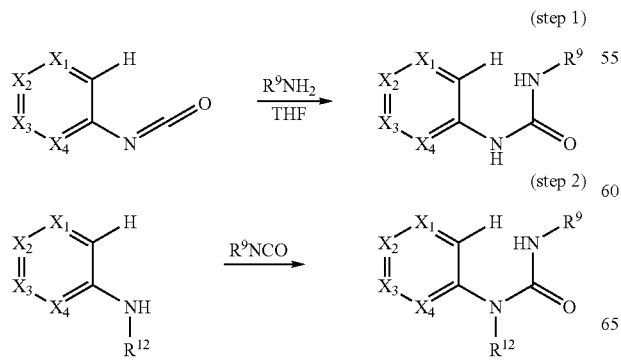

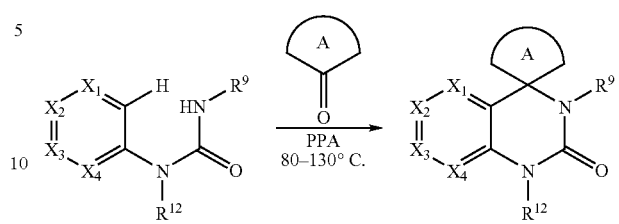

In scheme 1, $X_1$, $X_2$, $X_3$, $X_4$, A, $R^9$ and $R^{12}$ are as defined in the summary of the invention.

The starting materials are either commercially available or can be prepared according to routes known to the skilled person. If the starting urea in step 3 is not commercially available, it can be prepared by treating the corresponding isocyanate with a primary amine in a solvent such as tetrahydrofuran (step 1) or treating the corresponding aniline with a substituted isocyanate in an organic solvent such as dichloromethane or acetonitrile (step 2).

In step 3, the urea is converted into the desired quinazolinone by reacting it with a cyclic ketone in polyphosphoric acid at 80–130° C.

Protocol B:

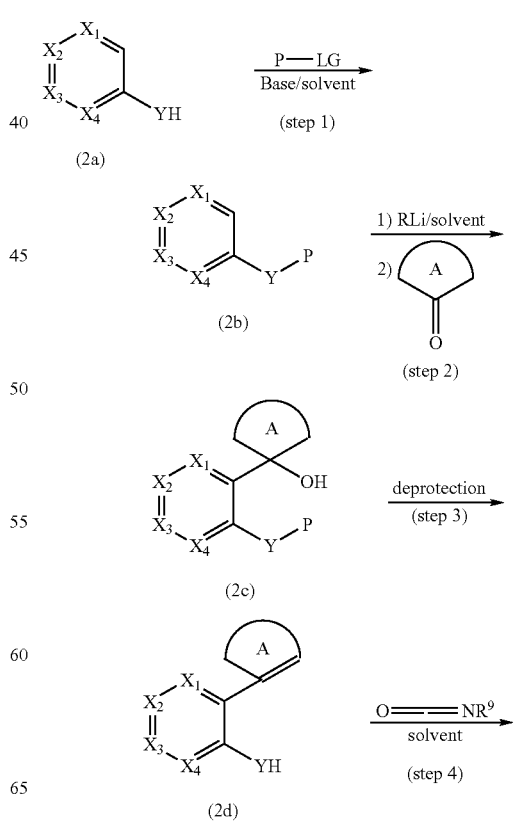

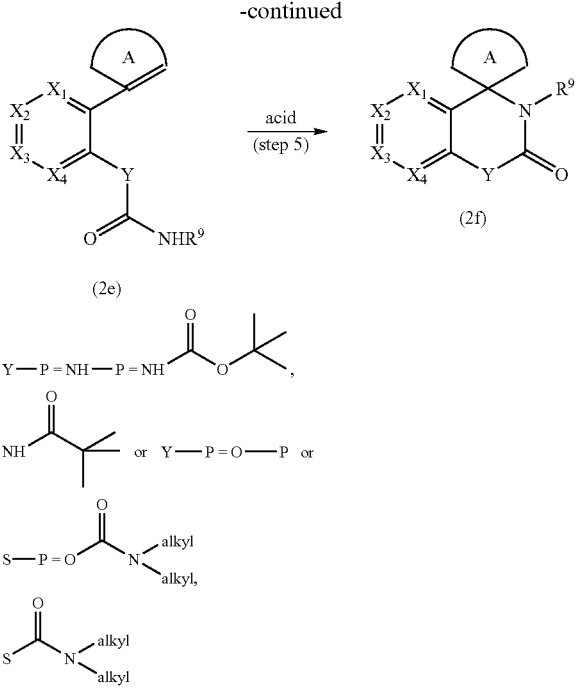

In scheme 2, $X_1$, $X_2$, $X_3$, $X_4$, A and $R^9$ are as defined in the summary of the invention, Y may be O, S or NH and LG is a leaving group and R is lower alkyl.

The starting compounds are either commercially available or can be prepared according to routes known to the skilled person.

In step 1, compound (2a) is reacted with dialkyl-carbamoyl chloride to form the desired N,N dialkyl-carbamate or thiocarbamate according to routes known to the skilled person. See Poirier, M. ; Simard, M. ; Wuest, J. D. ; *Organometallics*, 1996, 15 (4), 1296–1300.

Other protecting groups may be used as oxygen-based directed metalation groups such as OMe, OMOM, OP(OR$_2$), OPO(NMe)$_2$. See Snieckus, *Chem. Rev.*, 1990, 90, 879–933.

The aniline derivative is protected as a t-butyl carbamate or as a pivaloyl amide according to routes known to the skilled person. See *Tet. Lett.*, 1994, 35(48), 9003–9006. In step 2, compound (2b) is converted to a lithium salt (when Y is O or S) or to a dilithium salt thereof by reaction with an excess of lithium compound-forming agent such as t-butyllithium in a mixed solvent of anhydrous ether (for example, diethyl ether and tetrahydrofuran) and alkane (for example pentane), and reacted with an appropriate ketone. The reaction is carried out at low temperature (between –78° C. and 0° C.) to give the expected tertiary alcool. The organolithium intermediate can also be formed by halogen-metal exchange. The organolithium can also be transmetallated into another organometallic reagent such as a cerate (with anhydrous cerium trichloride for example) prior to treatment with the ketone.

In step 3, the protecting group is removed according to routes known to the skilled person either under reductive conditions (when Y=O—P or S—P), under acidic condition or under basic condition to give compound (2d).

In step 4, compound (2d) is reacted with an appropriate substituted isocyanate to obtain compound (2e).

In step 5, treating compound (2e) with an acid (mineral acid or lewis acid) triggers cyclisation to give compound (2f).

Protocol B':

Scheme 2'

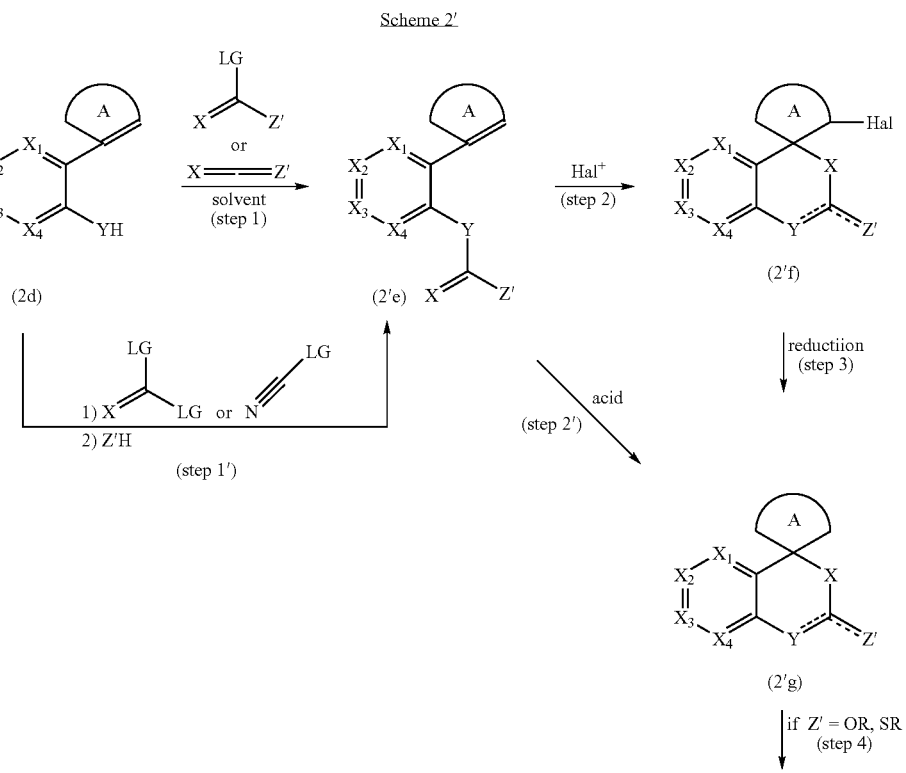

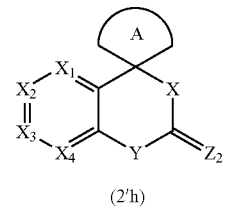

(2'h)

In scheme 2', $X_1$, $X_2$, $X_3$, $X_4$ and A are as defined in the summary of the invention, Y may be O, S or $NR^{12}$, X may be O, S, $NR^9$ and LG is a leaving group, Z' may be OR, SR, $NR^{16}R^{17}$ or $NR^{13}$, Hal is halogen, $Z^2$ may be O or S and where $R^{12}$, $R^{13}$, $R^{16}$, $R^{17}$ and $R^9$ are as defined in the summary of the invention and R is alkyl or benzyl.

In step 1, intermediate 2d obtained according to protocol B is reacted either with a carbonyl derivative such as a carbonate, a chloroformate, an isocyanate; a thiocarbonyl derivative such as an isothiocyanate, a thionochloroformate, or others such as cyanamide, 3,5-dimethyl-1H-pyrazole-1-carboximidamide nitrate, S-methylisothiourea or equivalent. Alternatively, as shown in step 1', intermediate 2'e can be prepared in two steps by treating 2d with either cyanogens bromide or a carbonyl (or thiocarbonyl) derivative activated by two leaving groups such as phosgene (or thiophosgene), 1,1'-carbonyldiimidazole (or 1,1'-thiocarbonyldiimidazole), nitrophenylchloroformate or carbon disulfide, followed by addition of a nucleophile such as an amine, an alcohol or a thiol to introduce Z'. The appropriate reaction conditions for each route can be easily determined by the skilled person. When desired, certain intermediates 2'e obtained can be derivatized into other intermediates 2'e according to routes known to the skilled person. For instance, an intermediate thiourea 2'e wherein Y=NH, X=S and Z'=$NH_2$ can be treated with an alkyl halide R—X according to reaction conditions known to the skilled person to give an intermediate 2'e wherein Y=NH, X=NH and Z'=SR.

In step 2, intermediate 2'e is treated with a source of halonium such as iodine, N-iodosuccinimide, bromine or N-bromosuccinimide to yield intermediate 2'f. Similarly to 2'e, intermediate 2'f can be derivatized into different intermediates 2'f according to routes known to the skilled person. The halide 2'f can be reduced to 2'g as shown in step 3 under reaction conditions known to the skilled person, such as treatment with trialkyl tin hydride and a radical initiator like azobisisobutyronitrile (AIBN) in an inert organic solvent. Alternatively, as shown in step 2', intermediate 2'e could be directly transformed into 2'g under acidic treatment according to conditions that can be determined by the skilled person. If necessary, intermediate 2'g can also be derivatized into different 2'g according to routes known to the skilled person. When Z' is OR or SR, intermediate 2'g can be converted to 2'h as shown in step 4. This can be done according to conditions known to the skilled person by hydrolysis under aqueous acidic media or by hydrogenolysis when R is benzyl.

Protocol C:

Scheme 3

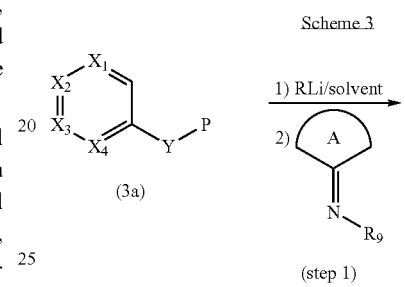

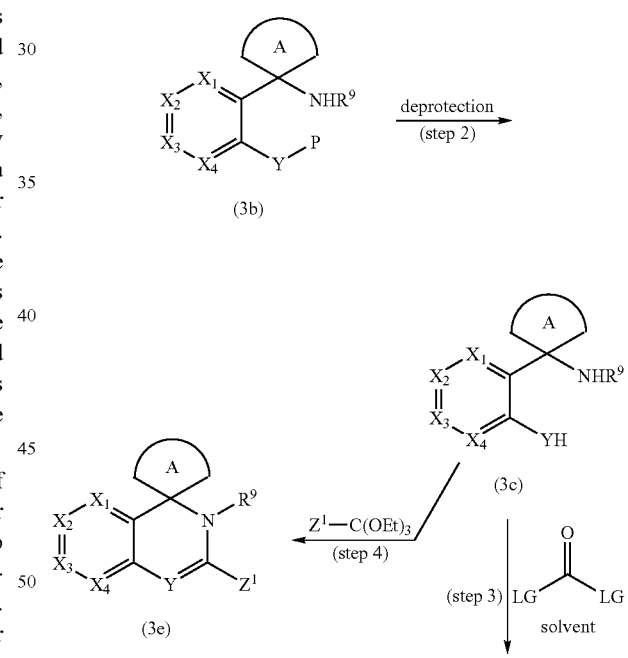

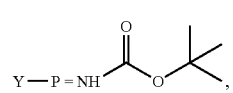

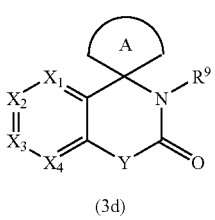

-continued

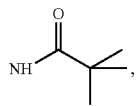

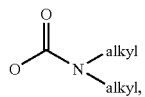

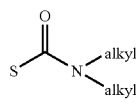

LG = leaving group
$Z^1$ = H or $CH_3$

In scheme 3, $X_1$, $X_2$, $X_3$, $X_4$ and A are as defined in the summary of the invention, $R^9$ is alkyl, aryl, alkylsulfonyl or arylsulfonyl, R is lower alkyl and Y may be O, S or NH.

An alternative method of preparing compound of the present invention is shown below and proceeds through the reaction of the organolithium intermediate with an imine.

In step 1, compound (3a) is converted to a lithium salt (when Y is O or S) or to a dilithium salt (when Y is NH) thereof by reaction with an excess of lithium compound-forming agent such as t-butyllithium in a mixed solvent of anhydrous ether (for example, diethyl ether and tetrahydrofuran) and alkane (for example pentane). The resulting organolithium is reacted with an appropriate imine at low temperature to give the expected tertiary amine (3b). The organolithium can also be transmetallated into another organometallic reagent such as a cerate (with anhydrous cerium trichloride for example) prior to treatment with the ketone.

In step 2, the protecting group is removed according to routes known to the skilled person either under reductive conditions (when Y=O—P or S—P), under acidic condition or under basic condition to give compound (3c). When $R^9$ is alkyl or arylsulfonyl, this group can be deprotected into the NH derivative by reductive methods or hydrolysis according to methods known to the skilled person.

In step 3, compound (3c) is reacted with a compound selected from a carbonic acid halide such as phosgene a carbonic acid diester, 1,1'-carbonyidiimidazole and so on to obtain compound (3d).

In step 4, compound (3c) is reacted with an orthoester, in the presence of an acid to obtain compound (3e) or its tautomeric forms. Protocol D:

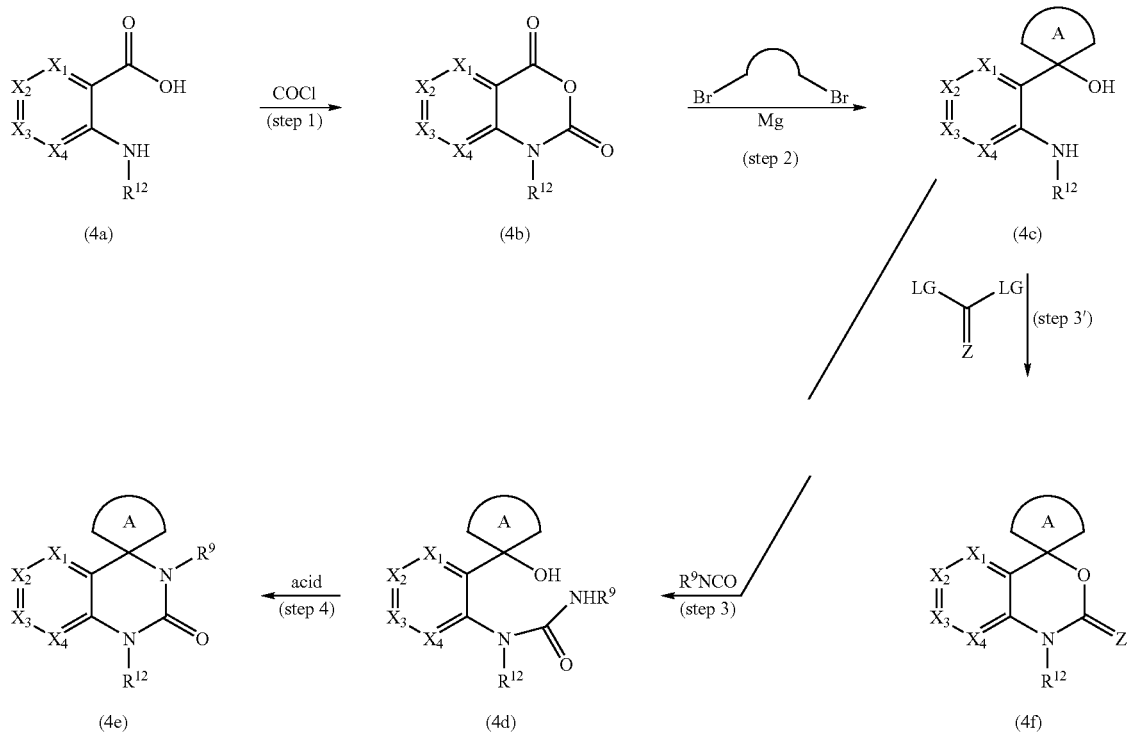

In scheme 4, $X_1$, $X_2$, $X_3$, $X_4$, A, $R^9$ and $R^{12}$ are as defined in the summary of the invention, Z is O or S.

The starting materials are either commercially available or can be prepared according to routes known to the skilled person. In step 1, the starting anthranilic acid is treated with phosgene or an equivalent source of carbonyl such as triphosgene or carbonyl diimidazole. Various solvents andreaction conditions can be used and will be easily determined by the skilled person. The resulting isatoic anhydride is treated with the Grignard reagent obtained from a dihalide and magnesium in a solvent such as tetrahydrofuran or ether (step 2). In step 3, the aniline is converted to an urea by treatment with a substituted isocyanate. Various solvents and reaction conditions can be used and will be easily determined by the skilled person. For example, the reaction can be performed at room temperature or reflux in an inert solvent such as dichloromethane, acetonitrile or tetrahydrofuran in the presence or not of a base such as triethylamine or pyridine. In step 4, the resulting hydroxyurea is subjected to an acid with or without an organic solvent. For example, the reaction can be carried out at 70–90° C. in sulfuric acid. A solvent such as toluene or acetic acid may be added.

In step 3', compound 4c is converted to compound 4f by treatment with a carbonyl (or thiocarbonyl) derivative activated by two leaving groups such as phosgene (or thiophosgene), 1,1'-carbonyidiimidazole (or 1,1'-thiocarbonyidiimidazole).

Protocol E:

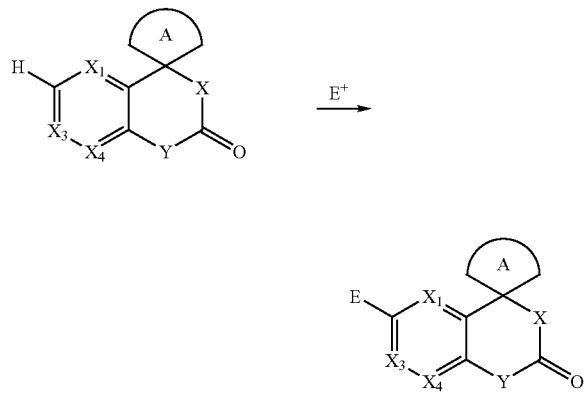

In scheme 5, $X_1$, $X_3$, $X_4$, X, Y and A are as defined in the summary of the invention.

The starting tricyclic compound is reacted with an electrophile $E^+$ such as halonium or acylium in presence or not of an activating agent in an organic solvent. Various solvents and reaction conditions for this aromatic electrophilic substitution can be used depending on the electrophile and will be easily determined by the skilled person. For instance, the starting material can be treated with a source of halonium such as N-iodo or N-bromosuccinimide in dimethylformamide at 60–70° C. to give the corresponding halide. In another example, the starting material can be reacted with an acyl halide and aluminium trichloride, as Lewis acid, in a solvent such as dichloroethane at 80° C.

Protocol F:

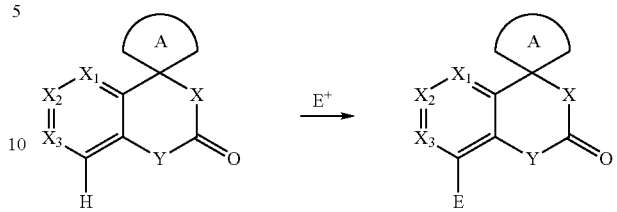

In scheme 6, $X_1$, $X_3$, X, Y and A are as defined in the summary of the invention and $X_2$ is not CH.

The starting tricyclic compound is reacted with an electrophile $E^+$ in presence or not of an activating agent in an organic solvent. This aromatic electrophilic substitution is similar to Protocol E except that in this case, since $X_2$ is different from CH, the substitution is oriented in position 8. Similarly to Protocol E, various solvents and reaction conditions for this aromatic electrophilic substituion can be used depending on the electrophile and will be easily determined by the skilled person.

Protocol G:

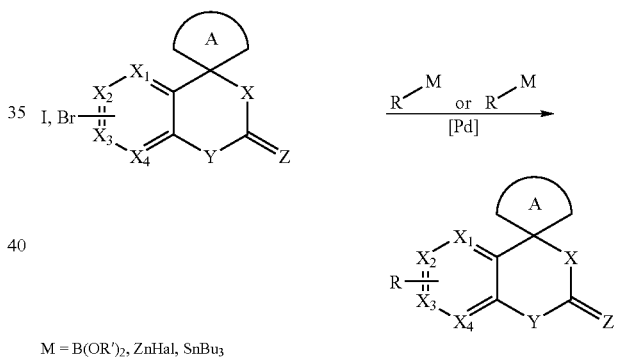

M = B(OR')$_2$, ZnHal, SnBu$_3$

In scheme 7, $X_1$, $X_2$, $X_3$ and $X_4$, X, Y, Z and A are as defined in the summary of the invention, R is alkenyl, alkynyl, aryl or heteroaryl and $R^1$ is H or alkyl.

The starting aryl or heteroaryl iodide or bromide is subjected to a palladium-catalyzed cross-coupling reaction with an organometallic species, such as a boronate ester, a boronic acid, an organozinc (Hal=halogen) or a trialkylstannane in the presence of base when needed. The organometallic species can be replaced with a terminal alkene or alkyne in the coupling reaction. When an alkyne is used, a source of copper(1), such as copper iodide, can be added. Various palladium catalysts, solvents and reaction conditions can be used for these coupling reactions and will be easily determined by the skilled person. For example, the starting aryl or heteroaryl iodide or bromide can be reacted with a boronic acid in dimethylformamide at 80° C. in the presence of tetrakis(triphenylphosphine)palladium as catalyst and an aqueous solution of potassium carbonate as a base.

Protocol H:

Scheme 8

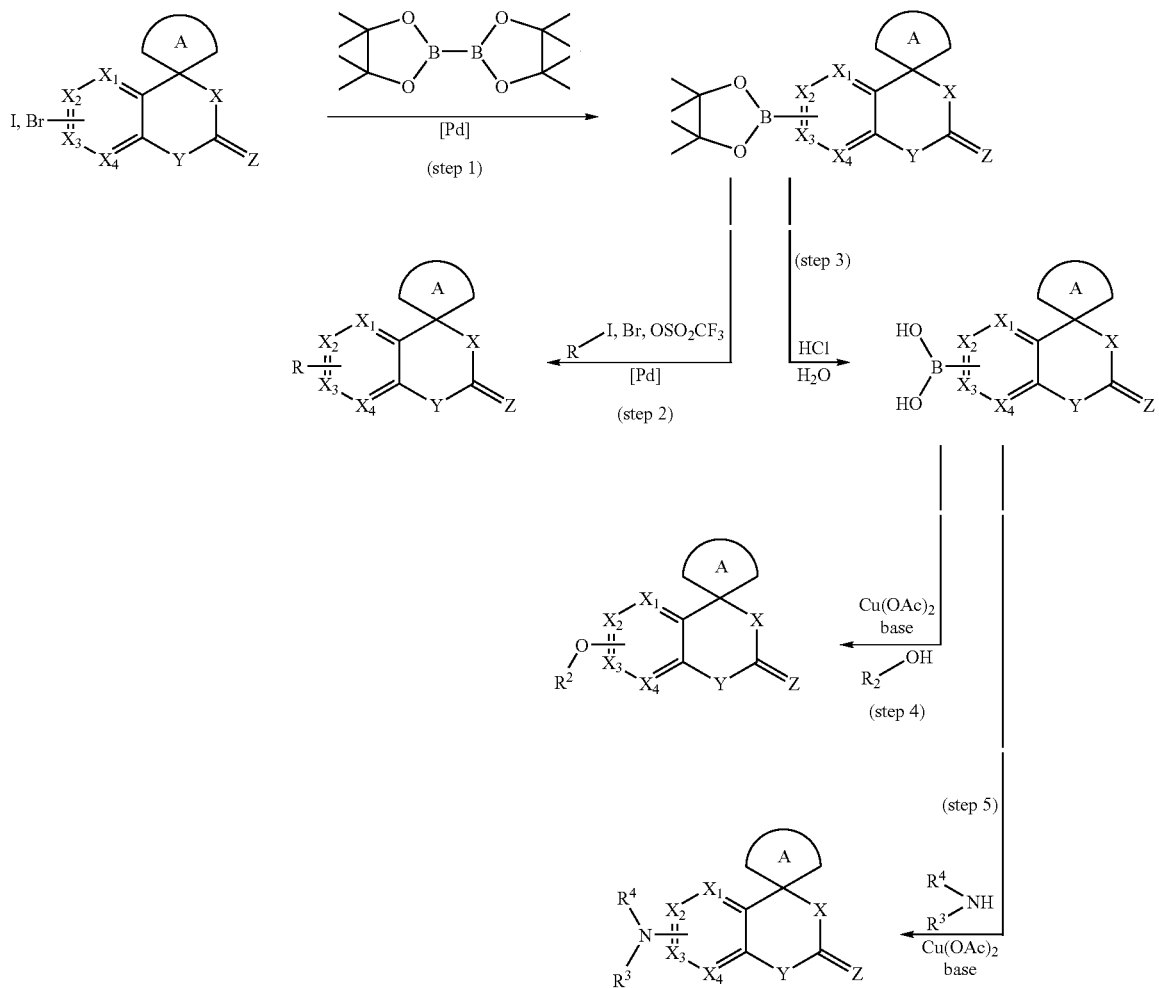

In scheme 8, $X_1$, $X_2$, $X_3$, $X_4$, X, Y, Z, $R^2$, $R^3$, $R^4$ and A are as defined in the summary of the invention and R is selected from aryl, alkenyl, alkynyl or heteroaryl.

In step 1, the starting aryl or heteroaryl iodide or bromide is treated with bis(pinacolato)diboron under palladium catalysis to give the corresponding boronate ester. Various paladium catalysts, solvents and reaction conditions can be used and will be easily determined by the skilled person. For example, the starting heteroaryl iodide or bromide can be reacted with bis(pinacolato)diboron in dimethylformamide at 80° C. in the presence of tetrakis(triphenylphosphine) palladium as catalyst. The resulting boronate ester is then coupled to an aryl, alkenyl, alkynyl or heteroaryl iodide, bromide or triflate catalyzed by a palladium species (step 2). Again, various palladium catalysts, solvents and reaction conditions can be used for this coupling reactions and will be easily determined by the skilled person. For instance, the boronate ester is reacted with an aryl, alkenyl, alkynyl or heteroaryl iodide in dimethylformamide at 80° C. in the presence of sodium acetate as base and tetrakis(triphenylphosphine)palladium as catalyst to give the coupled product.

In step 3, the boronate ester is hydrolyzed to the corresponding boronic acid. This can be done by treating it with acid, e.g. an aqueous solution of hydrochloric acid, in an organic solvent, e.g. methanol. The resulting boronic acid is coupled, (step 4) under air with a phenol or heteroaryl alcohol, or, (step 5) with a primary or secondary amine, heteroarylamine, aniline, amide, sulfonamide, urea, carbamate or imide, in the presence of a base such as triethylamine or pyridine and a source of copper(II) such as copper(II) acetate in a solvent like dichloromethane. Molecular sieves, 4 Å or 3 Å, can be added to the reaction mixture.

Protocol I:

Scheme 9

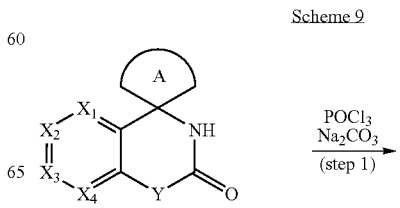

-continued

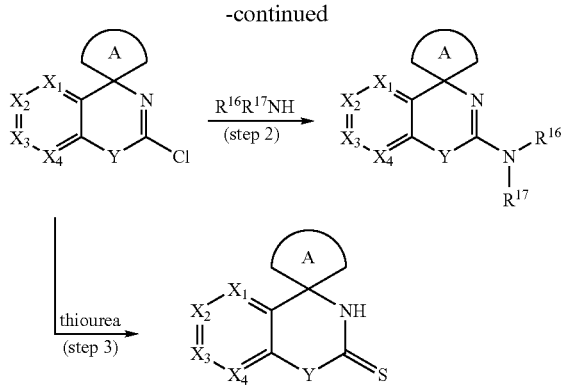

In scheme 9, $X_1$, $X_2$, $X_3$ and $X_4$, Y, $R^{16}$, $R^{17}$ and A are as defined in the summary of the invention.

In step 1, urea, carbamate or thio carbamate is initially converted into a halo-imine via a chlorinating agent such as $POCl_3$ which is then further reacted (step 2) with a suitable amine to form the final compound. The reaction can be carried out without solvent or in a solvent, for example an alcohol such as ethanol, at a temperature between 40 and 80° C. or under pressure for volatile amine, for example.

In step 3, the halo-imine is transformed into thio-derivative with thiourea.

The process of scheme 9 above can also be applied to compounds of formula (I) in which Y is NH and X is N—$R^9$.

Protocol J:

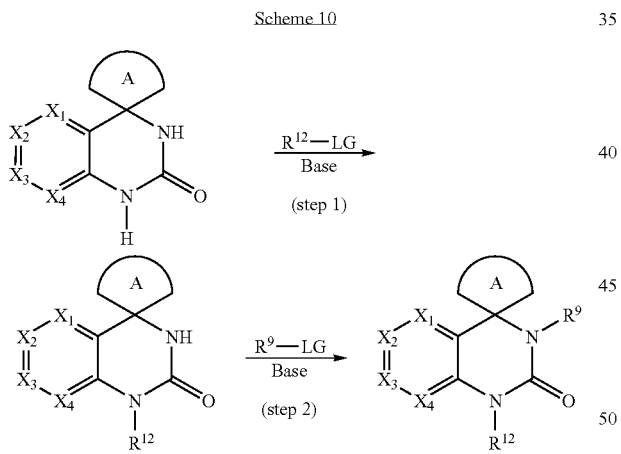

In scheme 10, $X_1$, $X_2$, $X_3$, $X_4$, $R^9$, $R^{12}$ and A are as defined in the summary of the invention and LG is a leaving group such as trifluoromethane sulfonate, mesylate or halogen.

In step 1, the quinazolinone is reacted with $R^{12}$-LG to obtain the N-substituted quinazoline In step 2, the N-substituted quinazolinone is reacted with $R^9$-LG.

Various solvents, operating conditions and bases can be used and will be easily determined by the skilled person. For example, and without any limitation, one can use for the reaction sodium hydride or cesium carbonate as base in dimethylformamide as solvent.

Step 2 of the above process can also be applied to compounds of formula (I) in which Y is O or S.

Step 1 of the above process can also be applied to compounds of formula (I) in which X is O or S.

Protocol K:

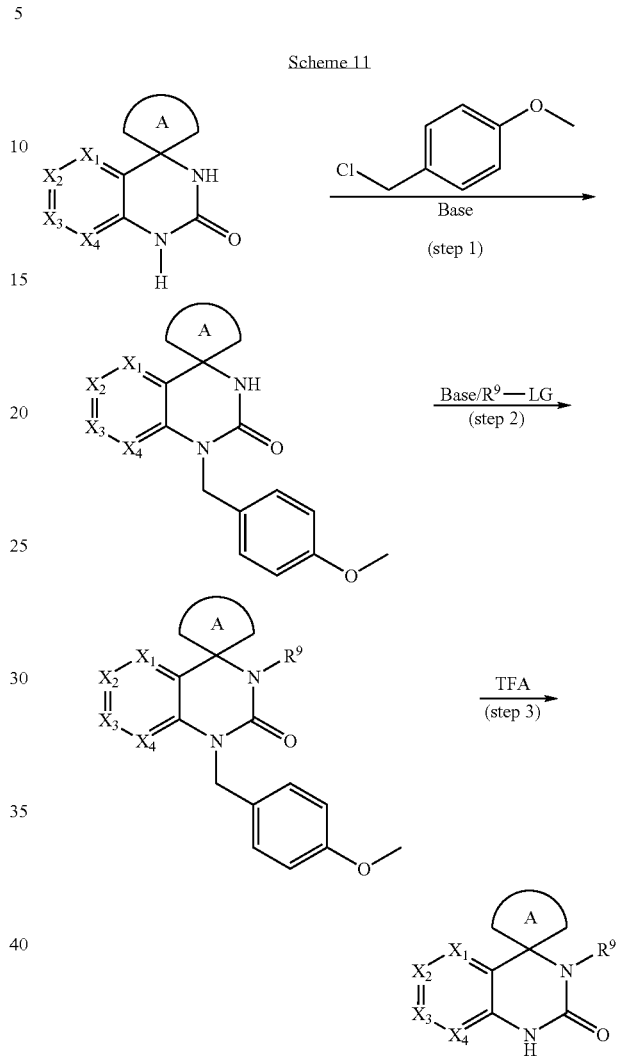

In scheme 11, $X_1$, $X_2$, $X_3$, $X_4$, $R^9$ and A are as defined in the summary of the invention and LG is a leaving group such as trifluoromethane sulfonate, mesylate or halogen.

In step 1, the quinazolinone is reacted with paramethoxybenzyl chloride (PMB). Other protecting group can be used. Various solvents, operating conditions, bases, can be used and will be easily determined by the skilled person. For example, and without any limitation, one can use for the reaction cesium carbonate as base in dimethylformamide as solvent.

In step 2, the protected quinazolinone is reacted with $R^9$-LG. Various solvents, operating conditions, bases, can be used and will be easily determined by the skilled person. For example, and without any limitation, one can use for the reaction sodium hydride as base in dimethylformamide as solvent.

In step 3, treatment of the N1-PMB protected quinazolinone with TFA removed the protecting group. Other protecting groups and deprotecting conditions can be used.

Protocol L:

Scheme 12

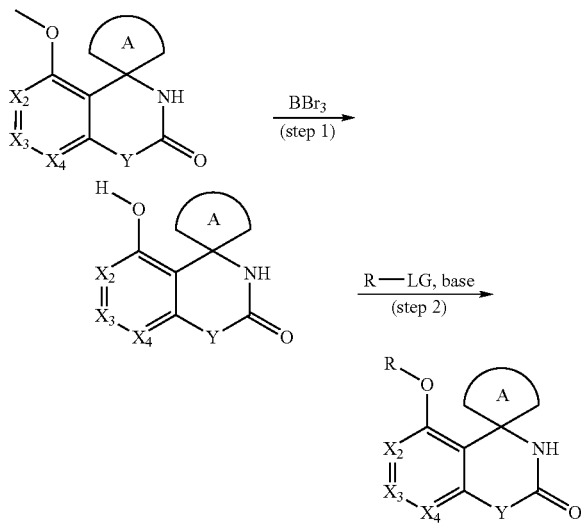

In scheme 12, $X_2$, $X_3$, $X_4$, and A and Y are as defined in the summary of the invention, R is alkyl or C(=O)-alkyl and LG is a leaving group.

In step 1, the starting methoxy derivative is demethylated with boron tribromide in a solvent such as dichloromethane. The resulting phenol intermediate is treated in step 2 with an electrophile such as an alkyl halide, an acyl halide or the like in the presence of a base such as potassium carbonate, cesium carbonate or sodium hydride in a solvent like dimethylformamide.

SYNTHESIS EXAMPLES

Examples 1 to 100 illustrate, without limiting it, the synthesis of particularly active compounds of formula (I) according to the invention.

In the following experimental protocols, the proton NMR data was acquired with a 400 MHz NMR apparatus unless specifically notified.

Example 1

Spiro[cyclohexane-1-4'-(3',4'-dihydro)quinazolin]-2'(1'H)-one $X_1$=CH, $X_2$=CH, $X_3$=CH, $X_4$=CH, A=cyclohexyl, X=NH, Z=O, Y=NH.

The title compound was prepared according to protocol A. Phenyl urea (13.6 g, 0.1 mol) was added portionwise to a solution of polyphosphoric acid (100 g) stirred at 100° C. After complete dissolution of the urea, cyclohexanone (10.3 mL, 0.1 mol) was added dropwise to the hot mixture. The mixture was stirred at 100–120° C. until completion and poured into cold water. The precipitate was filtered, washed with cold water, taken up in hot ethanol and neutralized with NH$_4$OH solution. Water was added to make a 50% ethanol/water solution and the precipitate was filtered, washed with water and dried. The crude material was purified by crystallization in ethanol. The title compound was obtained as a white powder. Melting point (mp)=224–226° C.

$^1$H NMR [(CD$_3$)$_2$SO] δ 9.11 (br s, 1H, NH), 7.24 (d, J=7.6 Hz, 1H), 7.09 (t, J=7.9 Hz, 1H), 6.88 (t, J=7.6 Hz, 1H), 6.78 (d, J=7.9 Hz, 1H), 6.74 (br s, 1H, NH), 1.79–1.63 (m, 7H), 1.50 (m, 2H),), 1.20 (m, 1H).

Example 2

6'-Methoxyspiro[cyclohexane-1-4'-(3',4'-dihydro)quinazolin]-2'(1'H)-one $X_1$=CH, $X_2$=C—O—CH$_3$, $X_3$=CH, $X_4$=CH, A=cyclohexyl, X=NH, Z=O, Y=NH.

The title compound was prepared according to protocol A, using 4-methoxyphenyl urea (30 g, 0.18 mol) and cyclohexanone (18.6 mL, 0.18 mol) in polyphosphoric acid (200 mL). The precipitate was filtered, washed with cold water, taken up in hot ethanol and neutralized with NH$_4$OH solution. Water was added to make a 50% ethanol/water solution and the precipitate was filtered, washed with water and dried. The crude material was purified by crystallization in ethanol. The title compound was obtained as a white powder (8.2 g, 18% yield). mp=233–235° C.

$^1$H NMR [(CD$_3$)$_2$SO] δ 8.94 (br s, 1H, NH), 6.80 (br s, 1H), 6.72 (m, 2H), 6.61 (m, 1H), 3.69 (s, 3H), 1.76–1.47 (m, 9H), 1.23 (m, 1H).

Example 3

Spiro[cycloheptane-1-4'-(3',4'-dihydro)quinazolin]-2'(1'H)-one $X_1$=CH, $X_2$=CH, $X_3$=CH, $X_4$=CH, A=cycloheptyl, X=NH, Z=O, Y=NH.

The title compound was prepared according to protocol A, using phenyl urea (27.2 g, 0.2 mol) and cycloheptanone (23.5 mL, 0.2 mol) in polyphosphoric acid (200 mL). The precipitate was filtered, washed with cold water, taken up in hot ethanol and neutralized with NH$_4$OH solution. Water was added to make a 50% ethanol/water solution and the precipitate was filtered, washed with water and dried. The crude material was purified by crystallization in ethanol. The title compound was obtained as a white powder (14.7 g, 32% yield) mp=198–200° C.

$^1$H NMR [(CD$_3$)$_2$SO] δ 9.11 (br s, 1H, NH), 7.21 (d, J=7.6 Hz, 1H), 7.09 (d, J=7.6 Hz, 1H), 6.88 (m, 2H), 6.78 (d, J=7.9 Hz, 1H), 1.94–1.72 (m, 6H), 1.54 (m, 6H).

Example 4

7'-Methoxyspiro[cyclohexane-1-4'-(3',4'-dihydro)quinazolin]-2'(1'H)-one $X_1$=CH, $X_2$=CH, $X_3$=C—O—CH$_3$, $X_4$=CH, A=cyclohexyl, X=NH, Z=O, Y=NH.

The title compound was prepared according to protocol A, using 3-methoxyphenyl urea (33.2 g, 0.2 mol) and cyclohexanone (20.7 mL, 0.2 mol) in polyphosphoric acid (200 mL). The precipitate was filtered, washed with cold water, taken up in hot ethanol and neutralized with NH$_4$OH solution. Water was added to make a 50% ethanol/water solution and the precipitate was filtered, washed with water and dried. The crude material was purified by crystallization in ethanol. The title compound was obtained as a white powder (9.8 g, 20% yield) mp=228–230° C.

$^1$H NMR [(CD$_3$)$_2$SO] δ 9.03 (br s, 1H, NH), 7.13 (d, J=8.5 Hz, 1H), 6.74 (br s, 1H, NH), 6.45 (dd, J=8.5, 2.3 Hz, 1H), 6.36 (d, J=2.3 Hz, 1H), 3.68 (s, 3H), 1.78–1.59 (m, 7H), 1.47 (m, 2H), 1.20 (m, 1H).

Example 5

6'-Phenylspiro[cycloheptane-1-4'-(3',4'-dihydro)quinazolin]-2'(1'H)-one

X$_1$=CH, X$_2$=C-phenyl, X$_3$=CH, X$_4$=CH, A=cycloheptyl, X=NH, Z=O, Y=NH.

The title compound was prepared according to protocol A, using 4-phenyl-phenyl urea (42.4 g, 0.2 mol) and cycloheptanone (23.5 mL, 0.2 mol) in polyphosphoric acid (400 g). The precipitate was filtered, washed with cold water, taken up in hot ethanol and neutralized with NH$_4$OH solution. Water was added to make a 50% ethanol/water solution and the precipitate was filtered, washed with water and dried. The crude material was purified by crystallization in ethanol. The title compound was obtained as a white powder (23.3 g, 38% yield). mp=180–182° C.

$^1$H NMR [(CD$_3$)$_2$SO] δ 9.28 (br s, 1H, NH), 7.59 (m, 2H), 7.43 (m, 4H), 7.30 (m, 1H), 7.0 (br s, 1H, NH), 6.88 (m, 1H), 2.01 (m, 2H), 1.89 (m, 2H), 1.77 (m, 2H), 1.58 (m, 6H).

Example 6

8'-Methoxyspiro[cyclohexane-1-4'-(3',4'-dihydro)quinazolin]-2'(1'H)-one

X$_1$=CH, X$_2$=CH, X$_3$=CH, X$_4$=C—O—CH$_3$, A=cyclohexyl, X=NH, Z=O, Y=NH.

The title compound was prepared according to protocol A, using 2-methoxyphenyl urea (49.8 g, 0.3 mol) and cyclohexanone (31 mL, 0.3 mol) in polyphosphoric acid (600 g). The precipitate was filtered, washed with cold water, taken up in hot ethanol and neutralized with NH$_4$OH solution. Water was added to make a 50% ethanol/water solution and the precipitate was filtered, washed with water and dried. The crude material was purified by crystallization in isopropanol. The title compound was obtained as a white powder (48.1 g, 65% yield). mp=209–211° C.

$^1$H NMR [(CD$_3$)$_2$SO] δ 7.79 (br s, 1H, NH), 6.87 (m, 4H), 3.79 (s, 3H), 1.79–1.60 (m, 7H), 1.48 (m, 2H), 1.22 (m, 1H).

Example 7

8'-Chlorospiro[cyclohexane-1-4'-(3',4'-dihydro)quinazolin]-2'(1'H)-one

X$_1$=CH, X$_2$=CH, X$_3$=CH, X$_4$=C—Cl, A=cyclohexyl, X=NH, Z=O, Y=NH.

The title compound was prepared according to protocol A, using 2-chlorophenyl urea (51.15 g, 0.3 mol) and cyclohexanone (29.4 g, 0.3 mol) in polyphosphoric acid (600 g). The precipitate was filtered, washed with cold water and recrystallized from ethyl acetate. The title compound was obtained as an orange solid (21% yield). mp=209–211° C.

$^1$H NMR [(CD$_3$)$_2$SO] δ 8.42 (br s, 1H, NH), 7.29 (d, J=7.9 Hz, 2H), 7.16 (br s, 1H), NH), 6.95 (t, J=7.9 Hz, 1H), 1.81–1.61 (m, 7H), 1.52–1.39 (m, 2H), 1.25–1.22 (m, 1H),

Example 8 and Example 9

7'-Chlorospiro[cyclohexane-1-4'-(3',4'-dihydro)quinazolin]-2'(1'H)-one (Example 8)

X$_1$=CH, X$_2$=CH, X$_3$=C—Cl, X$_4$=CH, A=cyclohexyl, X=NH, Z=O, Y=NH.

and 5'-chlorospiro[cyclohexane-1-4'-(3',4'-dihydro)quinazolin]-2'(1'H)-one (Example 9)

X$_1$=C—Cl, X$_2$=CH, X$_3$=CH, X$_4$=CH, A=cyclohexyl, X=NH, Z=O, Y=NH.

The title compounds were prepared according to protocol A, using 3-chlorophenyl urea (0.51 g, 3 mmol) and cyclohexanone (0.5 mL, 4.8 mmol, 1.6 equiv.) in polyphosphoric acid (11 g). The aqueous layer was extracted with CH$_2$Cl$_2$/MeOH (2/1). The combined organic extracts were dried over MgSO$_4$, filtered and concentrated under reduced pressure. The residue was purified by flash chromatography on silica gel (CH$_2$Cl$_2$/CH$_3$CN:90/10 to 60/40) followed by recrystallization in toluene to give 7'-chlorospiro[cyclohexane-1-4'-(3',4'-dihydro)quinazolin]-2'(1'H)-one as a white solid (110 mg, 15% yield). mp=254° C.

$^1$H NMR [(CD$_3$)$_2$SO] δ 9.28 (br s, 1H, NH), 7.27 (d, J=8.0 Hz, 1H), 6.91–6.89 (m, 2H), 6.82 (s, 1H, NH), 1.83–1.61 (m, 7H), 1.49 (m, 2H), 1.24 (m, 1H). and 5'-chlorospiro[cyclohexane-1-4'-(3',4'-dihydro)quinazolin]-2'(1'H)-one as a white solid (101 mg, 14% yield). mp=229° C.

$^1$H NMR [(CD$_3$)$_2$SO] δ 9.34 (br s, 1H, NH), 7.11 (t, J=8.0 Hz, 1H), 6.91 (d, J=8.0 Hz, 1H), 6.84 (br s, 1H, NH), 6.77 (d, J=8.0 Hz, 1H), 2.60 (td, J=13.0, 4.0 Hz, 2H), 1.82 (m, 2H), 1.64–1.49 (m, 5H), 1.22 (m, 1H).

Example 10

8'-Methylspiro[cyclohexane-1-4'-(3',4'-dihydro)quinazolin]-2'(1'H)-one

X$_1$=CH, X$_2$=CH, X$_3$=CH, X$_4$=C—CH$_3$, A=cyclohexyl, X=NH, Z=O, Y=NH.

The title compound was prepared according to protocol A, using o-tolyl urea (551 mg, 3.66 mmol) and cyclohexanone (430 μL, 4.15 mmol, 1.1 equiv.) in polyphosphoric acid (5 g). The aqueous layer was extracted with CH$_2$Cl$_2$/MeOH (2/1). The combined organic extracts were dried over MgSO$_4$, filtered and concentrated under reduced pressure. The residue was purified by flash chromatography on silica gel (CH$_2$Cl$_2$/MeOH:99/1 to 90/10) followed by recrystallization in toluene to give 290 mg (34% yield) of the title compound as a white solid. mp=204° C.

$^1$H NMR [(CD$_3$)$_2$SO] δ 8.32 (br s, 1H, NH), 7.10 (d, J=7.7 Hz, 1H), 6.97 (d, J=7.2 Hz, 1H), 7.10 (m, 2H), 1.82–1.61 (m, 7H), 1.50 (m, 2H), 1.23 (m, 1H).

Example 11

6'-Chlorospiro[cyclohexane-1-4'-(3',4'-dihydro)quinazolin]-2'(1'H)-one $X_1$=CH, $X_2$=C—Cl, $X_3$=CH, $X_4$=CH, A=cyclohexyl, X=NH, Z=O, Y=NH.

The title compound was prepared according to protocol A, using 4-chlorophenyl urea (0.85 g, 5 mmol) and cyclohexanone (0.55 mL, 5.5 mmol, 1.1 equiv.) in polyphosphoric acid (29 g). The aqueous layer was extracted with $CH_2Cl_2$/MeOH (2/1). The combined organic extracts were dried over $MgSO_4$, filtered and concentrated under reduced pressure. The residue was purified by flash chromatography on silica gel ($CH_2Cl_2$/MeOH:99/1 to 90/10) followed by recrystallization in toluene to give 79 mg (6% yield) of the title compound as a white solid. mp=241° C.

$^1$H NMR [$(CD_3)_2SO$] δ 9.28 (br s, 1H, NH), 7.29 (d, J=2.0 Hz, 1H), 7.16 (dd, J=8.5, 2.5 Hz, 1H), 6.87 (br s, 1H, NH), 6.81 (d, J=8.5 Hz, 1H), 1.76–1.60 (m, 7H), 1.49 (m, 2H), 1.25 (m, 1H).

Example 12

8'-Bromospiro[cyclohexane-1-4'-(3',4'-dihydro)quinazolin]-2'(1'H)-one $X_1$=CH, $X_2$=CH, $X_3$=CH, $X_4$=C—Br, A=cyclohexyl, X=NH, Z=O, Y=NH.

The title compound was prepared according to protocol A, using 2-bromophenyl urea (1.075 g, 5 mmol) and cyclohexanone (0.6 mL, 5.8 mmol, 1.2 equiv.) in polyphosphoric acid (39 g). The aqueous layer was extracted with $CH_2Cl_2$/MeOH (2/1). The combined organic extracts were dried over $MgSO_4$, filtered and concentrated under reduced pressure. The residue was purified by flash chromatography on silica gel ($CH_2Cl_2$/MeOH:99/1 to 90/10) followed by recrystallization in toluene to give 415 mg (28% yield) of the title compound as a white solid. mp=213° C.

$^1$H NMR [$(CD_3)_2SO$] δ 7.86 (br s, 1H, NH), 7.45 (d, J=8.0 Hz, 1H), 7.32 d, J=8.0 Hz, 1H), 7.17 (br s, 1H, NH), 6.90 (t, J=8.0 Hz, 1H), 1.81–1.49 (m, 9H), 1.23 (m, 1H).

Example 13

8'-Fluorospiro[cyclohexane-1-4'-(3',4'-dihydro)quinazolin]-2'(1'H)-one $X_1$=CH, $X_2$=CH, $X_3$=CH, $X_4$=C—F, A=cyclohexyl, X=NH, Z=O, Y=NH.

The title compound was prepared according to protocol A, using 2-fluorophenyl urea (0.77 g, 5 mmol) and cyclohexanone (0.55 mL, 5.5 mmol, 1.1 equiv.) in polyphosphoric acid (20 g). The aqueous layer was extracted with $CH_2Cl_2$/MeOH (2/1). The combined organic extracts were dried over $MgSO_4$, filtered and concentrated under reduced pressure. The residue was purified by flash chromatography on silica gel ($CH_2Cl_2$/MeOH:99/1 to 95/5) followed by recrystallization in toluene to give 272 mg (23% yield) of the title compound as a white solid. mp=221° C.

$^1$H NMR [$(CD_3)_2SO$] δ 9.12 (br s, 1H, NH), 7.11 (d, J=7.8 Hz, 1H), 7.05 (m, 1H), 6.94 (br s, 1H, NH), 6.90 (m, 1H), 1.81–1.61 (m, 7H), 1.50 (m, 2H), 1.25 (m, 1H).

Example 14

6'-Methylspiro[cyclohexane-1-4'-(3',4'-dihydro)quinazolin]-2'(1'H)-one $X_1$=CH, $X_2$=C—$CH_3$, $X_3$=CH, $X_4$=CH, A=cyclohexyl, X=NH, Z=O, Y=NH.

The title compound was prepared according to protocol A, using 4-methylphenyl urea (1.5 g, 10 mmol) and cyclohexanone (1.1 mL, 11 mmol, 1.1 equiv.) in polyphosphoric acid (38 g). The aqueous layer was extracted with $CH_2Cl_2$/MeOH (2/1). The combined organic extracts were dried over $MgSO_4$, filtered and concentrated under reduced pressure. The residue was purified by flash chromatography on silica gel ($CH_2Cl_2$/MeOH:99/1 to 90/10) followed by recrystallization in toluene to give 405 mg (18% yield) of the title compound as a white solid. mp=229° C.

$^1$H NMR [$(CD_3)_2SO$] δ 9.01 (br s, 1H, NH), 7.05 (s, 1H), 6.91 (d, J=8.0 Hz, 1H), 6.68–6.66 (m, 2H), 2.22 (s, 3H), 1.76–1.61 (m, 7H), 1.50 (m, 2H), 1.23 (m, 1H).

Example 15

5',8'-Dichlorospiro[cyclohexane-1-4'-3',4'-dihydro)quinazolin]-2'(1'H)-one $X_1$=C—Cl, $X_2$=CH, $X_3$=CH, $X_4$=C—Cl, A=cyclohexyl, X=NH, Z=O, Y=NH.

The title compound was prepared according to protocol A, using 2,5-dichlorophenyl urea (0.615 g, 3 mmol) and cyclohexanone (0.50 mL, 5 mmol, 1.6 equiv.) in polyphosphoric acid (15 g). The aqueous layer was extracted with $CH_2Cl_2$/MeOH (2/1). The combined organic extracts were dried over $MgSO_4$, filtered and concentrated under reduced pressure. The residue was purified by flash chromatography on silica gel ($CH_2Cl_2$/MeOH:99/1 to 92/8) followed by recrystallization in toluene to give 56 mg (7% yield) of the title compound as a white solid. mp=243° C.

$^1$H NMR [$(CD_3)_2SO$] δ 8.35 (br s, 1H, NH), 7.35 (d, J=8.5 Hz, 1H), 7.21 (br s, 1H, NH), 7.01 (d, J=9.0 Hz, 1H), 2.50 (ddd, J=13.5, 13.5, 4.5 Hz, 2H), 1.83 (m, 2H), 1.68–1.51 (m, 5H), 1.24 (m, 1H).

Example 16 and Example 17

6',7'-Dichlorospiro[cyclohexane-1-4'-(3',4'-dihydro)quinazolin]-2'(1'H)-one (Example 16)

$X_1$=CH, $X_2$=C—Cl, $X_3$=C—Cl, $X_4$=CH, A=cyclohexyl, X=NH, Z=O, Y=NH.

and 5',6'-dichlorospiro[cyclohexane-1-4'-(3',4'-dihydro)quinazolin]-2'(1'H)-one (Example 17)

$X_1$=C—Cl, $X_2$=C—Cl, $X_3$=CH, $X_4$=CH, A=cyclohexyl, X=NH, Z=O, Y=NH.

The title compounds were prepared according to protocol A, using 3,4-dichlorophenyl urea (0.61 g, 3 mmol) and cyclohexanone (0.50 mL, 5 mmol, 1.6 equiv.) in polyphosphoric acid (16 g). The aqueous layer was extracted with CH$_2$Cl$_2$/MeOH (2/1). The combined organic extracts were dried over MgSO$_4$, filtered and concentrated under reduced pressure. The residue was purified by flash chromatography on silica gel (CH$_2$Cl$_2$/CH$_3$CN:90/10 to 60/40) followed by recrystallization in toluene to give 6',7'-dichlorospiro[cyclohexane-1-4'-(3',4'-dihydro)quinazolin]-2'(1'H)-one as a white solid (55 mg, 6% yield). mp=269° C.

$^1$H NMR [(CD$_3$)$_2$SO] δ 9.40 (br s, 1H, NH), 7.51 (s, 1H), 7.03 (br s, 1H, NH), 6.98 (s, 1H), 1.75–1.59 (m, 7H), 1.48 (m, 2H), 1.24 (m, 1H).

and 5',6'-dichlorospiro[cyclohexane-1-4'-(3',4'-dihydro)quinazolin]-2'(1'H)-one as a white solid (26 mg, 3% yield). mp=240° C.

$^1$H NMR [(CD$_3$)$_2$SO] δ 9.47 (br s, 1H, NH), 7.43 (d, J=8.5 Hz, 1H), 6.91 (br s, 1H, NH), 6.81 (d, J=9.0 Hz, 1H), 2.64 (ddd, J=13.4, 13.4, 4.4 Hz, 2H), 1.83 (m, 2H), 1.65–1.53 (m, 5H), 1.26 (m, 1H).

Example 18

6'-Phenylspiro[cyclohexane-1-4'-(3',4'-dihydro)quinazolin]-2'(1'H)-one

X$_1$=CH, X$_2$=C-phenyl, X$_3$=CH, X$_4$=CH, A=cyclohexyl, X=NH, Z=O, Y=NH.

The title compound was prepared according to protocol A, using 4-phenyl-phenyl urea (0.67 g, 3.15 mmol) and cyclohexanone (0.50 mL, 5 mmol, 1.6 equiv.) in polyphosphoric acid (16 g). The aqueous layer was extracted with CH$_2$Cl$_2$/MeOH (2/1). The combined organic extracts were dried over MgSO$_4$, filtered and concentrated under reduced pressure. The residue was purified by flash chromatography on silica gel (CH$_2$Cl$_2$/MeOH:99/1 to 90/10) followed by recrystallization in toluene to give 410 mg (13% yield) of the title compound as a white solid. mp=213° C.

$^1$H NMR [(CD$_3$)$_2$SO] δ 9.25 (br s, 1H, NH), 7.62 (d, J=7.4 Hz, 2H), 7.52 (d, J=1.6 Hz, 1H), 7.42 (m, 3H), 7.30 (t, J=7.3 Hz, 1H), 6.88 (d, J=8.2 Hz, 1H), 6.83 (br s, 1H, NH), 1.84–1.79 (m, 6H), 1.63 (m, 1H), 1.53 (m, 2H), 1.30 (m, 1H).

Example 19

8'-Iodospiro[cyclohexane-1-4'-(3',4'-dihydro)quinazolin]-2'(1'H)-one

X$_1$=CH, X$_2$=CH, X$_3$=CH, X$_4$=C—I, A=cyclohexyl, X=NH, Z=O, Y=NH.

The title compound was prepared according to protocol A, using 2-iodophenyl urea (2 g, 7.6 mmol) and cyclohexanone (1 mL, 9.6 mmol, 1.25 equiv.) in polyphosphoric acid (25 g). The aqueous layer was extracted with CH$_2$Cl$_2$/MeOH (2/1). The combined organic extracts were dried over MgSO$_4$, filtered and concentrated under reduced pressure. The residue was purified by flash chromatography on silica gel (CH$_2$Cl$_2$/MeOH:99/1 to 90/10) followed by recrystallization in toluene to give 80 mg (3% yield) of the title compound as a white solid. mp=256° C.

$^1$H NMR [(CD$_3$)$_2$SO] δ 9.26 (br s, 1H, NH), 7.52 (m, 1H), 7.44 (dd, J=8.3, 1.6 Hz, 1H), 6.87 (br s, 1H, NH), 6.62 (d, J=8.3 Hz, 1H), 1.78–1.62 (m, 7H), 1.54 (m, 2H), 1.26 (m, 1H).

Example 20

8'-Bromospiro[cyclobutane-1-4'-(3',4'-dihydro)quinazolin]-2'(1'H)-one

X$_1$=CH, X$_2$=CH, X$_3$=CH, X$_4$=C—Br, A=cyclobutyl, X=NH, Z=O, Y=NH.

The title compound was prepared according to protocol A, using 2-bromophenyl urea (0.6 g, 2.8 mmol) and cyclobutanone (0.25 mL, 3.35 mmol, 1.2 equiv.) in polyphosphoric acid (22 g). The aqueous layer was extracted with CH$_2$Cl$_2$/MeOH (2/1). The organic extracts were dried over MgSO$_4$, filtered and concentrated. The crude material was purified by flash chromatography on silica gel (CH$_2$Cl$_2$/MeOH:99/1 to 90/10) and the resulting powder was washed with diisopropyl ether. The title compound was obtained as a white powder (0.03 g, 4% yield). mp=203–205° C.

$^1$H NMR [(CD$_3$)$_2$SO] δ 7.93 (br s, 1H, NH), 7.80 (br s, 1H, NH), 7.50 (d, J=7.7 Hz, 1H), 7.47 (d, J=7.7 Hz, 1H), 6.95 (t, J=7.7 Hz, 1H), 2.46–2.39 (m, 4H), 1.86 (m, 2H).

Example 21

8'-Bromospiro[cycloheptane-1-4'-(3',4'-dihydro)quinazolin]-2'(1'H)-one

X$_1$=CH, X$_2$=CH, X$_3$=CH, X$_4$=C—Br, A=cycloheptyl, X=NH, Z=O, Y=NH.

The title compound was prepared according to protocol A, using 2-bromophenyl urea (0.6 g, 2.8 mmol) and cycloheptanone (0.5 mL, 4.2 mmol, 1.5 equiv.) in polyphosphoric acid (22 g). The aqueous layer was extracted with CH$_2$Cl$_2$/MeOH (2/1). The organic extracts are dried over MgSO$_4$, filtered and concentrated. The crude material was purified by flash chromatography on silica gel (CH$_2$Cl$_2$/MeOH:99/1 to 90/10) and the resulting powder was washed with diisopropyl ether. The title compound was obtained as a white powder (0.12 g, 14% yield). mp=215–217° C.

$^1$H NMR [(CD$_3$)$_2$SO] δ 7.87 (br s, 1H, NH), 7.44 (d, J=7.8 Hz, 1H), 7.31 (br s, 1H, NH), 7.28 (d, J=7.8 Hz, 1H), 6.90 (t, J=7.8 Hz, 1H), 1.96–1.84 (m, 4H), 1.76–171 (m, 2H), 1.56 (m, 6H).

Example 22

8'-Bromo-4-methylspiro[cyclohexane-1-4'-3',4'-dihydro)quinazolin]-2'(1'H)-one

X$_1$=CH, X$_2$=CH, X$_3$=CH, X$_4$=C—Br, A=4-methyl-cyclohexyl, X=NH, Z=O, Y=NH.

The title compound was prepared according to protocol A, using 2-bromophenyl urea (0.6 g, 2.8 mmol) and 4-methylcyclohexanone (0.41 mL, 3.35 mmol, 1.2 equiv.) in polyphosphoric acid (22 g). The aqueous layer was extracted with CH$_2$Cl$_2$/MeOH (2/1). The organic extracts were dried over MgSO$_4$, filtered and concentrated. The crude material was purified by flash chromatography on silica gel (CH$_2$Cl$_2$/MeOH:99/1 to 90/10) and the resulting powder was washed with diisopropyl ether. The title compound was obtained as a white powder (0.11 g, 11% yield). mp=187–189° C.

$^1$H NMR [(CD$_3$)$_2$SO] δ 7.85 (br s, 1H, NH), 7.44 (d, J=7.8 Hz, 1H), 7.31 (d, J=7.8 Hz, 1H), 7.14 (br s, 1H, NH), 6.89 (t, J=7.8 Hz, 1H), 1.75 (m, 4H), 1.56–1.43 (m, 5H),), 1.85 (d, J=6.2 Hz, 3H).

Example 23

8'-Bromospiro[bicyclo[3,2,1]octane-2–4'-(3',4'-dihydro)quinazolin]-2'(1'H)-one $X_1$=CH, $X_2$=CH, $X_3$=CH, $X_4$=C—Br, A=bicyclo[3,2,1]octane, X=NH, Z=O, Y=NH.

The title compound was prepared according to protocol A, using 2-bromophenyl urea (0.6 g, 2.8 mmol) and bicyclo [3.2.1]octan-2-one (0.55 g, 4.47 mmol, 1.6 equiv.) in polyphosphoric acid (22 g). The aqueous layer was extracted with $CH_2Cl_2$/MeOH (2/1). The organic extracts were dried over $MgSO_4$, filtered and concentrated. The crude material was purified by flash chromatography on silica gel ($CH_2Cl_2$/MeOH:99/1 to 90/10) and the resulting powder was washed with diisopropyl ether. The title compound was obtained as a white powder (0.003 g, 1% yield). mp=276–278° C.

$^1$H NMR [$(CD_3)_2$SO] δ 7.92 (br s, 1H, NH), 7.48 (d, J=7.7 Hz, 1H), 7.42 (br s, 1H, NH), 7.39 (d, J=7.7 Hz, 1H), 6.92 (t, J=7.7 Hz, 1H), 2.33 (td, J=13.8, 5.7 Hz, 1H), 2.15–2.10 (m, 3H), 1.98 (d, J=11.5 Hz, 1H), 1.58–1.52 (m, 2H), 1.37–1.28 (m, 4H), 1.18 (m, 1H).

Example 24

6',8'-Dichlorospiro[cyclohexane-1-4'-(3',4'-dihydro)quinazolin]-2'(1'H)-one $X_1$=CH, $X_2$=C—Cl, $X_3$=CH, $X_4$=C—Cl, A=cyclohexyl, X=NH, Z=O, Y=NH A solution of Example 7 (100.2 mg, 0.4 mmol) in dimethylformamide (2 mL) was treated with N-chlorosuccinimide (80 mg, 0.6 mmol, 1.5 equiv.) at 60° C. overnight. The reaction mixture was concentrated then purified by flash chromatography on silica gel ($CH_2Cl_2$/MeOH:100/0 to 90/10) and reverse phase HPLC (C18 column, gradient of acetonitrile in water: 50/50 to 95:5) to give the title compound as a white solid (48% yield). mp=245° C.

$^1$H NMR [$CDCl_3$] δ 7.26 (m, 1H), 7.19 (br s, 1H, NH), 7.10 (m, 1H), 5.80 (br s, 1H, NH), 1.97 (m, 2H), 1.82–1.57 (m, 7H), 1.29 (m, 1H).

Example 25

8'-Chloro-6'-iodospiro[cyclohexane-1-4'-(3',4'-dihydro)quinazolin]-2'(1'H)-one $X_1$=CH, $X_2$=C—Cl, $X_3$=CH, $X_4$=C—Cl, A=cyclohexyl, X=NH, Z=O, Y=NH To a solution of Example 7 (5 g, 20 mmol) in trifluoroacetic acid (25 mL) were subsequently added N-iodosuccinimide (6 g, 22 mmol, 1.1 equiv.) and sulfuric acid (4 mL). The resulting solution was heated to 55° C. overnight, concentrated under reduced pressure, taken into dichloromethane and washed twice with water. The reaction mixture was concentrated and purified by flash chromatography on silica gel ($CH_2Cl_2$/MeOH:97/3) to give 4.5 g (73% yield) of the title compound as a yellowish solid. mp=261° C.

$^1$H NMR [$(CD_3)_2$SO] δ 8.64 (br s, 1H, NH), 7.64 (d, J=2.0 Hz, 1H), 7.56 (d, J=1.0 Hz, 1H), 7.22 (br s, 1H, NH), 1.76–1.59 (m, 7H), 1.49 (m, 2H), 1.25 (m, 1H).

Example 26

8'-Chloro-6'-phenylspiro[cyclohexane-1-4'-(3',4'-dihydro)quinazolin]-2'(1'H)-one $X_1$=CH, $X_2$=C-phenyl, $X_3$=CH, $X_4$=C—Cl, A=cyclohexyl, X=NH, Z=O, Y=NH A solution of Example 18 (232 mg, 0.79 mmol) in dimethylformamide (4 mL) was treated with N-chlorosuccinimide (80 mg, 0.6 mmol, 1.5 equiv.) at 60° C. overnight. The reaction mixture was concentrated then purified by flash chromatography on silica gel ($CH_2Cl_2$/MeOH:99/1 to 90/10) to give the title compound as a white solid (41% yield). mp=226° C.

$^1$H NMR [$(CD_3)_2$SO] δ 8.50 (br s, 1H, NH), 7.68 (d, J=7.3 Hz, 2H), 7.60 (s, 1H), 7.56 (s, 1H), 7.44 (t, J=7.1 Hz, 2H), 7.34 (m, 1H), 7.15 (br s, 1H, NH), 1.88–1.22 (m, 10H).

Example 27

8'-Chloro-6'-methoxyspiro[cyclohexane-1-4'-(3',4'-dihydro)quinazolin]-2'(1'H)-one $X_1$=CH, $X_2$=C—O—$CH_3$, $X_3$=CH, $X_4$=C—Cl, A=cyclohexyl, X=NH, Z=O, Y=NH A solution of Example 2 (500 mg, 2.03 mmol) in dimethylformamide (10 mL) was treated with N-chlorosuccinimide (300 mg, 2.24 mmol, 1.1 equiv.) at 60° C. overnight. The reaction mixture was concentrated and purified by flash chromatography on silica gel ($CH_2Cl_2$/MeOH:99/1 to 90/10) followed by recrystallization in toluene to give 76 mg (13% yield) of the title compound as a white solid. mp=226° C.

$^1$H NMR [$(CD_3)_2$SO] δ 8.20 (br s, 1H, NH), 6.96 (br s, 1H, NH), 6.92 (m, 1H), 6.87 (m, 1H), 3.73 (s, 3H), 1.72–1.61 (m, 7H), 1.62 (m, 2H), 1.26 (m, 1H).

Example 28

8'-Chloro-6'-phenylspiro[cycloheptane-1-4'-(3',4'-dihydro)quinazolin]-2'(1'H)-one $X_1$=CH, $X_2$=C-phenyl, $X_3$=CH, $X_4$=C—Cl, A=cycloheptyl, X=NH, Z=O, Y=NH A solution of Example 5 (150 mg, 0.49 mmol) in dimethylformamide (2 mL) was treated with N-chlorosuccinimide (75 mg, 0.56 mmol, 1.1 equiv.) at 60° C. overnight. The reaction mixture was concentrated then purified by flash chromatography on silica gel ($CH_2Cl_2$/MeOH:99/1 to 90/10) to give 158 mg (95% yield) of the title compound as a yellowish solid. mp=201° C.

$^1$H NMR [$CDCl_3$] δ 7.51–7.41 (m, 6H), 7.36 (m, 2H), 5.90 (br s, 1H, NH), 2.75–2.01 (m, 4H), 1.77–1.43 (m, 8H).

Example 29

8'-Chloro-6'-methylspiro[cyclohexane-1-4'-(3',4'-dihydro)quinazolin]-2'(1'H)-one $X_1$=CH, $X_2$=C—$CH_3$, $X_3$=CH, $X_4$=C—Cl, A=cyclohexyl, X=NH, Z=O, Y=NH A solution of Example 14 (350 mg, 1.51 mmol) in dimethylformamide (7 mL) was treated with N-chlorosuccinimide (305 mg, 2.3 mmol, 1.5 equiv.) at 60° C. overnight. The reaction mixture was concentrated and purified by flash chromatography on silica gel (CH$_2$Cl$_2$/MeOH:99/1 to 90/10). The resulting solid was triturated with methanol to give the title compound as a white solid (28% yield). mp=266° C.

$^1$H NMR [(CD$_3$)$_2$SO] δ 8.23 (br s, 1H, NH), 7.11 (m, 2H), 7.03 (br s, 1H, NH), 2.23 (s, 3H), 1.77–1.61 (m, 7H), 1.51 (m, 2H), 1.25 (m, 1H).

Example 30

8'-Chloro-6'-(3-pyridyl)spiro[cyclohexane-1-4'-(3',4'-dihydro)quinazolin]-2'(1'H)-one X$_1$=CH, X$_2$=C-(3-pyridyl), X$_3$=CH, X$_4$=C—Cl, A=cyclohexyl, X=NH, Z=O, Y=NH To a suspension of Example 25 (0.5 g, 1.4 mmol) in dimethylformamide (5 mL) were subsequently added 3-pyridylboronic acid (0.22 g, 1.7 mmol, 1.2 equiv.) and a 2M aqueous solution of potassium carbonate (1.5 mL). The mixture was degassed by bubbling nitrogen for 30 minutes and tetrakistriphenylphosphine palladium (60 mg, 0.05 mmol, 0.04 equiv.) was added. After heating to 90° C. overnight, the mixture was concentrated under reduced pressure, triturated with water and filtered. The resulting solid was triturated with ethyl acetate, filtered and purified by flash chromatography on silica gel (CH$_2$Cl$_2$/EtOAc:80/20 to 50/50) to give 140 mg (30% yield) of the title compound as white solid. mp=246° C.

$^1$H NMR [(CD$_3$)$_2$SO] δ 8.93 (br s, 1H, NH), 8.55 (m, 2H), 8.10 (m, 1H), 7.71 (d, J=1.5 Hz, 1H), 7.65 (d, J=1.5 Hz, 1H), 7.45 (dd, J=8.0, 5.0 Hz, 1H), 7.19 (br s, 1H, NH), 1.91–1.77 (m, 6H), 1.63 (m, 1H), 1.54 (m, 2H), 1.32 (m, 1H).

Example 31

8'-Chloro-6'-(4-pyridyl)spiro[cyclohexane-1-4'-(3',4'-dihydro)quinazolin]-2'(1'H)-one X$_1$=CH, X$_2$=C-(4-pyridyl), X$_3$=CH, X$_4$=C—Cl, A=cyclohexyl, X=NH, Z=O, Y=NH To a suspension of Example 25 (0.5 g, 1.4 mmol) in dimethylformamide (5 mL) were subsequently added 4-pyridylboronic acid (0.22 g, 1.7 mmol, 1.2 equiv.) and a 2M aqueous solution of potassium carbonate (1.5 mL). The mixture was degassed by bubbling nitrogen for 30 minutes and tetrakistriphenylphosphine palladium (60 mg, 0.05 mmol, 0.04 equiv.) was added. After heating to 90° C. overnight, the mixture was concentrated under reduced pressure, washed with water and ethyl acetate then purified by flash chromatography on silica gel (CH$_2$Cl$_2$/EtOAc:80/20 to CH$_2$Cl$_2$/MeOH:97/3) to give 40 mg (10% yield) of the title compound as white solid. mp=320–321° C.

$^1$H NMR [(CD$_3$)$_2$SO] δ 8.64 (br s, 1H, NH), 8.59 (d, J=6.0 Hz, 2H), 7.80–7.72 (m, 4H), 7.22 (br s, 1H, NH), 1.99–1.77 (m, 6H), 1.65 (m, 1H), 1.54 (m, 2H), 1.31 (m, 1H).

Example 32

6'-(4-Carboxyphenyl)-8'-chlorospiro[cyclohexane-1-4'-(3',4'-dihydro)quinazolin]-2'(1'H)-one X$_1$=CH, X$_2$=C-(4-carboxyphenyl), X$_3$=CH, X$_4$=C—Cl, A=cyclohexyl, X=NH, Z=O, Y=NH To a suspension of Example 25 (1 g, 2.8 mmol) in dimethylformamide (10 mL) were subsequently added 4-carboxyphenylboronic acid (0.55 g, 3.35 mmol, 1.2 equiv.) and a 2M aqueous solution of potassium carbonate (3 mL). The mixture was degassed by bubbling nitrogen for 30 minutes and tetrakistriphenylphosphine palladium (120 mg, 0.1 mmol, 0.04 equiv.) was added. After heating to 90° C. for 4 hours, the mixture was concentrated under reduced pressure, taken into ethyl acetate and washed with water. The aqueous layer was acidified to pH 2 and extracted with ethyl acetate. The organic layer was concentrated under reduced pressure to a third of its volume and filtered. The resulting solid was purified by flash chromatography on silica gel (CH$_2$Cl$_2$/MeOH:97/3 to 95/5) to give 250 mg (40% yield) of the title compound as white solid. mp=309° C.

$^1$H NMR [(CD$_3$)$_2$SO] δ 12.95 (br s, 1H, OH), 8.58 (br s, 1H, NH), 7.98 (d, J=8.5 Hz, 2H), 7.83 (d, J=8.5 Hz, 2H), 7.70 (d, J=1.5 Hz, 1H), 7.65 (s, 1H), 7.20 (br s, 1H, NH), 1.93–1.78 (m, 6H), 1.64 (m, 1H), 1.54 (m, 2H), 1.32 (m, 1H).

Example 33

6'-(3-Carboxyphenyl)-8'-chlorospiro[cyclohexane-1-4'-(3',4'-dihydro)quinazolin]-2'(1'H)-one X$_1$=CH, X$_2$=C-(3-carboxyphenyl), X$_3$=CH, X$_4$=C—Cl, A=cyclohexyl, X=NH, Z=O, Y=NH To a suspension of Example 25 (1 g, 2.8 mmol) in dimethylformamide (10 mL) were subsequently added 3-carboxyphenylboronic acid (0.55 g, 3.35 mmol, 1.2 equiv.) and a 2M aqueous solution of potassium carbonate (3 mL). The mixture was degassed by bubbling nitrogen for 30 minutes and tetrakistriphenylphosphine palladium (120 mg, 0.1 mmol, 0.04 equiv.) was added. After heating to reflux overnight, the mixture was concentrated under reduced pressure, taken into dichloromethane and washed with water. The aqueous layer was acidified to pH 1 and filtered to give 330 mg (58% yield) of the title compound as white solid. mp=300° C.

$^1$H NMR [(CD$_3$)$_2$SO] δ 13.10 (br s, 1H, OH), 8.54 (br s, 1H, NH), 8.14 (s, 1H), 7.92 (t, J=7.5 Hz, 2H), 7.64 (d, J=1.5 Hz, 1H), 7.59–7.55 (m, 2H), 7.17 (br s, 1H, NH), 1.89–1.78 (m, 6H), 1.64 (m, 1H), 1.55 (m, 2H), 1.32 (m, 1H).

Example 34

8'-Chloro-6'-(1H-indol-5-yl)spiro[cyclohexane-1-4'-(3',4'-dihydro)quinazolin]-2'(1H)-one X$_1$=CH, X$_2$=C-indol-5-yl, X$_3$=CH, X$_4$=C—Cl, A=cyclohexyl, X=NH, Z=O, Y=NH To a suspension of Example 25 (0.5 g, 1.4 mmol) in dimethylformamide (5 mL) were subsequently added 5-indolylboronic acid (0.26 g, 1.6 mmol, 1.2 equiv.) and a 2M aqueous solution of potassium carbonate (1.5 mL). The mixture was degassed by bubbling nitrogen for 30 minutes and tetrakistriphenylphosphine palladium (60 mg, 0.05 mmol, 0.04 equiv.) was added. After heating to 80° C. overnight, the mixture was concentrated under reduced pressure, taken into ethyl acetate and washed three times with water. The residue was then purified by flash chromatography on silica gel (CH$_2$Cl$_2$/EtOAc:80/20) to give 210 mg (44% yield) of the title compound as white solid. mp=257° C.

$^1$H NMR [(CD$_3$)$_2$SO] δ 11.12 (br s, 1H, NH), 8.40 (br s, 1H, NH), 7.83 (s, 1H), 7.56 (m, 2H), 7.44 (d, J=8.0 Hz, 1H), 7.39–7.36 (m, 2H), 7.11 (s, 1H), 6.47 (br s, 1H, NH), 1.89–1.78 (m, 6H), 1.64 (m, 1H), 1.55 (m, 2H), 1.32 (m, 1H).

Example 35

8'-Chloro-6'-(2-pyridyl)spiro[cyclohexane-1-4'-(3',4'-dihydro)quinazolin]-2'(1'H)-one $X_1$=CH, $X_2$=C-(2-pyridyl), $X_3$=CH, $X_4$=C—Cl, A=cyclohexyl, X=NH, Z=O, Y=NH To a solution of Example 25 (0.5 g, 1.3 mmol) in tetrahydrofuran (5 mL) was added a 0.5 M solution of 2-pyridyl zinc bromide in tetrahydrofuran (60 μL, 30 mmol, 23 equiv.). The mixture was degassed bubbling nitrogen for 30 minutes and tetrakis(triphenylphosphine)palladium (60 mg, 0.05 mmol, 0.04 equiv.) was added. After refluxing for 4 h, additional tetrakis(triphenylphosphine)palladium (100 mg) and toluene (5 mL) were added. After heating to 90° C. overnight, the mixture was diluted with dichloromethane and washed three times with water. The organic layer was concentrated under reduced pressure and purified by flash chromatography on silica gel ($CH_2Cl_2$/EtOAc:90/10) to give 50 mg (2% yield) of the title compound as a solid. mp=251° C.

$^1$H NMR [$(CD_3)_2$SO] δ 8.64 (br s, 1H, NH), 7.45 (dd, J=5.0, 1.0 Hz, 1H), 8.04–8.01 (m, 3H), 7.85 (td, J=7.5, 2.0 Hz, 1H), 7.32 (m, 1H), 7.21 (br s, 1H, NH), 1.89–1.83 (m, 6H), 1.66 (m, 1H), 1.56 (m, 2H), 1.32 (m, 1H).

Example 36

8'-Chloro-6'-(3-dimethylamino-prop-1-ynyl)spiro[cyclohexane-1-4'-(3',4'-dihydro)quinazolin]-2'(1'H)-one $X_1$=CH, $X_2$=C-(3-dimethylaminoprop-1-ynyl), $X_3$=CH, $X_4$=C—Cl, A=cyclohexyl, X=NH, Z=O, Y=NH To a suspension of Example 25 (0.5 g, 1.4 mmol) in pyrrolidine (10 mL) were subsequently added 1-dimethylamino-2-propyne (0.170 mL, 1.6 mmol, 1.2 equiv.), toluene (10 mL) and tetrakis(triphenylphosphine) palladium (80 mg, 0.07 mmol, 0.05 equiv.). After heating to 45° C. overnight, the mixture was filtered, diluted with ethyl acetate and washed twice with a 1 M aqueous solution of hydrochloric acid. The aqueous layer was basified to pH 9 and extracted twice with ethyl acetate. The combined extracts were dried over sodium sulfate, concentrated under reduced pressure and to give 60 mg (13% yield) of the title compound as yellowish solid. mp=208° C.

$^1$H NMR [$(CD_3)_2$SO] δ 8.63 (br s, 1H, NH), 7.37 (d, J=1.5 Hz, 1H), 7.34 (s, 1H), 7.19 (br s, 1H, NH), 3.43 (s, 2H), 2.24 (s, 6H), 1.81–1.72 (m, 6H), 1.62 (m, 1H), 1.50 (m, 2H), 1.27 (m, 1H).

Example 37

8'-Chloro-6'-(3-methylamino-prop-1-ynyl)spiro[cyclohexane-1-4'-(3',4'-dihydro)quinazolin]-2'(1'H)-one $X_1$=CH, $X_2$=C-(3-methylaminoprop-1-ynyl), $X_3$=CH, $X_4$=C—C, A=cyclohexyl, X=NH, Z=O, Y=NH To a solution of Example 25 (0.2 g, 0.5 mmol)) in dimethylformamide (3 mL) were subsequently added N-methylpropargylamine (0.1 mL, 1 mmol, 2 equiv.) and triethylamine (1 mL, 7 mmol, 14 equiv.). The mixture was degassed bubbling nitrogen for 30 minutes then tetrakis(triphenylphosphine)palladium (20 mg, 0.025 mmol, 0.05 equiv.) and copper(l) iodide (20 mg, 0.1 mmol, 0.02 equiv.) were added. After heating to 80° C. overnight, the mixture was diluted with dichloromethane and washed three times with water. The organic layer was dried over sodium sulfate, filtered, concentrated under reduced pressure and purified by flash chromatography on silica gel ($CH_2Cl_2$/MeOH:98/2 to $CH_2Cl_2$/MeOH/$NH_4$OH:96/3/1) to give 40 mg (25% yield) of the title compound as a solid. mp=188° C.

$^1$H NMR [$(CD_3)_2$SO] δ 8.62 (br s, 1H, NH), 7.33 (s, 1H), 7.32 (s, 1H), 7.19 (br s, 1H, NH), 3.50 (br s, 2H), 2.35 (br s, 3H), 1.76–1.73 (m, 6H), 1.61 (m, 1H), 1.50 (m, 2H), 1.26 (m, 1H).

Example 38

8'-Chloro-6'-[4-(4-methyl-piperazine-1-carbonyl)phenyl]spiro[cyclohexane-1-4'-(3',4'-dihydro)quinazolin]-2'(1'H)-one $X_1$=CH, $X_2$=C-(4-(4-methyl-piperazine-1-carbonyl)phenyl), $X_3$=CH, $X_4$=C—Cl, A=cyclohexyl, X=NH, Z=O, Y=NH To a suspension of Example 32 (100 mg, 0.27 mmol) in toluene (3 mL) was added thionyl chloride (0.03 mL, 0.4 mmol, 1.5 equiv.). The resulting mixture was heated to reflux for 2 hours, then twice concentrated under reduced pressure and taken into toluene. To the resulting solid in toluene (2 mL) was added triethylamine (0.1 mL, 0.54 mmol, 2 equiv.) and 1-methylpiperazine (0.04 mL, 0.32 mmol, 1.2 equiv.). After stirring overnight, the mixture was diluted with dichloromethane and washed twice with water. The organic layer was concentrated under reduced pressure and purified by flash chromatography on silica gel ($CH_2Cl_2$/MeOH:97/3) to give 20 mg (16% yield) of the title compound as white solid. mp=277° C.

$^1$H NMR [$(CD3)_2$SO] δ 8.55 (br s, 1H, NH), 7.80 (d, J=8.0 Hz, 2H), 7.67 (s, 1H), 7.61 (s, 1H), 7.50 (d, J=8.0 Hz, 2H), 7.18 (br s, 1H, NH), 3.60 (br m, 4H), 3.08 (br m, 4H), 2.67 (br s, 3H), 1.91–1.72 (m, 6H), 1.65 (m, 1H), 1.54 (m, 2H), 1.31 (m, 1H).

Example 39

8'-Chloro-6'-[4-(3-N-dimethylamino-propylcarboxamide)phenyl]-spiro[cyclohexane-1-4'-(3',4'-dihydro)quinazolin]-2'(1'H)-one $X_1$=CH, $X_2$=C-[4-(3-N-dimethylamino-propylcarboxamide)phenyl], $X_3$=CH, $X_4$=C—Cl, A=cyclohexyl, X=NH, Z=O, Y=NH To a suspension of Example 32 (122 mg, 0.33 mmol) in toluene (3 mL) was added thionyl chloride (0.04 mL, 0.5 mmol, 1.5 equiv.). The resulting mixture was heated to reflux overnight, then concentrated under reduced pressure. To the resulting solid in toluene (2 mL) was added triethylamine (0.1 mL, 0.54 mmol, 1.6 equiv.) and 3-dimethylaminopropylamine (0.037 mL, 0.26 mmol, 0.8 equiv.). After stirring for 4 h, the mixture was diluted with dichloromethane and washed twice with water and a 1N aqueous solution of hydrochloric acid. The aqueous layer was basified to pH 9 and extracted twice with dichloromethane. The combined organic extracts were concentrated under reduced pressure to give 40 mg (34% yield) of the title compound as white solid. mp=232° C.

$^1$H NMR [(CD$_3$)$_2$SO] δ 8.59–8.55 (m, 2H), 7.90 (d, J=8.5 Hz, 2H), 7.79 (d, J=8.5 Hz, 2H), 7.68 (d, J=1.5 Hz, 1H), 7.63 (s, 1H), 7.18 (br s, 1H, NH), 3.29 (m, 2H), 2.26 (t, J=7.0 Hz, 2H), 2.14 (s, 6H), 1.92–1.77 (m, 6H), 1.67 (m, 3H), 1.54 (m, 2H), 1.32 (m, 1H).

Example 40

8'-Chloro-6'-[4-(2-N-dimethylamino-ethylcarboxamide)phenyl]spiro-[cyclohexane-1-4'-(3',4'-dihydro)quinazolin]-2'(1'H)-one $X_1$=CH, $X_2$=C-[4-(2-N-dimethylamino-ethylcarboxamide)phenyl], $X_3$=CH, $X_4$=C—Cl, A=cyclohexyl, X=NH, Z=O, Y=NH To a suspension of Example 32 (150 mg, 0.4 mmol) in toluene (3 mL) was added thionyl chloride (0.03 mL, 0.41 mmol, 1.0 equiv.). The resulting mixture was heated to reflux for 3 h, then concentrated under reduced pressure. To the resulting solid in toluene (3 mL) was added triethylamine (0.14 mL, 0.8 mmol, 2 equiv.) and 2-dimethylaminoethylamine (0.04 mL, 0.32 mmol, 0.8 equiv.). After stirring overnight, the mixture was concentrated, diluted with dichloromethane and washed twice with water and a 1 N aqueous solution of hydrochloric acid. The aqueous layer was basified to pH 9 and extracted twice with dichloromethane. The combined organic extracts were concentrated under reduced pressure to give 100 mg (56% yield) of the title compound as white solid. mp=234° C.

$^1$H NMR [(CD$_3$)$_2$SO] 8.54 (br s, 1H, NH), 8.44 (t, J=5.5 Hz, 1H), 7.91 (d, J=8.5 Hz, 2H), 7.79 (d, J=8.5 Hz, 2H), 7.69 (d, J=1.5 Hz, 1H), 7.63 (d, J=1.5 Hz, 1H), 7.18 (br s, 1H, NH), 3.37 (q, J=6.5 Hz, 2H), 2.45 (t, J=6.5 Hz, 2H), 2.22 (s, 6H), 1.90–1.74 (m, 6H), 1.65 (m, 1H), 1.54 (m, 2H), 1.32 (m, 1H).

Example 41

8'-Chloro-6'-[3-(3-N-dimethylamino-propylcarboxamide)phenyl]spiro[-cyclohexane-1-4'-(3',4'-dihydro)quinazolin]-2'(1'H)-one $X_1$=CH, $X_2$=C-[3-(3-N-dimethylamino-propylcarboxamide)phenyl], $X_3$=CH, $X_4$=C—Cl, A=cyclohexyl, X=NH, Z=O, Y=NH To a suspension of Example 33 (100 mg, 0.27 mmol) in toluene (10 mL) was added thionyl chloride (0.1 mL, 1.3 mmol, 5 equiv.). The resulting mixture was heated to reflux for 2 h, then concentrated under reduced pressure. To the resulting solid in toluene (10 mL) was added triethylamine (0.1 mL, 0.54 mmol, 2 equiv.) and 3-dimethylaminopropylamine (0.03 mL, 0.21 mmol, 0.8 equiv.). After stirring for 3 h, the mixture was concentrated, diluted with dichloromethane and washed twice with water and a 1N aqueous solution of hydrochloric acid. The aqueous layer was washed with ethyl acetate, basified to pH 9 and extracted twice with dichloromethane. The combined organic extracts were concentrated under reduced pressure to give 30 mg (30% yield) of the title compound as white solid. mp=208° C.

$^1$H NMR [(CD$_3$)$_2$SO] δ 8.60 (m, 1H), 8.54 (br s, 1H, NH), 8.03 (br s, 1H, NH), 7.83 (d, J=7.5 Hz, 1H), 7.78 (d, J=8.0 Hz, 1H), 7.69 (d, J=1.5 Hz, 1H), 7.60 (s, 1H), 7.52 (t, J=7.5 Hz, 1H), 7.17 (br s, 1H, NH), 3.29 (m, 2H), 2.27 (t, J=7.0 Hz, 2H), 2.14 (s, 6H), 1.85–1.78 (m, 6H), 1.67 (m, 3H), 1.55 (m, 2H), 1.30 (m, 1H).

Example 42

8'-Chloro-6'-[3-(4-methyl-piperazine-1-carbonyl)-phenyl]spiro[cyclohexane-1-4'-(3',4'-dihydro)quinazolin]-2'(1'H)-one $X_1$=CH, $X_2$=C-[3-(4-methyl-piperazine-1-carbonyl)-phenyl], $X_3$=CH, $X_4$=C—Cl, A=cyclohexyl, X=NH, Z=O, Y=NH To a suspension of Example 33 (100 mg, 0.27 mmol) in toluene (5 mL) was added thionyl chloride (0.03 mL, 0.4 mmol, 1.5 equiv.). The resulting mixture was heated to reflux for 3 hours, then twice concentrated under reduced pressure and taken into toluene. To the resulting solid in toluene (5 mL) was added triethylamine (0.1 mL, 0.54 mmol, 2 equiv.) and 1-methylpiperazine (0.024 mL, 0.21 mmol, 0.8 equiv.). After stirring overnight, the mixture was diluted with dichloromethane and washed twice with water. The organic layer was concentrated under reduced pressure, taken into ethyl acetate and washed with a 1N aqueous solution of hydrochloric acid. The aqueous layer was washed with ethyl acetate, basified to pH 9 and extracted twice with dichloromethane. The combined organic extracts were concentrated under reduced pressure to give 60 mg (61% yield) of the title compound as white solid. mp=207° C.

$^1$H NMR [(CD$_3$)$_2$SO] δ 8.52 (br s, 1H, NH), 7.76 (d, J=8.0 Hz, 1H), 7.67 (s, 1H), 7.65 (d, J=1.5 Hz, 1H), 7.58 (d, J=1.5 Hz, 1H), 7.50 (t, J=7.5 Hz, 1H), 7.32 (d, J=7.5 Hz, 1H), 7.16 (br s, 1H, NH), 3.64 (br m, 4H), 2.32 (br m, 4H), 2.20 (s, 3H), 1.89–1.77 (m, 6H), 1.64 (m, 1H), 1.53 (m, 2H), 1.32 (m, 1H).

Example 43

8'-Chloro-6'-[3-(2-N-dimethylamino-ethylcarboxamide)phenyl]spiro-[cyclohexane-1-4'-(3',4'-dihydro)quinazolin]-2'(1'H)-one $X_1$=CH, $X_2$=C-[3-(2-N-dimethylamino-ethylcarboxamide)phenyl], $X_3$=CH, $X_4$=C—Cl, A=cyclohexyl, X=NH, Z=O, Y=NH To a suspension of Example 33 (100 mg, 0.27 mmol) in toluene (10 mL) was added thionyl chloride (0.1 mL, 1.3 mmol, 5 equiv.). The resulting mixture was heated to reflux for 2 h, then concentrated under reduced pressure. To the resulting solid in toluene (10 mL) was added triethylamine (0.1 mL, 0.54 mmol, 2 equiv.) and 2-dimethylaminoethyl amine (0.024 mL, 0.21 mmol, 0.8 equiv.). After stirring for 3 h, the mixture was concentrated, diluted with dichloromethane and washed twice with water and a 1N aqueous solution of hydrochloric acid. The aqueous layer was washed with ethyl acetate, basified to pH 9 and extracted twice with dichloromethane. The combined organic extracts were concentrated under reduced pressure to give 40 mg (40% yield) of the title compound as white solid. mp=225° C.

$^1$H NMR [(CD$_3$)$_2$SO] δ 8.55 (br s, 1H, NH), 8.51 (t, J=5.5 Hz, 1H), 8.05 (br s, 1H, NH), 7.84 (d, J=7.5 Hz, 1H), 7.79 (d, J=8.0 Hz, 1H), 7.70 (d, J=2.0 Hz, 1H), 7.59 (d, J=2.0 Hz, 1H), 7.52 (t, J=7.5 Hz, 1H), 7.18 (br s, 1H, NH), 3.39 (q, J=6.5 Hz, 2H), 2.42 (t, J=6.5 Hz, 2H), 2.19 (s, 6H), 1.89–1.78 (m, 6H), 1.65 (m, 1H), 1.54 (m, 2H), 1.31 (m, 1H).

Example 44

8'-Chlorospiro[cyclohexane-1-4'-(3',4'-dihydro)quinazolin]-2'(1'H)-thione $X_1$=CH, $X_2$=CH, $X_3$=CH, $X_4$=C—Cl, A=cyclohexyl, X=NH, Z=S, Y=NH a) Preparation of 2',8'-dichlorospiro[cyclohexane-1-4'-(3',4'-dihydro)quinazoline] (intermediate 1)

A solution of Example 7 (51 mg, 2 mmol) in phosphorus oxychloride (10 mL) containing Na$_2$CO$_3$ (32 mg, 3 mmol) was heated at 95° C. for 5 hours. After cooling to room temperature, the phosphorus oxychloride was removed under reduced pressure. The crude product was used without purification in the next step.

$^1$H NMR [(CD$_3$)$_2$SO] δ 8.31 (br s, 1H, NH), 7.28 (d, J=7.8 Hz, 1H), 7.23 (d, J=7.8 Hz, 1H), 7.04 (t, J=7.8 Hz, 1H), 1.89–1.61 (m, 7H), 1.51–1.48 (m, 2H), 1.28–1.24 (m, 1H).

b) Preparation of Example 44

A solution of 2',8'-dichlorospiro[cyclohexane-1-4'-(3',4'-dihydro)quinazoline] (2 mmol) and thiourea (88 mg, 10.4 mmol) was heated to reflux overnight, cooled to room temperature and concentrated. The material was dissolved in EtOAc and washed sequentially with saturated aqueous NaHCO$_3$ and saturated aqueous NaCl. The organic extracts were dried over Na$_2$SO$_4$, filtered and concentrated. The crude material was purified by flash chromatography on silica gel (cyclohexane/EtOAc:95/5) to afford the title compound as a white solid (288 mg, 54%). mp=209–211° C.

$^1$H NMR [(CD$_3$)$_2$SO] δ 9.15 (br s, 1H, NH), 8.69 (br s, 1H, NH), 7.39 (d, J=7.9 Hz, 1H), 7.35 (d, J=7.9 Hz, 1H), 7.09 (t, J=7.9 Hz, 1H), 1.85–1.51 (m, 9H), 1.26 (m, 1H).

Example 45

8'-Chloro-2'-cyanoiminospiro[cyclohexane-1-4'-(3',4'-dihydro)quinazoline]

$X_1$=CH, $X_2$=CH, $X_3$=CH, $X_4$=C—Cl, A=cyclohexyl, X=NH, $Z^1$=NH—CN, Y=N

2',8'-Dichlorospiro[cyclohexane-1-4'-(3',4'-dihydro)quinazoline] (2 mmol) and cyanamide (3 g) were heated to 60° C. overnight. The mixture was cooled to room temperature and water was added. The aqueous solution was extracted with CH$_2$Cl$_2$. The organic extracts were washed with saturated aqueous NaCl, dried over Na$_2$SO$_4$, filtered and concentrated. The crude material was purified by flash chromatography on silica gel (cyclohexane/EtOAc:90/10) to afford the title compound as a white solid (260 mg, 23%). mp=193–195° C.

$^1$H NMR [(CD$_3$)$_2$SO] δ 9.45 (br s, 1H, NH), 8.05 (br s, 1H, NH), 7.42 (d, J=7.8 Hz, 1H), 7.37 (d, J=7.8 Hz, 1H), 7.13 (t, J=7.8 Hz, 1H), 1.81–1.57 (m, 9H), 1.28 (m, 1H).

Example 46

8'-Chloro-2'-methoxyiminospiro[cyclohexane-1-4'-(3',4'-dihydro)-quinazoline]

$X_1$=CH, $X_2$=CH, $X_3$=CH, $X_4$=C—Cl, A=cyclohexyl, X=NH, $Z^1$=N—O—CH$_3$, Y=NH A solution of 2',8'-Dichlorospiro[cyclohexane-1-4'-(3',4'-dihydro)quinazoline] (2 mmol) in EtOH (10 mL) was added to a solution of methoxylamine hydrochloride (1 mg, 11.9 mmol) and triethylamine (1.67 mL, 11.9 mmol) in EtOH (3 mL) and heated to reflux overnight, cooled to room temperature and concentrated. The material was dissolved in EtOAc and washed sequentially with saturated aqueous NaHCO$_3$ and saturated aqueous NaCl. The organic extracts were dried over MgSO$_4$, filtered and concentrated. The crude material was purified by flash chromatography on silica gel (cyclohexane/EtOAc:80/20 to cyclohexane/EtOAc/MeOH:80/20/1) to afford the title compound as a white solid (120 mg, 22%). mp=113–115° C.

$^1$H NMR [(CD$_3$)$_2$SO] δ 8.17 (br s, 0.4H, NH), 7.64 (br s, 0.6H, NH), 7.33 (d, J=8.0 Hz, 0.6H), 7.27 (d, J=8.0 Hz, 0.6H), 7.25 (d, J=7.5 Hz, 0.4H), 7.22 (d, J=7.5 Hz, 0.4 H), 6.94 (t, J=8.0 Hz, 0.6H), 6.87 (t, J=7.5 Hz, 0.4H), 6.17 (br s, 0.6H, NH), 5.77 (br s, 0.4H, NH), 1.70 (m, 7H), 1.48 (m, 2H), 1.28 (m, 1H).

Example 47

8'-Chloro-2'-dimethylaminospiro[cyclohexane-1-4'-(3',4'-dihydro)-quinazoline]

$X_1$=CH, $X_2$=CH, $X_3$=CH, $X_4$=C—Cl, A=cyclohexyl, X=NH, $Z^1$=N(CH$_3$)$_2$, Y=N A solution of 2',8'-dichlorospiro[cyclohexane-1-4'-(3',4'-dihydro)quinazoline] (2 mmol) and dimethylamine (2M in ethanol) (3 mL, 6 mmol) was heated to 140° C. in a sealed tube overnight, cooled to room temperature and concentrated. The material was dissolved in CH$_2$Cl$_2$ and washed sequentially with saturated aqueous NaHCO$_3$ and saturated aqueous NaCl. The organic extracts were dried over MgSO$_4$, filtered and concentrated. The crude material was purified by flash chromatography on silica gel (cyclohexane/EtOAc/NH$_3$ (28% in water):70/30/1) to afford the title compound as a white solid (95 mg, 17%). mp=173–175° C.

$^1$H NMR [(CD$_3$)$_2$SO] δ 7.14 (d, J=7.8 Hz, 1H), 7.04 (d, J=7.8 Hz, 1H), 6.73 (t, J=7.8 Hz, 1H), 5.84 (br s, 1H, NH), 3.0 (s, 6H), 1.73–1.53-(m, 9H), 1.29–1.17 (m, 1H).

Example 48

8'-Chloro-1'-methylspiro[cyclohexane-1-4'-(3',4'-dihydro)quinazolin]-2'(1'H)-one $X_1$=CH, $X_2$=CH, $X_3$=CH, $X_4$=C—Cl, A=cyclohexyl, X=NH, Z=O, Y=N—CH$_3$ To a stirred solution Example 7 (150 mg, 0.59 mmol) in dimethylformamide (10 mL) was added sodium hydride (50% in grease, 35.4 mg, 0.73 mmol) under N$_2$. The mixture was stirred until hydrogen evolution ceased and methyl iodide (40 μl, 0.65 mmol) was added. The mixture was stirred overnight at room temperature. After removal of the solvent, the material was dissolved in CH$_2$Cl$_2$, washed with saturated aqueous NaCl solution, dried over Na$_2$SO$_4$, filtered and concentrated. The crude material was purified by flash chromatography on silica gel (cyclohexane/EtOAc 90/10) to afford the title compound as a white solid (55 mg, 43%). mp=163–165° C.

$^1$H NMR [(CD$_3$)$_2$SO] δ 7.34 (d, J=7.8 Hz, 1H), 7.31 (d, J=7.8 Hz, 1H), 7.08 (t, J=7.8 Hz, 1H), 6.94 (br s, 1H, NH), 3.37 (s, 3H), 1.80–1.62 (m, 7H), 1.53 (m, 2H), 1.19 (m, 1H).

Example 49

8'-Chloro-1'-(ethoxycarbonylmethyl)spiro[cyclohexane-1-4'-(3',4'-dihydro)-quinazolin]-2'(1'H)-one X$_1$=CH, X$_2$=CH, X$_3$=CH, X$_4$=C—Cl, A=cyclohexyl, X=NH, Z=O, Y=N-(ethoxycarbonylmethyl)

To a stirred Example 7 (500 mg, 2 mmol) in dimethylformamide (10 mL) was added sodium hydride (50% in grease, 96 mg, 2 mmol) under N$_2$. The mixture was stirred until hydrogen evolution ceased and ethyl bromoacetate (0.77 mL, 7 mmol) was added. The mixture was stirred overnight at 80° C. After removal of the solvent under reduced pressure, the material was dissolved in CH$_2$Cl$_2$, washed with saturated aqueous NaCl solution, dried over Na$_2$SO$_4$, filtered and concentrated. The crude material was purified by flash chromatography on silica gel (cyclohexane/EtOAc/toluene:70/30/100) to afford the title compound as a white solid (50 mg, 7%). mp=140–142° C.

$^1$H NMR [(CD$_3$)$_2$SO] δ 7.35 (d, J=8.0 Hz, 1H), 7.32 (d, J=8.0 Hz, 1H), 7.23 (br s, 1H, NH), 7.07 (t, J=8.0 Hz, 1H), 4.71 (s, 2H), 4.09 (q, J=7.5 Hz, 2H), 1.95–1.92 (m, 2H), 1.78–1.62 (m, 5H), 1.54–1.51 (m, 2H), 1.23 (m, 1H), 1.15 (t, J=7.5 Hz, 3H).

Example 50

8'-Chloro-3'-methylspiro[cyclohexane-1-4'-(3',4'-dihydro)quinazolin]-2'(1'H)-one X$_1$=CH, X$_2$=CH, X$_3$=CH, X$_4$=C—Cl, A=cyclohexyl, X=N—CH$_3$, Z=O, Y=NH Preparation of 8'-Chloro-1'-(4-methoxybenzyl)spiro[cyclohexane-1-4'-(3',4'-dihydro)quinazolin]-2'(1'H)-one (intermediate 2)

A solution of Example 7 (5 g, 19.9 mmol), cesium carbonate (7.8 g, 23.9 mmol) and 4-methoxybenzylchloride (2.9 mL, 21.93 mmol) in dimethylformamide (250 mL) was stirred at room temperature for 3 days. The mixture was concentrated. The residue was dissolved in CH$_2$Cl$_2$, washed with saturated aqueous NaCl solution, dried over Na$_2$SO$_4$, filtered and concentrated. AcOEt was added and the precipitate was filtered off to afford the title compound as a white solid (6.33 g, 86%).

$^1$H NMR [(CD$_3$)$_2$SO] 7.33 (d, J=7.8 Hz, 1H), 7.26 (d, J=7.8 Hz, 1H), 7.06 (m, 3H), 6.77 (d, J=8.7 Hz, 2H), 5.25 (s, 2H), 3.66 (s, 3H), 1.67–1.47 (m, 5H), 1.40–1.27 (m, 4H), 1.13 (m, 1H).

Preparation of 8'-Chloro-3'-methyl-1'-(4-methoxybenzyl)spiro[cyclohexane-1-4'-(3',4'-dihydro) quinazolin]-2'(1'H)-one (intermediate 3)

To a stirred solution of 8'-chloro-1'-(4-methoxybenzyl) spiro[cyclohexane-1-4'-(3',4'-dihydro)quinazolin]-2'(1'H)-one (260 mg, 0.7 mmol) in dimethylformamide (15 mL) was added sodium hydride (50% in grease, 48 mg, 1 mmol) under N$_2$. The mixture was stirred until hydrogen evolution ceased and methyl iodide (60 µl, 0.96 mmol) was added. The mixture was stirred overnight at room temperature. After removal of the solvent, the material was dissolved in CH$_2$Cl$_2$, washed with saturated aqueous NaCl, dried over Na$_2$SO$_4$, filtered and concentrated. The crude material was purified by flash chromatography on silica gel (cyclohexane/EtOAc/28% aqueous NH$_3$:90/10/1) to afford the title compound as a white solid (190 mg, 70%).

$^1$H NMR [(CD$_3$)$_2$SO] δ 7.45 (d, J=7.9 Hz, 1H), 7.40 (d, J=7.9 Hz, 1H), 7.12 (t, J=7.9 Hz, 1H), 7.07 (d, J=8.2 Hz, 2H), 6.79 (d, J=8.2 Hz, 2H), 5.25 (s, 2H), 3.67 (s, 3H), 2.85 (s, 3H), 1.66–1.35 (m, 10H).

Preparation of Example 50

To a solution of 8'-Chloro-3'-methyl-1'-(4-methoxybenzyl)spiro[cyclohexane-1-4'-(3',4'-dihydro)quinazolin]-2'(1'H)-one (180 mg, 047 mmol) in CH$_2$Cl$_2$ (4 mL) cooled at −10° C. was added dropwise trifluoroacetic acid (4 mL). The mixture was stirred at −10° C. for 1 hour and at room temperature for 20 min. The mixture was poured into a saturated aqueous NaHCO$_3$ solution and extracted with CH$_2$Cl$_2$. The organic extracts were washed with saturated aqueous NaCl solution, dried over MgSO$_4$, filtered and concentrated. The crude material was purified by flash chromatography on silica gel (cyclohexane/EtOAc/NH$_3$ (28% in water):90/10/1 to 70/30/1) to afford the title compound as a white solid (21 mg, 17%). mp=135–137° C.

$^1$H NMR [(CD$_3$)$_2$SO] δ 8.80 (br s, 1H, NH), 7.46 (d, J=7.7 Hz, 1H), 7.29 (d, J=7.7 Hz 1H), 7.00 (t, J=7.7 Hz, 1H), 2.96 (s, 3H), 1.96 (m, 4H), 1.66 (m, 2H), 1.56–1.39 (m, 4H).

Example 51

8'-Chloro-6'-[4-(4-pyrimidin-2-yl-piperazine-1-carbonyl)phenyl]spiro[-cyclohexane-1-4'-(3',4'-dihydro) quinazolin]-2'(1'H)-one X$_1$=CH, X$_2$=C-[4-(4-pyrimidin-2-yl-piperazine-1-carbonyl)phenyl], X$_3$=CH, X$_4$=C—Cl, A=cyclohexyl, X=NH, Z=O, Y=NH To a suspension of Example 32 (185 mg, 0.5 mmol) in toluene (10 mL) was added thionyl chloride (0.19 mL, 1.9 mmol, 5 equiv.). The resulting mixture was heated to reflux for 2 h, then concentrated under reduced pressure. To the resulting solid in toluene (4 mL) was added triethylamine (0.15 mL, 1 mmol, 2 equiv.) and 2-(1-piperazinyl)pyrimidine (100 mg, 0.6 mmol, 1.2 equiv.). After heating to 80° C. for 1 h, the mixture was diluted with dichloromethane and washed with water. The organic layer was concentrated under reduced pressure and the resulting solid was purified by flash chromatography on silica gel (CH$_2$Cl$_2$/MeOH:97/3) to give 210 mg (81% yield) of the title compound as white solid. mp=271° C.

$^1$H NMR [(CD$_3$)$_2$SO] δ 8.30 (br s, 1H, NH), 8.15 (d, J=4.5 Hz, 2H), 7.55 (d, J=8.0 Hz, 2H), 7.44 (s, 1H), 7.39 (s, 1H), 7.27 (d, J=8.5 Hz, 2H), 6.94 (br s, 1H, NH), 6.43 (t, J=4.5 Hz, 1H), 3.57–3.27 (m, 8H), 1.69–1.54 (m, 6H), 1.41 (m, 1H), 1.30 (m, 2H), 1.07 (m, 1H).

Example 52

8'-Chloro-6'-[4-(4-(2-morpholin-4-yl-ethyl)-piperazine-1-carbonyl)-phenyl]spiro[-cyclohexane-1-4'-(3', 4'-dihydro)quinazolin]-2'(1'H)-one X$_1$=CH, X$_2$=C-[4-(4-(2-morpholin-4-yl-ethyl)-piperazine-1-carbonyl)-phenyl], X$_3$=CH, X$_4$=C—Cl, A=cyclohexyl, X=NH, Z=O, Y=NH To a suspension of Example 32 (150 mg, 0.4 mmol) in toluene (2 mL) was added thionyl chloride (0.06 mL, 0.8 mmol, 2 equiv.). The resulting mixture was heated to reflux for 2 h, then concentrated under reduced pressure. To the resulting solid in toluene (2 mL) was added triethylamine (0.11 mL, 0.8 mmol, 2 equiv.) and 1-[2-(morpholin-4-yl)-ethyl]-piperazine (64 mg, 0.3 mmol, 0.8 equiv.). After stirring for 2 h, the mixture was diluted with dichloromethane, washed with water and washed with a 1M aqueous solution of sodium hydroxyde. The organic layer was dried over sodium sulfate, concentrated under reduced pressure and the resulting solid was triturated with ethyl acetate/methanol to give 106 mg (50% yield) of the title compound as white solid. mp=264° C.

$^1$H NMR [(CD$_3$)$_2$SO] δ 8.53 (br s, 1H, NH), 7.75 (m, 2H), 7.65 (s, 1H), 7.60 (s, 1H), 7.43 (m, 2H), 7.17 (br s, 1H, NH), 3.53 (m, 8H), 2.50–2.36 (m, 12H), 1.84–1.78 (m, 6H), 1.63 (m, 1H), 1.56 (m, 2H), 1.29 (m, 1H).

Example 53

8'-Chloro-6'-[4-(4-(2-morpholin-4-yl-2-oxo-ethyl)-piperazine-1-carbonyl)-phenyl]spiro[-cyclohexane-1-4'-(3',4'-dihydro)quinazolin]-2'(1'H)-one $X_1$=CH, $X_2$=C-[4-(4-(2-morpholin-4-yl-2-oxo-ethyl)-piperazine-1-carbonyl)-phenyl], $X_3$=CH, $X_4$=C—Cl, A=cyclohexyl, X=NH, Z=O, Y=NH To a suspension of Example 32 (150 mg, 0.4 mmol) in toluene (2 mL) was added thionyl chloride (0.06 mL, 0.8 mmol, 2 equiv.). The resulting mixture was heated to reflux for 3 h, then concentrated under reduced pressure. To the resulting solid in toluene (2 mL) was added triethylamine (0.11 mL, 0.8 mmol, 2 equiv.) and 4-[2-(piperazin-1-yl)-acetyl]-morpholine (130 mg, 0.6 mmol, 1.5 equiv.). After stirring overnight, the mixture was diluted with dichloromethane, washed with water and washed with a saturated aqueous solution of sodium bicarbonate. The organic layer was dried over sodium sulfate, concentrated under reduced pressure and the resulting solid was triturated with ethyl acetate/methanol to give 0.1 g (45% yield) of the title compound as white solid. mp=239° C.

$^1$H NMR [(CD$_3$)$_2$SO] δ 8.53 (br s, 1H, NH), 7.74 (d, J=8.0 Hz, 2H), 7.66 (s, 1H), 7.60 (s, 1H), 7.44 (d, J=8.0 Hz, 2H), 7.17 (br s, 1H, NH), 3.58–3.22 (m, 14H), 2.50 (m, 4H), 1.88–1.79 (m, 6H), 1.64 (m, 1H), 1.55 (m, 2H), 1.30 (m, 1H).

Example 54

8'-Chloro-6'-[4-(4-(2-hydroxy-ethoxy)-ethyl)-piperazine-1-carbonyl)-phenyl]spiro[-cyclohexane-1-4'-(3',4'-dihydro)quinazolin]-2'(1'H)-one $X_1$=CH, $X_2$=C-[4-(4-(2-hydroxy-ethoxy)-ethyl)-piperazine-1-carbonyl)-phenyl], $X_3$=CH, $X_4$=C—Cl, A=cyclohexyl, X=NH, Z=O, Y=NH To a suspension of Example 32 (150 mg, 0.4 mmol) in toluene (2 mL) was added thionyl chloride (0.06 mL, 0.8 mmol, 2 equiv.). The resulting mixture was heated to reflux for 3 h, then concentrated under reduced pressure. To the resulting solid in toluene (2 mL) was added triethylamine (0.11 mL, 0.8 mmol, 2 equiv.) and 1-hydroxyethylethoxypiperazine (77 mg, 0.4 mmol, 1.1 equiv.). After stirring for 2 h, the mixture was diluted with dichloromethane and washed with water and washed with a 1M aqueous solution of sodium hydroxyde. The organic layer was dried over sodium sulfate, concentrated under reduced pressure to give 0.06 g (29% yield) of the title compound as white solid. mp=100° C.

$^1$H NMR [(CD$_3$)$_2$SO] δ 8.53 (br s, 1H, NH), 7.75 (d, J=8.0 Hz, 2H), 7.65 (s, 1H), 7.60 (s, 1H), 7.43 (d, J=8.0 Hz, 2H), 7.17 (br s, 1H, NH), 4.58 (br s, 1H), 3.59–3.39 (m, 10H), 2.45 (m, 6H), 1.88–1.77 (m, 6H), 1.64 (m, 1H), 1.54 (m, 2H), 1.30 (m, 1H).

Example 55

9'-Chlorospiro[cyclohexane-1-5'-(5',10'-dihydro)]-imidazo[2,1-b]quinazoline

Formula (I), $X_1$=CH, $X_2$=CH, $X_3$=CH, $X_4$=C—Cl, A=cyclohexyl, X-Z=NCH=CHNH, Y=NH Preparation of 8'-Chloro-2'-(2,2-dimethoxy-ethylamino)spirorcyclohexane-1-4'-(3',4'-dihydro) quinazoline] (intermediate 4)

A solution of Example 7 (1.34 mmol, 0.5 g) in phosphorus oxychloride (7 mL) containing Na$_2$CO$_3$ (21 mg, 2 mmol) is heated to 95° C. for 4 hours. After cooling to room temperature, the phosphorus oxychloride was removed under reduced pressure. The residue was taken into EtOH (10 mL), amino acetaldehyde dimethyl acetal (1 mL, 8.04 mmol) was added and the resulting mixture is refluxed overnight. CH$_2$Cl$_2$ and a saturated aqueous solution of NaHCO$_3$ were added. The layers were separated, the aqueous one being extracted three times with CH$_2$Cl$_2$. The combined organic layers were washed with brine, dried over Na$_2$SO$_4$ and concentrated. The crude material was purified by flash chromatography on silica gel (cyclohexane/EtOAc/MeOH: 80/20/5) to give 0.43 g (96%) of intermediate 4.

$^1$H NMR [(CD$_3$)$_2$SO] δ 7.12 (d, J=7.5 Hz, 1H), 7.04 (d, J=7.5 Hz, 1H), 6.70 (t, J=7.5 Hz, 1H), 6.46 (br s, 1H), 6.08 (br s, 1H), 4.48 (t, J=5.3 Hz, 1H), 3.41 (t, J=5.3 Hz, 2H), 3.32 (m, 6H), 1.72–1.56 (m, 9H), 1.22 (m, 1H).

Preparation of Example 55

A solution of intermediate 4 (0.436 g, 1.29 mmol) in a mixture of isopropyl alcohol (10 mL) and 3M aqueous HCl (4 mL) was refluxed overnight. The reaction mixture was allowed to cool to room temperature, was concentrated under reduced pressure and taken into CH$_2$Cl$_2$ and an aqueous saturated solution of NaHCO$_3$. The layers were separated, the aqueous one being extracted three times with CH$_2$Cl$_2$. The combined organic layers were washed with brine, dried over Na$_2$SO$_4$ and concentrated. The crude material was recrystallised in EtOAc to afford the title compound as a white solid (0.07 g, 23%) (purity=95.4%) mp=197–199° C.

$^1$H NMR [(CD$_3$)$_2$SO] δ 9.58 (br s, 1H), 7.52 (m, 1H), 7.34 (d, J=7.7 Hz, 1NH), 7.23 (d, J=1.5 Hz, 1H), 6.92 (t, J=7.7 Hz, 1H), 6.71 (d, J=1.5 Hz, 1H), 2.03 (m 4H), 1.37–1.45 (m, 6H).

Example 56

9'-Chlorospiror[cyclohexane-1-5'-(5',10'-dihydro)]-[-1,2,4]triazolo[3,4-b]quinazoline Formula (I), $X_1$=CH, $X_2$=CH, $X_3$=CH, $X_4$=C—Cl, A=cyclohexyl, X-Z: NCH=NN, Y=NH Preparation of 8'-Chlorospiro[cyclohexane-1-4'-(3',4'-dihydro)-quinazolin-2'-yl]-hydrazine A solution of Example 7 (1.8 mmol, 0.45 g) in phosphorus oxychloride (9 mL) containing Na$_2$CO$_3$ (0.28 g, 2.7 mmol) is heated at 95° C. for 4 hours. After cooling to room temperature, the phosphorus oxychloride was removed under reduced pressure. The residue was taken into EtOH (10 mL), hydrazine (35% wt. solution in water, 2 mL) was added and the resulting mixture was refluxed overnight. $CH_2Cl_2$ and a saturated aqueous solution of $NaHCO_3$ were added. The layers were separated, the aqueous one being extracted three times with $CH_2Cl_2$. The combined organic layers were washed with brine, dried over $Na_2SO_4$ and concentrated. The crude material (0.43 g, 91%) was used without further purification in the next step. 1H NMR [$(CD_3)_2SO$] δ 7.12 (d, 1H), 7.08 (m, 1H), 6.75 (t, 1H), 1.83–1.60 (m, 7H), 1.47 (m, 2H), 1.25 (m, 1H).

Preparation of Example 56

A solution of 8'-Chlorospiro[cyclohexane-1-4'-(3',4'-dihydro)-quinazolin-2'-yl]-hydrazine (0.58 g, 2.19 mmol), triethyl orthoformate (1.82 mL, 10.95 mmol) and $H_2SO_4$ (0.05 mL) in butanol (20 mL) was refluxed for 24 h. The reaction mixture was allowed to cool to room temperature, was concentrated under reduced pressure and taken into a mixture of $CH_2Cl_2$ and an aqueous saturated solution of $NaHCO_3$. The layers were separated, the aqueous one being extracted three times with $CH_2Cl_2$. The combined organic layers were washed with brine, dried over $Na_2SO_4$ and concentrated. The crude material was recrystallized in EtOAc to afford the title compound as a white solid (0.13 g, 21%). (purity=96.6%) mp=237–239° C.
$^1$H NMR [$(CD_3)_2SO$] δ 9.99 (br s, 1H), 8.72 (s, 1H), 7.55 (dd, J=7.9, 1.0 Hz, 1H), 7.37 (dd, J=7.9, 1.0 Hz, 1H), 6.97 (t, J=7.9 Hz, 1H), 2.07 (m, 4H), 1.72 (m, 5H), 1.53 (m, 1H).

Example 57

9'-Chlorospiro[cyclohexane-1-5'-(4',5'-dihydro)]-[1,2,4]triazolo[4,3-a]quinazoline Formula (I), $X_1$=CH, $X_2$=CH, $X_3$=CH, $X_4$=C—Cl, A=cyclohexyl, X=NH, Y-Z: NCH=NN To a solution of 8'-Chlorospiro[cyclohexane-1-4'-(3',4'-dihydro)-quinazolin-2'-yl]-hydrazine (0.35 g, 1.32 mmol) and triethyl orthoformate (1.2 mL, 7.22 mmol) in $CHCl_3$ (16 mL) was added $H_2SO_4$ (0.04 mL). The mixture was stirred at room temperature for 3 h, was concentrated under reduced pressure and taken into a mixture of $CH_2Cl_2$ and an aqueous saturated solution of $NaHCO_3$. The layers were separated, the aqueous one being extracted three times with $CH_2Cl_2$. The combined organic layers were washed with brine, dried over $Na_2SO_4$ and concentrated. The residue was taken into butanol (10 mL) and refluxed overnight. After completion, the solvent was evaporated under reduced pressure to give a mixture of 9'-Chlorospiro[cyclohexane-1–5'-(4',5'-dihydro)]-[1,2,4]triazolo[4,3-a]quinazoline and 9'-Chlorospiro[cyclohexane-1–5'-(5',10'-dihydro)]-[1,2,4]triazolo[3,4-b]quinazoline as a 88/12 ratio. Crystallization in $CH_2Cl_2$ afford the title compound as a white powder (0.045 g, 43%). (purity=97.2%) mp=285–287° C.
$^1$H NMR [$(CD_3)_2SO$] δ 9.14 (s, 1H), 7.55 (m, 2H), 7.46 (s, 1H), 7.35 (t, J=8.0 Hz, 1H), 1.85–1.64 (m, 7H), 1.50 (m, 2H), 1.23 (m, 1H).

Example 58

Spiro[cyclohexane-1-9'-8',9'-dihydro)-pyrazolo[4',3'-f]quinazolin]-7'(6'H)-one

Formula (I): $X_1$13 $X_2$=C—CH: NNH—C, $X_3$=CH, $X_4$=CH, A=cyclohexyl, X=NH, Z=O, Y=NH
The title compound was prepared according to protocol A using (N-(1H-indazol-5-yl)urea (1 g, 5.67 mmol), polyphosphoric acid (20 g) and cyclohexanone (0.9 mL, 1.5 equiv.). The crude product was purified by flash chromatography on silica gel ($CH_2Cl_2$/MeOH:99/01 to 97/3) followed by recrystallization in toluene to give the title compound as a white solid (14 mg, 1% yield) (purity 98.8%).
$^1$H NMR [$(CD_3)_2SO$] δ 12.97 (br s, 1H, NH), 8.98 (br s, 1H, NH), 8.16 (s, 1H), 7.33 (d, J=8.5 Hz, 1H), 6.88 (d, J=9.0 Hz, 1H), 6.70 (br s, 1H, NH), 2.33–2.20 (m, 2H), 1.89–1.78 (m, 4H), 1.68–1.41 (m, 4H).

Example 59

8'-Chloro-5'-methoxyspirorcyclohexane-1-4'-(3',4'-dihydro)quinazolinl-2'(1'H)-one Formula (I): $X_1$=C—OCH$_3$, $X_2$=CH, $X_3$=CH, $X_4$=C—Cl, A=cyclohexyl, X=NH, Z=O, Y=NH Preparation of (2-Chloro-5-methoxy-phenyl)-urea (intermediate 5)

A solution of 2-chloro-5-methoxyaniline (5 g, 25.76 mmol) and potassium cyanate (5.22 g, 64.41 mmol) in a mixture of acetic acid (125 mL) and water (12.5 mL) was stirred at room temperature overnight. The solvent was evaporated, and the residue taken into a mixture of $CH_2Cl_2$ and an aqueous saturated solution of $NaHCO_3$. The layers were separated, the aqueous one being extracted three times with $CH_2Cl_2$. The combined organic layers were washed with brine, dried over $Na_2SO_4$ and concentrated. The crude material was purified by flash chromatography on silica gel (cyclohexane/EtOAc/MeOH:80/20/2) to give 2.06 g (40%) of intermediate 5.
$^1$H NMR [$(CD_3)_2SO$] δ 7.97 (br s, 1H, NH), 7.85 (d, J=3.0 Hz, 1H), 7.27 (d, J=9.0 Hz, 1H), 6.54 (dd, J=9.0, 3.0 Hz, 1H), 6.4 (br s, 2H), 3.71 (s, 3H).

Preparation of Example 59

Example 59 was prepared according to protocol A using intermediate 5 (1 g, 4.98 mmol), polyphosphoric acid (15 g) and cyclohexanone (0.88 mL, 7.47 mmol). After completion, ice was added, the precipitate was filtered and washed with cold water. The residue was recrystallized in ethanol to afford the title compound as a white powder (0.6 g, 78% yield) (purity 99.54%) mp=228.5–230.5° C.
$^1$H NMR [$(CD_3)_2SO$] δ 7.93 (br s, 1H, NH), 7.27 (d, J=8.9 Hz, 1H), 7.00 (br s, 1H, NH), 6.65 (d, J=8.9 Hz, 1H), 3.79 (s, 3H), 2.45–2.38 (m, 2H), 1.84–1.74 (m, 2H), 1.63–1.56 (m, 3H), 1.46 (m, 2H), 1.23–1.13 (m, 1H).

Example 60

5'-Difluorospiro[cyclohexane-1-4'-(3',4'-dihydro)quinazolin]-2'(1'H)-one

Formula (I): $X_1$=C—F, $X_2$=CH, $X_3$=CH, $X_4$=C—F, A=cyclohexyl, X=NH, Z=O, Y=NH Preparation of 2,5-difluorophenyl urea (intermediate 6)

To a solution of 2,5-difluorophenyl isocyanate (1 g, 6.45 mmol) in tetrahydrofuran (50 mL) at 0° C. was added a 28% aqueous solution of ammonia (30 mL). The mixture was stirred for 1 h allowing the temperature to warm up to room temperature, then concentrated under reduced pressure, taken into water and filtered. The solid was washed twice with water and with ether, then dried at 65° C. under reduced pressure to give 740 mg (67%) of intermediate 6.

$^1$H NMR [(CD$_3$)$_2$SO] δ 8.53 (br s, 1H, NH), 8.02 (m, 1H), 7.21 (m, 1H), 6.72 (m, 1H), 6.29 (br s, 2H, NH$_2$).

Preparation of Example 60

The title compound was prepared according to protocol A using intermediate 6 (740 mg, 4.3 mmol), polyphosphoric acid (20 g) and cyclohexanone (0.70 mL, 6.75 mmol). The crude product was purified by flash chromatography on silica gel (CH$_2$Cl$_2$/MeOH:100/0 to 95/5) followed by recrystallization in toluene to give the title compound as a white solid (28 mg, 3% yield) (purity 99%) mp=194–195° C.

$^1$H NMR [(CD$_3$)$_2$SO] δ 9.26 (br s, 1H, NH), 7.13 (m, 1H), 7.05 (br s, 1H, NH), 6.71 (m, 1H), 2.01 (m, 2H), 1.86–1.75 (m, 4H), 1.64 (m, 1H), 1.49 (m, 2H), 1.18 (m, 1H).

Example 61

8'-Chloro-5'-methylspiro[cyclohexane-1-4'-(3',4'-dihydro)quinazolin]-2'(1'H)-one Formula (I): X$_1$=C—CH$_3$, X$_2$=CH, X$_3$=CH, X$_4$=C—C, A=cyclohexyl, X=NH, Z=O, Y=NH Preparation of (2-chloro-5-methyl-phenyl)urea (intermediate 7)

A solution of 2-chloro-5-methylaniline (10 g, 70.6 mmol) and potassium cyanate (14.3 g, 176 mmol) in a mixture of acetic acid (340 mL) and water (34 mL) was stirred at room temperature during 4 hours. The solvent was evaporated and the residue taken into a mixture of CH$_2$Cl$_2$ and an aqueous saturated solution of NaHCO$_3$. The precipitate was filtered, washed with dichloromethane and dried under vacuum to give 12.6 g (97%) of intermediate 7.

$^1$H NMR [(CD$_3$)$_2$SO] δ 8.05 (s, 1H, NH), 7.96 (s, 1H), 7.23 (d, 1H), 6.75 (d, 1H), 6.37 (br s, 2H), 2.24 (s, 3H).

Preparation of Example 61

The title compound was prepared according to protocol A using intermediate 7 (12.6 g, 68.2 mmol), polyphosphoric acid (150 g) and cyclohexanone (8.5 mL, 81.9 mmol). After completion, the mixture was poured into ice and water and stirred 45 minutes. The precipitate was filtered and washed with cold water, with diethyl ether and dried under vacuum to give 3.1 g of the title product. The residue (100 mg) was recrystallized in ethanol to afford the title compound as a white powder (0.06 g, 17% yield) (purity with HPLC: 99.9%).

$^1$H NMR [(CD$_3$)$_2$SO] δ 8.02 (br s, 1H, NH), 7.20 (d, J=8.04 Hz, 1H), 6.89 (br s, 1H, NH), 6.57 (d, J=8.03 Hz, 1H), 2.47 (s, 3H), 2.02–2.18 (m, 2H), 1.70–1.90 (m, 4H), 1.62–1.70(m, 1H), 1.1.48–1.60 (m, 2H), 1.20–1.35 (m, 1H).

Example 62

8'-Chloro-6'-(morpholin-4-yl)methylspiro[cyclohexane-1-4'-(3',4'-dihydro)quinazolin]-2'(1'H)-one Formula (I): X$_1$=CH, X$_2$=C—CH$_2$-morpholinyl, X$_3$=CH, X$_4$=C—Cl, A=cyclohexyl, X=NH, Z=O, Y=NH The title compound was prepared according to protocol E. To a stirred solution of Example 7 (1 g, 4 mmol) in glacial acetic acid (15 mL) was sequentially added trioxane (0.55 g, 6 mmol, 1.5 equiv.) and a 48% aqueous solution of hydrobromic acid (5 mL). The mixture was heated to 95° C. overnight, poured on ice. The precipitate was filtered, washed twice with water then with ether to give 1.39 g of 8'-Chloro-6'-bromomethylspiro[cyclohexane-1-4'-(3',4'-dihydro)quinazolin]-2'(1'H)-one as a white solid. The crude bromomethyl derivative (150 mg, 0.43 mmol) was treated with morpholine (0.100 mL, 1.1 mmol, 2.6 equiv.) in DMF (3 mL) overnight. The mixture was concentrated under reduced pressure, taken into ethyl acetate, extracted with 1N aqueous HCl. The aqueous layer was washed twice with ethyl acetate, basified to pH 9 and extracted three times with ethyl acetate. The combined organic layers were washed three times with water and brine and concentrated under reduced pressure. The crude material was purified by recrystallization in toluene to give the title compound (102 mg, 68%) (purity 97%) as a white solid. mp=223° C.

$^1$H NMR [(CD$_3$)$_2$SO] δ 8.33 (br s, 1H, NH), 7.21 (s, 1H), 7.18 (s, 1H), 7.08 (br s, 1H, NH), 3.56 (m, 4H), 3.39 (s, 2H), 2.32 (m, 4H), 1.84–1.49 (m, 9H), 1.25 (m, 1H).

Example 63

8'-Chloro-5'-hydroxyspiro[cyclohexane-1-4'-(3',4'-dihydro)quinazolin]-2'(1'H)-one Formula (I): X$_1$=C—OH, X$_2$=CH, X$_3$=CH, X$_4$=C—Cl, A=cyclohexyl, X=NH, Z=O, Y=NH The title compound was prepared according to protocol L. To a stirred solution Example 59 (0.83 g, 2.95 mmol) in CH$_2$Cl$_2$ (100 mL) boron tribromide (1N in CH$_2$Cl$_2$, 21.8 mL, 21.8 mmol) was added at 0° C. The mixture was stirred at room temperature for 48 h, poured into a saturated aqueous solution of NaHCO$_3$ and extracted with CH$_2$Cl$_2$. The combined organic layers were washed with brine, dried over Na$_2$SO$_4$, filtered and concentrated. The crude material was purified by precipitation in Et$_2$O to afford the title compound as a white solid (0.25 g, 32%). (purity 97.6%) mp=252–254° C.

$^1$H NMR [(CD$_3$)$_2$SO] δ 9.90 (br s, 1H), 7.75 (br s, 1H), 7.08 (d, J=8.7 Hz, 1H), 6.97 (br s, 1H, NH), 6.43 (d, J=8.7 Hz, 1 H), 2.58–2.54 (m, 2H), 1.83–1.72 (m, 2H), 1.62–1.53 (m, 3H), 1.46 (m, 2H), 1.24–1.07 (m, 1H).

Example 64

8'-Chloro-5'-hydroxy-6'-iodo-spiro[cyclohexane-1-4'-(3',4'-dihydro)quinazolin]-2'(1'H)-one X$_1$=C—OH, X$_2$=C—I, X$_3$=CH, X$_4$=C—Cl, A=cyclohexyl, X=NH, Z=O, Y=NH To a stirred suspension of Example 63 (10 g, 37.5 mmol) in trifluoroacetic acid (150 mL) at 0 to 5° C. was added N-iodosuccinimide (9.47 g, 41.2 mmol) in portions over 10 minutes. The reaction mixture was stirred at 0 to 5° C. for 2 hours. The mixture was poured onto a mixture of water (700 mL) and ice (300 mL). The resulting brown solid was filtered and washed with water (250 mL) followed by heptane (4×40 mL). The solid was pulled dry on the filter bed for 2 hours and then slurried in a mixture of dichloromethane (30 mL) and methanol (5 mL). The dark pink precipitate was filtered and washed with dichloromethane (3×20 mL) to afford the titled compound (12.2 g, 31.0 mmol, 83%).

$^1$H NMR [(CD$_3$)$_2$SO] δ 9.10 (s, 1H), 8.25 (s, 1H), 7.81 (s, 1H), 7.18 (s, 1H), 2.70 (m, 2H), 1.95 (m, 2H), 1.75 (m, 3H), 1.60 (m, 2H), 1.28 (m, 1H).

Example 65

8'-Chloro-6'-iodo-5'-methoxy-spiro[cyclohexane-1-4'-(3',4'-dihydro)quinazolin]-2'(1'H)-one Formula (I): $X_1$=C—$OCH_3$, $X_2$=C—CN, $X_3$=CH, $X_4$=C—Cl, A=cyclohexyl, X=NH, Z=O, Y=NH To a stirred suspension of Example 64 (16.27 g, 41.4 mmol) in DMF (325 mL) was added DBU (7.5 mL, 50.1 mmol) followed by methyl iodide (6.8 mL, 109 mmol) at 20 to 25° C. The reaction mixture was stirred for 3 hours. The mixture was poured into water (1625 mL) and the resulting solid was filtered and washed with water (500 mL) followed by heptane (2×150 mL). The solid was stirred in ethyl acetate containing 10% methanol (100 mL) for 10 minutes. The precipitate was filtered and washed with EtOAc (25 mL), TBME (10 mL) and dried in vacuo at 50° C. to afford the titled compound as a fawn solid (14.4 g, 35.5 mmol, 86%).

$^1$H NMR [$CDCl_3$] δ 7.67 (s, 1H), 7.18 (s, 1H), 5.68 (s, 1H), 3.83 (s, 3H), 2.23 (td, J=13.6, 4.5, 2H), 1.90 (m, 2H), 1.70 (m, 3H), 1.51 (m, 2H), 1.25 (m, 1H).

Example 66

8'-Chloro-6'-cyano-5'-methoxy-spiro[cyclohexane-1-4'-(3',4'-dihydro)quinazolin]-2'(1'H)-one Formula (I): $X_1$=C—$OCH_3$, $X_2$=C—CN, $X_3$=CH, $X_4$=C—Cl, A=cyclohexyl, X=NH, Z=O, Y=NH To a stirred solution of Example 65 (3 g, 7.38 mmol) in NMP (60 mL) at 18 to 20° C. was added copper (I) cyanide (555 mg, 6.2 mmol). The mixture was heated to 150° C. for 4 days, quenched into ice/water (300 mL) and the crude product filtered off. The crude product was dissolved in EtOAc (500 mL) and washed with 33% $NH_3$(aq) solution (2×200 mL). The organic layer was further washed with brine (2×100 mL) and water (2×100 mL) and dried over $MgSO_4$, filtered and concentrated in vacuo at 40° C. to give the crude product (1.2 g, 3.92 mmol). The crude product (650 mg, 2.12 mmol) was purified by preparative HPLC to yield the title compound as a pale yellow solid (97 mg, 3.27 mmol, 4%) (purity 96%).

$^1$H NMR (360 MHz, $d^6$-DMSO) δ 1.29–1.43 (m, 1H), 1.50–1.70 (m, 2H), 1.73–1.95 (m, 5H), 2.25 (ddd, J=4.5, 13.5 & 13.5 Hz, 2H), 4.17 (s, 3H), 5.62–5.68 (br s, 1H), 7.25–7.29 (br s, 1H), 7.54 (s, 1H).

Example 67

8'-Chloro-5'-[2-(4-morpholino)ethoxy]spiro[cyclohexane-1-4'-(3',4'-dihydro)quinazolin]-2'(1'H)-one Formula (I): $X_1$=C—$OCH_2CH_2$-(4-morpholinyl), $X_2$=CH, $X_3$=CH, $X_4$=C—, A=cyclohexyl, X=NH, Z=O, Y=NH The title compound was prepared according to protocol L. To a stirred solution of Example 63 (1 g, 3.93 mmol) in DMF (30 mL) under nitrogen at 18 to 20° C. was added 60% sodium hydride dispersion (0.16 g, 3.93 mmol). The mixture was stirred for 15 minutes before 4-(2-chloroethyl)morpholine (0.59 g, 3.93 mmol) was added. The mixture was then heated to 100° C. for 1.5 hours. After cooling to room temperature the reaction mixture was added to water (300 mL). The resulting solid was filtered and washed with water (50 mL). The crude solid was dried in vacuo at 45° C. and subsequent purification by column chromatography (silica 60 g, eluting with 5% methanol in dichloromethane) afforded the title compound (0.48 g, 1.23 mmol, 32%) as a cream solid after drying in vacuo at 50° C. (purity 96.9%)

$^1$H NMR (360 MHz, $CDCl_3$) δ 7.20 (d, J=8.8 Hz, 1H), 7.04 (s, 1H), 6.50 (d, J=8.8 Hz, 1 H), 5.65 (s, 1H), 4.10 (t, J=5.5 Hz, 2H), 3.73 (t, J=4.5 Hz, 4H), 2.84 (t, J=5.5 Hz, 2H), 2.68 (td, J=13.5, 4.5 Hz, 2H), 2.56 (t, J=4.5 Hz, 4H), 1.74 (m, 5H), 1.56 (m, 2H), 1.32 (m, 1H).

Example 68

8'-Chloro-5'-[2-dimethylaminoethoxy]spiro[cyclohexane-1-4'-(3',4'-dihydro)quinazolin]-2'(1'H)-one Formula (I): $X_1$=C—$OCH_2CH_2N(CH_3)_2$, $X_2$=CH, $X_3$=CH, $X_4$=C—Cl, A=cyclohexyl, X=NH, Z=O, Y=NH To a stirred solution of Example 63 (6 g, 22.5 mmol) in DMF (20 mL) at 18 to 20° C. was added a solution of potassium carbonate (2M, 9.42 mL, 18.84 mmol) followed by 2-dimethyl-aminoethyl chloride hydrochloride (2M, 37.7 mL, 75.4 mmol). The mixture was heated to 100° C. for 18 hours and allowed to cool to 18 to 20° C. The reaction mixture was added to water (1.5 L) and extracted with EtOAc (2×1 L). The combined organic layer was back washed with water (1 L) and separated. The combined organic fractions were dried over with $MgSO_4$, filtered and concentrated in vacuo at 40° C. to give the crude material (4.7 g, 13.9 mmol). The crude product was purified by TBME wash (60 mL) and charcoal (5 g) treatment in DCM (200 mL) and column chromatography (silica; gradient elution, 100% EtOAc to 50% in DCM to EtOAc:DCM:MeOH; 2:10:1) to yield the title compound as a pale yellow solid (2.34 g, 6.93 mmol, 31%) (purity 99%)

$^1$H NMR (360 MHz, $d^6$-DMSO) δ1.21–1.33 (m, 1H), 1.40–1.55 (m, 2H), 1.60–1.72 (m, 5H), 2.29 (s, 6H), 2.57 (ddd, J=4.5, 13.5, 13.5 Hz, 2H), 2.72 (t, J=6.1 Hz, 2H), 4.02 (t, J=6.1 Hz, 2H), 5.48–5.54 (br s, 1H), 6.45 (d, J=9.0 Hz, 1H), 6.92–6.97 (br s, 1H), 7.14 (d, J=9.0 Hz, 1H);

Example 69

8'-Chloro-5'-(2-aminoethoxy)-spiro[cyclohexane-1-4'-(3',4'-dihydro)quinazolin]-2'(1'H)-one Formula (I): $X_1$=C—$OCH_2CH_2NH_2$, $X_2$=CH, $X_3$=CH, $X_4$=C—Cl, A=cyclohexyl, X=NH, Z=O, Y=NH Preparation of 8'-Chloro-5'-(2-methanesulphonylethoxy)-spiro[cyclohexane-1-4'-(3',4'-dihydro)quinazolin]-2'(1'H)-one (intermediate 8)

To a stirred solution of Example 78 (5 g, 1.61 mmol) and triethylamine (1.95 g, 1.93 mmol) in dichloromethane (200 mL) at 0 to 5° C. was added a solution of methanesulphonyl chloride (2.21 g, 1.93 mmol) in dichloromethane (10 mL). The reaction mixture was stirred at 20 to 25° C. for 5 hours. The mixture was washed with water (2×100 mL) and the organic phase was dried over magnesium sulphate. Filtration and concentration in vacuo at 40° C. afforded intermediate 8 as an off-white solid (5.4 g, 1.39 mmol, 86%).

$^1$H NMR [$CDCl_3$] δ 7.13 (d, J=9.1 Hz, 1H), 6.99 (s, 1H), 6.38 (d, J=9.1 Hz, 1H), 5.60 (s, 1H), 4.53 (m, 2H), 4.20 (m, 2H), 3.00 (s, 3H), 2.47 (td, J=13.6, 4.5 Hz, 2H), 1.59–1.78 (m, 5H), 1.48 (m, 2H), 1.28 (m, 1H).

Preparation of Example 69

Intermediate 8 (1.0 g, 2.57 mmol) was stirred with a solution of ammonia in ethanol (40 mL) at 70° C. in a sealed pressure vessel for 21 hours. The ethanol was removed by evaporation in vacuo at 40° C. to leave a fawn coloured solid residue (0.81 g). 2N-Hydrochloric acid (40 mL) was added (no dissolution occurred), the acidic aqueous suspension was treated with 2N-sodium hydroxide to pH 12. The aqueous mixture was extracted twice with ethyl acetate containing 10% methanol (45 mL and 80 mL). The combined ethyl acetate was washed once with water (50 mL), dried over magnesium sulphate, filtered and concentrated in vacuo at 40° C. to low volume (10 mL). An off-white solid was filtered off and washed with ethyl acetate (5 mL). The crude amine was purified by column chromatography (silica 20 g, eluting with 20% methanol in dichloromethane) to yield the title compound as an off-white solid after drying in vacuo at 50° C. (0.30 g, 0.97 mmol, 38%) (purity 98.7%).

$^1$H NMR [(CD$_3$)$_2$SO] δ 7.80 (br s, 1H), 7.10 (d, J=8.8 Hz, 1H), 6.90 (s, 1H), 6.48 (d, J=8.8 Hz, 1H), 3.78 (t, J=5.6, 2H), 2.78 (t, J=5.6, 2H), 2.40 (m, 2H), 1.65 (m, 2H), 1.25 to 1.51 (m, 7H), 1.01 (m, 1H);

Example 70

8'-Chloro-5'-[2-(methylamino)ethoxy]-spiro[cyclohexane-1-4'-(3',4'-dihydro)quinazolin]-2'(1'H)-one Formula (I): X$_1$=C—OCH$_2$CH$_2$NHCH$_3$, X$_2$=CH, X$_3$=CH, X$_4$=C—Cl, A=cyclohexyl, X=NH, Z=O, Y=NH Intermediate 8 (0.4 g, 1.03 mmol) was stirred with a solution of methylamine in ethanol (27 mL) at 70° C. for 7 hours. The ethanol was removed by evaporation in vacuo at 40° C. and the residue was partitioned between water (25 mL) and ethyl acetate (50 mL), adding 2M-sodium hydroxide (2 mL) to ensure the pH was >12. The ethyl acetate was washed once with water (15 mL), dried over magnesium sulphate and concentrated in vacuo at 40° C. to give a pink solid residue. The crude amine was purified by column chromatography (silica 20 g, eluting with 4% triethylamine and 16% methanol in ethyl acetate) to yield the title compound (0.23 g, 0.71 mmol, 69%) as an off-white solid after drying in vacuo at 50° C. (purity 99%)

$^1$H NMR (d$_6$ DMSO) δ 1.21 (m, 1H), 1.54 (m, 2H), 1.68 (m, 3H), 1.85 (m, 2H), 2.41 (s, 3H), 2.58 (m, 2H), 2.95 (t, J=5.7 Hz, 2H), 4.08 (t, J=5.7 Hz, 2H), 6.70 (d, J=8.9 Hz, 1H), 7.12 (s, 1H), 7.31 (d, J=8.9 Hz, 1H), 8.02 (s, 1H).

Example 71

8'-Chloro-5'-[2-(2-aminoethoxy)ethoxy]spiro[cyclohexane-1-4'-(3',4'-dihydro)quinazolin]-2'(1'H)-one Formula (I): X$_1$=C—OCH$_2$CH$_2$OCH$_2$CH$_2$NH$_2$, X$_2$=CH, X$_3$=CH, X$_4$=C—Cl, A=cyclohexyl, X=NH, Z=O, Y=NH To a stirred solution of Example 63 (1.07 g, 4.0 mmol) in DMF (20 mL) at room temperature was added potassium carbonate (1.22 g, 8.8 mmol) and 2-[2-(2-chloroethoxy)ethyl]-1H-isoindole-1,3(2H)-dione (1.22 g, 4.8 mmol). The mixture was heated at 100° C. for 8 hours. More potassium carbonate (1.22 g) and 2-[2-(2-chloroethoxy)ethyl]-1H-isoindole-1,3(2H)-dione (1.22 g) were added and the stirred mixture was heated at 100° C. for a further 9 hours. After cooling to 18 to 20° C. the reaction mixture was added to water (200 mL). The resulting solid was filtered and washed with water (50 mL). The solid was purified by column chromatography (silica 50 g, eluting with 5% methanol in dichloromethane) to yield the phthalimide intermediate (1.0 g, 2.06 mmol, 52%) as a pink glassy solid. To a stirred suspension of the phthalimide intermediate (0.9 g, 1.86 mmol) in ethanol (23 mL) was added hydrazine hydrate (0.28 mL, 5.64 mmol). The mixture was heated at 60° C. for 4 hours. 2M-Hydrochloric acid (36 mL) was added and the reaction was heated at reflux for 1.25 hours. Cooling to 18 to 20° C. afforded a solid that was isolated by filtration and washed with water (10 mL). The pH of the filtrate was adjusted to 14 by the addition of 2M-sodium hydroxide (2 mL), the crude amine precipitated and was filtered and washed with water (10 mL) and TBME (10 mL). The amine was purified by column chromatography (silica 20 g, eluting with 4% triethylamine and 16% methanol in ethyl acetate) to yield the title compound (0.43 g, 1.21 mmol, 65%) as a white solid after drying in vacuo at 50° C. (purity 98%)

$^1$H NMR (360 MHz, d$_6$ DMSO) δ 1.40 (m, 1H), 1.65 (m, 2H), 1.75 (m, 3H), 2.00 (m, 2H), 2.77 (m, 2H), 2.87 (t, J=5.9 Hz, 2H), 3.65 (t, J=5.9 Hz, 2H), 3.95 (m, 2H), 4.29 (m, 2H), 6.81 (d, J=9.0 Hz, 1H), 7.22 (s, 1H), 7.44 (d, J=9.0 Hz, 1H), 8.13 (s, 1H).

Example 72

8'-Chloro-5'-[3-dimethylaminopropoxy]spiro[cyclohexane-1-4'-(3',4'-dihydro)quinazolin]-2'(1'H)-one Formula (I): X$_1$=C—OCH$_2$CH$_2$CH$_2$N(CH$_3$)$_2$, X$_2$=CH, X$_3$=CH, X$_4$=C—Cl, A=cyclohexyl, X=NH, Z=O, Y=NH To a stirred solution of Example 63 (1.5 g, 5.63 mmol) in DMF (20 mL) at 18 to 20° C. was added a solution of potassium carbonate (2M, 9.42 mL, 18.84 mmol) followed by 3-dimethyl-aminopropyl chloride hydrochloride (1.02 g, 6.45 mmol). The mixture was heated to 100° C. for 18 h. It was then added to water (400 mL) and extracted with EtOAc (2×400 mL). The combined organic layer was back washed with water (300 mL) and separated. Dried with MgSO$_4$, concentrated in vacuo at 40° C. to give crude material (1.27 g, 3.61 mmol). The crude product was purified by charcoal (1 g) treatment in DCM (120 mL) and column chromatography (silica; gradient elution, 100% EtOAc to 50% in DCM to EtOAc:DCM:MeOH; 2:10:1) to yield the desired product as an off white solid (305 mg, 0.87 mmol, 15%) (purity 99%)

$^1$H NMR (360 MHz, d$^6$-DMSO) δ 1.40–1.53 (m, 1H), 1.65–1.78 (m, 2H), 1.85–2.0 (m, 5H), 2.2 (m, J=7.3, 6.3 Hz, 2H), 2.45 (s, 6H), 2.67 (t, J=7.3 Hz, 2H), 2.75 (ddd, J=4.6, 13.6 & 13.6 Hz, 2H), 4.22 (t, J=6.3 Hz, 2H), 5.71–5.75 (br s, 1H), 6.68 (d, J=9.1 Hz, 1H), 7.16–7.20 (br s, 1H), 7.35 (d, J=9.1 Hz, 1H).

Example 73

8'-Chloro-5'-ethoxycarbonylmethoxyspiro[cyclohexane-1-4'-(3',4'-dihydro)quinazolin]-2'(1'H)-one Formula (I): X$_1$=C—OCH$_2$CO$_2$CH$_2$CH$_3$, X$_2$=CH, X$_3$=CH, X$_4$=C—Cl, A=cyclohexyl, X=NH, Z=O, Y=NH The title compound was prepared according to protocol L. To a stirred solution of Example 63 (0.5 g, 1.96 mmol) in DMF (10 mL) at 18 to 20° C. was added potassium carbonate (0.6 g, 4.31 mmol) and ethyl bromoacetate (0.36 g, 2.16 mmol). The mixture was heated at 100° C. for 1.5 hours, cooled to room temperature and then added to water (100 mL). The resulting solid was filtered and washed with water (50 mL) and heptane (20 mL). Drying in vacuo at 50° C. afforded the title compound (0.6 g, 1.7 mmol, 87%) as an off-white solid.

$^1$H NMR (360 MHz, CDCl$_3$) δ 7.2 (d, J=9.1 Hz, 1H), 7.03 (s, 1H), 6.37 (d, J=9.1 Hz, 1H), 5.60 (s, 1H), 4.64 (s, 2H), 4.30 (q, J=7.3 Hz, 2H), 2.70 (td, J=13.2, 4.1 Hz, 2H), 1.80 (m, 4H), 1.55 (m, 3H), 1.45 (m, 1H), 1.35 (t, J=7.3 Hz, 3H).

Example 74

5'-Carboxymethoxy-8'-chloro-spiro[cyclohexane-1-4'-(3',4'-dihydro)quinazolin]-2'(1'H)-one Formula (I): $X_1$=C—OCH$_2$CO$_2$H, $X_2$=CH, $X_3$=CH, $X_4$=C—Cl, A=cyclohexyl, X=NH, Z=O, Y=NH A solution of potassium hydroxide (0.32 g, 5.65 mmol) in water (1.1 mL) was added to a stirred suspension of the crude Example 73 (0.4 g, 1.13 mmol) in THF (30 mL) at room temperature. The mixture was stirred for 24 hours before the THF was removed by evaporation in vacuo at 40° C. Water (20 mL) was added to the residue and the mixture was washed once with ethyl acetate (10 mL). The aqueous solution was acidified to pH 1 with concentrated hydrochloric acid to afford an off-white solid. The solid was filtered and washed with water (10 mL) and heptane (5 mL). The solid was purified by column chromatography (silica 10 g, eluting with 10% acetic acid in ethyl acetate) to yield the title (0.15 g, 0.46 mmol, 41%) as an off-white solid after drying in vacuo at 50° C. (purity 98.9%) mp=284–286° C.

$^1$H NMR [(CD$_3$)$_2$SO] δ 13.05 (br s, 1H), 7.95 (br s, 1H), 7.24 (d, J=9.0 Hz, 1H), 6.99 (br s, 1H, NH), 6.54 (d, J=9.0 Hz, 1H), 4.69 (s, 2H), 2.61 (m, 2H), 1.77 (m, 2H), 1.55 (m, 3H), 1.45 (m, 2H), 1.30 (m, 1H).

Example 75

5'-Carboxypropoxy-8'-chloro-spiro[cyclohexane-1-4'-(3',4'-dihydro)quinazolin]-2'(1'H)-one Formula (I): $X_1$=C—OCH$_2$CH$_2$CH$_2$CO$_2$H, $X_2$=CH, $X_3$=CH, $X_4$=C—Cl, A=cyclohexyl, X=NH, Z=O, Y=NH To a stirred solution of Example 63 (1.07 g, 4 mmol) in DMF (20 mL) at 18 to 20° C. was added potassium carbonate (1.22 g, 8.8 mmol) and ethyl 4-bromobutyrate (0.82 g, 4.2 mmol). The mixture was heated at 100° C. for 2 hours, cooled to room temperature and added to water (200 mL). The mixture was extracted with ethyl acetate (2×200 mL). The combined extracts were washed with water (100 mL), dried over magnesium sulfate and evaporated in vacuo at 50° C. to afford a solid residue. Trituration of the residue with heptane (10 mL) afforded the intermediate ethyl ester (1.27 g, 3.33 mmol, 84%) as a pink solid after drying in vacuo at 50° C.

$^1$H NMR (360 MHz, CDCl$_3$) δ 1.11 (t+m, 4H), 1.38 (m, 2H), 1.58 (m, 5H), 2.01 (m, 2H), 2.38 (m, 4H), 3.87 (t, J=5.7 Hz, 2H), 4.01 (q, J=6.3 Hz, 2H), 5.46 (s, 1H), 6.32 (d, J=8.1 Hz, 1H), 6.87 (s, 1H), 7.02 (d, J=8.1 Hz, 1H).

6N-Hydrochloric acid (10 mL) was added to a stirred suspension of the ethyl ester (0.9 g, 2.36 mmol) in dioxane (6 mL) at 18 to 20° C. The mixture was stirred under reflux for 2.5 hours. After cooling to 18 to 20° C. the solid was filtered and washed with water (50 mL) and TBME (5 mL). The solid was triturated with TBME (30 mL) to afford the title compound (0.64 g, 1.79 mmol, 76%) as an off-white solid after drying in vacuo at 50° C. (purity 98%).

$^1$H NMR (360 MHz, d$_6$ DMSO) δ 1.03 (m, 1H), 1.34 (m, 2H), 1.47 (m, 3H), 1.68 (m, 2H), 1.80 (m, 2H), 2.30 (m, 4H), 3.87 (t, J=6.3 Hz, 2H), 6.40 (d, J=9.0 Hz, 1H), 6.90 (s, 1H), 7.11 (d, J=9.0 Hz, 1H), 7.80 (s, 1H), 12.05 (br s, 1H).

Example 76

8'-Chloro-5'-(3-sulphopropoxy)-spiro[cyclohexane-1-4'-(3',4'-dihydro)quinazolin]-2'(1'H)-one Formula (I): $X_1$=C—OCH$_2$CH$_2$CH$_2$SO$_3$H, $X_2$=CH, $X_3$=CH, $X_4$=C—Cl, A=cyclohexyl, X=NH, Z=O, Y=NH The title compound was prepared according to protocol L. To a stirred solution of Example 63 (1 g, 3.93 mmol) in DMF (20 mL) at 18 to 20° C. was added potassium carbonate (1.19 g, 8.65 mmol) followed by sodium 3-bromopropane-sulphonate (0.97 g, 4.32 mmol). The mixture was heated at 100° C. for 6 hours, cooled to room temperature and then added to water (300 mL). The resulting solution was acidified to pH 1 with concentrated hydrochloric acid. The aqueous mixture was washed with ethyl acetate (200 mL) and evaporated in vacuo to dryness at 70° C. The residue was treated with TBME (200 mL) and a small amount of white solid was filtered and discarded. Decanting away the TBME from the filtrate isolated a pale yellow insoluble oil. Remaining DMF was removed from the oil by further evaporation in vacuo at 70° C. The resulting gum was triturated with acetonitrile (10 mL) to yield the title compound (0.11 g, 0.28 mmol, 7%) as a white solid after drying in vacuo at 50° C. (purity=99.7%)

$^1$H NMR (360 MHz, (CD$_3$)$_2$SO) δ 8.27 (br s, 1H), 7.95 (s, 1H), 7.25 (d, J=8.6 Hz, 1H), 7.04 (s, 1H), 6.63 (d, J=8.6 Hz, 1H), 4.09 (t, J=6.5 Hz, 2H), 2.64 (t, J=7.5 Hz, 2H), 2.58 (m, 2H), 2.08 (m, 2H), 1.80 (br m, 2H), 1.60 (br m, 3H), 1.38 (br d, J=12.6 Hz, 2H), 1.22 (m, 1H).

Example 77

8'-Chloro-5'-[2-(tetrahydro-pyran-2-yloxy)-ethoxy]-spiro[cyclohexane-1-4'-(3',4'-dihydro)quinazolin]-2'(1'H)-one Formula (I): $X_1$=C—OCH$_2$CH$_2$O-(tetrahydro-pyran-2-yl), $X_2$=CH, $X_3$=CH, $X_4$=C—Cl, A=cyclohexyl, X=NH, Z=O, Y=NH The title compound was prepared according to protocol L. To a stirred solution of Example 63 (0.5 g, 1.96 mmol) in DMF (10 mL) at 18 to 20° C. was added potassium carbonate (0.6 g, 4.31 mmol) followed by 2-(2-bromoethoxy)tetrahydro-2H-pyran (0.45 g, 2.16 mmol). The mixture was heated at 100° C. for 3.2 hours, cooled to room temperature and then added to water (100 mL). The resulting solid was filtered and washed with water (50 mL) followed by heptane (20 mL). Drying in vacuo at 50° C. afforded the title compound (0.69 g, 1.75 mmol, 90%) as an off-white solid.

$^1$H NMR (360 MHz, (CD$_3$)$_2$SO) δ 7.94 (s, 1H), 7.21 (d, J=8.9 Hz, 1H), 6.99 (s, 1H), 6.59 (d, J=8.9 Hz, 1H), 4.68 (m, 1H), 4.08 (m, 2H), 3.92 (m, 1H), 3.70 (m, 2H), 3.41 (m, 1H), 2.56 (td, J=13.6, 4.1 Hz, 2H), 1.33–1.84 (m, 13H), 1.19 (m, 1H),

Example 78

8'-Chloro-5'-(2-hydroxy-ethoxy)-spiro[cyclohexane-1-4'-(3',4'-dihydro)quinazolin]-2'(1'H)-one Formula (I): $X_1$=C—OCH$_2$CH$_2$OH, $X_2$=CH, $X_3$=CH, $X_4$=C—Cl, A=cyclohexyl, X=NH, Z=O, Y=NH Example 77 (0.69 g, 1.75 mmol) was stirred in a mixture of THF (20 mL) and water (4 mL). Concentrated hydrochloric acid (0.4 mL) was added and the mixture was stirred at room temperature for 24 h then heated under reflux for 2 hours. The THF was removed by evaporation in vacuo at 40°

C. and the residue was partitioned between water (25 mL) and ethyl acetate (40 mL). The aqueous phase was separated and extracted with ethyl acetate (20 mL). The combined extracts were washed with water (20 mL), dried over $MgSO_4$ and concentration in vacuo at 40° C. afforded the title compound (0.32 g, 1.03 mmol, 59%) as a cream solid after drying in vacuo at 50° C. (purity=95.7%) mp=176–178° C.

$^1$H NMR [$(CD_3)_2SO$] δ 7.89 (br s, 1H), 7.23 (d, J=9.0 Hz, 1H), 6.98 (br s, 1H, NH), 6.63 (d, J=9.0 Hz, 1H), 4.81 (t, J=5 Hz, 2H), 4.00 (t, J=5 Hz, 2H), 3.76 (q, J=5 Hz, 2H), 2.58 (m, 2H), 1.77 (m, 2H), 1.53 (m, 3H), 1.45 (m, 2H), 1.30 (m, 1H).

Example 79

8'-Chloro-5'-(5-ethoxycarbonyl-furan-2-ylmethoxy)-spiro[cyclohexane-1-4'-3',4'-dihydro)quinazolin]-2'(1'H)-one Formula (I): $X_1$=C—$OCH_2$-(5-ethoxycarbonyl-furan-2-yl), $X_2$=CH, $X_3$=CH, $X_4$=C—Cl, A=cyclohexyl, X=NH, Z=O, Y=NH The title compound was prepared according to protocol L. To a stirred solution of Example 63 (0.5 g, 1.87 mmol) and sodium iodide (0.14 g, 1.87 mmol) in DMF (10 mL) at 18 to 20° C. was added potassium carbonate (0.258 g, 0.95 mmol) and 5-Chloromethyl-furan-2-carboxylic acid ethyl ester (0.29 mL, 1.87 mmol). The mixture was stirred at room temperature for 2 h. After completion, the solvent was removed under reduced pressure and a mixture of water and EtOAc was added. The layer were separated, the aqueous one being extrated three times with EtOAc. The combined organic layers were washed with brine, dried over $Na_2SO_4$, filtered and concentrated. The solid was purified by column chromatography (silica 10 g, eluting with $CH_2Cl_2$/MeOH: 99/1 to 98/2) to yield the title compound (0.75 g, 96%) as a white solid after drying in vacuo at 50° C.

$^1$H NMR [$(CD_3)_2SO$] δ 7.98 (br s, 1H NH), 7.30–7.28 (m, 2H), 7.01 (br s, 1H NH), 6.80–6.76 (m, 2H), 5.2 (s, 2H), 4.28 (q, J=7.0 Hz, 2H), 2.43–2.4 (m, 2H), 1.75–1.72 (m, 2H), 1.56–1.53 (m, 3H), 1.40 (m, 2H), 1.28 (t, J=7.0 Hz, 3H), 0.97 (m, 1H).

Example 80

8'-Chloro-5'-(5-carboxy-furan-2-ylmethoxy)-spiro[cyclohexane-1-4'-(3',4'-dihydro)quinazolin]-2'(1'H)-one Formula (I): $X_1$=C—$OCH_2$-(5-carboxy-furan-2-yl), $X_2$=CH, $X_3$=CH, $X_4$=C—Cl, A=cyclohexyl, X=NH, Z=O, Y=NH A solution of lithium hydroxide monohydrate (0.85 g, 20 mmol) in water (1.35 mL), EtOH (11 mL) and MeOH (67 mL) was added to a stirred suspension of the crude Example 79 (0.6 g, 1.43 mmol) in $CH_2Cl_2$ (17 mL) at room temperature. The mixture was stirred for 48 h before the solvents were removed by evaporation in vacuo at 40° C. Water was added to the residue and the mixture was acidified with concentrated aqueous HCl and extracted with $CH_2Cl_2$. The combined organic layers were dried over $Na_2SO_4$, filtered and concentrated. The solid was purified by column chromatography (silica 5 g, eluting with $CH_2Cl_2$/MeOH:70/30) to yield the title compound (0.05 g, 9%) as a white solid after drying in vacuo at 50° C. (purity 98%)

$^1$H NMR [$(CD_3)_2SO$] δ 13.10 (s, 1H), 7.96 (br s, 1H, NH), 7.29 (d, J=9.1 Hz, 1H), 7.12 (br s, 1H, NH), 6.99 (s, 1H), 6.79 (d, J=9.1 Hz, 1H), 6.70 (br s , 1H), 5.15 (s, 1H). 2.43–2.40 (m, 2H), 1.70 (m, 2H), 1.55–1.52 (m, 3H), 1.40 (m, 2H), 0.98–1.00 (m, 1H),

Example 81

8'-Chloro-5'-cyanomethoxyspiro[cyclohexane-1-4'-(3',4'-dihydro)quinazolin]-2'(1'H)-one Formula (I): $X_1$=C—$OCH_2CN$, $X_2$=CH, $X_3$=CH, $X_4$=C—Cl, A=cyclohexyl, X=NH, Z=O, Y=NH The title compound was prepared according to protocol L. To a stirred solution of Example 63 (2 g, 7.85 mmol) in DMF (30 mL) at 18 to 20° C. was added potassium carbonate (2.39 g, 17.3 mmol) followed by bromoacetonitrile (1.04 g, 8.64 mmol). The mixture was heated at 100° C. for 2 hours, cooled to 18 to 20° C. and added to water (300 mL). The resulting solid was filtered and washed with water (60 mL). Drying in vacuo at 50° C. afforded crude title compound (2.35 g). The crude product was purified by column chromatography (silica 70 g eluting with 10% methanol in dichloromethane) to yield title compound (1.72 g, 5.6 mmol, 72%) as a fawn solid after drying in vacuo at 50° C. (purity=97%) mp=193–195° C.

$^1$H NMR [$(CD_3)_2SO$] δ 8.12 (br s, 1H), 7.36 (d, J=9.0 Hz, 1H), 7.07 (br s, 1H, NH), 6.75 (d, J=9.0 Hz, 1H), 5.24 (s, 2H), 2.34 (m, 2H), 1.80 (m, 2H), 1.63 (m, 3H), 1.47 (m, 2H), 1.20 (m, 1H).

Example 82

8'-Chloro-5'-(1H-tetrazol-5-ylmethoxy)-spiro[cyclohexane-1-4'-(3',4'-dihydro)quinazolin]-2'(1'H)-one Formula (I): $X_1$=C—$OCH_2$-(1H-tetrazol-5-yl), $X_2$=CH, $X_3$=CH, $X_4$=C—Cl, A=cyclohexyl, X=NH, Z=O, Y=NH Example 81 (0.05 g, 0.16 mmol), trimethyltin azide (0.05 mL, 0.179 mmol) and toluene (2 mL) were mixed and refluxed under nitrogen for 15 h. 10M NaOH (0.02 mL, 0.2 mmol) was added and the mixture was stirred at room temperature overnight. The upper layer was removed, hexane was added to the residue, the resulting mixture was stirred for 30 min, hexane was removed. This operation was repeated three times, and EtOAc was added, the precipitate was filtered and washed with EtOAc. The residue was taken into $CH_2Cl_2$ and 1M HCl (1 mL, 1 mmol) and concentrated under reduced pressure. The precipitate was washed successively with water and MeOH to give the title compound (0.04 g, 71%) as a white powder (purity=98.1%) mp=287–289° C.

$^1$H NMR [$(CD_3)_2SO$] δ 8.02 (br s, 1H), 7.34 (d, J=8.9 Hz, 1H), 7.01 (br s, 1H 6.82 (d, J=8.9 Hz, 1H), 5.47 (s, 2H), 2.35 (m, 2H), 1.73 (m, 2H), 1.50 (m, 3H), 1.36 (m, 2H), 0.88 (m, 1H).

Example 83

8'-Chloro-5'-(5-hydroxy-[1,2,4]oxadiazol-3-ylmethoxy)-spiro[cyclohexane-1-4'-3',4'-dihydro)quinazolin]-2'(1'H)-one Formula (I): $X_1$=C—$OCH_2$-(5-hydroxy-[1,2,4]oxadiazol-3-yl), $X_2$=CH, $X_3$=CH, $X_4$=C—Cl, A=cyclohexyl, X=NH, Z=O, Y=NH Preparation of 8'-chloro-5'-(N-hydroxycarbamimidoylmethoxy)-spiro[cyclohexane-1-4'-(3',4'-dihydro)quinazolin]-2'(1'H)-one (intermediate 9)

To a mixture of Example 81 (0.6 g, 1.96 mmol) and hydroxylamine hydrochloride (0.186 g, 2.94 mmol) in ethanol (7 mL) was added sodium hydroxyde (0.114 g, 2.85 mmol) dissolved in the minimum of water. The reaction mixture was heated to reflux for 24 h with stirring. After cooling, the solvent was concentrated under reduced pressure. The residue was taken into $CH_2Cl_2$, the precipitate was filtered, washed with $CH_2Cl_2$ and dried under vacuum at 45° C. to afford intermediate 9 in a quantitative yield.

$^1$H NMR [$(CD_3)_2$SO] δ 9.34 (br s, 1H, OH), 7.94 (br s, 1H NH), 7.73 (d, J=9.0 Hz, 1H), 6.98 (br s, 1H, NH), 6.70 (d, J=9.0 Hz, 1H), 5.61 (s, 2H), 4.40 (br s, 2H, $NH_2$), 2.56–2.54 (m, 2H), 1.83–1.72 (m, 2H), 1.62–1.53 (m, 3H), 1.46 (m, 2H), 1.24–1.07 (m, 1H).

Preparation of Example 83

To a mixture of intermediate 9 (0.3 g, 0.885 mmol) and ethyl chloroformate (0.13 mL, 1.3 mmol) in anhydrous $CHCl_3$ (4 mL) was added triethylamine (0.22 mL, 1.6 mmol). The reaction mixture was stirred at room temperature for 5 h. After completion, the precipitate was filtered to afford the (ethoxycarbonyl)oxy]amino intermediate (0.275 mg, 76%), which was used directly in the next step without further purification.

$^1$H NMR [$(CD_3)_2$SO] δ 7.98 (br s, 1H, NH), 7.30 (d, J=9.0 Hz, 1H), 6.98 (br s, 1H, NH), 6.78 (br s, 2H, $NH_2$), 6.70 (d, J=9.0 Hz, 1H), 4.48 (s, 2H), 4.20 (q, J=7.7 Hz, 2H), 2.58–2.54 (m, 2H), 1.83–1.72 (m, 2H), 1.62–1.53 (m, 3H), 1.46 (m, 2H), 1.28–1.20 (m, 1H), 1.23(t, J=7.7 Hz, 3H).

A mixture [(ethoxycarbonyl)oxy]amino intermediate (0.275 g, 0.67 mmol) and 1,8-diazabicyclo[5,4,0]undec-7-ene (0.4 mL, 2.67 mmol) in $CH_3CN$ (4 mL) was refluxed for 24 h with stirring. The reaction mixture was concentrated under reduced pressure and taken into a mixture of $CH_2Cl_2$ and aqueous 1M HCl. The layers were separated and the aqueous one being extracted three times with $CH_2Cl_2$. The combined organic layers were dried over $Na_2SO_4$, filtered and concentrated to yield the title compound (0.17 g, 70%) as a white solid after drying in vacuo at 50° C.

$^1$H NMR [$(CD_3)_2$SO] δ 12.86 (br s, 1H), 8.04 (br s, 1H), 7.32 (d, J=9.0 Hz, 1H), 7.03 (br s, 1H), 6.72 (d, J=9.0 Hz, 1H), 5.07 (s, 2H), 2.42–2.36 (m, 2H), 1.78–1.74 (m, 2H), 1.59–1.56 (m, 3H), 1.44 (m, 2H), 1.11 (m, 1H).

Example 84

8'-Chloro-6'-iodo-5'-[2-dimethylamino-ethoxy]spiro [cyclohexane-1-4'-(3',4'-dihydro)quinazolin]-2'(1'H)-one Formula (I): $X_1$=C—$OCH_2CH_2N(CH_3)_2$, $X_2$=C—I, $X_3$=CH, $X_4$=C—Cl, A=cyclohexyl, X=N Z=O, Y=NH The title compound was prepared according to protocol L. To a stirred solution of Example 68 (1.5 g, 4.44 mmol) in trifluoroacetic acid (15 mL) were subsequently added N-iodosuccinimide (1.1 g, 4.89 mmol, 1.1 equiv.) and sulfuric acid (4 mL). The resulting solution was stirred for 4 h, and then ethyl acetate and water were added. The organic layer was separated. The aqueous layer was twice washed with ethyl, basified to pH 9 with 30% aqueous sodium hydroxide then extracted three times with ethyl acetate. The combined organic extracts were washed with water, brine and concentrated under reduced pressure to give 1.95 g (95%) of the title compound as a white solid. (purity 99%)

$^1$H NMR (CDCl3) δ 7.71 (s, 1H), 7.06 (br s, 1H), 5.43 (br s, 1H), 4.06 (t, J=6.0 Hz, 2H), 2.82 (t, J=6.0 Hz, 2H), 2.36 (s, 6H), 2.34 (m, 2H), 1.93 (m, 2H), 1.80–1.71 (m, 3H), 1.59–1.50 (m, 2H), 1.33 (m, 1H).

Example 85

6'-(4-Carboxyphenyl)-8'-chloro-5'-methoxyspiro [cyclohexane-1-4'-(3',4'-dihydro)quinazolin]-2'(1'H)-one Formula (I): $X_1$=C—$OCH_3$, $X_2$=C-(4-carboxyphenyl), $X_3$=CH, $X_4$=C—Cl, A=cyclohexyl, X=NH, Z=O, Y=NH The title compound was prepared according to protocol G. To a stirred solution of Example 65 (7 g, 17.2 mmol) in DMF (84 mL) at 18 to 20° C. was added a solution of 4-carboxyphenyl-boronic acid (343 mg, 20.64 mmol) and potassium carbonate (2M, 34 mL, 68 mmol) under N2. After degassing the mixture by bubbling with N2 for 2 h, tetrakis (triphenylphosphine) palladium (1.33 g, 1.147 mmol) was added. The solution was heated to 100° C. for 18 h. It was then added to water (1 L) and EtOAc (1 L). The desired product was precipitated and collected by filtration to give the crude product (3.5 g, 51%). The aqueous filtrate was separated and acidified to pH 1 with concentrated HCl (20 mL). The white solid was collected by filtration (2.7 g, 39%). The crude products were combined and purified by column chromatography (silica 80 g; gradient elution, 20% DCM in EtOAc to 50% DCM in MeOH) to give the title compound (1.77 g, 4.41 mmol, 18%) as an off-white solid. (purity=99.4%) mp=309–311° C.

$^1$H NMR [$(CD_3)_2$SO] δ 8.27 (s, 1H), 7.98 (d, J=8.0 Hz, 2H), 7.50 (d, J=8.0 Hz, 2H), 7.29 (s, 1H), 6.98 (s, 1H), 3.18 (s, 3H), 2.25 (m, 2H), 1.80 (m, 4H), 1.61 (m, 1H), 1.48 (m, 2H), 1.19 (m, 1H).

Example 86

6'-(3-Carboxyphenyl)-8'-chloro-5'-methoxyspiro [cyclohexane-1-4'-(3',4'-dihydro)quinazolin]-2'(1'H)-one Formula (I): $X_1$=C—$OCH_3$, $X_2$=C-(3-carboxyphenyl), $X_3$=CH, $X_4$=C—Cl, A=cyclohexyl, X=NH,Z=O,Y=NH The title compound was prepared according to protocol G. To a stirred solution of Example 65 (1.75 g, 4.30 mmol) in DMF (30 mL) at 18 to 20° C. was added a solution of 3-carboxyphenyl-boronic acid (0.86 g, 5.18 mmol) and potassium carbonate (2M, 8.5 mL, 17 mmol) under N2. The mixture was degassed by bubbling N2 for 2 h and tetrakis (triphenylphosphine)palladium (331 mg, 0.286 mmol) was added. The solution was heated to 100° C. for 24 h and allowed to cool to 18 to 20° C. The reaction mixture was added to water (200 mL) and EtOAc (300 mL). The desired product was precipitated and collected by filtration, dried in vacuo at 40° C. to yield the title compound (567 mg, 1.42 mmol, 33%) as a light brown solid. (purity=96%)

$^1$H NMR (($CD_3$)$_2$SO) δ 13.06 (br s, 1H), 8.30 (br s, 1H), 8.04 (s, 1H), 7.94 (d, J=8.1 Hz, 1H), 7.74 (d, J=8.0 Hz, 1H), 7.58 (t, J=8.0 Hz, 1H), 7.34 (s, 1H), 7.01 (br s, 1H), 3.21 (s, 3H), 2.30 (m, 2H), 1.87–1.78 (m, 4H), 1.67–1.64 (m, 1H), 1.53–1.50 (m, 2H), 1.24 (m, 1H).

Example 87

8'-Chloro-6'-[2-(4-methyl-piperazine-1-carbonyl) phenyl]spiro[cyclohexane-1-4'-(3',4'-dihydro) quinazolin]-2'(1'H)-one Formula (I): $X_1$=CH, $X_2$=C-(2-(4-methyl-piperazine-1-carbonyl)phenyl), $X_3$=CH, $X_4$=C—Cl, A=cyclohexyl, X=NH, Z=O, Y=NH Preparation of (2-bromo-phenyl)-(4-methyl-piperazin-1-yl)-methanone (intermediate 10)

To a solution of 2-bromobenzoyl chloride (2 g, 9 mmol) in toluene (30 mL) was added N-methylpiperazine (2 mL, 18 mmol, 2 equiv.). The resulting mixture was stirred overnight. The precipitate was filtered and the filtrate was concentrated under reduced pressure. The residue was taken into dichloromethane, washed with water. The organic layer was concentrated under reduced pressure to give 2 g (77% yield) of intermediate 10.

$^1$H NMR [CDCl3] δ 7.60 (m, 1H), 7.35 (m, 1H), 7.20 (m, 2H), 3.90–3.80 (m, 2H), 3.40–3.20 (m, 2H), 2.60–2.40 (m, 3H), 2.30 (s, 3H), 2.30–2.25 (m, 1H).

Preparation of Example 87

To a suspension of Example 25 (200 mg, 0.5 mmol) in dimethylformamide (6 mL) were subsequently added sodium acetate (130 mg, 1.6 mmol, 3 equiv.) and bis (pinacolato)diboron (152 mg, 0.6 mmol). The mixture was degassed by bubbling nitrogen and tetrakis(triphenylphosphine)palladium (30 mg, 0.026 mmol, 0.05 equiv.) was added. The resulting mixture was heated to 45° C. overnight and to 90° C. for 2 h, concentrated under reduced pressure. The residue was taken into dichloromethane, washed once with water. The organic layer was dried over sodium sulfate, concentrated under reduced pressure and purified by flash chromatography on silica gel (heptane/ethyl acetate:80/20), the resulting solid was hydrolized by hydrochloric acid (1N) in methanol and concentrated under reduced pressure to give 400 mg (66% yield) of the boronic acid. To a suspension of the crude boronic acid (40 mg, 0.14 mmol ) in dimethylformamide (2 mL) were subsequently added intermediate 10 (46 mg, 0.16 mmol, 1.2 equiv.) and a 2M aqueous solution of potassium carbonate (0.2 mL, 0.4 mmol, 3 equiv.). The mixture was degassed by bubbling nitrogen and tetrakis (triphenylphosphine)palladium (8 mg, 0.007 mmol, 0.05 equiv.) was added. After heating to 90° C. for 3 hours, the mixture was concentrated under reduced pressure, taken into ethyl acetate and washed with water. The organic layer was washed three times with HCl (1N). The aqueous layer was basified to pH 9 and extracted three times with dichlomethane. The organic layer was concentrated under reduced pressure, the resulting solid was crystallized in toluene/methanol to give 10 mg (16% yield) of the title compound as a white solid. mp=250° C.

$^1$H NMR [(CD$_3$)$_2$SO] δ 8.58 (br s, 1H, NH), 7.50–7.49 (m, 2H), 7.43 (m, 1H), 7.33–7.28 (m, 3H), 7.18(br s, 1H, NH), 3.70 (m, 1H), 3.20 (m, 1H), 2.95 (m, 1H), 2.78 (m, 1H), 2.38 (m, 1H), 2.10 (m, 1H), 1.98 (s, 3H), 1.86–1.75 (m, 6H), 1.62–1.48 (m, 4H), 1.24–1.16 (m, 2H),

Example 88

8'-Chloro-6'-[2-methyl-4-(4-methyl-piperazine-1-carbonyl)phenyl]spiro[cyclohexane-1-4'-(3',4'-dihydro)quinazolin]-2'(1'H)-one Formula (I): $X_1$=CH, $X_2$=C-(2-methyl-4-(4-methyl-piperazine-1-carbonyl)phenyl), $X_3$=CH, $X_4$=C—Cl, A=cyclohexyl, X=NH, Z=O, Y=NH Preparation of (4-Bromo-3-methyl-phenyl)-(4-methyl-piperazin-1-yl)-methanone (intermediate 11)

To a solution of 4-bromo-3-methylbenzoyl chloride (0.5 g, 2 mmol) in toluene (6 mL) was added N-methylpiperazine (0.5 mL, 4 mmol, 2 equiv.). The resulting mixture was stirred overnight, The precipitate was filtered and the filtrate was concentrated under reduced pressure. The residue was taken into ethyl acetate and washed with water. The organic layer was dried over sodium sulfate, concentrated under reduced pressure to give 0.2 g (34% yield) of intermediate 11.

Preparation of Example 88

To a suspension of Example 25 (1 g, 2.5 mmol) in dimethylformamide (25 mL) were subsequently added sodium acetate (650 mg, 8 mmol, 3 equiv.) and bis(pinacolato)diboron (760 mg, 3 mmol, 1.2 equiv.). The mixture was degassed by bubbling nitrogen and tetrakis(triphenylphosphine) palladium (150 mg, 0.13 mmol, 0.05 equiv.) was added . The resulting mixture was heated to 45° C. overnight, then additional bis(pinacolato)diboron (635 mg, 2.5 mmol, 1 equiv.) and tetrakis(triphenylphosphine) palladium (100 mg, 0.087 mmol, 0.035 equiv.) was added. The mixture was heated to 90° C. overnight and concentrated under reduced pressure. The residue was taken into ethyl acetate, washed once with water. The organic layer was concentrated under reduced pressure and the resulting solid was washed with ethyl acetate to give 0.7 g (78% yield) of boronate. To a suspension of the boronate (200 mg, 0.5 mmol) in dimethylformamide (3 mL) were subsequently added intermediate 11 (200 mg, 0.7 mmol, 1.4 equiv.) and sodium acetate (123 mg, 1.5 mmol, 3 equiv.). The mixture was degassed by bubbling nitrogen and tetrakis(triphenylphosphine)palladium (29 mg, 0.025 mmol, 0.05 equiv.) was added. After heating to 90° C. overnight, the mixture was concentrated under reduced pressure, taken into dichloromethane and washed with water. The organic layer was concentrated under reduced pressure and purified by flash chromatography on silica gel (dichloromethane/methanol:97/3 to 95/5) and the resulting solid was crystallized in toluene/methanol to give 10 mg (6% yield) of the title compound as a white solid. mp=184° C.

$^1$H NMR [(CD$_3$)$_2$SO] δ 8.50 (br s, 1H, NH), 7.30–7.23 (m, 5H), 7.15 (br s, 1H, NH), 3.60–3.37 (m, 4H), 2.33–2.27 (m, 7H), 2.20 (s, 3H), 1.78 (m, 6H), 1.62 (m, 1H), 1.5 (m, 2H), 1.24 (m, 1H).

Example 89

8'-Chloro-6'-[4-(piperazine-1-carbonyl)phenyl]spiro [cyclohexane-1-4'-(3',4'-dihydro)quinazolin]-2'(1'H)-one Formula (I): $X_1$=CH, $X_2$=C-(4-(piperazine-1-carbonyl)phenyl), $X_3$=CH, $X_4$=C—Cl, A=cyclohexyl, X=NH, Z=O, Y=NH To a suspension of Example 32 (400 mg, 1.08 mmol) in toluene (4 mL) was added thionyl chloride (0.2 mL, 2.16 mmol, 2 equiv.). The resulting mixture was heated to reflux for 3 h, then concentrated under reduced pressure taken into THF (8 mL). To a 0.135 M solution of the acyl chloride in THF (4 mL, 0.54 mmol) was added triethylamine (0.1 mL, 0.15 mmol, 3 equiv.) and piperazine (70 mg, 0.81 mmol, 1.5 equiv.). After stirring for 2 days, the mixture was concentrated, taken into dichloromethane, washed with water and extracted with a 1N aqueous solution of HCl. The aqueous layer was washed twice with dichloromethane, basified to pH 9 and extracted three times with dichloromethane. The combined organic extracts were concentrated under reduced pressure and purified by flash chromatography on silica gel ($CH_2Cl_2$/MeOH:99/1 to 95/5) to give 181 mg (75% yield) of the title compound as a white solid.

$^1$H NMR [(CD3)$_2$SO] δ 8.54 (br s, 1H, NH), 7.78 (d, J=8.5 Hz, 2H), 7.66 (s, 1H), 7.63 (s, 1H), 7.48 (d, J=8.0 Hz, 2H), 7.17 (br s, 1H, NH), 3.57 (br m, 4H), 2.96 (br m, 4H), 1.88–1.77 (m, 6H), 1.64 (m, 1H), 1.54 (m, 2H), 1.28 (m, 1H).

Example 90

8'-Chloro-6'-[4-carbamoyl-phenyl]spiro[cyclohexane-1-4'-(3',4'-dihydro)quinazolin]-2'(1'H)-one Formula (I): $X_1$=CH, $X_2$=C-(4-carbamoyl-phenyl), $X_3$=CH, $X_4$=C—Cl, A=cyclohexyl, X=NH, Z=O, Y=NH To a suspension of Example 32 (1 g, 2,7 mmol) in toluene (10 mL) was added thionyl chloride (0.4 mL, 5.4 mmol, 2 equiv.). The resulting mixture was heated to reflux overnight. The precipitate was isolated by filtration, washed with toluene and dried under reduced pressure to give 0.9 g (90% yield) of the acyl chloride. To a suspension of the acyl chloride (100 mg, 0.25 mmol) in toluene (2 mL) was added a 0.5M solution of ammonia in dioxane (1 mL, 0.5 mmol, 2 equiv.). The mixture was stirred overnight and concentrated under reduced pressure. The residue was taken into dichloromethane and washed with water. The organic layer was concentrated under reduced pressure and the resulting solid was purified by flash chromatography on silica gel (dichloromethane/methanol:97/3) to give 10 mg (66% yield) of the title compound as a white solid. mp=327° C.

$^1$H NMR [(CD$_3$)$_2$SO] δ 8.55 (br s, 1H, NH), 8.02 (br s, 1H, NH), 7.95–7.93 (d, J=8.5 Hz, 2H), 7.80–7.77 (d, J=8.5 Hz, 2H), 7.69 (s, 1H), 7.63 (s, 1H), 7.36 (br s, 1H, NH), 7.17 (br s, 1H, NH), 1.92–1.77 (m, 6H), 1.66–1.63 (m, 1H), 1.55–1.53 (m, 2H), 1.32–1.23 (m, 1H),

Example 91

8'-Chloro-6'-[4-((1-methyl-piperidin-4-yl)-piperazine-1-carbonyl)phenyl]spiro[cyclohexane-1-4'-(3',4'-dihydro)quinazolin]-2'(1'H)-one Formula (I): $X_1$=CH, $X_2$=C-(4-((1-methyl-piperidin-4-yl)-piperazine-1-carbonyl)phenyl), $X_3$=CH, $X_4$=C—Cl, A=cyclohexyl, X=NH, Z=O, Y=NH To a suspension of Example 32 (150 mg, 0.4 mmol) in toluene (2 mL) was added thionyl chloride (0.06 mL, 0.8 mmol, 2 equiv.). The resulting mixture was heated to reflux for 3 hours, and then concentrated under reduced pressure. The resulting solid was added to a solution of 1-(N-methyl-piperidin-4-yl) piperazine (100 mg, 0.6 mmol, 1.5 equiv.) and triethylamine (0.1 mL, 0.8 mmol, 2 equiv.) in toluene (2 mL). After stirring overnight, the mixture was diluted with dichloromethane and washed with a saturated solution of sodium bicarbonate. The organic layer was concentrated under reduced pressure. The resulting solid was washed with ethyl acetate/methanol and crystallized in ethyl acetate/methanol to give 70 mg (33% yield) of the title compound as a white solid. mp=181° C.

$^1$H NMR [(CD$_3$)$_2$SO] δ 8.53 (br s, 1H, NH), 7.75 (d, J=8 Hz, 2H), 7.65 (s, 1H) 7.60 (s, 1H), 7.43 (d, J=8 Hz, 2H), 7.17 (br s, 1H, NH), 3.59–3.31 (br m, 7H), 2.78–2.75 (m, 2H), 2.16–2.12 (m, 4H), 1.88–1.29 (m, 17H).

Example 92

8'-Chloro-5'-methoxy-6'-[4-(4-methyl-piperazine-1-carbonyl)phenyl]spiro[cyclohexane-1-4'-(3',4'-dihydro)quinazolin]-2'(1'H)-one Formula (I): $X_1$=C—OCH$_3$, $X_2$=C-(4-(4-methyl-piperazine-1-carbonyl)phenyl), $X_3$=CH, $X_4$=C—Cl, A=cyclohexyl, X=NH, Z=O, Y=NH To a stirred solution of Example 85 (1 g, 2.55 mmol) in DCM (15 mL) at 18 to 20° C. was added a solution of thionyl chloride (0.6 g, 5 mmol) and DMF (0.8 mL). The mixture was stirred at 18 to 20° C. for 2 h. The resulting mixture was concentrated in vacuo at 55° C. Toluene (10 mL) was added to the intermediate and concentrated in vacuo at 55° C. (This procedure was repeated to ensure all the unreacted thionyl chloride was removed.). The crude intermediate was dissolved in toluene (10 mL) and N-methyl piperazine (0.5 g, 5 mmol) was added. The reaction was stirred for 15 h at 18 to 20° C. and concentrated in vacuo at 55° C. The crude product was purified by column chromatography (silica 35 g; 60% EtOAc in MeOH) to yield title compound as a pale brown solid (170 mg, 0.35 mmol, 14%) (purity 95%).

$^1$H NMR [(CD$_3$)$_2$SO] δ 1.25 (m, 1H), 1.54 (m, 2H), 1.68 (m, 1H), 1.83 (m, 4H), 2.22 (s, 3H), 2.32 (m, 6H), 3.25 (s, 3H), 3.36–3.40 (br s, 2H), 3.56–3.70 (br s, 2H), 7.05–7.09 (br s, 1H), 7.36 (s, 1H), 7.47 (d, J=8.3 Hz, 2H), 7.58 (d, J=8.3 Hz, 2H), 8.36–8.40 (br s, 1H).

Example 93

8-Chloro-5-methoxyspiro[4H-benzo[d][1,3]oxazin-2-ylamine-4'-4'-(tetrahydro-pyran-4'-yl)]

Formula (III), $X_1$=C—OCH$_3$, $X_2$=CH, $X_3$=CH, $X_4$=C—Cl, A=tetrahydro-pyran-4-yl, X=O, $Z^1$=NH$_2$, Y=N Preparation of N-(2-chloro-5-methoxy-phenyl)-2,2-dimethyl-propionamide (intermediate 12)

To a solution of 2-chloro-5-methoxyaniline hydrochloride (8 g, 41.1 mmol) and triethylamine (12.6 mL, 90.42 mmol) in $CH_2Cl_2$ (200 mL) under nitrogen pivaloyl chloride (5.57 mL, 45.22 mmol) was added dropwise at 0° C. The reaction mixture was stirred at room temperature overnight. The mixture was poured into a saturated aqueous NaHCO$_3$ solution and extracted with $CH_2Cl_2$. The organic extracts were washed with saturated aqueous NaCl solution, dried over Na$_2$SO$_4$, filtered and concentrated. The crude material was purified by flash chromatography on silica gel (cyclohexane/EtOAc:98/2) to afford intermediate 12 as a pink oil (7.54 g, 76%).

$^1$H NMR [CDCl$_3$] δ 8.15 (d, J=3.0 Hz, 1H), 8.0 (br s, 1H), 7.17 (d, J=9.0 Hz, 1H), 6.57 (dd, J=9.0, 3.0 Hz, 1H), 3.79 (s, 3H), 1.33 (s, 9H).

Preparation of N-[6-chloro-2-(4-hydroxy-tetrahydro-pyran-4-yl)-3-methoxy-phenyl]-2,2-dimethyl-propionamide (intermediate 13)

To a stirred solution of intermediate 12 (1 g, 4.13 mmol) in THF (25 mL) under nitrogen at −20° C. was added dropwise n-butyllithium (2.5M in hexane, 4.13 mL, 10.34 mmol). The reaction mixture was stirred at −10° C. for 4 h and n-butyllithium (2.5M in hexane, 4.13 mL, 10.34 mmol) was added dropwise at −10° C. The mixture was further stirred for 7 h and tetrahydropyran-4-one was added dropwise at 0° C. The mixture was stirred overnight at room temperature, poured into water and extracted with EtOAc. The organic extracts were washed with saturated aqueous NaCl solution, dried over $Na_2SO_4$, filtered and concentrated. The crude material was purified by precipitation in EtOAc to afford intermediate 13 as a white powder (0.25 g, 18%).

$^1$H NMR [$CDCl_3$] δ 8.08 (br s, 1H, NH), 7.32 (d, J=8.5 Hz, 1H), 6.82 (d, J=8.5 Hz, 1H), 3.95 (t, J=11.5 Hz, 2H), 3.84 (s, 3H), 3.79 (m, 2H), 3.35 (m, 1H, OH), 2.86 (m, 1H), 2.33 (m, 1H), 1.84 (m, 2H), 1.33 (s, 9H).

Preparation of 6-chloro-2-(3,6-dihydro-2H-pyran-4-yl)-3-methoxy-phenylamine (intermediate 14)

A solution of intermediate 13 (0.365 g, 1.06 mmol) and potassium hydroxide (0.24 g, 4.27 mmol) in glycol (0.5 mL) was stirred at 100° C. overnight. The reaction mixture was poured into water and extracted three times with $CH_2Cl_2$. The combined organic layers were washed with brine, dried over $Na_2SO_4$ and concentrated. The crude product was purified by flash column chromatography (eluent: cyclohexane/EtOAc:90/10) to give title compound (0.187 g, 73%) as a white solid.

$^1$H NMR [$CDCl_3$] δ 7.09 (d, J=9.0 Hz, 1H), 6.24 (d, J=9.0 Hz, 1H), 5.71 (m, 1H), 4.29 (m, 2H), 4.20 (m, 2H), 3.92 (m, 2H), 3.73 (s, 3H), 2.29 (m, 2H).

Preparation of [6-chloro-2-(3,6-dihydro-2H-pyran-4-yl)-3-methoxy-phenyl]-urea (intermediate 15)

A solution of intermediate 14 (0.187 g, 0.78 mmol) and potassium cyanate (0.15 g, 1.95 mmol) in a mixture of acetic acid (5 mL) and water (0.5 mL) was stirred at room temperature overnight. The solvent was evaporated, and the residue taken into a mixture of $CH_2Cl_2$ and an aqueous saturated solution of $NaHCO_3$. The layers were separated, the aqueous one being extracted three times with $CH_2Cl_2$. The combined organic layers were washed with brine, dried over $Na_2SO_4$ and concentrated to give 0.15 g (68%) of crude intermediate 15.

$^1$H NMR [$(CD_3)_2SO$] δ 7.51 (br s, 1H), 7.32 (d, J=8.5 Hz, 1H), 6.89 (d, J=8.5 Hz, 1H), 5.75 (br s, 2H), 5.49 (m, 1H), 4.12 (m, 2H), 3.74 (m, 5H), 2.16 (m, 2H).

Preparation of 8-chloro-5-methoxyspiro[4H-benzo[d][1,3]oxazin-2-ylamine-4-4'-(3'-iodo-tetrahydro-pyran-4'-yl)] (intermediate 16)

A solution of iodine (0.23 g, 0.9 mmol) and sodium iodide (0.2 g, 1.35 mmol) in an aqueous solution of $NaHCO_3$ (10%) (3 mL) was added dropwise to a stirred solution of crude intermediate 15 (0.128 g, 0.45 mmol) in $CH_2Cl_2$ (5 mL) at room temperature. After a further 3 h, the reaction mixture was treated with a small amount of $Na_2S_2O_3$. The layers were separated and the aqueous one being extracted three times with $CH_2Cl_2$. The combined organic layers were dried over $Na_2SO_4$, filtered and concentrated. The crude material was precipitate in $Et_2O$ to yield intermediate 16 (0.1 g, 56%) as a white solid after drying in vacuo at 50° C.

$^1$H NMR [$(CD_3)_2SO$] δ 7.26 (d, J=8.8 Hz, 1H), 7.17 (br s, 2H), 6.59 (d, J=8.8 Hz, 1H), 4.47 (m, 1H), 4.25 (dd, J=10.3, 2.0 Hz, 1H), 3.97 (m, 1H), 3.82–3.79 (m, 2H), 3.75 (s, 3H), 3.70–3.62 (m, 1H), 1.81 (d, J=14.6 Hz, 1H).

Preparation of Example 93

To a mixture of intermediate 16 (100 mg, 0.24 mmol) and AIBN (0.02 g, 0.12 mmol) in toluene (4 mL) under argon was added tributyltin hydride (0.08 mL, 0.29 mmol). The reaction mixture was heated to 80° C. for 10 h. After completion, the mixture was concentrated under reduced pressure, the residue was taken into $CH_3CN$ and washed three times with hexane. The crude product was purified by flash column chromatography (eluent: $CH_2Cl_2$/MeOH:95/5) to give the title compound (31 mg, 46%) as a white solid.

$^1$H NMR [$CDCl_3$] δ 7.22 (d, J=9.0 Hz, 1H), 6.48 (d, J=9.0 Hz, 1H), 5.29 (br s, 2H), 3.88–3.85 (m, 4H), 3.80 (s, 3H), 2.81–2.73 (m, 2H), 1.81 (d, J=14 Hz, 2H).

Example 94

8'-Trifluoromethylspiro[cyclohexane-1-4'-3',4'-dihydro)quinazolin]-2'(1'H)-one Formula (I): $X_1$=CH, $X_2$=CH; $X_3$=CH, $X_4$=C—$CF_3$, A=cyclohexyl, X=NH, Z=O, Y=NH The title compound was prepared according to protocol A using 2-trifluoromethylphenylurea (500 mg, 2.45 mmol), polyphosphoric acid (3 g) and cyclohexanone (0.3 mL, 2.89 mmol). The crude product was purified by flash chromatography on silica gel (hexane/EtOAc:100/0 to 50/50) followed by reverse-phase chromatography on a C18 column (water/acetonitrile:90/10 to 0/100) to give the title compound (13 mg, 2% yield).

$^1$H NMR [$CDCl_3$] δ 7.46 (m, 2H), 7.07 (m, 1H), 7.01 (br s, 1H, NH), 5.60 (br s, 1H, NH), 2.00 (m, 2H), 1.83–1.57 (m, 7H), 1.30 (m, 1H).

Example 95

8'-Chloro-6'-cyanomethylspiro[cyclohexane-1-4'-(3',4'-dihydro)quinazolin]-2'(1'H)-one Formula (I): $X_1$=CH, $X_2$=C—$CH_2CN$, $X_3$=CH, $X_4$=C—Cl, A=cyclohexyl, X=NH, Z=O, Y=NH The title compound was prepared according to protocol E. To a stirred solution of Example 7 (1 g, 4 mmol) in glacial acetic acid (15 mL) was sequentially added trioxane (0.55 g, 6 mmol, 1.5 equiv.) and a 48% aqueous solution of hydrobromic acid (5 mL). The mixture was heated to 95° C. overnight, poured on ice. The precipitate was filtered, washed twice with water then with ether to give 1.39 g of 8'-Chloro-6'-bromomethylspiro[cyclohexane-1-4'-(3',4'-dihydro)quinazolin]-2'(1'H)-one as a white solid. The crude bromomethyl derivative (256 mg, 74 mmol) was treated with sodium cyanide (40 mg, 82 mmol, 1.1 equiv.) in DMF (10 mL) and was heated to 60° C. for two hours. The mixture was concentrated under reduced pressure, taken into water, extracted twice with $CH_2Cl_2$, dried over $Na_2SO_4$, filtered and concentrated under reduced pressure. The crude material was purified twice by flash chromatography on silica gel ($CH_2Cl_2$/MeOH:99/1 followed by cyclohexane/EtOAc:60/

40+2% NH$_4$OH), to give the title compound (60 mg,28%) (purity 95%) as a white solid. mp=239° C.

$^1$H NMR [(CD$_3$)$_2$SO] δ 8.50 (br s, 1H, NH), 7.30–7.29 (d, 2H), 7.15 (br s, 1H, NH) 3.94 (s, 2H), 1.81–1.68 (m, 7H), 1.54–1.50 (m, 2H), 1.25 (m, 1H).

Example 96

8'-Chloro-5'-(3-dimethylamino-2-hydroxy-propoxy)-spiro[cyclohexane-1-4'-(3',4'-dihydro)quinazolin]-2' (1'H)-one X$_1$=C—OCH$_2$CH(OH)CH$_2$N(CH$_3$)$_2$, X$_2$=CH, X$_3$=CH, X$_4$=C—Cl, A=cyclohexyl, X=NH, Z=O Y=NH Preparation of 8'-Chloro-5'-(oxiran-2-ylmethoxy)-spiro[cyclohexane-1-4'-(3',4'-dihydro)quinazolin]-2' (1'H)-one (intermediate 17)

To a stirred solution of Example 63 (5 g, 18.75 mmol) in DMF (80 mL) at 18 to 20° C. was added anhydrous potassium carbonate (6.5 g, 46.9 mmol) followed by epibromohydrin (2.83 g, 20.6 mmol) in one portion. The mixture was heated to 80° C. for 2 h and then 90° C. for 2 h. The crude mixture was quenched into water (800 ml) and extracted with EtOAc (2×1 L). The organic layer was dried over anhydrous MgSO$_4$, filtered and concentrated in vacuo at 40° C. to give the crude product (3.4 g, 57% yield). The crude product was subjected to column chromatography (silica 100 g, eluting with 30% to 50% EtOAc in heptane) to afford intermediate 17 (2.7 g, 45% yield) as a white solid after drying in vacuo at 45° C. (purity 98.9%).

$^1$H NMR [CDCl$_3$] δ 6.96 (d, J=8.8 Hz, 1H), 6.76–6.79 (br s, 1H), 6.24 (d, J=8.8 Hz, 1H), 5.30–5.35 (br s, 1H), 4.09 (dd, J=2.8, 10.9 Hz, 1H), 3.67 (dd, J=6.3, 10.9 Hz, 1H), 3.16 (m, 1H), 2.73 (dd, J=4.3, 4.8 Hz, 1H), 2.53 (dd, J=2.5, 4.8 Hz, 1H), 2.28–2.38 (m, 2H), 1.45–1.61 (m, 5H), 1.23–1.36 (m, 2H), 1.04–1.15 (m, 1H).

Preparation of Example 96

To a stirred solution of dimethylamine in EtOH (17 mL, 5.6M, 95.2 mmol) at 18 to 20° C. was added intermediate 17 (730 mg, 2.26 mmol) in one portion. The mixture was heated to 40° C. for 2.6 h. The solid was filtered, washed with EtOH (40 mL) and dried in vacuo at 40° C. to yield the desired product as a white solid (515 mg, 1.40 mmol, 62%)(purity 99%).

$^1$H NMR [(CD$_3$)$_2$SO] δ 7.10 (d, J=9.0 Hz, 1H), 6.90–6.94 (br s, 1H), 6.42 (d, J=9.0 Hz, 1H), 5.44–5.50 (br s, 1H), 3.99 (m, 1H), 3.91 (m, 2H), 3.50–3.54 (br s, 1H), 2.52 (m, 3H), 2.33 (dd, J=12.1, 3.5 Hz, 1H), 2.27, (s, 6H), 1.59–1.76 (m, 5H), 1.38–1.52 (m, 2H), 1.18–1.30 (m, 1H).

Example 97

8'-Chloro-5'-(3-methylamino-2-hydroxy-propoxy)-spiro[cyclohexane-1-4'-(3',4'-dihydro)quinazolin]-2' (1'H)-one X$_1$=C—OCH$_2$CH(OH)CH$_2$NHCH$_3$, X$_2$=CH, X$_3$=CH, X$_4$=C—Cl, A=cyclohexyl, X=NH, Z=O, Y=NH To a stirred solution of methylamine in EtOH (12 mL, 8M, 96 mmol) at 18 to 20° C. was added intermediate 17 (500 mg, 1.55 mmol) in one portion. The mixture was heated to 40° C. for 2 h. A further portion of methylamine in EtOH (10 mL, 8M, 80 mmol) was added and the reaction heated at 40° C. for another 20 mins. The mixture was concentrated in vacuo at 40° C. and TBME (30 mL) was added. The white solid (390 mg, 1.1 mmol) formed was filtered to give the crude product (390 mg, 1.1 mmol). The material was dissolved in DCM (20 mL) and heated to 35° C. for ten minutes in the presence of charcoal (2 g). The suspension was filtered through a pad of celite, washed with DCM (20 mL) and concentrated in vacuo at 40° C. to yield the title compound as a white solid (200 mg, 36% yield) (purity 97.3%).

$^1$H NMR [(CD$_3$)$_2$SO] δ 7.21 (d, J=9.0 Hz, 1H), 7.00–7.06 (br s, 1H), 6.54 (d, J=9.0 Hz, 1H), 5.55–5.59 (br s, 1H), 4.04 (m, 2H), 4.13 (m, 1H), 2.90 (dd, J=3.8, 12.0 Hz, 1H), 2.80 (dd, J=8.4, 12.0 Hz, 1H), 2.60 (m, 2H), 2.54 (s, 3H), 2.05–2.25 (br s, 2H), 1.70–1.88 (m, 5H), 1.48–1.63 (m, 2H), 1.25–1.38 (m, 1H).

Example 98

8'-Chloro-5'-[2-(ethoxycarbonylmethyl-amino)-ethoxy]-spiro[cyclohexane-1-4'-(3',4'-dihydro)quinazolin]-2'(1'H)-one X$_1$=C—OCH$_2$CH$_2$NHCH$_2$COOCH$_2$CH$_3$, X$_2$=CH, X$_3$=CH, X$_4$=C—Cl, A=cyclohexyl, X=NH Z=O, Y=NH To a stirred suspension of intermediate 8 (2.0 g, 5.14 mmol) in acetonitrile (28 mL) was added a solution of ethyl glycinate (3.72 g, 3.6 mmol) in acetonitrile (12 mL). The mixture was stirred under reflux for 24 hours. Concentration in vacuo at 40° C. afforded an orange oil (5 g) which was subjected to column chromatography (silica 110 g, eluting with 50% to 100% EtOAc in heptane followed by 90% EtOAc in DCM) to give the title compound (450 mg, 22% yield) as a white solid after drying in vacuo at 45° C.

$^1$H NMR [(CD$_3$)$_2$SO] δ 7.94–7.98 (br s, 1H), 7.24 (d, J=9.0 Hz, 1H), 7.01–7.05 (br s, 1H), 6.62 (d, J=9.0 Hz, 1H), 4.08 (t, J=7.1 Hz, 2H), 4.01 (t, J=5.6 Hz, 2H), 3.41 (s, 2H), 2.95 (t, J=5.6 Hz, 2H), 2.45–2.55 (m, 2H), 2.12 (br s, 1H), 1.70–1.85 (m, 2H), 1.52–1.63 (m, 3H), 1.40–1.49 (m, 2H), 1.21–1.25 (m, 1H), 1.18 (t, J=7.1 Hz, 3H).

Example 99

8'-Chloro-5'-[2-(carboxymethyl-amino)-ethoxy]-spiro[cyclohexane-1-4'-(3',4'-dihydro)quinazolin]-2' (1'H)-one hydrochloride X$_1$=C—OCH$_2$CH$_2$NHCH$_2$COOH, X$_2$=CH, X$_3$=CH, X$_4$=C—Cl, A=cyclohexyl, X=NH, Z=O, Y=NH To a stirred solution of Example 98 (600 mg, 1.52 mmol) in 1,4-dioxane (8 mL) was added a solution of HCl (6N, 10.5 mL) at 18 to 20° C. The reaction mixture was heated to 90° C. for 2 h. It was then quenched onto water (100 mL) and washed with DCM (200 mL). The aqueous layer was concentrated and dried in vacuo at 60° C. to give title compound (614 mg, 99.9% yield) as a white solid (purity 95.9%).

$^1$H NMR (400 MHz, CD$_3$OD) δ 7.07 (d, J=9.1 Hz, 1H), 6.56 (d, J=9.1 Hz, 1H), 4.17 (t, J=5.6 Hz, 2H), 3.86 (s, 2H), 3.39 (t, J=5.6 Hz, 2H), 2.24–2.34 (m, 2H), 1.40–1.60 (m, 7H), 1.15–1.26 (m, 1H).

Biological Results

In vitro Inhibition of the Phosphodiesterase 7 and of other Phosphodiesterases

The capacity of the compounds of the invention to inhibit cyclic nucleotide phosphodiesterases was evaluated by measuring their IC$_{50}$ (concentration necessary to inhibit the enzymatic activity by 50%).

PDE3A3, PDE4D3, PDE7A1 were cloned and expressed in insect cells Sf21 using using the baculovirus expression system and we uses directly the cell culture supernatant as enzyme source. The source of PDE1 and of PDE5 were human cell lines (respectively TPH1 human monocytes and MCF7 human caucasian breast adenocarcinoma).

They were obtained partially purified on an anion exchange column (Mono Q) according to a method adapted from Lavan B. E., Lakey T., Houslay M. D. Biochemical pharmacology, 1989, 38 (22), 4123–4136.

Measurement of the enzymatic activity for the various types of PDE was then made according to a method adapted from W. J. Thompson et al. 1979, Advances in Cyclic Nucleotide Research, Vol. 10: 69–92, ed. G. Brooker et al. Raven Press, NY.

The substrate used was cGMP for PDE1 and PDE5 and cAMP for PDE 3, PDE 4 and PDE 7. The substrate concentration was 0.2 µM for PDE 1, PDE 3 and PDE 5, 0,25 µM for PDE 4 and 50 nM for PDE 7.

The enzymatic reaction was stopped after 1 hour for PDE 1, PDE 3 and PDE 5 and 10 minutes for PDE 4 and PDE 7.

In order to determine their $IC_{50}$, compounds of the invention were assayed at 8 to 11 concentrations ranging from 0.02 nM to 100 µM for PDE 4 and PDE 7 and at least at 6 concentrations ranging from 0,1 µM to 30 µM for PDE 1, 3 and 5.

The $IC_5$ (µM) were determined for some of the compounds of the invention, and the $IC_{50}$ of most of the compounds of examples 1 to 99 were comprise between 0.008 µM and 18 µM.

The activity of some of the most active compounds are summarized in the following table:

| Example number | $IC_{50}$ PDE7 (µM) |
|---|---|
| 15 | 0.014 |
| 26 | 0.016 |
| 34 | 0.012 |
| 38 | 0.018 |
| 41 | 0.02 |
| 51 | 0.008 |
| 52 | 0.015 |
| 53 | 0.013 |
| 54 | 0.013 |

These results show that the compounds of the invention inhibit PDE7 at very low concentrations, with some $IC_{50}$ values lower than 100 nM. The results of the assays with other PDE (1, 3, 4 and 5) show $IC_{50}$ values often superior to 1 µM or even 10 µM. It demonstrates that compounds of the invention are strong and selective PDE7 inhibitors.

What is claimed is:

1. Compounds having the following formula (I):

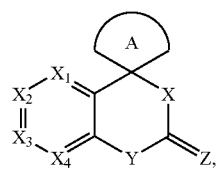

(I)

in which,
a) $X_1$, $X_2$, $X_3$ and $X_4$ are the same or different and are selected from:
C—$R^1$, in which $R^1$ is selected from:
Q1, or lower alkyl, lower alkenyl or lower alkynyl, these groups being unsubstituted or substituted with one or several groups Q2;
the group $X^5$—$R^5$ in which,
$X_5$ is selected from:
a single bond,
lower alkylene, lower alkenylene or lower alkynylene, optionally interrupted with 1 or 2 heteroatoms chosen from O, S, S(=O), $SO_2$ or N, the carbon atoms of these groups being unsubstituted or substituted with one or several groups, identical or different, selected from $SR^6$, $OR^6$, $NR^6R^7$, =O, =S or =N—$R^6$ which $R^6$ and $R^7$ are the same or different and are selected from hydrogen or lower alkyl, and,
$R^5$ is selected from aryl, heteroaryl, cycloalkyl optionally interrupted with C(=O) or with 1, 2, or 3 heteroatoms chosen from O, S, S(=O), $SO_2$ or N, cycloalkenyl optionally interrupted with C(=O) or with 1, 2, or 3 heteroatoms chosen from O, S, S(=O), $SO_2$ or N, or a bicyclic group,
these groups being unsubstituted or substituted with one or several groups selected from Q3, heteroaryl or lower alkyl optionally substituted with Q3;
in which Q1, Q2, Q3 are the same or different and are selected from
hydrogen, halogen, CN, $NO_2$, $SO_3H$, P(=O)$(OH)_2$ $OR^2$, OC(=O)$R^2$, C(=O)$OR^2$, $SR^2$, S(=O)$R^2$, C(=O)—NH—$SO_2$—$CH_3$, $NR^3R^4$, Q-$R^2$, Q-$NR^3R^4$, $NR^2$-Q-$NR^3R^4$ or $NR^3$-Q-$R^2$ in which Q is selected from C(=NR), C(=O), C(=S) or $SO_2$, R is selected from hydrogen, CN, $SO_2NH_2$ or lower alkyl and $R^2$, $R^3$ and $R^4$ are the same or different and are selected from:
hydrogen,
lower alkyl optionally interrupted with C(=O), Q4-aryl, Q4-heteroaryl, Q4-cycloalkyl optionally interrupted with C(=O) or with 1 or 2 heteroatoms chosen from O, S, S(=O), $SO_2$ or N, or Q4-cycloalkenyl optionally interrupted with C(=O) or with 1 or 2 heteroatoms chosen from O, S, S(=O), $SO_2$ or N, in which
Q4 is selected from $(CH_2)_n$, lower alkyl interrupted with one heteroatom selected from O, S or N, lower alkenyl or lower alkynyl, these groups being optionally substituted with lower alkyl, OR' or NR=R" in which R' and R" are the same or different and are selected from hydrogen or lower alkyl;
n is an integer selected from 0, 1, 2, 3 or 4;
these groups being unsubstituted or substituted with one or several groups selected from lower alkyl, halogen, CN, $OH_3$, $SO_3H$, $SO_2OH_3$, C(=O)—NH—$SO_2$—$CH_3$, $OF_3$, $OR^6$, $COOR_6$, C(=O)$R^6$, $NR^6R^7$, $NR^6C$(=O)$R^7$, C(=O)$NR^6R^7$ or $SO_2NR^6R^7$, in which $R^6$ and $R^7$ are the same or different and are selected from hydrogen or lower alkyl optionally substituted with one or two groups selected from OR, COOR or $NRR^8$ in which R and $R^8$ are hydrogen or lower alkyl, and,
$R^6$ and $R^7$, and/or, $R^3$ and $R^4$, together with the nitrogen atom to which they are linked, can form a 4- to 8-membered heterocyclic ring, which may contain one or two heteroatoms selected from O, S, S(=O), $SO_2$, or N, and which may be substituted with,
$(CH_2)_n$-Q5, in which n is an integer selected from 0, 1, 2 and 3, and Q5 is a 4- to 8-membered heterocyclic ring which may contain one or two heteroatoms selected from O, S or N and which may be substituted with a lower alkyl, or, a lower alkyl optionally substituted with OR', NR'R", C(=O)NR'R" or COOR' in which R' and R" are the same or different and are selected from, H, or, lower alkyl optionally substituted with OR or COOR in which R is hydrogen or lower alkyl and, R' and R" together with the nitrogen atom to which they are linked, can form a 4- to 8-membered heterocyclic ring, which may contain one or two heteroatoms selected from O, S or N; or, when $X_1$, and $X_2$ both represent C—$R^1$, the 2 substituents $R^1$ may form together with the carbon atoms to which they are attached, a 5-membered heterocyclic ring comprising a nitrogen atom and optionally a second heteroatom selected from O, S or N;

b) X is $NR^9$, in which $R^9$ is hydrogen, c) Y is N—$R^{12}$, in which $R^{12}$ is hydrogen, d) Z is O, S or $NR^{13}$ in which $R^{13}$ is CN, e) A is a cycle chosen from:

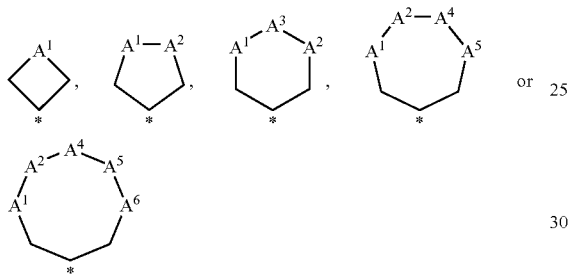

in which, $A^1$, $A^2$, $A^3$, $A^4$, $A^5$ and $A^6$ represent a carbon atom,

* represents the carbon atom which is shared between the cycle A and the backbone cycle containing X and/or Y;

each carbon atom of the cycle A is unsubstituted or substituted with 1 or 2 groups, identical or different, selected from lower alkyl;

2 atoms of the cycle A, which are not adjacent, may be linked by a 2, 3 or 4 carbon atom chain;

or their tautomeric forms, their racemic forms or their isomers and their pharmaceutically acceptable derivatives.

2. A compound of formula (I) according to claim 1 in which a) $X_1$, $X_2$ and $X_3$ are the same or different and are C—$R^1$, in which $R^1$ is selected from:

hydrogen, halogen, CN, $SO_3H$, $NO_2$, $CF_3$, $OR^2$, $SR^2$, $NR^2R^3$, $COR^2$, $COOR^2$, $CONR^2R^3$, $SO_2CH_3$, $SO_2NR^2R^3$ in which $R^2$ and $R^3$ are the same or different and are selected from hydrogen or lower alkyl optionally substituted with halogen, CN, $OR^6$, $COOR^6$, $NR^6R^7$, $SO_2NR^6R^7$ or C(=O)$NR^6R^7$ in which $R^6$ and $R^7$ are the same or different and are selected from hydrogen or lower alkyl, and, $R^6$ and $R^7$, together with the nitrogen atom to which they are linked, can form a 4- to 8-membered heterocyclic ring;

lower alkyl, lower alkenyl or lower alkynyl, these groups being unsubstituted or substituted with 1, 2 or 3 groups selected from halogen, CN, $SO_3$ H, $OR^2$, $COOR^2$, $NR^3R^4$, $SO_2NR^3R^4$ or C(=O)$NR^3R^4$ in which $R^2$, $R^3$ and $R^4$ are the same or different and are selected from hydrogen or lower alkyl, and, $R^3$ and $R^4$, together with the nitrogen atom to which they are linked, can form a 4- to 8-membered heterocyclic ring;

the group $X_5$—$R^5$ in which, $X_5$ is selected from a lower alkylene or a single bond, and, $R^5$ is selected from phenyl, pyridyl or indolyl, these groups being unsubstituted or substituted with 1, 2 or 3 groups selected from Q3, heteroaryl or lower alkyl optionally substituted with Q3 in which Q3 is selected from:

halogen, CN, $SO_3H$, $NO_2$, $CF_3$, $OR^2$, $OC(=O)R^2$, $C(=O)R^2$, $C(=O)OR^2$, NH—$C(=O)R^2$, $NR^3R^4$, $SO_2NR^3R^4$ or $C(=O)NR^3R^4$ in which $R^2$, $R^3$ and $R^4$ are the same or different and are selected from:

hydrogen, lower alkyl unsubstituted or substituted with one or several groups selected from halogen, $OR^6$, $COOR^6$ or $NR^6R^7$ in which $R^6$ and $R^7$ are the same or different and are selected from hydrogen or lower alkyl and, $R^6$ and $R^7$, and/or, $R^3$ and $R^4$, together with the nitrogen atom to which they are linked, can form a 4- to 8-membered heterocyclic ring, which may contain one or two heteroatoms selected from O, S or N, and which may be substituted with, a 4- to 8-membered heterocyclic ring, which may contain one or two heteroatoms selected from O, S or N and which may be substituted with a lower alkyl, or, a lower alkyl optionally substituted with OR', NR'R", C(=O)NR'R" or COOR' in which R' and R" are the same or different and are selected from, H, or, lower alkyl optionally substituted with OR or COOR in which R is hydrogen or lower alkyl and, R' and R" together with the nitrogen atom to which they are linked, can form a 4- to 8-membered heterocyclic ring, which may contain one or two heteroatoms selected from O, S or N;

b) $X_4$ is C—$R^1$ in which $R^1$ is selected from hydrogen, halogen, CN, $NO_2$, $SO_2CH_3$, $SO_3H$, $CH_3$, $CF_3$, $OR^2$, $SR^2$, $NR^2R^3$, $COOR^2$, $CONR^2R^3$ or $SO_2NR^2R^3$ in which $R^2$ and $R^3$ are the same or different and are selected from hydrogen or lower alkyl;

c) X is NH;

d) Y is NH;

e) Z is chosen from O, S or $NR^{13}$ in which $R^{13}$ is CN;

f) A is a cycle chosen from:

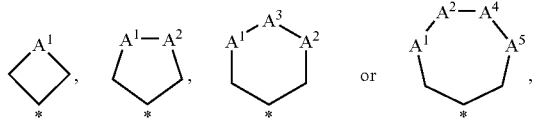

$A^1$, $A^2$, $A^3$, $A^4$ and $A^5$ are the same or different and are selected from:

a carbon atom, unsubstituted or substituted with 1 or 2 groups, identical or different, selected from lower alkyl,

* represents the carbon atom which is shared between the cycle A and the backbone cycle containing X and/or Y; and 2 atoms of the cycle A, which are not adjacent, may be linked by a 2, 3 or 4 carbon atom chain.

3. A compound of formula (I), according to claim 1 in which, $X_1$, $X_2$, $X_3$ and $X_4$ are the same or different and are C—$R^1$, in which $R^1$ is selected from:
Q1, or
lower alkyl, lower alkenyl or lower alkynyl, these groups being unsubstituted or substituted with 1, 2 or 3 groups Q2;
the group $X_5$—$R^5$ in which,
$X_5$ is selected from:
a single bond,
a lower alkylene, optionally interrupted with 1 heteroatom chosen from O, S and N;
$R^5$ is selected from aryl, heteroaryl, cycloalkyl optionally interrupted with C(=O) or with 1, 2, or 3 heteroatoms chosen from O, S, S(=O), $SO_2$ or N, cycloalkenyl optionally interrupted with C(=O) or with 1, 2, or 3 heteroatoms chosen from O, S, S(=O), $SO_2$ or N, or a bicyclic group,
these groups being unsubstituted or substituted with 1, 2 or 3 groups selected from Q3, heteroaryl or lower alkyl optionally substituted with Q3;
in which Q1, Q2, Q3 are the same or different and are selected from
hydrogen, halogen, CN, $NO_2$, $SO_3H$,
$OR^2$, OC(=O)$R^2$, C(=O)$OR^2$, $SR^2$, S(=O)$R^2$, C(=O)—NH—$SO_2$—$CH_3$, $NR^3R^4$, Q-$R^2$, Q-$NR^3R^4$, $NR^2$-Q-$NR^3R^4$ or $NR^3$-Q-$R^2$ in which Q is selected from C(=NR), C(=O), C(=S) or $SO_2$, R is selected from hydrogen or lower alkyl and $R^2$, $R^3$ and $R^4$ are the same or different and are selected from:
hydrogen,
lower alkyl optionally interrupted with C(=O), Q4-aryl, Q4-heteroaryl, Q4-cycloalkyl optionally interrupted with C(=O) or with 1 or 2 heteroatoms chosen from O, S, S(=O), $SO_2$ or N, or Q4-cycloalkenyl optionally interrupted with C(=O) or with 1 or 2 heteroatoms chosen from O, S, S(=O), $SO_2$ or N, in which
Q4 is selected from $(CH_2)_n$, lower alkyl interrupted with one heteroatom selected from O, S or N, lower alkenyl or lower alkynyl, these groups being optionally substituted with lower alkyl, OR' or NR'R" in which R' and R" are the same or different and are selected from hydrogen or lower alkyl;
n is an integer selected from 0, 1, 2, 3 or 4;
these groups being unsubstituted or substituted with 1 or 2 groups selected from lower alkyl, halogen, CN, $CH_3$, $SO_3H$, $SO_2CH_3$, $CF_3$, C(=O)NH—$SO_2CH_3$, $OR^6$, $COOR^6$, C(=O)$R^6$, $NR^6R^7$, C(=O)$NR^6R^7$ or $SO_2NR^6R^7$, in which $R^6$ and $R^7$ are the same or different and are selected from hydrogen or lower alkyl optionally substituted with one or two groups selected from OR, COOR or $NRR^8$ in which R and $R^8$ are hydrogen or lower alkyl, and,
$R^6$ and $R^7$, and/or, $R^3$ and $R^4$, together with the nitrogen atom to Which they are linked, can form a 4- to 8-membered heterocyclic ring, which may contain one or two heteroatoms selected from O, S, S(=O), $SO_2$ or N, and which may be substituted with,
$(CH_2)_n$-Q5, in which n is an integer selected from 0, 1, 2 and 3, and Q5 is a 4- to 8-membered heterocyclic ring which may contain one or two heteroatoms selected from O, S or N and which may be substituted with a lower alkyl, or,
a lower alkyl optionally substituted with OR', NR'R", C(=O)NR'R" or COOR' in which R' and R" are the same or different and are selected from,
H, or,
lower alkyl optionally substituted with OR or COOR in which R is hydrogen or lower alkyl and, R' and R" together with the nitrogen atom to which they are linked, can form a 4- to 8-membered heterocyclic ring, which may contain one or two heteroatoms selected from O, S or N.

4. A compound of formula (I) according to claim 1, in which $X_1$, $X_2$, $X_3$ and $X_4$ are the same or different and are C—$R^1$, in which $R^1$ is selected from:
Q1, or
lower alkyl or lower alkynyl, these groups being unsubstituted or substituted with 1, 2 or 3 fluorine atoms, $OR^3$, $COOR^3$ or $NR^3R^4$ in which $R^3$ and $R^4$ are the same or different and are selected from hydrogen or lower alkyl;
$R^3$ and $R^4$ together with the nitrogen atom to which they are linked, may also form a 6-membered heterocyclic ring, which may contain one or two heteroatoms selected from O or N;
the group $X_5$—$R^5$ in which $X_5$ is a single bond and $R^5$ is selected from aryl, heteroaryl, or a bicyclic group, these groups being unsubstituted or substituted with 1, 2 or 3 groups selected from Q3,
in which Q1 and Q3 are the same or different and are selected from
hydrogen, halogen, CN, lower alkyl,
OR, C(=O)$OR^2$, $NR^3R^4$, C(=O)$NR^3R^4$ or $SO_2NR^3R^4$ in which $R^2$, $R^3$ and $R^4$ are the same or different and are selected from:
hydrogen,
lower alkyl, Q4-heteroaryl in which Q4 is selected from lower alkyl interrupted with one heteroatom selected from O, S or N and $(CH_2)_n$ in which n is an integer selected from 0, 1, 2 or 3;
these groups being unsubstituted or substituted with 1 or 2 groups selected from lower alkyl, CN, $SO_3H$, C(=O)—NH—$SO_2$—$CH_3$, $OR^6$, $COOR^6$ or $NR^6R^7$, in which $R^6$ and $R^7$ are the, same or different and are selected from hydrogen or lower alkyl optionally substituted with one or two groups selected from OR, COOR or $NRR^8$ in which R and $R^8$ are hydrogen or lower alkyl, and,
$R^6$ and $R^7$, and/or, $R^3$ and $R^4$, together with the nitrogen atom to which they are linked, can form a 4- to 6-membered heterocyclic ring, which may contain one or two heteroatoms selected from O or N, and which may be substituted with,
a 6-membered heterocyclic ring, which may contain one or two heteroatoms selected from O or N and which may be substituted with a lower alkyl, or,
a lower alkyl optionally substituted with OR', NR'R", C(=O)NR'R" or COOR' in which R' and R" are the same or different and are selected from,
H, or,
lower alkyl optionally substituted with OR or COOR in which R is hydrogen or lower alkyl and,
R' and R" together with the nitrogen atom to which they are linked, can form a 6-membered heterocyclic ring, which may contain one or two heteroatoms selected from O or N.

5. A compound of formula (I) according to claim 3, in which, $X_1$ is C—$R^1$, in which $R^1$ is selected from
hydrogen, halogen, $OR^2$, $COR^2$, $COOR^2$, $CONR^2R^3$ in which $R^2$ and $R^3$ are the same or different and are selected from
hydrogen,
lower alkyl, Q4-aryl, Q4-heteroaryl, Q4-cycloalkyl optionally interrupted with C(=O) or with 1 or 2 heteroatoms chosen from O, S, or N, or Q4-cycloalkenyl optionally interrupted with C(=O) or with 1 or 2 heteroatoms chosen from O, S, or N, in which Q4 is selected from $(CH_2)_n$, lower alkyl interrupted with one heteroatom selected from O, S or N, lower alkenyl or lower alkynyl;

n is an integer selected from 0, 1, 2 or 3;

these groups being unsubstituted or substituted with lower alkyl, CN, $OR^6$, $SO_3H$, $C(=O)$—NH—$SO_2$—$CH_3$, $CONR^6R^7$, $COOR^6$, $COR^6$ or $NR^6R^7$, in which and $R^6$ and $R^7$ are the same or different and are selected from hydrogen or lower alkyl, optionally substituted with $NH_2$, COOH, OH;

$R^6$ and $R^7$ together with the nitrogen atom to which they are linked, can form a 4- to 8-membered heterocyclic ring, which may contain one or two heteroatoms selected from O, S or N and which may be substituted with, $(CH_2)_n$-Q5, in which n is an integer selected from 0, 1, 2 and 3, and Q5 is a 4- to 8-membered heterocyclic ring which may contain one or two heteroatoms selected from O, S or N and which may be substituted with a lower alkyl, or, COR' or lower alkyl optionally substituted with OR', NR'R", C(=O)NR'R" or COOR' in which R' and R" are the same or different and are selected from hydrogen or lower alkyl;

lower alkyl optionally substituted with CN, $SO_3H$, $OR^3$, $NR^3R^4$, $COOR^3$ or $CONR^3R^4$ in which $R^3$ and $R^4$ are the same or different and are selected from hydrogen and, lower alkyl optionally substituted with OH, COOH or $NH_2$;

the group $X_5$—$R^5$ in which $X_5$ is a lower alkylene optionally interrupted with a heteroatom selected from O and N and $R^5$ is selected from aryl, heteroaryl, cycloalkyl optionally interrupted with C(=O) or with 1, 2, or 3 heteroatoms chosen from O, S or N and cycloalkenyl optionally interrupted with C(=O) or with 1,2, or 3 heteroatoms chosen from O, S or N, these groups being unsubstituted or substituted $OR^3$ or $COOR^3$ in which $R^3$ is selected from hydrogen and lower alkyl;

$R^3$ and $R^4$, together with the nitrogen atom to which they are linked, can form a 4- to 6-membered heterocyclic ring, which may contain one or two heteroatoms selected from O or N, and which may be substituted with, $(CH_2)_n$-Q5, in which n is an integer selected from 0, 1, 2 and 3, and Q5 is a 4- to 8-membered heterocyclic ring which may contain one or two heteroatoms selected from O, S or N and which may be substituted with a lower alkyl, or, C(=O)—R' or a lower alkyl optionally substituted with OR', NR'R", C(=O)NR'R" or COOR' in which R' and R" are the same or different and are selected from hydrogen or lower alkyl.

6. A compound of formula (I) according to claim 3 in which $X_1$ is C—$R^1$, in which $R^1$ is selected from hydrogen, halogen or $OR^2$ in which $R^2$ is selected from hydrogen, lower alkyl, unsubstituted or substituted with CN, C(=O)—NH—$SO_2$—$CH_3$, $OR^6$, $SO_3H$, $COOR^6$ or $NR^6R^7$;

Q4-oxadiazole, Q4-tetrazole, Q4-morpholine, Q4-furan, Q4-isoxazole, in which Q4 is selected from lower alkyl interrupted with one heteroatom selected from O, S or N and $(CH_2)_n$ in which n is an integer selected from 1 and 2;

these groups being unsubstituted or substituted with $CH_3$, $OR^6$ or $COOR^6$, in which $R^6$ and $R^7$ are the same or different and are selected from hydrogen or lower alkyl, optionally substituted with $NH_2$ or COOH.

7. A compound of formula (I) according to claims 3 in which $X_2$ is C—$R^1$, in which $R^1$ is $X_5$—$R^5$, in which $X_5$ is a single bond, $R^5$ is phenyl or pyridyl, optionally substituted with a lower alkyl, and, substituted with $C(=O)NR^3R^4$ in which $R^3$ and $R^4$ together with the nitrogen atom to which they are linked, form a 4- to 8-membered heterocyclic ring, which may contain one or two heteroatoms selected from O, S, S(=O), $SO_2$ or N, and which may be substituted with, a 4- to 8-membered heterocyclic ring, which may contain one or two heteroatoms selected from O, S or N and which may be substituted with a lower alkyl, or, a lower alkyl optionally substituted with OR', NR'R", C(=O)NR'R" or COOR' in which R' and R" are the same or different and are selected from, H, or, lower alkyl optionally substituted with OR or COOR in which R is hydrogen or lower alkyl and, R' and R" together with the nitrogen atom to which they are linked, can form a 4- to 8-membered heterocyclic ring, which may contain one or two heteroatoms selected from O, S or N.

8. A compound of formula (I) according to claim 3 in which one of $X_1$, $X_2$, $X_3$ and $X_4$ is C—$R^1$ in which $R^1$ is hydrogen while the others are identical or different and are C—$R^1$ in which $R^1$ is other than hydrogen.

9. A compound of formula (I) according to claim 8, in which $X_3$ is C—$R^1$ in which $R^1$ is hydrogen.

10. A compound of formula (I) according to claim 3 in which $X_3$ is C—$R^1$, in which $R^1$ is selected from:

hydrogen or halogen, or, $X_5$—$R^5$ in which $R^5$ is a single bond and $R^5$ is aryl or heteroaryl, optionally substituted with one, two or three groups which are the same or different and which are selected from halogen, CN, $CF_3$, $SO_2Me$, $OR^2$, $COOR^2$, $NR^2R^3$, $SO_2NR^2R^3$ and $CONR^2R^3$ in which $R^2$ and $R^3$ are the same or different and are selected from hydrogen or lower alkyl.

11. A compound of formula (I) according to claim 10 in which $X_3$ is C—$R^1$, in which $R^1$ is selected from hydrogen or halogen.

12. A compound of formula (I) according to claim 8 in which $X_4$ is C—$R^1$, in which $R^1$ is selected from hydrogen, halogen, $CF_3$, O-lower alkyl, $COOR^2$ or, lower alkyl optionally substituted with $OR^2$, $COOR^2$ or $SO_2NR^2R^3$ in which $R^2$ and $R^3$ are the same or different and are selected from hydrogen or lower alkyl.

13. A compound of formula (I) according to claim 1 in which Z is O.

14. A compound of formula (I) according to claim 1 in which A is selected from cyclohexyl or cycloheptyl, unsubstituted or substituted with $CH_3$.

15. A compound of formula (I) according to claim 1 in which A is selected from unsubstituted cyclohexyl or cycloheptyl.

16. A compound selected from the group consisting of

Spiro[cyclohexane-1-4'-(3',4'-dihydro)quinazolin]-2' (1'H)-one,

6'-Methoxyspiro[cyclohexane-1-4'-(3',4'-dihydro) quinazolin]-2'(1'H)-one,

Spiro[cycloheptane-1-4'-(3',4'-dihydro)quinazolin]-2' (1'H)-one,

7'-Methoxyspiro[cyclohexane-1-4'-(3',4'-dihydro) quinazolin]-2'(1'H)-one,

6'-Phenylspiro[cycloheptane-1-4'-(3',4'-dihydro)quinazolin]-2'(1'H)-one,

8'-Methoxyspiro[cyclohexane-1-4'-(3',4'-dihydro) quinazolin]-2'(1'H)-one,

8'-Chlorospiro[cyclohexane-1-4'-(3',4'-dihydro)quinazolin]-2'(1'H)-one,

7'-chlorospiro[cyclohexane-1-4'-(3',4'-dihydro)quinazolin]-2'(1'H)-one,
5'-chlorospiro[cyclohexane-1-4'-(3',4'-dihydro)quinazolin]-2'(1'H)-one,
8'-methylspiro[cyclohexane-1-4'-(3',4'-dihydro)quinazolin]-2'(1'H)-one,
6'-chlorospiro[cyclohexane-1-4'-(3',4'-dihydro)quinazolin]-2'(1'H)-one,
8'-bromospiro[cyclohexane-1-4'-(3',4'-dihydro)quinazolin]-2'(1'H)-one,
8'-fluorospiro[cyclohexane-1-4'-(3',4'-dihydro)quinazolin]-2'(1'H)-one,
6'-methylspiro[cyclohexane-1-4'-(3',4'-dihydro)quinazolin]-2'(1'H)-one,
5',8'-dichlorospiro[cyclohexane-1-4'-(3',4'-dihydro)quinazolin]-2'(1'H)-one,
6',7'-dichlorospiro[cyclohexane-1-4'-(3',4'-dihydro)quinazolin]-2'(1'H)-one,
5',6'-dichlorospiro[cyclohexane-1-4'-(3',4'-dihydro)quinazolin]-2'(1'H)-one,
6'-phenylspiro[cyclohexane-1-4'-(3',4'-dihydro)quinazolin]-2'(1'H)-one,
8'-iodospiro[cyclohexane-1-4'-(3',4'-dihydro)quinazolin]-2'(1'H)-one,
8'-Bromospiro[cyclobutane-1-4'-(3',4'-dihydro)quinazolin]-2'(1'H)-one,
8'-Bromospiro[cycloheptane-1-4'-(3',4'-dihydro)quinazolin]-2'(1'H)-one,
8'-Bromo-4-methylspiro[cyclohexane-1-4'-(3',4'-dihydro)quinazolin]-2'(1'H)-one,
8'-Bromospiro[bicyclo[3,2,1]octane-2-4'-(3',4'-dihydro)quinazolin]-2'(1'H)-one,
6',8'-dichlorospiro[cyclohexane-1-4'-(3',4'-dihydro)quinazolin]-2'(1'H)-one,
8'-chloro-6'-iodospiro[cyclohexane-1-4'-(3',4'-dihydro)quinazolin]-2'(1'H)-one,
8'-chloro-6'-methoxyspiro[cyclohexane-1-4'-(3',4'-dihydro)quinazolin]-2'(1'H)-one,
8'-chloro-6'-phenylspiro[cycloheptane-1-4'-(3',4'-dihydro)quinazolin]-2'(1'H)-one,
8'-chloro-6'-phenylspiro[cyclohexane-1-4'-(3',4'-dihydro)quinazolin]-2'(1'H)-one,
8'-chloro-6'-methylspiro[cyclohexane-1-4'-(3',4'-dihydro)quinazolin]-2'(1'H)-one,
8'-chloro-6'-(3-pyridyl)spiro[cyclohexane-1-4'-(3',4'-dihydro)quinazolin]-2'(1'H)-one,
8'-chloro-6'-(4-pyridyl)spiro[cyclohexane-1-4'-(3',4'-dihydro)quinazolin]-2'(1'H)-one,
6'-(4-carboxyphenyl)-8'-chlorospiro[cyclohexane-1-4'-(3',4'-dihydro)quinazolin]-2'(1'H)-one,
6'-(3-carboxyphenyl)-8'-chlorospiro(cyclohexane-1-4'-(3',4'-dihydro)-quinazolin]-2'(1'H)-one,
8'-chloro-6'-(1H-indol-5yl)spiro[cyclohexane-1-4'-(3',4'-dihydro)quinazolin]-2'(1'H)-one,
8'-chloro-6'-(2-pyridyl)spiro[cyclohexane-1-4'-(3',4'-dihydro)quinazolin]-2'(1'H)-one,
8'-chloro-6'-(3-dimethylamino-prop-1-ynyl)spiro[cyclohexane-1-4'-(3',4'-dihydro)-quinazolin]-2'(1'H)-one,
8'-chloro-6'-(3-methylamino-prop-1-ynyl)spiro[cyclohexane-1-4'-(3',4'-dihydro)quinazolin]-2'(1'H)-one,
8'-chloro-6'-[4-(4-methyl-piperazine-1-carbonyl)phenyl]spiro[cyclohexane-1-4'-(3',4'-dihydro)quinazolin]-2'(1'H)-one,
8'-chloro-6'-[4-(3-N-dimethylamino-propylcarboxamide)phenyl]-spiro-[cyclohexane-1-4'-(3',4'-dihydro)quinazolin]-2'(1'H)-one,
8'-chloro-6'-[4-(2-N-dimethylamino-ethylcarboxamide)phenyl]-spiro-[cyclohexane-1-4'-(3',4'-dihydro)quinazolin]-2'(1'H)-one,
8'-chloro-6'-[3-(3-N-dimethylamino-propylcarboxamide)phenyl]-spiro-[cyclohexane-1-4'-(3',4'-dihydro)quinazolin]-2'(1'H)-one,
8'-chloro-6'-[3-(4-methyl-piperazine-1-carbonyl)-phenyl]spiro-[cyclohexane-1-4'-(3',4'-dihydro)quinazolin]-2'(1'H)-one,
8'-chloro-6'-[3-(2-N-dimethylamino-ethylcarboxamide)phenyl]spiro-[cyclohexane-1-4'-(3',4'-dihydro)quinazolin]-2'(1'H)-one,
8'-Chlorospiro[cyclohexane-1-4'-(3',4'-dihydro)quinazolin]-2'(1'H)-thione,
8'-Chloro-2'-cyanoiminospiro[cyclohexane-1-4'-(3',4'-dihydro)quinazoline,
8'-chloro-6'-[4-(4-pyrimidin-2-yl-piperazine-1-carbonyl)phenyl]spiro[-cyclohexane-1-4'-(3',4'-dihydro)quinazolin]-2'(1'H)-one,
8'-chloro-6'-[4-(4-(2-morpholin-4-yl-ethyl)-piperazine-1-carbonyl)-phenyl]spiro[-cyclohexane-1-4'-(3',4'-dihydro)quinazolin]-2'(1'H)-one,
8'-chloro-6'-[4-(4-(2-morpholin-4-yl-2-oxo-ethyl)-piperazine-1-carbonyl)-phenyl]spiro[-cyclohexane-1-4'-(3',4'-dihydro)quinazolin]-2'(1'H)-one,
8'-chloro-6'-[4-(4-(2-hydroxy-ethoxy)-ethyl)-piperazine-1-carbonyl)-phenyl]spiro[-cyclohexane-1-4'-(3',4'-dihydro)quinazolin]-2'(1'H)-one,
Spiro[cyclohexane-1-9'-(8',9'-dihydro)-pyrazolo[4',3'-f]quinazolin]-7'(6'H)-one,
8'-Chloro-5'-methoxyspiro[cyclohexane-1-4'-(3',4'-dihydro)quinazolin]-2'(1'H)-one,
5',8'-difluorospiro[cyclohexane-1-4'-(3',4'-dihydro)quinazolin]-2'(1'H)-one,
8'-Chloro-5'-methylspiro[cyclohexane-1-4'-(3',4'-dihydro)quinazolin]-2'(1'H)-one,
8'-Chloro-6'-(morpholin-4-yl)methylspiro[cyclohexane-1-4'-(3',4'-dihydro)quinazolin]-2'(1'H)-one,
8'-Chloro-5'-hydroxyspiro[cyclohexane-1-4'-(3',4'-dihydro)quinazolin]-2'(1'H)-one,
8'-Chloro-5'-hydroxy-6'-iodo-spiro[cyclohexane-1-4'-(3',4'-dihydro)quinazolin]-2'(1'H)-one,
8'-Chloro-6'-iodo-5'-methoxy-spiro[cyclohexane-1-4'-(3',4'-dihydro)quinazolin]-2'(1'H)-one,
8'-Chloro-6'-cyano-5'-methoxy-spiro[cyclohexane-1-4'-(3',4'-dihydro)quinazolin]-2'(1'H)-one,
8'-Chloro-5'-[2-(4-morpholino)ethoxy]spiro[cyclohexane-1-4'-(3',4'-dihydro)quinazolin]-2'(1'H)-one,
8'-Chloro-5'-[2-dimethylaminoethoxy]spiro[cyclohexane-1-4'-(3',4'-dihydro)quinazolin]-2'(1'H)-one,
8'-Chloro-5'-(2-aminoethoxy)-spiro[cyclohexane-1-4'-(3',4'-dihydro)quinazolin]-2'(1'H)-one,
8'-Chloro-5'-[2-(methylamino)ethoxy]-spiro[cyclohexane-1-4'-(3',4'-dihydro)quinazolin]-2'(1'H)-one,
8'-Chloro-5'-[2-(2-aminoethoxy)ethoxy]spiro[cyclohexane-1-4'-(3',4'-dihydro)quinazolin]-2'(1'H)-one,
8'-Chloro-5'-[3-dimethylaminopropoxy]spiro[cyclohexane-1-4'-(3',4'-dihydro)quinazolin]-2'(1'H)-one,
8'-Chloro-5'-ethoxycarbonylmethoxyspiro[cyclohexane-1-4'-(3',4'-dihydro)quinazolin]-2'(1'H)-one,
5'-carboxymethoxy-8'-chloro-spiro[cyclohexane-1-4'-(3',4'-dihydro)quinazolin]-2'(1'H)-one,
5'-carboxypropoxy-8'-chloro-spiro[cyclohexane-1-4'-(3',4'-dihydro)quinazolin]-2'(1'H)-one,
8'-chloro-5'-(3-sulphopropoxy)-spiro[cyclohexane-1-4'-(3',4'-dihydro)quinazolin]-2'(1'H)-one,
8'-Chloro-5'-[2-(tetrahydro-pyran-2-yloxy)-ethoxy]-spiro[cyclohexane-1-4'-(3',4'-dihydro)quinazolin]-2'(1'H)-one,
8'-Chloro-5'-(2-hydroxy-ethoxy)-spiro[cyclohexane-1-4'-(3',4'-dihydro)quinazolin]-2'(1'H)-one, 8'-Chloro-5'-(5-ethoxycarbonyl-furan-2-ylmethoxy)-spiro[cyclohexane-1-4'-(3',4'-dihydro)quinazolin]-2'(1'H)-one,
8'-Chloro-5'-(5-carboxy-furan-2-ylmethoxy)-spiro[cyclohexane-1-4'-(3',4'-dihydro)quinazolin]-2'(1'H)-one,
8'-Chloro-5'-cyanomethoxyspiro[cyclohexane-1-4'-(3',4'-dihydro)quinazolin]-2'(1'H)-one,
8'-Chloro-5'-(1H-tetrazol-5-ylmethoxy)-spiro[cyclohexane-1-4'-(3',4'-dihydro)quinazolin]-2'(1'H)-one,
8'-Chloro-5'-(5-hydroxy-[1,2,4]oxadiazol-3-ylmethoxy)-spiro[cyclohexane-1-4'-(3',4'-dihydro)quinazolin]-2'(1'H)-one,
8'-Chloro-6'-iodo-5'-[2-dimethylamino-ethoxy]spiro[cyclohexane-1-4'-(3',4'-dihydro)quinazolin]-2'(1'H)-one,
6'-(4-carboxyphenyl)-8'-chloro-5'-methoxyspiro[cyclohexane-1-4'-(3',4'-dihydro)quinazolin]-2'(1'H)-one,
6'-(3-carboxyphenyl)-8'-chloro-5'-methoxyspiro[cyclohexane-1-4'-(3',4'-dihydro)quinazolin]-2'(1'H)-one,
8'-chloro-6'-[2-(4-methyl-piperazine-1-carbonyl)phenyl]spiro[cyclohexane-1-4'-(3',4'-dihydro)quinazolin]-2'(1'H)-one,
8'-chloro-6'-[2-methyl-4-(4-methyl-piperazine-1-carbonyl)phenyl]spiro[cyclohexane-1-4'-(3',4'-dihydro)quinazolin]-2'(1'H)-one,
8'-chloro-6'-[4-(piperazine-1-carbonyl)phenyl]spiro[cyclohexane-1-4'-(3',4'-dihydro)quinazolin]-2'(1'H)-one,
8'-chloro-6'-[4-carbamoyl-phenyl]spiro[cyclohexane-1-4'-(3',4'-dihydro)quinazolin]-2'(1'H)-one,
8'-chloro-6'-[4-((1-methyl-piperidin-4-yl)-piperazine-1-carbonyl)phenyl]spiro[cyclohexane-1-4'-(3',4'-dihydro)quinazolin]-2'(1'H)-one,
8'-chloro-5'-methoxy-6'-[4-(4-methyl-piperazine-1-carbonyl)phenyl]spiro[cyclohexane-1-4'-(3',4'-dihydro)quinazolin]-2'(1'H)-one,
8'-Trifluoromethylspiro[cyclohexane-1-4'-(3',4'-dihydro)quinazolin]-2'(1'H)-one,
8'-Chloro-6'-cyanomethylspiro[cyclohexane-1-4'-(3',4'-dihydro)quinazolin]-2'(1'H)-one,
8'-Chloro-5'-(3-dimethylamino-2-hydroxy-propoxy)-spiro[cyclohexane-1-4'-(3',4'-dihydro)quinazolin]-2'(1'H)-one,
8'-Chloro-5'-(3-methylamino-2-hydroxy-propoxy)-spiro[cyclohexane-1-4'-(3',4'-dihydro)quinazolin]-2'(1'H)-one,
8'-Chloro-5'-[2-(ethoxycarbonylmethyl-amino)-ethoxy]-spiro[cyclohexane-1-4'-(3',4'-dihydro)quinazolin]-2'(1'H)-one,
8'-Chloro-5'-[2-(carboxymethyl-amino)-ethoxy]-spiro[cyclohexane-1-4'-(3',4'-dihydro)quinazolin]-2'(1'H)-one hydrochloride,
8'-Chloro-5'-(2-methanesulfonylamino-2-oxo-ethoxy)-spiro[cyclohexane-1-4'-(3',4'-dihydro)quinazolin]-2'(1'H)-one,
8'-Chloro-5'-(2-[(5-methyl-isoxazol-3-ylmethyl)-amino]ethoxy)-spiro[cyclohexane-1-4'-(3',4'-dihydro)quinazolin]-2'(1'H)-one.

17. A pharmaceutical composition comprising a compound according to claim 1 or a pharmaceutically acceptable salt thereof and a pharmaceutically acceptable carrier.

18. A method for preparing a compound of formula (I) according to claim 1 in which $X_1$, $X_2$, $X_3$, $X_4$, A and $R^9$ are as defined in claim 1 and Y is NH, said method comprising, (1) reacting a compound (2a)

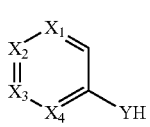

(2a)

in which $X_1$, $X_2$, $X_3$, $X_4$ are as defined in claim 1 and Y is NH, with a group P-LG in which P is a protecting group and LG is a leaving group to obtain compound (2b)

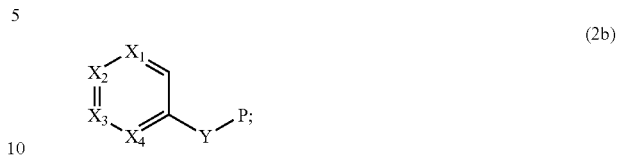

(2b)

(2) reacting compound (2b) with R-Li in which R is lower alkyl and then with a ketone of formula

in which A is as defined in claim 1 to obtain compound (2c)

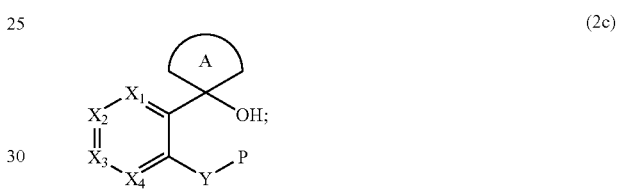

(2c)

(3) removing the protecting group P either under reductive conditions, acidic condition or basic condition to obtain compound (2d)

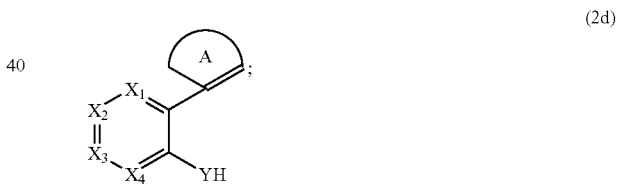

(2d)

(4) reacting compound (2d) with a group O=C=N—$R^9$ in which $R^9$ is as defined in claim 1 to obtain compound (2e)

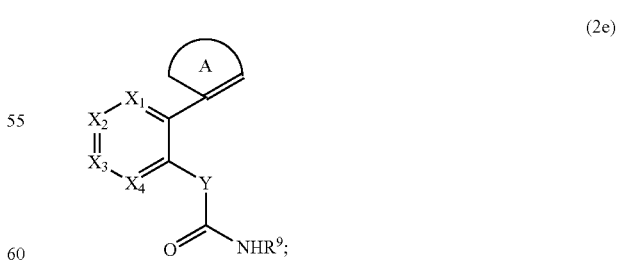

(2e)

(5) reacting compound (2e) with an acid to obtain said compound of formula (I),
(6) isolating said compound of formula (I).

* * * * *